United States Patent
Wu et al.

(10) Patent No.: US 11,466,013 B2
(45) Date of Patent: Oct. 11, 2022

(54) ERK INHIBITOR AND USE THEREOF

(71) Applicant: Betta Pharmaceuticals Co., LTD, Zhejiang (CN)

(72) Inventors: Hao Wu, Zhejiang (CN); Wei Gu, Zhejiang (CN); Xiaojing Tang, Zhejiang (CN); Wei Wang, Zhejiang (CN); Bo Zhan, Zhejiang (CN); Dongjie Feng, Zhejiang (CN); Yongxin Ke, Zhejiang (CN); Zhongyan Chen, Zhejiang (CN); Yifei Shen, Zhejiang (CN); Wenmao Wu, Zhejiang (CN); Xintao Zhao, Zhejiang (CN); Hong Lan, Beijing (CN); Jiabing Wang, Beijing (CN); Lieming Ding, Zhejiang (CN)

(73) Assignee: Betta Pharmaceuticals Co., Ltd, Zhejiang (CN)

( * ) Notice: Subject to any disclaimer, the term of this patent is extended or adjusted under 35 U.S.C. 154(b) by 0 days.

(21) Appl. No.: 16/973,335

(22) PCT Filed: Jun. 6, 2019

(86) PCT No.: PCT/CN2019/090221
§ 371 (c)(1),
(2) Date: Dec. 8, 2020

(87) PCT Pub. No.: WO2019/233457
PCT Pub. Date: Dec. 12, 2019

(65) Prior Publication Data
US 2021/0261552 A1 Aug. 26, 2021

(30) Foreign Application Priority Data

Jun. 8, 2018 (WO) ............... PCT/CN2018/090385
Dec. 13, 2018 (WO) ............... PCT/CN2018/120975

(51) Int. Cl.
| | |
|---|---|
| *C07D 487/04* | (2006.01) |
| *A61P 35/00* | (2006.01) |
| *C07D 401/04* | (2006.01) |
| *C07D 403/14* | (2006.01) |
| *C07D 417/04* | (2006.01) |
| *C07D 487/20* | (2006.01) |
| *C07D 491/20* | (2006.01) |
| *C07D 513/04* | (2006.01) |
| *C07D 519/00* | (2006.01) |

(52) U.S. Cl.
CPC ............ *C07D 487/04* (2013.01); *A61P 35/00* (2018.01); *C07D 401/04* (2013.01); *C07D 403/14* (2013.01); *C07D 417/04* (2013.01); *C07D 487/20* (2013.01); *C07D 491/20* (2013.01); *C07D 513/04* (2013.01); *C07D 519/00* (2013.01)

(58) Field of Classification Search
CPC .. C07D 487/04; C07D 519/00; C07D 487/20; C07D 403/14; C07D 513/04; C07D 491/20; C07D 401/04; C07D 417/04
USPC ................................................... 514/210.16
See application file for complete search history.

(56) References Cited

FOREIGN PATENT DOCUMENTS

| WO | 2008006793 A1 | 1/2008 |
|---|---|---|
| WO | 2016026078 A1 | 2/2016 |
| WO | 2016205418 A1 | 12/2016 |

OTHER PUBLICATIONS

Bueno, et al., "Design, synthesis and antimalarial evaluation of novel thiazole derivatives," Bioorganic & Medicinal Chemistry Letters, 2016; 17 pgs.

(Continued)

*Primary Examiner* — Kahsay Habte
(74) *Attorney, Agent, or Firm* — Umberg Zipser LLP; Jason Tejani

(57) ABSTRACT

Disclosed are a compound (as shown in formula I) as an extracellular signal-regulated kinase (ERK) inhibitor, a pharmaceutical composition thereof, a preparation method therefor, and use thereof in treating ERK-mediated diseases. Said compound plays a role by regulating a plurality of processes such as cell proliferation, apoptosis, migration and angiogenesis.

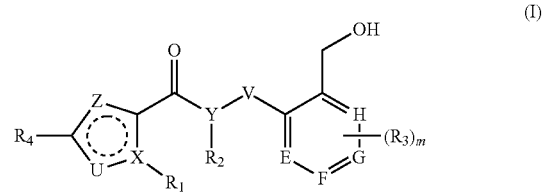

(I)

27 Claims, No Drawings

(56) References Cited

OTHER PUBLICATIONS

Guerrero, et al., "Discovery, Design and Synthesis of the First Reported Potent and Selective Sphingosine-1-Phosphate 4 (S1P4) Receptor Antagonists," Bioorg Med Chem Lett., Jun. 15, 2011;21(12):3632-3636.
CAS Registry No. 1292085-13-2; STN Entry Date May 9, 2011; Ryan Scientific et al: 4-Thiazolecarboxamide derivative; XP055889041; 1 page.
CAS Registry No. 1305600-17-2; STN Entry Date Jun. 5, 2011; Ryan Scientific et al: 4-Thiazolecarboxamide derivative; XP055889054; 1 page.
CAS Registry No. 1308080-08-1; STN Entry Date Jun. 9, 2011; Ryan Scientific et al: 4-Thiazolecarboxamide derivative; XP055889049; 1 page.
CAS Registry No. 1308581-88-5; STN Entry Date Jun. 10, 2011; Ryan Scientific et al: "3-soxazolecaboxamide derivative"; XP055889037; 1 page.
CAS Registry No. 1974983-61-3; STN Entry Date Aug. 18, 2016; Aurora Fine Chemicals: "1,2,4-Dxadiazole-3-carboxamide derivative"; XP055889023; 1 page.
European Patent Office. Extended European Search Report, dated Feb. 18, 2022, European Application No. 19815477.5, 12 pages.

ERK INHIBITOR AND USE THEREOF

TECHNICAL FIELD

The invention relates to a series of compounds as inhibitors of extracellular signal-regulated kinase (ERK), preparation methods and pharmaceutical compositions thereof. The invention also relates to the use of the above-mentioned compound or its pharmaceutical composition in the treatment of ERK-mediated diseases.

BACKGROUND TECHNIQUE

Cells have extremely complex life activities, and these life activities must be strictly regulated. As an open system, it not only communicates information with the external environment, but also transmits information between cells. In the process of long-term evolution and development and natural selection, a complex signal transduction network has been gradually established. It is formed by the interaction and interaction of different signal transmission pathways, that is, there are different signal transduction pathways "cross-talking". In the signal network, the mitogen-activated protein kinase (MAPK) signaling pathway plays an extremely important role, controlling various physiological processes of cells, such as cell growth, development, division, and death.

Extracellular signal-regulated kinase (ERK) is a member of the MAPK family. Its signal transmission pathway is the core of the signal network involved in regulating cell growth, development and division. From extracellular stimulus to cells. The corresponding biological effects of cells must go through the three-stage kinase cascade reaction of the MAPK signal transduction pathway, that is, the upstream activator protein→MAPK kinase kinase (MAPKKK)→MAPK kinase (MAP-KK)→MAPK. In the transmission pathway of ERKs, Ras acts as an upstream activator protein, Raf acts as MAPKKK, MAPK/ERK kinase (MEK) acts as MAPKK, and ERK stands for MAPK, that is, the Ras-Raf-MEK-ERK pathway. MAPKKK phosphorylates both serine and threonine of MAPKK and activates it, which in turn causes MAPKK to phosphorylate both threonine and serine on MAPK. Phosphorylation activated ERK1/2 is translocated from the cytoplasm to the nucleus, and then mediates the activation of various transcription factors and genes such as Elk-1, ATF, NF-κ B, Ap-1, c-fos and c-Jun And transcription, participate in a variety of biological reactions such as cell proliferation and differentiation, cell morphology maintenance, cytoskeleton construction, cell apoptosis and cell canceration.

ERK includes ERK1 and ERK2, and is the key to signal transmission from surface receptors to the nucleus. MAPK kinases ERK1 and ERK2 are widely expressed and participated in the RAS-RAF-MEK-ERK signal cascade. They both contain unique N- and C-termini that provide signal specificity. The kinase domain also has a 31-amino acid residue that makes it functionally specific. In multiple cell types, multiple mitogens or other stimuli can activate multiple subtypes of RAS (HRAS, NRAS, and KRAS), and activated RAS can recruit and activate various RAF subunits (including ARAF, BRAF, and CRAF), therefore, the cascade activates MEK1/2, mediates the phosphorylation of downstream ERK1 and ERK2 to activate ERK1/2, regulates the activation and transcription of hundreds of cytoplasmic and nuclear substrates, and the occurrence of related biological effects. (Reference Yoon S, Seger R. The extracellular signal-regulated kind: multiple substrates regulate diverse cellular functions; Growth Factors 2006, 24, 21-44).

The RAS-RAF-MEK-ERK signaling cascade plays a key role in the occurrence and development of a variety of diseases, including brain injury, cancer, cardiac hypertrophy, diabetes, and inflammation. Especially in cancers, approximately 98% of pancreatic cancers, 52% of colorectal cancers, and 32% of lung adenocarcinomas have KRAS mutations, and 28% of melanomas have NRAS gene mutations. In addition, about 40-60% of melanomas, 40% of thyroid cancers, and 20% of colorectal cancers have BRAF mutations (Reference Vakiani E, solit DB. KRAS and BraF; KRAS and BRAF; drug targets and predictive biomarkers; Journal of Pathology 2011, 223, 219-29). Mutations in the RAS and RAF genes cause ERK in tumor cells to be continuously activated, causing excessive cell proliferation. Therefore, for a wide range of human tumors, the RAS-RAF-MEK-ERK signaling pathway is a very attractive approach for anti-tumor treatment.

ERK inhibitors currently in clinical development include BVD-523, GDC-0994, KO-947, LY-3214996, and LTT462, etc., but they are all in the early stage of clinical I/II phase research and development. There are currently no drugs on the market and urgently need to be developed effective ERK inhibitor.

We have discovered a series of new compounds that can selectively inhibit ERK in the same signaling cascade. In the present invention, the ERK inhibitor should be understood to inhibit ERK1 and/or ERK2.

SUMMARY

The invention relates to a compound as an inhibitor of extracellular signal-regulated kinase (ERK), or a pharmaceutically acceptable salt, solvate, chelate, non-covalent complex or prodrug thereof. The general structural formula of the compound of the present invention is shown in formula (I):

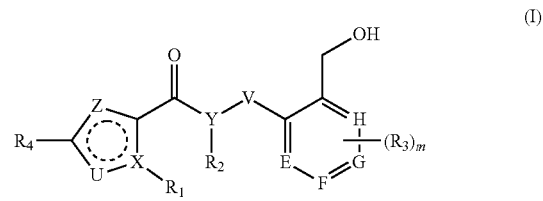

wherein,
--- stands for a single or double bond;
X and Y are independently N or C;
Z and U are independently selected from the group consisting of O, S, $NR_{10}$ and $C(R_{10})_2$, wherein $R_{10}$ is independently H, or unsubstituted or substituted $C_{1-8}$ alkyl;
V is $(CH_2)_n$;
E, F, G and H are independently N or CH;
$R_1$ and $R_2$ are independently absent or are selected from the group consisting of H, halogen, hydroxyl, CN, $C_{1-4}$ alkyl, $C_{1-8}$ alkoxy, $C_{2-8}$ alkenyl, $C_{2-8}$ alkynyl, $C_{3-10}$ cycloalkyl, $C_{6-10}$ aryl, $C_{5-10}$ heteroaryl and $C_{3-10}$ heterocyclyl, wherein any of the $C_{1-8}$ alkyl, $C_{1-8}$ alkoxy, $C_{2-8}$ alkenyl, $C_{2-8}$ alkynyl, $C_{3-10}$ Cycloalkyl, $C_{6-10}$ aryl, $C_{5-10}$ heteroaryl or $C_{3-10}$ heterocyclyl is unsubstituted or substituted with halogen, hydroxy or $C_{1-8}$ alkyl; or
$R_1$ and $R_2$ together with the atoms to which they are attached form a $C_{5-10}$ cycloalkyl, $C_{5-10}$ heterocyclyl or $C_{5-10}$ heteroaryl group, wherein any of the $C_{5-10}$cycloalkyl, $C_{5-10}$ heterocyclyl or $C_{5-10}$ heteroaryl is unsubstituted or substituted with halogen, hydroxy, CN, $C_{1-8}$alkyl, —$C_{1-8}$alkyl-hydroxy, —$C_{1-8}$alkyl-halogen, —$C_{1-8}$alkyl-$C_{1-8}$ alkoxy, —$C_{1-8}$alkyl-$C_{1-8}$alkoxy-$C_{1-8}$alkoxy, —(C═O)OC$_{1-8}$ alkyl, $C_{1-8}$ alkoxy, $C_{2-8}$ alkenyl, $C_{2-8}$ alkynyl, $C_{3-10}$ cycloalkyl, $C_{6-10}$ aryl, $C_{5-10}$ heteroaryl or $C_{3-10}$ heterocyclyl; or any of the $C_{5-10}$ cycloalkyl, $C_{5-10}$ heterocyclyl or $C_{5-10}$ heteroaryl group and an additional $C_{3-10}$ cycloalkyl group, $C_{3-10}$ heterocyclyl, $C_{6-10}$ aryl group or $C_{5-10}$ heteroaryl group form a spiro ring, wherein any of the additional $C_{3-10}$ cycloalkyl group, $C_{3-10}$ heterocyclyl, $C_{6-10}$ aryl or $C_{5-10}$ heteroaryl is unsubstituted or substituted with $C_{1-8}$ alkyl;

$R_3$ is selected from the group consisting of halogen, hydroxy, CN, $C_{1-8}$ alkyl, $C_{1-8}$ alkoxy, $C_{2-8}$ alkenyl, $C_{2-8}$ alkynyl, $C_{3-10}$cycloalkyl, $C_{6-10}$ aryl, $C_{5-10}$ heteroaryl and $C_{3-10}$ heterocyclyl, wherein any of the $C_{1-8}$ alkyl, $C_{1-8}$alkoxy, $C_{2-8}$ alkenyl, $C_{2-8}$ alkynyl, $C_{3-10}$cycloalkyl, $C_{6-10}$ aryl, $C_{5-10}$ heteroaryl or $C_{3-10}$ heterocyclyl is unsubstituted or substituted with halogen, hydroxy or $C_{1-8}$ alkyl;

$R_4$ is selected from the group consisting of $C_{5-10}$ cycloalkyl, $C_{6-10}$ aryl, $C_{5-10}$ heteroaryl and $C_{1-10}$ heterocyclyl, wherein any of the $C_{5-10}$ cycloalkyl, $C_{6-10}$ aryl, $C_{5-10}$ heteroaryl or $C_{5-10}$ heterocyclyl is unsubstituted or substituted with halogen, hydroxy, amino, CN, $C_{1-8}$ alkyl, $C_{1-8}$ haloalkyl or NR$_5$R$_6$, wherein $R_5$ and $R_6$ are independently selected from the group consisting of H, halogen, hydroxyl, CN, $C_{1-8}$ alkyl, —(C═O)C$_{1-8}$ alkyl, $C_{3-10}$ cycloalkyl, $C_{6-10}$ aryl, $C_{5-10}$ heteroaryl, $C_{3-10}$ heterocyclyl, —(C═O)C$_{5-10}$ heteroaryl or —(C═O)C$_{3-10}$ heterocyclyl, wherein any of the $C_{1-8}$ alkyl, —(C═O)C$_{1-8}$ alkyl, $C_{3-10}$ cycloalkyl, $C_{6-10}$ aryl, $C_{5-10}$ heteroaryl, $C_{3-10}$ heterocyclyl, —(C═O)C$_{5-10}$ heteroaryl or —(C═O)C$_{3-10}$ heterocyclyl is unsubstituted or substituted with halogen, hydroxy, amino, CN, $C_{1-8}$ alkyl, $C_{1-8}$ haloalkyl, —(C═O)C$_{1-8}$ alkyl, $C_{1-8}$ alkoxy, $C_{5-10}$ heteroaryl or $C_{3-10}$ heterocyclyl;

Each heterocyclyl or heteroaryl contains 1, 2 or 3 heteroatoms independently selected from the group consisting of N, O and S;

m and n are independently 0, 1, 2, 3, or 4.

In one aspect, in formula (I), both X and Y are N.

In one aspect, both Z and U in formula (I) are CH.

In one aspect, Z in formula (I) is S, U is CH; Z is CH, U is N; or Z is N, U is CH.

In one aspect, X in formula (I) is C, Z is S, and U is N.

In one aspect, both $R_1$ and $R_2$ in formula (I) are H.

In one aspect, $R_1$ in formula (I) is absent, and $R_2$ is H.

In one aspect, $R_1$ and $R_2$ in formula (I) together with the atoms to which they are attached form $C_{5-8}$ cycloalkyl or $C_{5-8}$ heterocyclyl, wherein any of the $C_{5-8}$ cycloalkyl or $C_{5-8}$ heterocyclyl is unsubstituted or substituted with F, Cl, hydroxy, CN, $C_{1-6}$ alkyl, —$C_{1-6}$ alkyl-hydroxy, —$C_{1-6}$ alkyl-chloro, —$C_{1-6}$alkyl-$C_{1-6}$ alkoxy, —(C═O)OC$_{1-6}$ alkyl, $C_{1-6}$ alkoxy, $C_{3-6}$ cycloalkyl, phenyl, $C_{5-8}$ heteroaryl or $C_{3-6}$ heterocyclyl; or any of the $C_{5-8}$ cycloalkyl or $C_{5-8}$ heterocyclyl and an additional $C_{3-7}$ cycloalkyl, $C_{3-7}$ heterocyclyl, phenyl or $C_{5-8}$ heteroaryl group forms a spiro ring, wherein any of the additional $C_{3-7}$ cycloalkyl, $C_{3-7}$ heterocyclyl, phenyl or $C_{5-8}$ heteroaryl is unsubstituted or substituted with $C_{1-6}$ alkyl, and each heterocyclyl or heteroaryl contains 1 or 2 heteroatoms independently selected from the group consisting of N, O and S.

In one aspect,

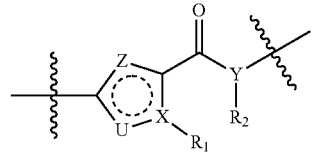

in formula (I) is selected from the group consisting of

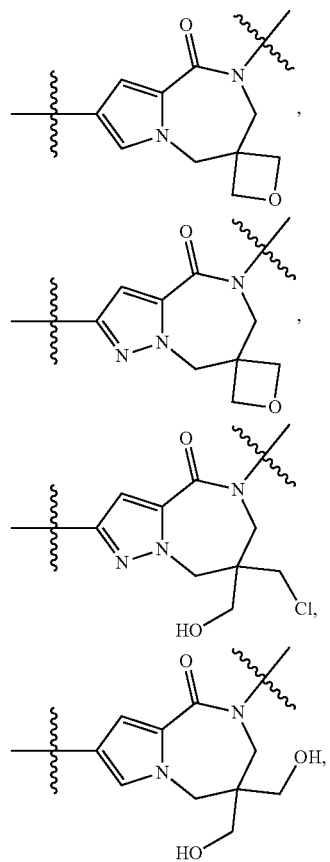

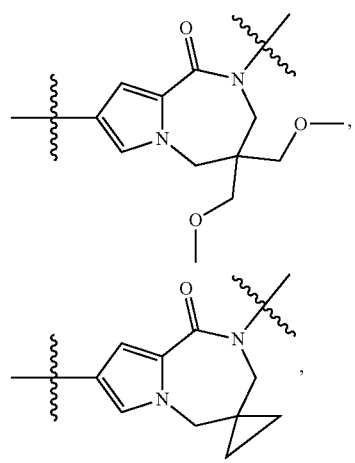

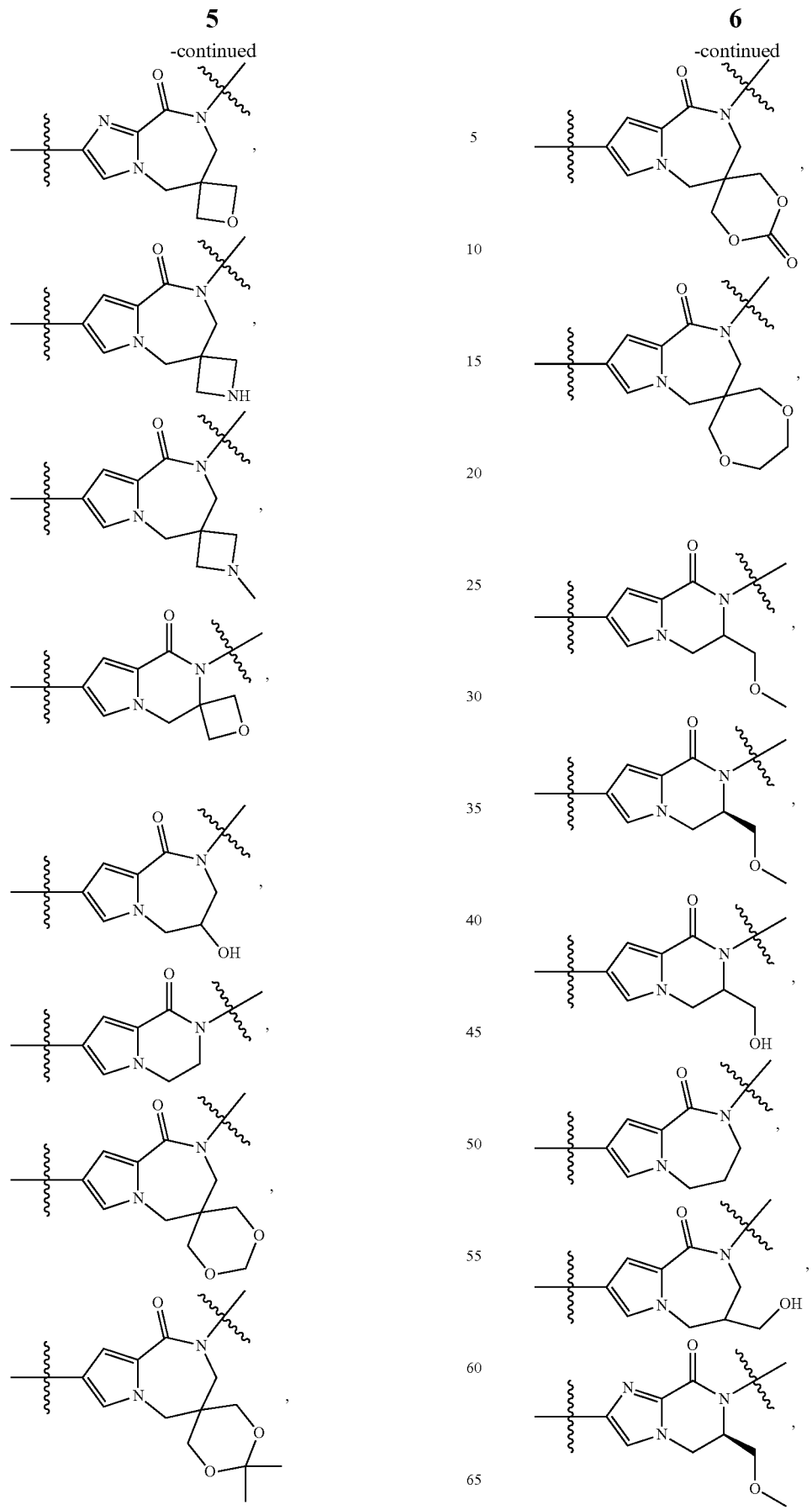

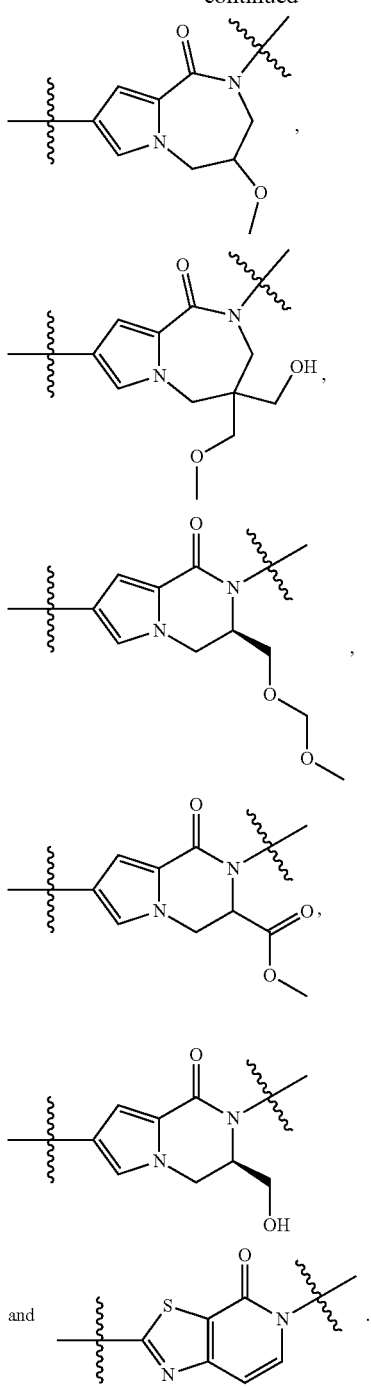

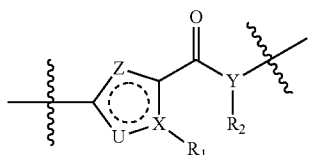

In one aspect, in formula (I) is

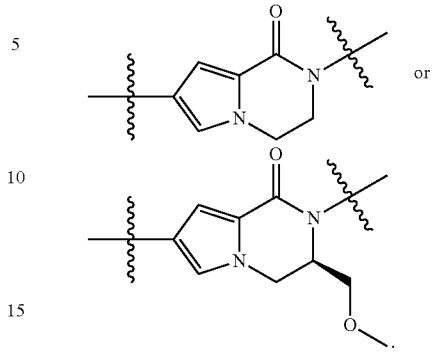

In one aspect, n in formula (I) is 1.

In one aspect, E, F, G, and H in formula (I) are defined in the following group:
(i) E, F, G and H are all CH;
(ii) E, F, G are CH, H is N;
(iii) E is N, and F, G, H are CH; or
(iv) F is N, and E, G, and H are CH.

In one aspect, E, F, G and H in formula (I) are all CH.

In one aspect, $R_3$ in formula (I) is optionally selected from hydroxy, CN, halogen, $C_{1-6}$ alkyl or $C_{1-6}$ haloalkyl.

In one aspect, $R_3$ in formula (I) is independently selected from the group consisting of hydroxyl, CN, F, Cl, methyl or trifluoromethyl.

In one aspect, $R_4$ in formula (I) is selected from the group consisting of $C_{5-6}$ cycloalkyl, phenyl, $C_{5-6}$ heteroaryl and $C_{5-6}$ heterocyclyl, wherein any of the $C_{5-6}$ cycloalkyl, phenyl, $C_{5-6}$ heteroaryl or $C_{5-6}$ heterocyclyl is unsubstituted or substituted with halogen, hydroxy, amino, CN, $C_{1-6}$ alkyl, $C_{1-6}$ haloalkyl or $NR_5R_6$.

In one aspect, $R_4$ in formula (I) is selected from the group consisting of phenyl, pyridyl or pyrimidinyl, wherein any of the phenyl, pyridyl or pyrimidinyl is unsubstituted or is substituted with F, Cl, CN, methyl, trifluoromethyl or $NR_5R_6$.

In one aspect, $R_5$ and $R_6$ are independently selected from the group consisting of H, halogen, hydroxyl, $C_{1-6}$ alkyl, —(C═O)$C_{1-6}$ alkyl, $C_{3-7}$ cycloalkyl, phenyl, $C_{5-10}$ heteroaryl and $C_{3-10}$ heterocyclyl, wherein any of the $C_{1-6}$ alkyl, —(C═O)$C_{1-6}$ alkyl, $C_{3-7}$ cycloalkyl, phenyl, $C_{5-10}$ heteroaryl or $C_{3-10}$ heterocyclyl is unsubstituted or substituted with F, Cl, hydroxy, amino, CN, $C_{1-6}$alkoxy, $C_{1-6}$ alkyl, —(C═O)$C_{1-6}$ alkyl, $C_{1-6}$ haloalkyl, —$C_{1-6}$ heterocyclyl, —$C_{5-6}$ heteroaryl, —$C_{5-6}$ heterocyclyl-$C_{1-6}$ alkyl or —$C_{5-6}$ heteroaryl-$C_{1-6}$ alkyl.

In one aspect, $R_5$ and $R_6$ are independently selected from the group consisting of H, methyl, ethyl, propyl, isopropyl,

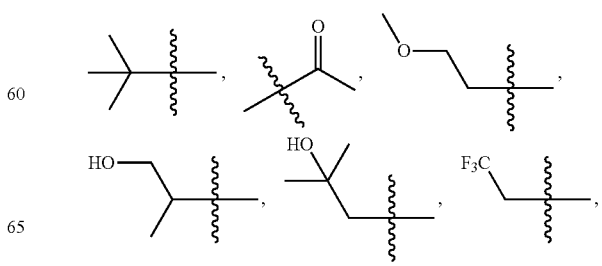

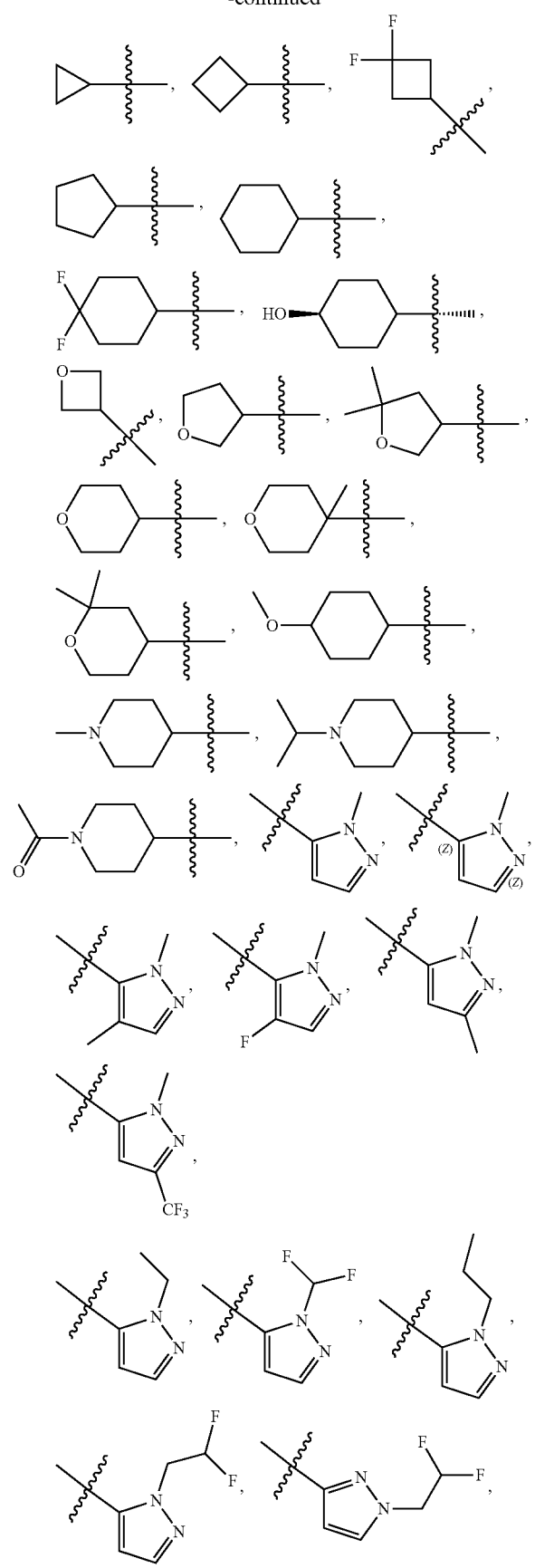
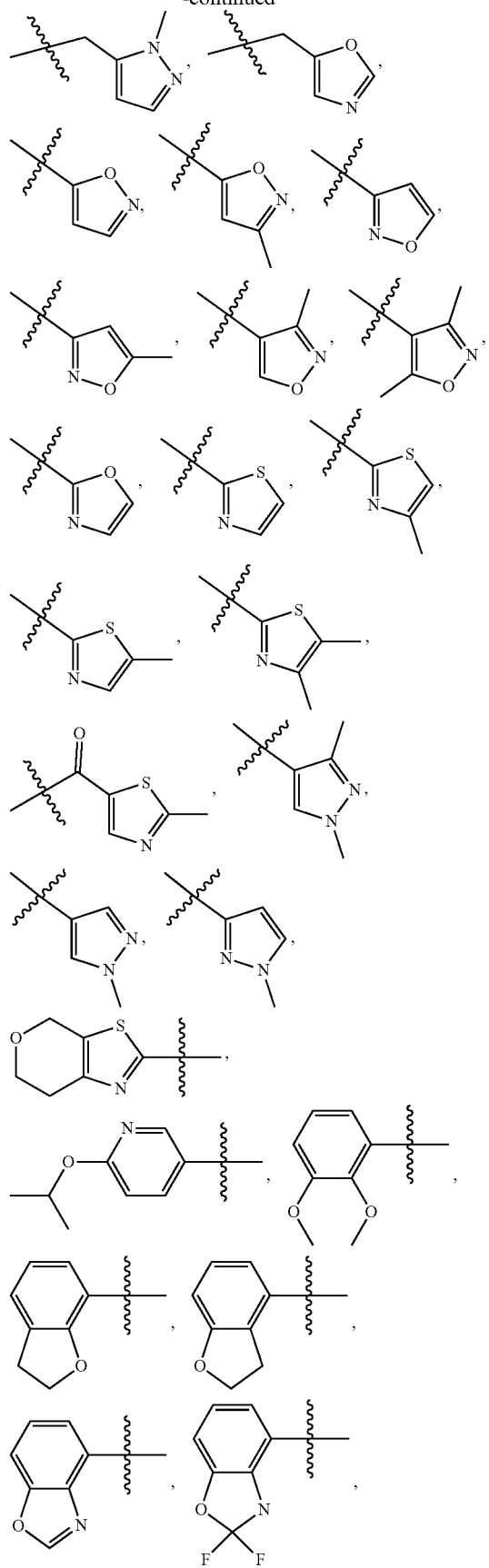

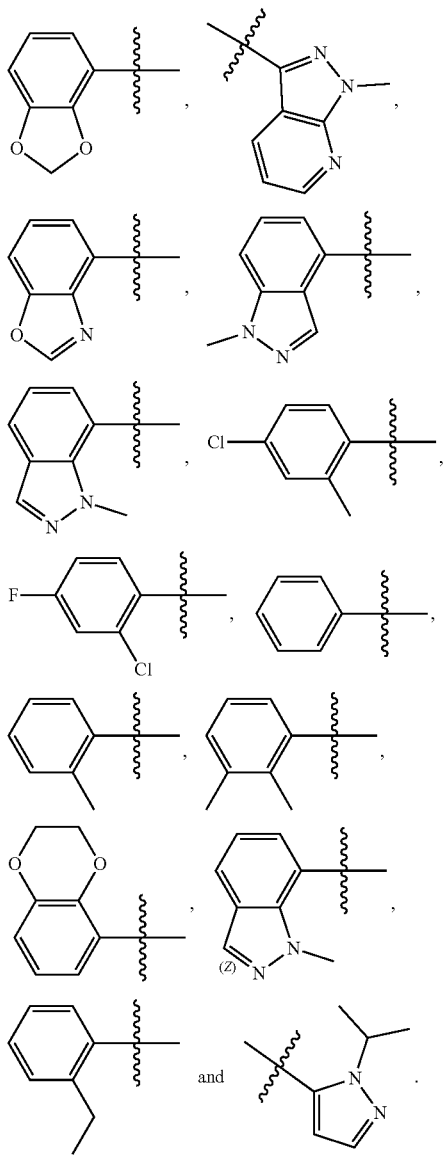
In one aspect, R$_4$ in formula (I) is selected from the group consisting of
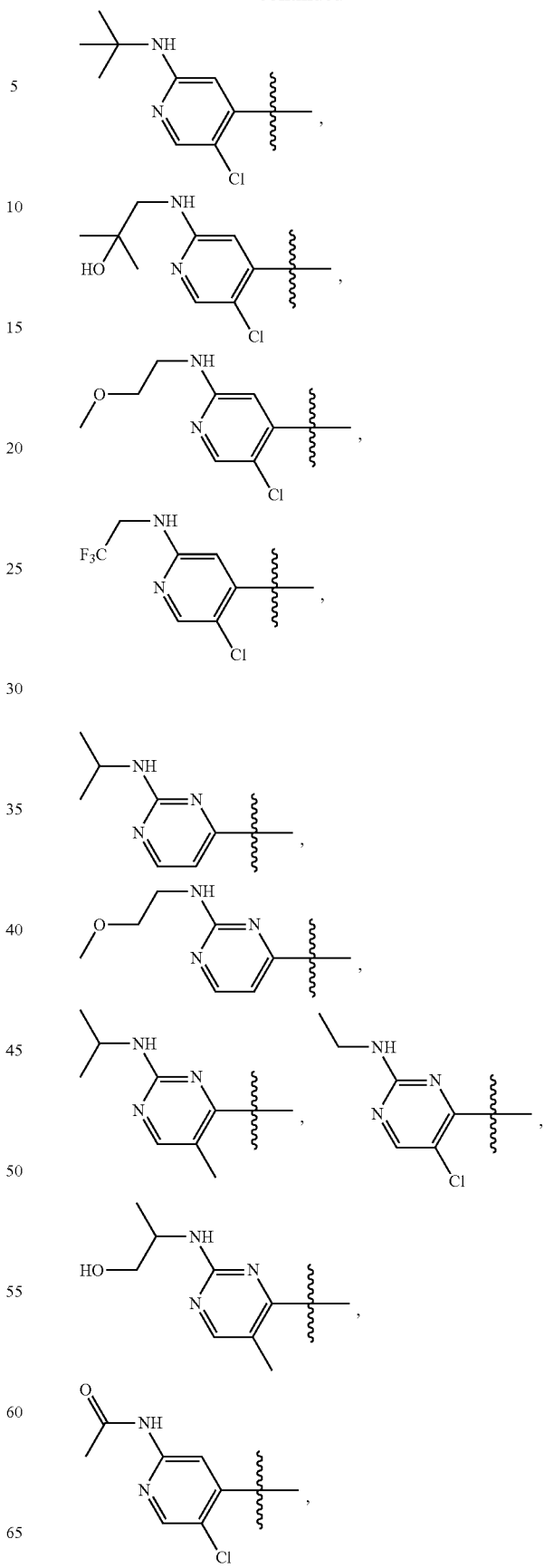

-continued
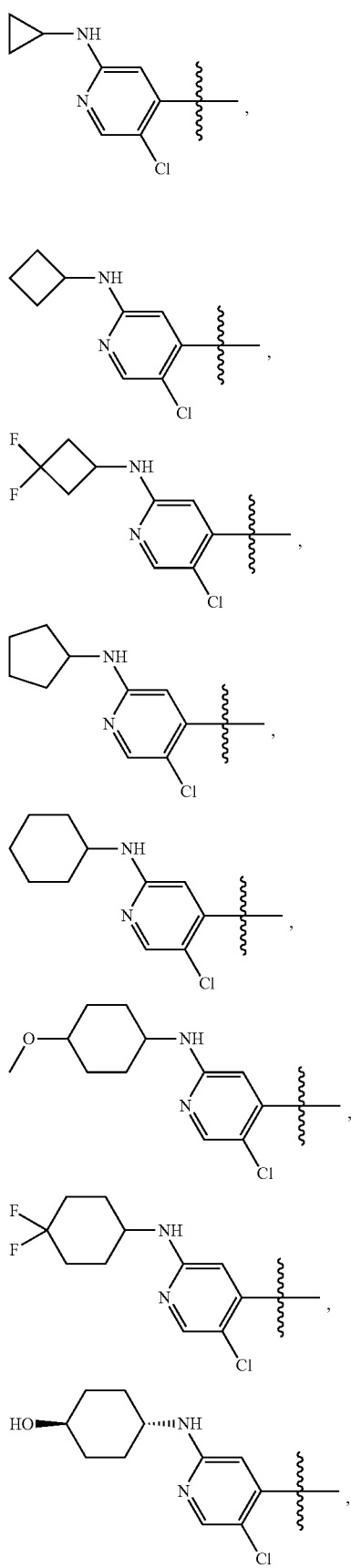
-continued
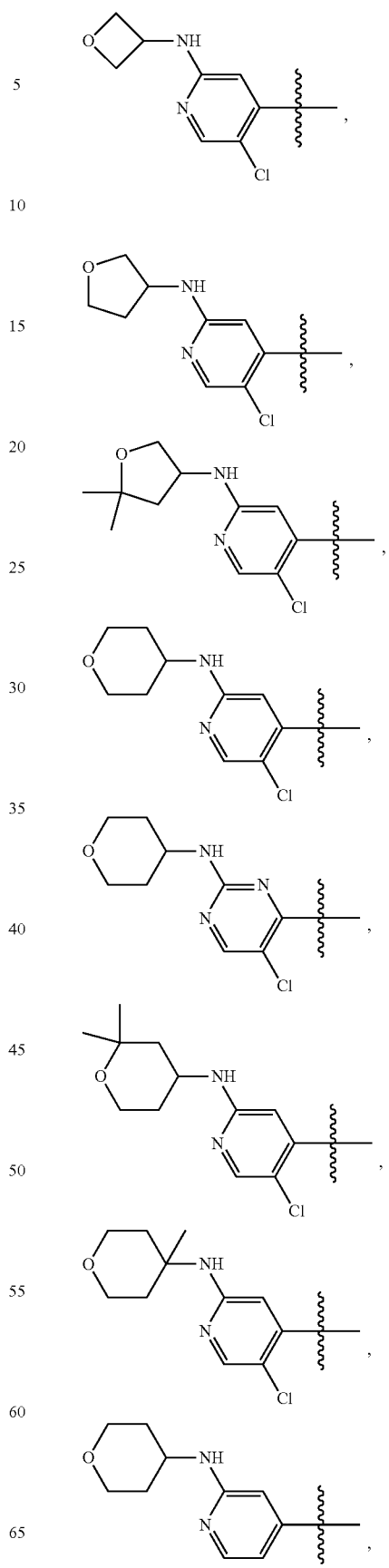

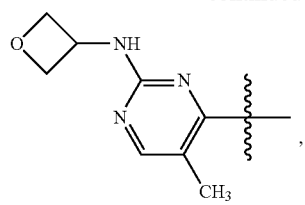,
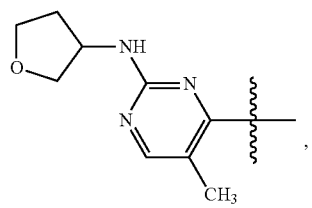,
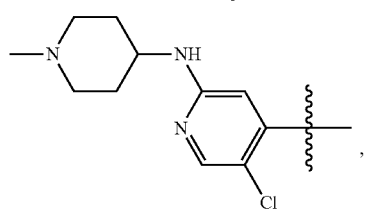,
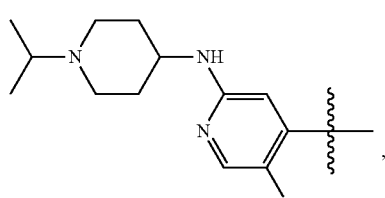,
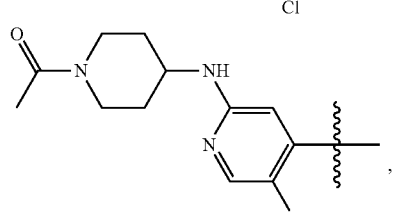,
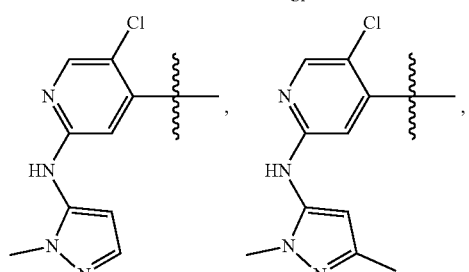,
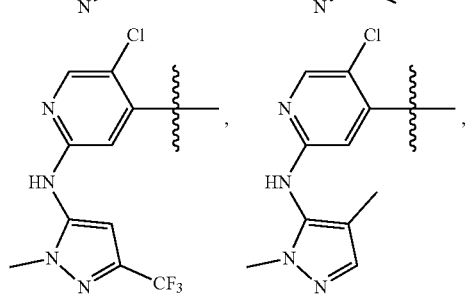
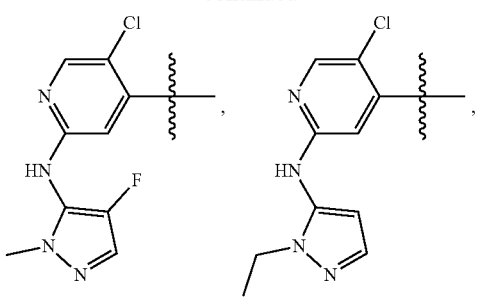,
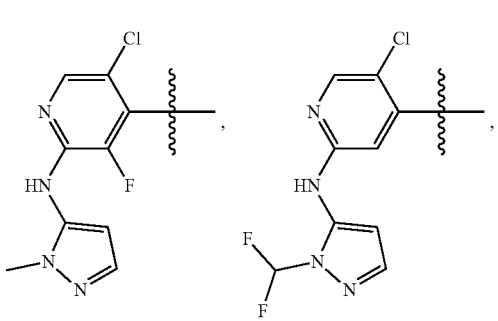,
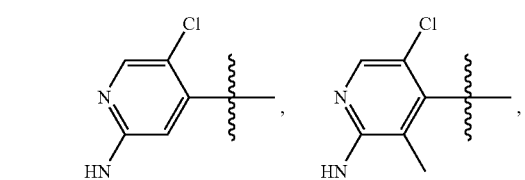,
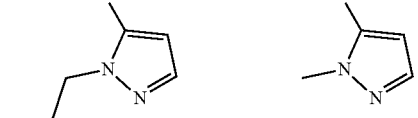,
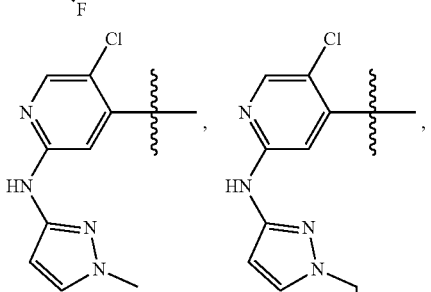,
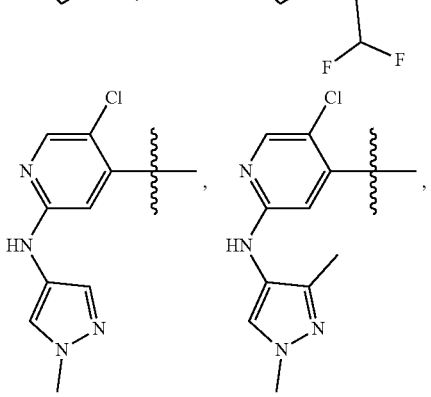,

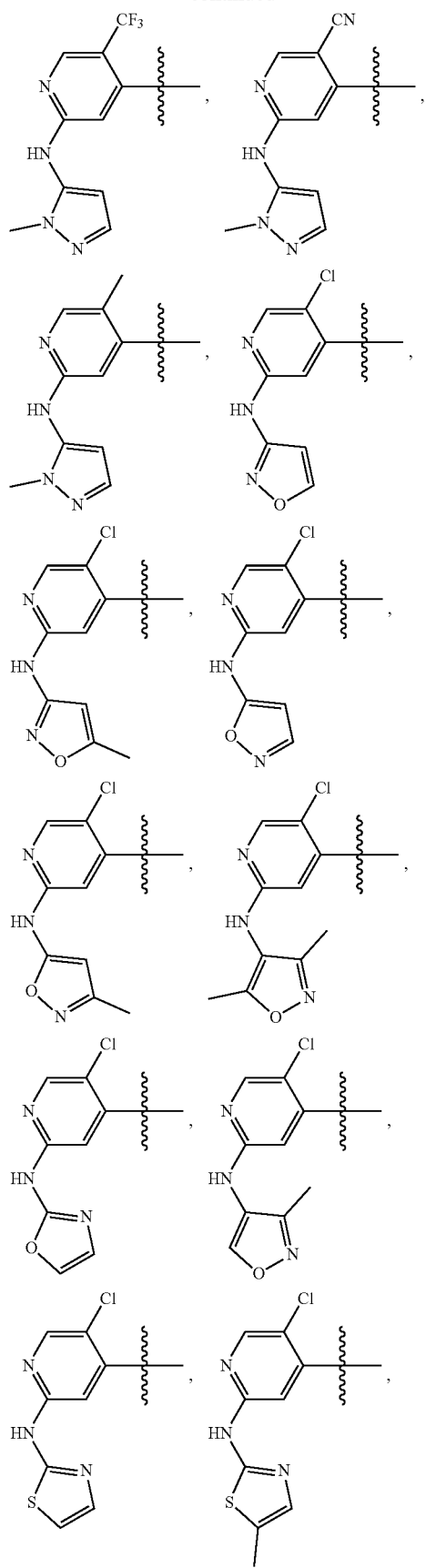
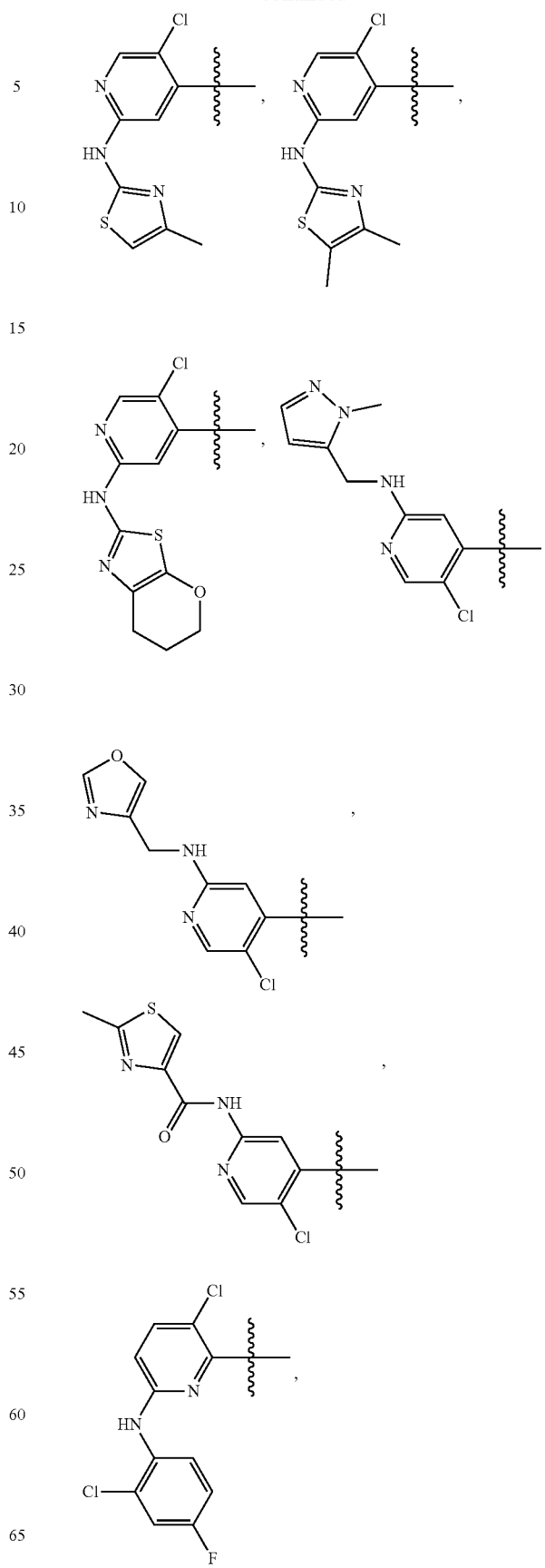

-continued
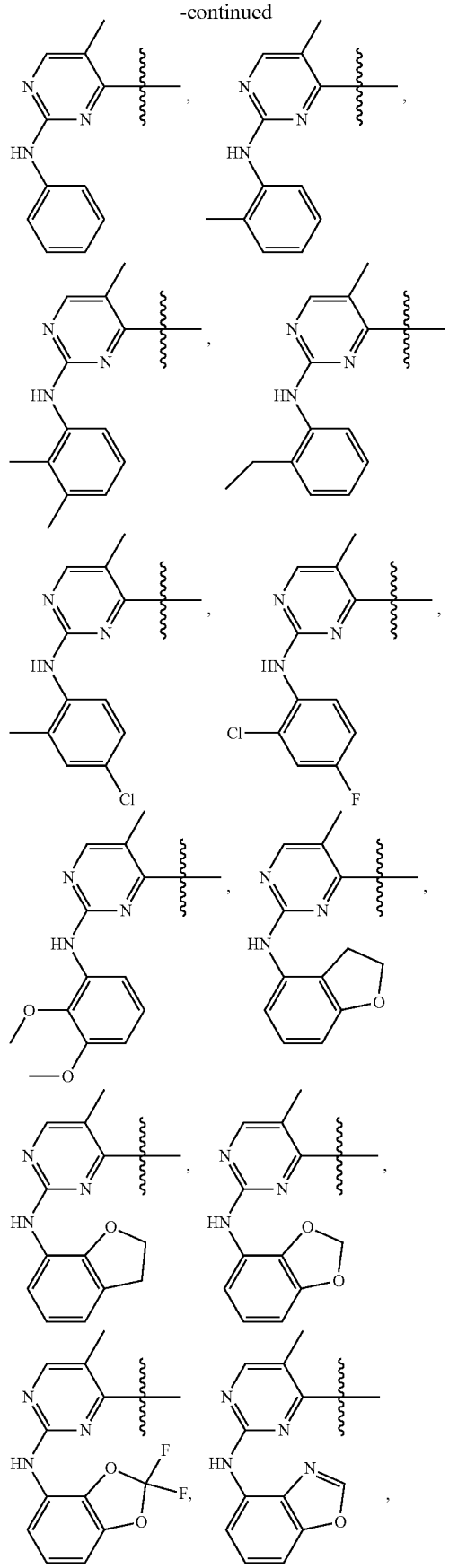
-continued
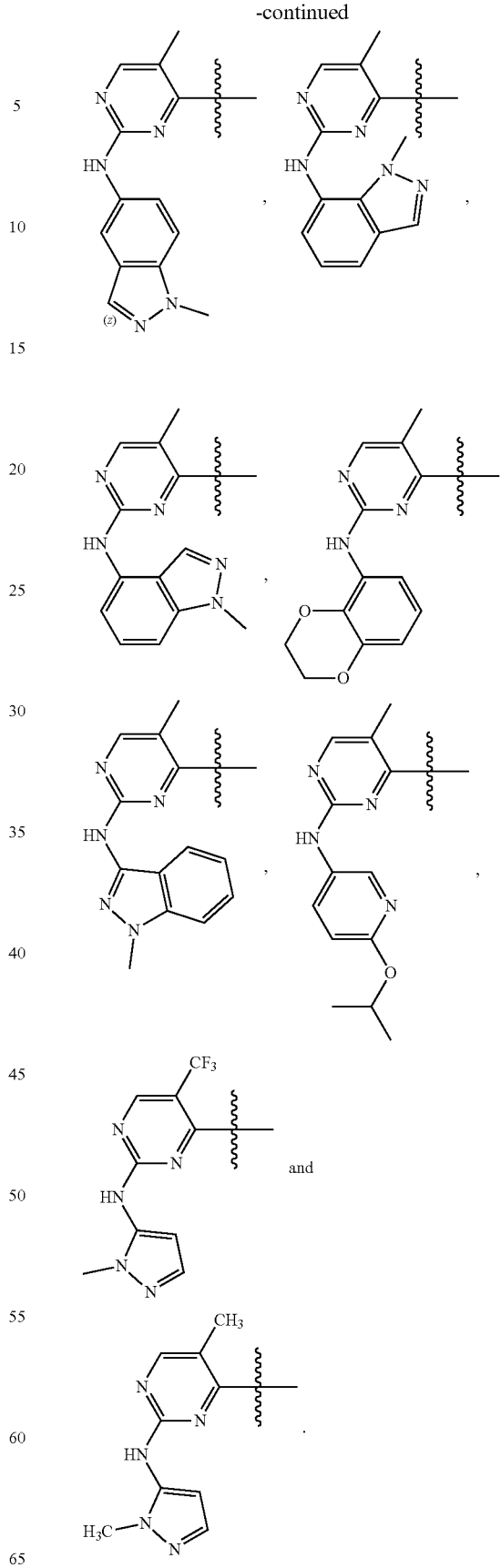

In one aspect, $R_4$ in formula (I) is

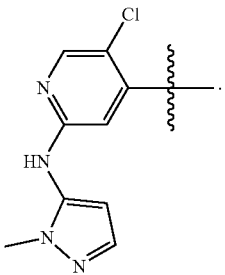 [SMILES: *c1cc(Nc2ccnn2C)ncc1Cl]

In one aspect, m in formula (I) is 0, 1, or 2.

The present invention further provides a compound or a pharmaceutically acceptable salt thereof, wherein the compound is selected from the group consisting of:
1) 4-(5-Chloro-2-(isopropylamino)pyridin-4-yl)-1H-(2-(hydroxymethyl)benzyl)-1H-pyrrole-2-carboxamide;
2) 5-(5-Chloro-2-(isopropylamino)pyridin-4-yl)-N-(5-fluoro-2-(hydroxymethyl)benzyl)thiazole-2-carboxamide;
3) 5-(5-Chloro-2-(isopropylamino)pyridin-4-yl)-1H-(2-(hydroxymethyl)benzyl)thiazole-2-carboxamide,
4) 5-(5-Chloro-2-(isopropylamino)pyridin-4-yl)-1H-(4-fluoro-2-(hydroxymethyl)benzyl)thiazole-2-carboxamide;
5) 5-(5-Chloro-2-(isopropylamino)pyridin-4-yl)-1H-(3-fluoro-2-(hydroxymethyl)benzyl)thiazole-2-carboxamide;
6) 8'-(5-Chloro-2-(isopropylamino)pyridin-4-yl)-2'-(2-(hydroxymethyl)benzyl)-2',3'-dihydro-1'H,5'H-spiro[oxetane-3,4'-pyrrolo[1,2-a][1,4]diazepine]-1'-one;
7) 2'-(5-Chloro-2-(isopropylamino)pyridin-4-yl)-5'-(2-(hydroxymethyl)benzyl)-5',6'-dihydro-4'H,8'H-spiro[oxetane-3,7'-pyrazolo[1,5-a][1,4]diazepine]-4'-one;
8) 2-(5-Chloro-2-(isopropylamino)pyridin-4-yl)-7-(chloromethyl)-7-(hydroxymethyl)-5-(2-(hydroxymethyl)benzyl)-5,6,7,8-Tetrahydro-4H-pyrazolo[1,5-a][1,4]diazepine-4-one;
9) 2'-(4-Chloro-2-(hydroxymethyl)benzyl)-8'-(5-chloro-2-(isopropylamino)pyridin-4-yl)-2',3'-dihydro-1'H,5'H-spiro[cyclopropane-1,4'-pyrrolo[1,2-a][1,4]diazepine]-1'-one;
10) 8'-(5-Chloro-2-(isopropylamino)pyridin-4-yl)-2'-(5-fluoro-2-(hydroxymethyl)benzyl)-2',3'-dihydro-1'H,5'H-spiro[oxetane-3,4'-pyrrolo[1,2-a][1,4]diazepine]-1'-one;
11) 2-(5-Chloro-2-(isopropylamino)pyridin-4-yl)-8-(2-(hydroxymethyl)benzyl)-7,8-dihydro-5H,9H-spiro[imidazo[1,2-a][1,4]diazepine-6,3'-oxetane]-9-one;
12) 8'-(5-Chloro-2-(isopropylamino)pyridin-4-yl)-2'-(3-fluoro-2-(hydroxymethyl)benzyl)-2',3'-dihydro-1'H,5'H-spiro[oxetane-3,4'-pyrrolo[1,2-a][1,4]diazepine]-1'-one,
13) 8'-(5-Chloro-2-(isopropylamino)pyridin-4-yl)-2'-(2-(hydroxymethyl)benzyl)-2',3'-dihydro-1'H,5'H-spiro[azetidine-3,4'-pyrrolo[1,2-a][1,4]diazepine]-1'-one;
14) 7-(5-Chloro-2-(isopropylamino)pyridin-4-yl)-2-(2-(hydroxymethyl)benzyl)-3,4-dihydro pyrrolo[1,2-a]pyrazine-1(2H)-one;
15) 2-(4-Chloro-2-(hydroxymethyl)benzyl)-7-(5-chloro-2-(isopropylamino)pyridin-4-yl)-3,4-dihydropyrrolo[1,2-a]pyrazine-1(2H)-one;
16) 8-(5-Chloro-2-(isopropylamino)pyridin-4-yl)-2-(2-(hydroxymethyl)benzyl)-2,3,4,5-tetra hydro-1H-pyrrolo[1,2-a][1,4]diazepine-1-one;
17) 8'-(5-Chloro-2-(isopropylamino)pyridin-4-yl)-2'-(4,5-difluoro-2-(hydroxymethyl)benzyl)-2',3'-dihydrogen-1'H,5'H-spiro[oxetane-3,4'-pyrrolo[1,2-a][1,4]diazepine-1'-one;
18) 7-(5-Chloro-2-(isopropylamino)pyridin-4-yl)-2-(5-fluoro-2-(hydroxymethyl)benzyl)-3,4-dihydropyrrolo[1,2-a]pyrazine-1(2H)-one;
19) 7-(5-Chloro-2-(isopropylamino)pyridin-4-yl)-2-(4,5-difluoro-2-(hydroxymethyl)benzyl)-3,4-dihydropyrrolo[1,2-a]pyrazine 1(2H)-one;
20) 8-(5-Chloro-2-(isopropylamino)pyridin-4-yl)-2-<5-fluoro-2-(hydroxymethyl)benzyl)-4-hydroxy-2,3,4,5-tetrahydro-1H-pyrrolo[1,2-a][1,4]diazepine-1-one;
21) 8-(5-Chloro-2-(isopropylamino)pyridin-4-yl)-2-(4,5-difluoro-2-(hydroxymethyl)benzyl)-2,3,4,5-tetrahydro-1H-pyrrolo[1,2-a][1,4]diazepine-1-one;
22) N-(5-Fluoro-2-(hydroxymethyl)benzyl)-4-(5-methyl-2-((1-methyl-1H-pyrazol-5-yl)amino)pyrimidine-4-yl)-1H-pyrrole-2-carboxamide;
23) 2-(5-Fluoro-2-(hydroxymethyl)benzyl)-7-(5-methyl-2-((1-methyl-1H-pyrazol-5-yl)amino)pyrimidin-4-yl)-3,4-dihydropyrrolo[1,2-a]pyrazine-1(2H)-one; or
24) 8'-(5-Chloro-2-(isopropylamino)pyridin-4-yl)-2'-(2-(hydroxymethyl)benzyl)-1-methyl-2',3'-dihydro-1'H,5'H-spiro[azetidine-3,4'-pyrrolo[1,2-a][1,4]diazepine]-1'-one
25) 8'-(5-Chloro-2-(isopropylamino)pyridin-4-yl)-2'-(2-(hydroxymethyl)benzyl)-2',3'-dihydro-1'H,5'H-spiro[azetidine-3,4'-pyrrolo[1,2-a][1,4]diazepine]-1'-one;
26) 8-(5-Chloro-2-(isopropylamino)pyridin-4-yl)-2-(2-(hydroxymethyl)benzyl)-2',2'-dimethyl-2,3-dihydrogen-1H,5H-spiro[pyrrolo[1,2-a][1,4]diazepine-4,5'-[1,3]dioxane]-1-one;
27) 8-(5-Chloro-2-(isopropylamino)pyridin-4-yl)-4,4-bis(hydroxymethyl)-2-(2-(hydroxymethyl)benzyl)-2,3,4,5-tetrahydro-1H pyrrolo[1,2-a][1,4]diazepine-1-one;
28) 8-(5-Chloro-2-(isopropylamino)pyridin-4-yl)-2-(5-fluoro-2-(hydroxymethyl)benzyl)-2',2'-dimethyl-2,3-dihydro-1H,5H-spiro[pyrrolo[1,2-a][1,4]diazepine-4,5'-[1,3]dioxane]-1-one;
29) 8-(5-Chloro-2-(isopropylamino)pyridin-4-yl)-2-(5-fluoro-2-(hydroxymethyl)benzyl)-4,4-bis(hydroxymethyl)-2,3,4,5-tetrahydro-1H-pyrrolo[1,2-a][1,4]diazepine-1-one;
30) 7-(5-Chloro-2-(oxetan-3-ylamino)pyridin-4-yl)-2-(5-fluoro-2-(hydroxymethyl)benzyl)-3,4-dihydropyrrolo[1,2-a]pyrazine-1(2H)-one;
31) 7-(5-Chloro-2-((tetrahydrofuran-3-yl)amino)pyridin-4-yl)-2-(5-fluoro-2-(hydroxymethyl)benzyl)-3,4-dihydropyrrole[1,2-a]pyrazine-1(2H)-one;
32) 2-(5-Fluoro-2-(hydroxymethyl)benzyl)-7-(5-methyl-2-(oxetan-3-ylamino)pyrimidin-4-yl)-3,4-dihydropyrrolo[1,2-a]pyrazine-1(2H)-one;
33) 2-(5-Fluoro-2-(hydroxymethyl)benzyl)-7-(5-methyl-2-((tetrahydrofuran-3-yl)amino)pyrimidin-4-yl)-3,4-dihydropyrrolo[1,2-a]pyrazine-1(2H)-one;
34) (R)-7-(5-chloro-2-(isopropylamino)pyridin-4-yl)-2-(5-fluoro-2-(hydroxymethyl)benzyl)-3-(methoxy(methyl))-3,4-dihydropyrrolo[1,2-a]pyrazine-1(2H)-one;
35) (R)-2-(5-Fluoro-2-(hydroxymethyl)benzyl)-3-(methoxymethyl)-7-(5-methyl-2-((1-methyl-1H-pyrazol-5-yl)amino)pyrimidin-4-yl)-3,4-dihydropyrrolo[1,2-a]pyrazine-1(2H)-one;
36) (R)-2-(5-Fluoro-2-(hydroxymethyl)benzyl)-7-(2-(isopropylamino)-5-methylpyrimidin-4-yl)-3-(methoxymethyl)-3,4-dihydropyrrolo[1,2-a]pyrazine-1(2H)-one;

37) 2-(5-Fluoro-2-(hydroxymethyl)benzyl)-3-(hydroxymethyl)-7-(5-methyl-2-(oxetan-3-ylamino)pyrimidine-4-yl)-3,4-dihydropyrrolo[1,2-a]pyrazine-1(2H)-one;

38) 2'-(4,5-Difluoro-2-(hydroxymethyl)benzyl)-8'-(5-methyl-2-(oxetan-3-ylamino)pyrimidin-4-yl)-2',3'-dihydro-1'H,5'H spiro[oxetane-3,4'-pyrrolo[1,2-a][1,4]diazepine]-1'-ketone;

39) 2'-(4,5-Difluoro-2-(hydroxymethyl)benzyl)-8'-(5-methyl-2-((tetrahydrofuran-3-yl)amino)pyrimidin-4-yl)-2',3'dihydro-1'H,5'H spiro[oxetane-3,4'-pyrrolo[1,2-a][1,4]diazepine]-1'-one; or 40) 2-(5-Fluoro-2-(hydroxymethyl)benzyl)-3-(hydroxymethyl)-7-(5-methyl-2-((tetrahydro furan-3-yl)amino)pyrimidin-4-yl)-3,4-dihydropyrrolo[1,2-a]pyrazine-1(2H)-one;

41) 7-(5-Chloro-2-(oxetan-3-ylamino)pyridin-4-yl)-2-(4,5-difluoro-2-(hydroxymethyl)benzyl)-3,4-dihydropyrrolo[1,2-a]pyrazine-1(2H)-one;

42) 8-(5-Chloro-2-(isopropylamino)pyridin-4-yl)-2-(5-fluoro-2-(hydroxymethyl)benzyl)-4-(hydroxymethyl)-2,3,4,5-tetrahydro-1H-pyrrolo[1,2-a][1,4]diazepine-1-one;

43) 8-(5-Chloro-2-(isopropylamino)pyridin-4-yl)-2-(5-fluoro-2-(hydroxymethyl)benzyl)-2,3-dihydro-1H,5H-Spiro[pyrrolo[1,2-a][1,4]diazepine-4,5'-[1,3]dioxane]-1-one;

44) 8-(5-Chloro-2-(isopropylamino)pyridin-4-yl)-2-(5-fluoro-2-(hydroxymethyl)benzyl)-4,4-bis(methoxymethyl))-2,3,4,5-tetrahydro-1H-pyrrolo[1,2-a][1,4]diazepine-1-one;

45) (R)-7-(5-chloro-2-((1-methyl-1H-pyrazol-5-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;

46) (R)-2-(5-Chloro-2-(isopropylamino)pyridin-4-yl)-7-(5-fluoro-2-(hydroxymethyl)benzyl)-6-(methoxy(methyl)-6,7-dihydroimidazo[1,2-a]pyrazine-8-(5H)-one;

47) (R)-7-(5-chloro-3-fluoro-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

48) (R)-7-(5-chloro-3-methyl-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

49) 2-(5-Fluoro-2-(hydroxymethyl)benzyl)-7-(5-methyl-2-(o-tolylamino)pyrimidin-4-yl)-3,4-dihydropyrrolo[1,2-a]pyrazine-1(2H)-one;

50) 7-(5-chloro-2-((1-methyl-1H-pyrazol-5-yl)amino)pyridin-4-yl)-2-(5-fluoro-2-(hydroxymethyl)benzyl)-3,4-Dihydropyrrolo[1,2-a]pyrazine-1(2H)-one;

51) (R)-7-(5-chloro-2-((4-fluoro-1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

52) (R)-7-(5-chloro-2-((1-ethyl-1H-pyrazol-5-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;

53) (R)-7-(5-chloro-2-((1-methyl-1H-pyrazol-5-yl)amino)pyridin-4-yl)-2-(5-fluoro-2-(hydroxymethyl)benzyl)-3-((methoxymethoxy)methyl)-3,4-dihydropyrrolo[1,2-a]pyrazine-1(2H)-one;

54) (R)-7-(5-chloro-2-((1-(difluoromethyl)-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

55) 8-(5-Chloro-2-(isopropylamino)pyridin-4-yl)-2-(5-fluoro-2-(hydroxymethyl)benzyl)-4-methoxy-2,3,4,5-tetrahydro-1H-pyrrolo[1,2-a][1,4]diazepine-1-one;

56) 8-(5-Chloro-2-(isopropylamino)pyridin-4-yl)-2-(5-fluoro-2-(hydroxymethyl)benzyl)-4-(hydroxymethyl)-4-(methoxymethyl)-2,3,4,5-4,5-tetrahydro-1H-pyrrolo[1,2-a][1,4]diazepine-1-one;

57) Methyl 7-(5-chloro-2-(isopropylamino)pyridin-4-yl)-2-(5-fluoro-2-(hydroxymethyl)benzyl)-1-oxo-1,2,3,4-tetrahydropyrrolo[1,2-a]pyrazine-3-carboxylic acid ethyl ester;

58) 8-(5-Chloro-2-(isopropylamino)pyridin-4-yl)-2-(4-chloro-5-fluoro-2-(hydroxymethyl)benzyl)-4,4-bis(hydroxy(methyl)-2,3,4,5-tetrahydro-1H-pyrrolo[1,2-a][1,4]diazepine-1-one;

59) (R)-7-(5-chloro-2-(isopropylamino)pyridin-4-yl)-2-(5-fluoro-2-(hydroxymethyl)benzyl)-3-(hydroxymethyl)-3,4-dihydropyrrolo[1,2-a]pyrazine-1(2H)-one;

60) (R)-7-(5-chloro-2-(oxetan-3-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;

61) (3R)-7-(5-chloro-2-((tetrahydrofuran-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

62) (R)-7-(5-chloro-2-((tetrahydro-2H-pyran-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

63) (R)-7-(5-chloro-2-((3,3-difluorocyclobutyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

64) (R)-7-(2-(tert-butylamino)-5-chloropyridin-4-yl)-2-(5-fluoro-2-(hydroxymethyl)benzyl)-3-(methoxy(methyl)-3,4-dihydropyrrolo[1,2-a]pyrazine-1(2H)-one;

65) (R)-7-(5-chloro-2-((2-hydroxy-2-methylpropyl)amino)pyridin-4-yl)-2-(5-fluoro-2-(hydroxymethyl)benzyl yl)-3-(methoxymethyl)-3,4-dihydropyrrolo[1,2-a]pyrazine-1(2H)-one;

66) (R)-7-(5-Chloro-2-((1-methylpiperidin-4-yl)amino)pyridin-4-yl)-2-(5-fluoro-2-(hydroxymethyl)benzyl yl)-3-(methoxymethyl)-3,4-dihydropyrrolo[1,2-a]pyrazine-1(2H)-one;

67) (R)-2-(5-Fluoro-2-(hydroxymethyl)benzyl)-3-(methoxymethyl)-7-(2-((tetrahydro-2H-pyran-4-yl)amino)pyridin-4-yl)-3,4-dihydropyrrolo[1,2-a]pyrazine-1(2H)-one;

68) (R)-7-(5-chloro-2-((4,4-difluorocyclohexyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

69) (R)-7-(5-chloro-2-((4-methyltetrahydro-2H-pyran-4-yl)amino)pyridin-4-yl)-2-(5-fluoro-2-((hydroxymethyl)benzyl)-3-(methoxymethyl)-3,4-dihydropyrrolo[1,2-a]pyrazine-1(2H)-one;

70) (R)-7-(5-chloro-2-(cyclobutylamino)pyridin-4-yl)-2-(5-fluoro-2-(hydroxymethyl)benzyl)-3-(methoxy(methyl)-3,4-dihydropyrrolo[1,2-a]pyrazine-1 (2H)-one;

71) (R)-7-(5-chloro-2-(((1R,4R)-4-hydroxycyclohexyl)amino)pyridin-4-yl)-2-<5-fluoro-2-(hydroxymethyl)benzyl)-3-(methoxymethyl)-3,4-dihydropyrrolo[1,2-a]pyrazine-1(2H)-one;

72) (R)-7-(5-chloro-2-(cyclohexylamino)pyridin-4-yl)-2-(5-fluoro-2-(hydroxymethyl)benzyl)-3-(methoxymethylyl)-3,4-dihydropyrrolo[1,2-a]pyrazine-1(2H)-one;

73) 7-(5-Chloro-2-((1-isopropylpiperidin-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

74) (R)-7-(5-chloro-2-(cyclopropylamino)pyridin-4-yl)-2-(5-fluoro-2-(hydroxymethyl)benzyl)-3-(methoxy (methyl)-3,4-dihydropyrrolo[1,2-a]pyrazine-1(2H)-one;

75) (R)-2-(5-Fluoro-2-(hydroxymethyl)benzyl)-7-(5-fluoro-2-(isopropylamino)pyridin-4-yl)-3-(methoxy(methyl)-3,4-dihydropyrrolo[1,2-a]pyrazine-1(2H)-one;

76) (R)-2-(5-Fluoro-2-(hydroxymethyl)benzyl)-7-(2-(isopropylamino)-5-(trifluoromethyl)pyridin-4-yl)-3-(methoxymethyl)-3,4-dihydropyrrolo[1,2-a]pyrazine-1(2H)-one;

77) (R)-7-(5-chloro-2-(cyclopentylamino)pyridin-4-yl)-2-(5-fluoro-2-(hydroxymethyl)benzyl)-3-(methoxy (methyl)-3,4-dihydropyrrolo[1,2-a]pyrazine-1(2H)-one;

78) (3R)-7-(5-chloro-2-((2,2-dimethyltetrahydro-2H-pyran-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

79) (3R)-7-(5-chloro-2-((5,5-dimethyltetrahydrofuran-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

80) (R)-7-(5-chloro-2-((5-methylisoxazol-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

81) (R)-7-(5-Chloro-2-((3,5-dimethylisoxazol-4-yl)amino)pyridin-4-yl)-2-(5-fluoro-2-(hydroxy(methyl)benzyl)-3-(methoxymethyl)-3,4-dihydropyrrolo[1,2-a]pyrazine-1(2H)-one;

82) (R)-7-(5-chloro-2-(oxazol-2-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;

83) (R)-7-(5-chloro-2-((3-methylisoxazol-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

84) (R)-7-(5-chloro-2-(thiazol-2-ylamino)pyridin-4-yl)-2-(5-fluoro-2-(hydroxymethyl)benzyl)-3-(methyl(oxymethyl)-3,4-dihydropyrrolo[1,2-a]pyrazine-1(2H)-one;

85) (R)-7-(5-chloro-2-((5-methylthiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

86) (R)-7-(5-chloro-2-((1-methyl-1H-pyrazol-3-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;

87) (R)-7-(5-chloro-2-((3-methylisoxazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

88) (R)-7-(5-chloro-2-((1-methyl-1H-pyrazol-4-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;

89) (R)-7-(5-chloro-2-((1,3-dimethyl-1H-pyrazol-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

90) (R)-7-(5-chloro-2-((4,5-dimethylthiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

91) (R)-7-(5-chloro-2-((4-methylthiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

92) (R)-7-(5-Chloro-2-(isoxazol-3-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;

93) (R)-7-(5-Chloro-2-(isoxazol-5-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;

94) (R)-7-(5-Chloro-2-((6,7-dihydro-4H-pyrano[4,3-d]thiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-ketone;

95) (R)-7-(5-Chloro-2-((1-methyl-1H-pyrazol-5-yl)amino)pyridin-4-yl)-2-(4,5-difluoro-2-(hydroxymethyl)benzyl)-3-(methoxymethyl)-3,4-dihydropyrrolo[1,2-a]pyrazine-1(2H)-one;

96) (R)-7-(5-chloro-2-((1,3-dimethyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

97) (R)-7-(5-chloro-2-((1,4-dimethyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

98) (R)-7-(5-chloro-2-((1-methyl-1H-pyrazol-5-yl)amino)pyridin-4-yl)-2-(3-fluoro-2-(hydroxymethyl(yl)benzyl)-3-(methoxymethyl)-3,4-dihydropyrrolo[1,2-a]pyrazine-1(2H)-one;

99) (R)-7-(5-chloro-2-((1-methyl-1H-pyrazol-5-yl)amino)pyridin-4-yl)-2-(4-fluoro-2-(hydroxymethyl(yl)benzyl)-3-(methoxymethyl)-3,4-dihydropyrrolo[1,2-a]pyrazine-1(2H)-one;

100) (R)-2-(5-fluoro-2-(hydroxymethyl)benzyl)-3-(methoxymethyl)-7-(2-((1-methyl-1H-pyrazole-5-yl)amino)-5-(trifluoromethyl)pyridin-4-yl)-3,4-dihydropyrrolo[1,2-a]pyrazine-1 (2H)-one;

101) (R)-4-(2-(5-Fluoro-2-(hydroxymethyl)benzyl)-3-(methoxymethyl)-1-oxo-1,2,3,4-tetrahydro pyrrolo[1,2-a]pyrazin-7-yl)-6-((1-methyl-1H-pyrazol-5-yl)amino)nicotinonitrile;

102) (R)-2-(5-Fluoro-2-(hydroxymethyl)benzyl)-3-(methoxymethyl)-7-(5-methyl-2-((1-methyl-1H-pyrazol-5-yl)amino)pyridin-4-yl)-3,4-dihydropyrrolo[1,2-a]pyrazine-1(2H)-one;

103) (R)-7-(5-Chloro-2-((1-methyl-1H-pyrazol-5-yl)amino)pyridin-4-yl)-2-(2-(hydroxy methyl)-5-(trifluoromethyl)benzyl)-3-(methoxymethyl)-3,4-dihydropyrrolo[1,2-a]pyrazine-1(2H)-one;

104) (R)-7-(5-Chloro-2-((1-methyl-1H-pyrazol-5-yl)amino)pyridin-4-yl)-2-((3-(hydroxymethyl)-6-methylpyridin-2-yl)methyl)-3-(methoxymethyl)-3,4-dihydropyrrolo[1,2-a]pyrazine-1(2H)-one;

105) (R)-7-(5-chloro-2-((1-methyl-1H-pyrazol-5-yl)amino)pyridin-4-yl)-2-((4-(hydroxy methyl)-6-methylpyridin-3-yl)methyl)-3-(methoxymethyl)-3,4-dihydropyrrolo[1,2-a]pyrazine-1(2H)-one;

106) (R)-7-(5-chloro-2-((1-methyl-1H-pyrazol-5-yl)amino)pyridin-4-yl)-2-((2-(hydroxy methyl)-6-(trifluoromethyl)pyridin-3-yl)methyl)-3-(methoxymethyl)-3,4-dihydropyrrolo[1,2-a]pyrazine-1(2H)-ketone;

107) (R)-7-(5-chloro-2-((1-methyl-1H-pyrazol-5-yl)amino)pyridin-4-yl)-2-((3-(hydroxymethyl)pyridine-2-yl)methyl)-3-(methoxymethyl)-3,4-dihydropyrrolo[1,2-a]pyrazine-1(2H)-one;

108) (R)-7-(5-chloro-2-((1-methyl-1H-pyrazol-5-yl)amino) pyridin-4-yl)-2-((4-(hydroxymethyl)pyridine-3-yl) methyl)-3-(methoxymethyl)-3,4-dihydropyrrolo[1,2-a] pyrazine-1(2H)-one;

109) (R)-7-(5-chloro-3-fluoro-2-(isopropylamino)pyridin-4-yl)-2-(5-fluoro-2-(hydroxymethyl)benzyl)-3-(methoxymethyl)-3,4-dihydropyrrolo[1,2-a]pyrazine-1(2H)-one;

110) 7-(2-((1-Acetylpiperidin-4-yl)amino)-5-chloropyridin-4-yl)-2-(5-fluoro-2-(hydroxymethyl)benzyl)-3-(methoxymethyl)-3,4-dihydropyrrolo[1,2-a]pyrazine-1(2H)-one;

111) (R)-7-(5-chloro-2-((4-methoxycyclohexyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

112) (R)-N-(5-chloro-4-(2-(5-fluoro-2-(hydroxymethyl) benzyl)-3-(methoxymethyl)-1-oxo-1,2,3,4-Tetrahydropyrrolo[1,2-a]pyrazin-7-yl)pyridin-2-yl)acetamide;

113) (R)-7-(5-chloro-2-(((1-methyl-1H-pyrazol-5-yl) methyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

114) (R)-7-(5-chloro-2-((1-(2,2-difluoroethyl)-1H-pyrazol-3-yl)amino)pyridin-4-yl)-2-(5-fluoro-2-(hydroxymethyl) benzyl)-3-(methoxymethyl)-3,4-dihydropyrrolo[1,2-a] pyrazine-1(2H)-one;

115) (R)-7-(5-chloro-2-((1-(2,2-difluoroethyl)-1H-pyrazol-5-yl)amino)pyridin-4-yl)-2-(5-fluoro-2-(hydroxymethyl) benzyl)-3-(methoxymethyl)-3,4-dihydropyrrolo[1,2-a] pyrazine-1(2H)-one;

116) (R)-7-(5-chloro-2-((oxazole-4-methylene)amino)pyridin-4-yl)-2-(5-fluoro-2-(hydroxymethyl)benzyl)-3-(methoxymethyl)-3,4-dihydropyrrole[1,2-a]pyrazine-1(2H)-one;

117) (R)-N-(5-chloro-4-(2-(5-fluoro-2-(hydroxymethyl) benzyl)-3-(methoxymethyl)-1-oxo-1,2,3,4-tetrahydropyrrolo[1,2-a]pyrazin-7-yl)pyridin-2-yl)-2-methylthiazole-4-carboxamide;

118) (R)-7-(5-chloro-2-((1-methyl-3-(trifluoromethyl)-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

119) (R)-3-((7-(5-chloro-2-((1-methyl-1H-pyrazol-5-yl) amino)pyridin-4-yl)-3-(methoxy methyl)-1-oxo-3,4-dihydropyrrolo[1,2-a]pyrazine-2(1H)-yl)methyl)-4-(hydroxymethyl)benzonitrile;

120) (R)-7-(5-chloro-2-((1-methyl-1H-pyrazol-5-yl)amino) pyridin-4-yl)-2-((2-(hydroxymethyl)pyridine-3-yl) methyl)-3-(methoxymethyl)-3,4-dihydropyrrolo[1,2-a] pyrazine-1(2H)-one;

121) 2-(5-Fluoro-2-(hydroxymethyl)benzyl)-7-(2-((1-hydroxyprop-2-yl)amino)-5-methyl pyrimidin-4-yl)-3,4-dihydropyrrolo[1,2-a]pyrazine-1(2H)-one;

122) N-(5-Fluoro-2-(hydroxymethyl)benzyl)-4-(5-methyl-2-(oxetan-3-ylamino)pyrimidin-4-yl)-1H-pyrrole-2-carboxamide;

123) 2-(5-Fluoro-2-(hydroxymethyl)benzyl)-7-(2-(isopropylamino)-5-methylpyrimidin-4-yl)-3,4-dihydropyrrolo[1,2-a]pyrazine-1(2H)-one;

124) 7-(5-Chloro-2-((2,2,2-trifluoroethyl)amino)pyridin-4-yl)-2-(5-fluoro-2-(hydroxymethyl)benzyl)-3,4-dihydropyrrolo[1,2-a]pyrazine-1(2H)-one;

125) 7-(2-((2-Chloro-4-fluorophenyl)amino)-5-methylpyrimidin-4-yl)-2-(5-fluoro-2-(hydroxymethyl)benzyl)-3,4-dihydropyrrolo[1,2-a]pyrazine-1(2H)-one;

126) 7-(5-Chloro-2-((tetrahydro-2H-pyran-4-yl)amino)pyridin-4-yl)-2-(5-fluoro-2-(hydroxymethyl)benzyl)-3,4-dihydropyrrolo[1,2-a]pyrazine-1(2H)-one;

127) (R)-2-(5-Fluoro-2-(hydroxymethyl)benzyl)-7-(2-(isopropylamino)pyrimidin-4-yl)-3-(methoxymethyl)-3,4-dihydropyrrolo[1,2-a]pyrazine-1(2H)-one;

128) 7-(5-Chloro-2-((3,3-difluorocyclobutyl)amino)pyridin-4-yl)-2-(5-fluoro-2-(hydroxymethyl)benzyl)-3,4-dihydropyrrolo[1,2-a]pyrazine-1(2H)-one;

129) 7-(5-Chloro-2-((2-chloro-4-fluorophenyl)amino)pyridin-4-yl)-2-(5-fluoro-2-(hydroxymethyl)benzyl)-3,4-dihydropyrrolo[1,2-a]pyrazine-1(2H)-one;

130) (R)-7-(5-chloro-2-((tetrahydro-2H-pyran-4-yl)amino) pyrimidin-4-yl)-2-(5-fluoro-2-(hydroxymethyl)benzyl)-3-(methoxymethyl)-3,4-dihydropyrrolo[1,2-a]pyrazine-1(2H)-one;

131) (R)-7-(5-chloro-2-(ethylamino)pyrimidin-4-yl)-2-(5-fluoro-2-(hydroxymethyl)benzyl)-3-(methoxymethylyl)-3,4-dihydropyrrolo[1,2-a]pyrazine-1 (2H)-one;

132) 7-(2-((2-ethylphenyl)amino)-5-methylpyrimidin-4-yl)-2-(5-fluoro-2-(hydroxymethyl)benzyl)-3,4-dihydropyrrolo[1,2-a]pyrazine-1(2H)-one;

133) 7-(2-(Benzo[d][1,3]dioxol-4-ylamino)-5-methylpyrimidin-4-yl)-2-(5-fluoro-2-(hydroxyl(methyl)benzyl)-3,4-dihydropyrrolo[1,2-a]pyrazine-1(2H)-one;

134) 2-(5-Fluoro-2-(hydroxymethyl)benzyl)-7-(5-methyl-2-((1-methyl-1H-indazol-5-yl)amino)pyrimidin-4-yl)-3,4-dihydropyrrolo[1,2-a]pyrazine-1(2H)-one;

135) 7-(2-((2,3-Dihydrobenzo[b][1,4]dioxen-5-yl)amino)-5-methylpyrimidin-4-yl)-2-(5-fluoro-2-(hydroxymethyl) benzyl)-3,4-dihydropyrrolo[1,2-a]pyrazine-1(2H)-one;

136) 7-(2-((2,3-Dimethylphenyl)amino)-5-methylpyrimidin-4-yl)-2-(5-fluoro-2-(hydroxymethyl)benzyl)-3,4-dihydropyrrolo[1,2-a]pyrazine-1(2H)-one;

137) 2-(5-Fluoro-2-(hydroxymethyl)benzyl)-7-(5-methyl-2-(phenylamino)pyrimidin-4-yl)-3,4-dihydropyrrolo[1,2-a]pyrazine-1(2H)-one;

138) 7-(2-((4-Chloro-2-methylphenyl)amino)-5-methylpyrimidin-4-yl)-2-(5-fluoro-2-(hydroxymethyl)benzyl)-3,4-dihydropyrrolo[1,2-a]pyrazine-1(2H)-one;

139) 4-(5-Chloro-2-((1-methyl-1H-pyrazol-5-yl)amino) pyridin-4-yl)-N-(4,5-difluoro-2-(hydroxymethyl)benzyl)-1H-pyrrole-2-carboxamide;

140) 2-(5-Fluoro-2-(hydroxymethyl)benzyl)-7-(5-methyl-2-((1-methyl-1H-indazol-7-yl)amino)pyrimidin-4-yl)-3,4-dihydropyrrolo[1,2-a]pyrazine-1(2H)-one;

141) 2-(5-Fluoro-2-(hydroxymethyl)benzyl)-7-(5-methyl-2-((1-methyl-1H-indazol-4-yl)amino)pyrimidin-4-yl)-3,4-dihydropyrrolo[1,2-a]pyrazine-1(2H)-one;

142) 7-(2-((2,2-Difluorobenzo[d][1,3]dioxol-4-yl)amino)-5-methylpyrimidin-4-yl)-2-(5-fluoro-2-(hydroxymethyl) benzyl)-3,4-dihydropyrrolo[1,2-a]pyrazine-1(2H)-one;

143) 7-(2-(Benzo[d]oxazol-4-ylamino)-5-methylpyrimidin-4-yl)-2-(5-fluoro-2-(hydroxymethyl)benzyl)-3,4-dihydropyrrolo[1,2-a]pyrazine-1(2H)-one;

144) 2-(5-Fluoro-2-(hydroxymethyl)benzyl)-7-(5-methyl-2-((1-methyl-1H-pyrazolo[3,4-b]pyridine-3-(yl)amino)pyrimidinepiperidin-4-yl)-3,4-dihydropyrrolo[1,2-a]pyrazine-1(2H)-one;

145) 7-(2-((2,3-Dihydrobenzofuran-4-yl)amino)-5-methylpyrimidin-4-yl)-2-(5-fluoro-2-(hydroxymethyl)benzyl)-3,4-dihydropyrrolo[1,2-a]pyrazine-1(2H)-one;

146) 7-(2-((2,3-Dihydrobenzofuran-7-yl)amino)-5-methylpyrimidin-4-yl)-2-(5-fluoro-2-(hydroxymethyl)benzyl)-3,4-dihydropyrrolo[1,2-a]pyrazine-1(2H)-one;

147) 7-(5-Chloro-2-((1-methyl-1H-pyrazol-5-yl)amino) pyridin-4-yl)-2-(4-chloro-5-fluoro-2-(hydroxymethyl) benzyl)-3,4-dihydropyrrolo[1,2-a]pyrazine-1(2H)-one;
148) 7-(5-Chloro-2-((1-methyl-1H-pyrazol-5-yl)amino) pyridin-4-yl)-2-(3,5-difluoro-2-(hydroxymethyl)benzyl)-3,4-dihydropyrrolo[1,2-a]pyrazine-1(2H)-one;
149) 7-(5-Chloro-2-((1-methyl-1H-pyrazol-5-yl)amino) pyridin-4-yl)-2-(4-fluoro-2-(hydroxymethyl)benzyl)-3,4-dihydropyrrolo[1,2-a]pyrazine-1(2H)-one;
150) 7-(5-Chloro-2-((1-methyl-1H-pyrazol-5-yl)amino) pyridin-4-yl)-2-(3-fluoro-2-(hydroxymethyl)benzyl)-3,4-dihydropyrrolo[1,2-a]pyrazine-1(2H)-one;
151) 4-(2-(5-Fluoro-2-(hydroxymethyl)benzyl)-1-oxo-1,2,3,4-tetrahydropyrrolo[1,2-a]pyrazine-7-yl)-6-((1-methyl-1H-pyrazol-5-yl)amino)nicotinonitrile;
152) 2-(5-Fluoro-2-(hydroxymethyl)benzyl)-7-(5-methyl-2-((1-methyl-1H-pyrazol-5-yl)amino)pyridin-4-yl)-3,4-dihydropyrrolo[1,2-a]pyrazine-1(2H)-one;
153) 7-(5-Chloro-2-((1-methyl-1H-pyrazol-5-yl)amino) pyridin-4-yl)-2-(2-hydroxymethyl)-5-(trifluoromethyl(yl) benzyl)-3,4-dihydropyrrolo[1,2-a]pyrazine-1(2H)-one;
154) 7-(5-Chloro-2-((1-methyl-1H-pyrazol-5-yl)amino) pyridin-4-yl)-2-((3-(hydroxymethyl)-6-methylpyridine-2-yl)methyl)-3,4-dihydropyrrolo[1,2-a]pyrazine-1(2H)-one;
155) 7-(5-Chloro-2-((1-methyl-1H-pyrazol-5-yl)amino) pyridin-4-yl)-2-((2-(hydroxymethyl)pyridin-3-yl) (methyl)-3,4-dihydropyrrolo[1,2-a]pyrazine-1(2H)-one;
156) 7-(5-Chloro-2-((2-methoxyethyl)amino)pyridin-4-yl)-2-(5-fluoro-2-(hydroxymethyl)benzyl)-3,4-di hydropyrrolo[1,2-a]pyrazine-1(2H)-one;
157) (R)-2-(5-Fluoro-2-(hydroxymethyl)benzyl)-7-(2-((2-methoxy ethyl)amino)pyrimidin-4-yl)-3-(methyl(oxymethyl)-3,4-dihydropyrrolo[1,2-a]pyrazine-1(2H)-one;
158) 7-(2-((2,3-Dimethoxyphenyl)amino)-5-methylpyrimidin-4-yl)-2-(5-fluoro-2-(hydroxylmethyl)benzyl)-3,4-dihydropyrrolo[1,2-a]pyrazine-1(2H)-one;
159) 2-(5-Fluoro-2-(hydroxymethyl)benzyl)-7-(2-((6-isopropoxypyridin-3-yl)amino)-5-meth ylpyrimidin-4-yl)-3,4-dihydropyrrolo[1,2-a]pyrazine-1(2H)-one;
160) 7-(5-Chloro-2-((1-methyl-1H-pyrazol-5-yl)amino) pyridin-4-yl)-2-(4,5-difluoro-2-(hydroxymethyl)benzyl)-3,4-dihydropyrrolo[1,2-a]pyrazine-1(2H)-one;
161) 2-(5-Fluoro-2-(hydroxymethyl)benzyl)-7-(2-((1-methyl-1H-pyrazol-5-yl)amino)-5-(trifluoromethyl)pyridine-4-yl)-3,4-dihydropyrrolo[1,2-a]pyrazine-1(2H)-one;
162) 2-(5-Fluoro-2-(hydroxymethyl)benzyl)-7-(2-(isopropylamino)-5-(trifluoromethyl)pyridin-4-yl)-3,4-dihydropyrrolo[1,2-a]pyrazine-1(2H)-one;
163) (R)-2-(5-Fluoro-2-(hydroxymethyl)benzyl)-3-(methoxymethyl)-7-(2-((1-methyl-1H-pyrazole-5-yl) amino)-5-(trifluoromethyl)pyrimidin-4-yl)-3,4-dihydropyrrolo[1,2-a]pyrazine-1(2H)-one;
164) 2-(5-Fluoro-2-(hydroxymethyl)benzyl)-7-(2-((1-methyl-1H-pyrazol-5-yl)amino)-5-(trifluoromethyl)pyrimidine-4-yl)-3,4-dihydropyrrolo[1,2-a]pyrazine-1(2H)-one;
165) 7-(5-Chloro-2-((1-methyl-1H-pyrazol-5-yl)amino) pyridin-4-yl)-2-((3-(hydroxymethyl)pyridin-2-yl) (methyl)-3,4-dihydropyrrolo[1,2-a]pyrazine-1(2H)-one;
166) 7-(5-Chloro-2-((1-methyl-1H-pyrazol-5-yl)amino) pyridin-4-yl)-2-((2-(hydroxymethyl)pyridin-3-yl) (methyl)-3,4-dihydropyrrolo[1,2-a]pyrazine-1(2H)-one;
167) 2-(5-Chloro-2-(isopropylamino)pyridin-4-yl)-5-(4,5-difluoro-2-(hydroxymethyl)benzyl) thiazolo[5,4-c]pyridine-4(5H)-one, and 168) (R)-7-(5-chloro-2-((1-methyl-1H-pyrazol-5-yl)amino) pyridin-4-yl)-3-(methoxymethyl)-2-(3,4,5-trifluoro-2-(hydroxymethyl)benzyl)-3,4-dihydropyrrolo[1,2-a]pyrazine-1(2H)-one.

The present invention also provides a pharmaceutical composition comprising a therapeutically effective amount of at least one compound represented by the structural formula (I) and at least one pharmaceutically acceptable carrier.

The present invention further provides a pharmaceutical composition in which the weight ratio of the compound represented by the structural formula (I) to the pharmaceutically acceptable carrier is 0.0001:1-10.

The invention provides the application of the compound or pharmaceutical composition represented by the structural formula (I) in the preparation of a medicament.

The present invention further provides a preferred technical solution for the application:

In a further embodiment, the medicament is to treat, prevent, delay or restrain the occurrence or progression of cancer or cancer metastasis.

In a further embodiment, the medicament is used for treating a disease mediated by ERK. In a further embodiment, the disease is cancer.

In a further embodiment, the cancer is selected from the group consisting of breast cancer, multiple myeloma, bladder cancer, endometrial cancer, gastric cancer, cervical cancer, rhabdomyosarcoma, non-small cell lung cancer, small cell lung cancer, pleomorphic lung cancer, ovarian cancer, esophagus cancer, melanoma, colorectal cancer, hepatocellular carcinoma, head and neck cancer, hepatobiliary cell carcinoma, myelodysplastic syndrome, malignant glioma, prostate cancer, thyroid cancer, Schwann cell tumor, lung squamous cell carcinoma, lichenoid keratosis, synovial sarcoma, skin cancer, pancreatic cancer, testicular cancer and liposarcoma.

In a further embodiment, the medicament is used as an ERK inhibitor.

In a further embodiment, the ERK includes ERK1 and/or ERK2.

The present invention also provides a method for treating and/or preventing a disease mediated by ERK, comprising administering to a subject in need thereof a therapeutically effective amount of the compound or pharmaceutical compositions represented by structural formula (I).

In a further embodiment, in the above-mentioned method, the ERK includes ERK1 and/or ERK2.

In a further embodiment, in the above-mentioned method, the disease mediated by ERK is cancer.

In a further embodiment, in the above-mentioned method, the cancer is selected from the group consisting of breast cancer, multiple myeloma, bladder cancer, endometrial cancer, gastric cancer, cervical cancer, rhabdomyosarcoma, non-small cell lung cancer, small cell lung cancer, pleomorphic lung cancer, ovarian cancer, esophageal cancer, melanoma, colorectal cancer, hepatocellular carcinoma, head and neck cancer, hepatobiliary cell carcinoma, myelodysplastic syndrome, malignant glioma, prostate cancer, thyroid cancer, schwann cell tumor, lung squamous cell carcinoma, lichenoid keratosis, synovial sarcoma, skin cancer, pancreatic cancer, testicular cancer, and liposarcoma.

The present invention also provides a method for treatmenting cancer, comprising administering to a subject in need thereof a therapeutically effective amount of at least any one of the compounds represented by the structural formula (I) or the pharmaceutical composition to the subject, and the cancer is selected from the group consisting of breast cancer, multiple myeloma, bladder cancer, endometrial cancer, stomach cancer, cervical cancer, rhabdomyosarcoma, non-small cell lung cancer, small cell lung cancer, pleomorphic lung cancer, ovarian cancer, esophageal cancer, melanoma, colorectal cancer, hepatocellular carcinoma, head and neck tumors, hepatobiliary cell carcinoma, myelodysplastic syndrome, malignant glioma, prostate cancer, thyroid cancer, schwann cell tumor, lung squamous cell carcinoma, lichenoid keratosis, synovial sarcoma, skin cancer, pancreatic cancer, testicular cancer and liposarcoma.

In a further embodiment, in the above-mentioned method, the subject in need thereof is a human.

The general chemical terms used in the general structural formula above have their usual meanings. For example, unless otherwise stated, the term "halogen" will be understood to mean fluorine, chlorine, bromine, or iodine.

In a further aspect, halogen groups include fluorine, chlorine and bromine.

As used herein, unless otherwise specified, "alkyl" will be understood to mean a linear or branched monovalent saturated hydrocarbon group. For example, alkyl includes methyl, ethyl, propyl, isopropyl, n-butyl, iso-butyl, sec-butyl, tert-butyl, n-pentyl, 3-(2-methyl)butyl, 2-pentyl, 2-methylbutyl, neo-pentyl, n-hexyl, 2-hexyl, 2-methylpentyl, etc. Similarly, the "$C_{1-8}$" in "$C_{1-8}$ alkyl" refers to a straight or branched group containing 1, 2, 3, 4, 5, 6, 7 or 8 carbon atoms.

Alkenyl and alkynyl include straight-chain or branched alkenyl and alkynyl. Similarly, "$C_{2-8}$ alkenyl" and "$C_{2-8}$ alkynyl" refer to alkenyl or alkynyl groups containing 2, 3, 4, 5, 6, 7 or 8 carbon atoms arranged in a straight or branched chain.

"Alkoxy" refers to the oxyether form of the aforementioned linear or branched alkyl group, that is, —O-alkyl.

In this document, "a", "an", "the", "at least one" and "one or more" are used interchangeably. Thus, for example, a composition comprising "a" pharmaceutically acceptable carrier can be understood to mean that the composition includes "one or more" pharmaceutically acceptable excipients.

The term "aryl", as used herein, unless otherwise specified, will be understood to mean an unsubstituted or substituted monocyclic or condensed ring aromatic group including carbon ring atoms. In a further aspect, the aryl group is a 6 to 10 membered monocyclic or bicyclic aromatic ring group. In a further aspect, it is phenyl and naphthyl. Most aspect is phenyl.

The term "heterocyclyl", as used herein, unless otherwise specified, will be understood to mean an unsubstituted or substituted 3-8 membered stable monocyclic ring consisting of carbon atoms and 1-3 heteroatoms selected from N, O or S. The system in which nitrogen or sulfur heteroatoms can be selectively oxidized, and nitrogen heteroatoms can be selectively quaternized. The heterocyclyl can be attached to any heteroatom or carbon atom to form a stable structure. Examples of these heterocyclyls include, but are not limited to azetidinyl, pyrrolidinyl, piperidinyl, piperazinyl, oxopiperazinyl, oxopiperidinyl, tetrahydrofuranyl, dioxolane, tetrahydroimidazolyl, tetrahydrothiazolyl, tetrahydrooxazolyl, tetrahydropyranyl, morpholinyl, thiomorpholinyl, thiomorpholinyl sulfoxide, thiomorpholinylsulfone and tetrahydro oxadiazolyl.

The term "heteroaryl", as used herein, unless otherwise specified, will be understood to mean an unsubstituted or substituted stable 5- or 6-membered monocyclic aromatic ring system or an unsubstituted or substituted 9- or 10-membered benzo-fused heteroaromatic ring system or bicyclic heteroaromatic ring system, which consists of carbon atoms and 1-4 heteroatoms selected from N, O or S, and wherein the nitrogen or sulfur heteroatoms can be selectively oxidized. The nitrogen heteroatoms can be selectively quaternized. The heteroaryl group can be attached to any heteroatom or carbon atom to form a stable structure Examples of heteroaryl groups include, but are not limited to thienyl, furyl, imidazolyl, isoxazolyl, oxazolyl, pyrazolyl, pyrrolyl, thiazolyl, thiadiazolyl, triazolyl, pyridyl, pyridyl Azinyl, indolyl, azaindolyl, indazolyl, benzimidazolyl, benzofuranyl, benzothienyl, benzisoxazolyl, benzothiazolyl, benzothiazolyl, benzene and thiadiazolyl, benzotriazolyl adenine, quinolinyl or isoquinolinyl.

The term "cycloalkyl" will be understood to mean a cyclic saturated alkyl chain having 3-10 carbon atoms, for example, cyclopropyl, cyclobutyl, cyclopentyl or cyclohexyl.

The term "substituted" will be understood to mean that one or more hydrogen atoms in the group are replaced by the same or different substituents. Typical substituents include, but are not limited to halogen (F, Cl, Br or I), $C_{1-8}$ alkyl, $C_{3-12}$ cycloalkyl, —$OR_1$, —$SR_1$, =O, =S, —$C(O)R_1$, —$C(S)R_1$, =$NR_1$, —$C(O)OR_1$, —$C(S)OR_1$, —$NR_1R_2$, —$C(O)NR_1R_2$, cyano, nitro, —$S(O)_2R_1$, —$OS(O_2)\ OR_1$, —$OS(O)_2R_1$, —$OP(O)(OR_1)(OR_2)$. Wherein $R_1$ and $R_2$ are independently selected from —H, $C_{1-6}$ alkyl, and $C_{1-6}$ haloalkyl. In a further aspect, the substituents are independently selected from the group comprising —F, —Cl, —Br, —I, —OH, trifluoromethoxy, ethoxy, propoxy, isopropoxy, n-butoxy group, isobutoxy, tert-butoxy, —$SCH_3$, —$SC_2H_5$, formaldehyde, —$C(OCH_3)$, cyano, nitro, —$CF_3$, —$OCF_3$, amino, dimethylamino, methylthio, sulfonyl and acetyl groups.

Examples of substituted alkyl groups include, but are not limited to 2-aminoethyl, 2-hydroxyethyl, pentachloroethyl, trifluoromethyl, methoxymethyl, pentafluoroethyl, and piperazinyl methyl.

Examples of substituted alkoxy groups include, but are not limited to aminomethoxy, trifluoromethoxy, 2-diethylaminoethoxy, 2-ethoxycarbonylethoxy, 3-hydroxypropoxy.

The term "pharmaceutically acceptable salt" will be understood to mean a salt prepared from a pharmaceutically acceptable non-toxic base or acid. When the compound provided by the present invention is an acid, its corresponding salt can be conveniently prepared from pharmaceutically acceptable non-toxic bases, including inorganic bases and organic bases. Salts derived from inorganic bases include aluminum, ammonium, calcium, copper (high and low prices), ferric, ferrous, lithium, magnesium, manganese (high and low prices), potassium, sodium, zinc and the like. Particularly preferred are ammonium, calcium, magnesium, potassium and sodium salts. Pharmaceutically acceptable non-toxic organic bases that can be derivatized into salts include primary, secondary and tertiary amines, as well as cyclic amines and amines containing substituents, such as naturally occurring and synthetic amines containing substituents. Other pharmaceutically acceptable non-toxic organic bases capable of forming salts, including ion exchange resins and arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, reduced glucosamine, glucosamine, histidine, hexamine, isopropylamine, lysine, methyl glucamine, morpholine, piperazine, piperidine, polyamine resin, procaine, purine, theobromine, triethylamine, trimethylamine, tripropylamine, tromethamine, etc.

When the compound provided by the present invention is a base, the corresponding salt can be conveniently prepared from pharmaceutically acceptable non-toxic acids, including inorganic acids and organic acids. Such acids include, for example, acetic acid, benzenesulfonic acid, benzoic acid, camphorsulfonic acid, citric acid, ethanesulfonic acid, isethionic acid, formic acid, fumaric acid, gluconic acid, glutamic acid, hydrobromic acid, Hydroiodic acid, perchloric acid, hydrochloric acid, isethionic acid, propionic acid, glycolic acid, lactic acid, maleic acid, malic acid, mandelic acid, methanesulfonic acid, mucic acid, nitric acid, oxalic acid, hexanoic acid, pantothenic acid, phosphoric acid, succinic acid, sulfuric acid, 2-naphthalenesulfonic acid, cyclohexylamine sulfonic acid, salicylic acid, saccharic acid, trifluoroacetic acid, tartaric acid and p-toluenesulfonic acid. Preferably, citric acid, hydrobromic acid, formic acid, hydrochloric acid, maleic acid, phosphoric acid, sulfuric acid and tartaric acid. More preferably, formic acid and hydrochloric acid.

Since the compound represented by formula (I) will be used as a medicine, it is preferable to use a certain purity, for example, at least 60% purity, more suitable purity is at least 75%, and particularly suitable purity is at least 98% (% is weight ratio).

The prodrug of the compound of the present invention is included in the protection scope of the present invention. Generally, the prodrug refers to a functional derivative that is easily converted into a desired compound in the body. For example, any pharmaceutically acceptable salt, ester, salt of ester or other derivative of the compound of the present application can directly or indirectly provide the compound of the present application or its pharmaceutically active metabolite or residues. Particularly preferred derivatives or prodrugs are those compounds that can improve the bioavailability of the compounds of the present application when administered to patients (for example, can make oral compounds more easily absorbed into the blood), or promote the transfer of parent compounds to biological organs or those compounds delivered at the site of action (for example, the brain or lymphatic system). Therefore, the term "administration" in the treatment method provided by the present invention refers to the administration of the compound disclosed in the present invention that can treat different diseases, or although it is not clearly disclosed but can be converted into the present disclosure in vivo after administration to a subject compound of compound.

The conventional methods for selecting and preparing suitable prodrug derivatives have been described in, for example, "Design of Prodrugs" (Design of Prodrugs, ed. H. Bundgaard, Elsevier, 1985) such books.

Obviously, the definition of any substituent or variable at a specific position in a molecule is independent of other positions in the molecule. It is easy to understand that those skilled in the art can select the substituents or substituted forms of the compounds of the present invention through the existing technical means and the methods described in the present invention to obtain chemically stable and easy-to-synthesize compounds.

The compound of the present invention may contain one or more asymmetric centers, and may produce diastereomers and optical isomers from this. The present invention includes all possible diastereomers and their racemic mixtures, their substantially pure resolved enantiomers, all possible geometric isomers and their pharmaceutically acceptable salts.

The above formula (I) does not exactly define the three-dimensional structure of a certain position of the compound. The present invention includes all stereoisomers of the compound represented by formula (I) and pharmaceutically acceptable salts thereof. Further, mixtures of stereoisomers and specific isolated stereoisomers are also included in the present invention. In the synthetic process of preparing such compounds, or in the process of racemization or epimerization known to those skilled in the art, the product obtained may be a mixture of stereoisomers.

When the compound represented by formula (I) has tautomers, unless otherwise stated, the present invention includes any possible tautomers, pharmaceutically acceptable salts thereof, and mixtures thereof.

When the compound represented by formula (I) and its pharmaceutically acceptable salt have solvates or polymorphs, the present invention includes any possible solvates and polymorphs. The type of solvent that forms the solvate is not particularly limited, as long as the solvent is pharmaceutically acceptable. For example, water, ethanol, propanol, acetone and similar solvents can be used.

The term "composition", as used herein, will be understood to mean a product comprising a specified amount of each specified ingredient, and any product produced directly or indirectly from a combination of specified amounts of each specified ingredient. Therefore, pharmaceutical compositions containing the compounds of the present invention as active ingredients and methods for preparing the compounds of the present invention are also part of the present invention. In addition, some crystalline forms of the compound may exist in polymorphs, and this polymorph is included in the present invention. In addition, some compounds can form solvates with water (ie, hydrates) or common organic solvents, and such solvates also fall within the scope of the present invention.

The pharmaceutical composition provided by the present invention includes as an active component a compound represented by formula (I) (or a pharmaceutically acceptable salt thereof), a pharmaceutically acceptable carrier and other optional therapeutic components or accessories. Although in any given case, the most suitable way of administering the active ingredient depends on the particular subject to be administered, the nature of the subject and the severity of the disease, the pharmaceutical composition of the present invention includes oral, rectal, topical and a pharmaceutical composition for parenteral administration (including subcutaneous administration, intramuscular injection, and intravenous administration). The pharmaceutical composition of the present invention can be conveniently prepared in a unit dosage form known in the art and prepared by any preparation method known in the pharmaceutical field.

In fact, according to conventional drug mixing technology, the compound represented by formula (I) of the present invention, or prodrug, or metabolite, or pharmaceutically acceptable salt, can be used as an active component and mixed with a drug carrier to form a drug combination Things. The pharmaceutical carrier can take various forms, depending on the desired mode of administration, for example, oral or injection (including intravenous injection). Therefore, the pharmaceutical composition of the present invention may adopt a separate unit suitable for oral administration, such as a capsule, cachet or tablet containing a predetermined dose of the active ingredient. Further, the pharmaceutical composition of the present invention may take the form of powder, granule, solution, aqueous suspension, non-aqueous liquid, oil-in-water emulsion, or water-in-oil emulsion. In addition, in addition to the common dosage forms mentioned above, the compound represented by formula (I) or a pharmaceutically acceptable salt thereof can also be administered by a controlled release method and/or a delivery device. The pharmaceutical composition of the present invention can be prepared by any pharmaceutical method. Generally, this method includes the step of associating the active ingredient with the carrier which constitutes one or more necessary ingredients. In general, the pharmaceutical composition is prepared by uniformly and intimately mixing the active ingredient with a liquid carrier or a finely divided solid carrier or a mixture of both. In addition, the product can be easily prepared into the desired appearance.

Therefore, the pharmaceutical composition of the present invention includes a pharmaceutically acceptable carrier and a compound represented by formula (I) or its stereoisomers, tautomers, polymorphs, solvates, and pharmaceutically acceptable salt and its prodrug. The combination of the compound represented by formula (I) or its pharmaceutically acceptable salt, and one or more other compounds with therapeutic activity is also included in the pharmaceutical composition of the present invention.

The drug carrier used in the present invention can be, for example, a solid carrier, a liquid carrier or a gas carrier. Solid carriers include, but are not limited to lactose, gypsum powder, sucrose, talc, gelatin, agar, pectin, acacia, magnesium stearate, and stearic acid. Liquid carriers include but are not limited to syrup, peanut oil, olive oil and water. Gas carriers include but are not limited to carbon dioxide and nitrogen. When preparing oral pharmaceutical preparations, any pharmacologically convenient medium can be used. For example, water, ethylene glycol, oils, alcohols, flavoring agents, preservatives, coloring agents, etc. can be used for oral liquid preparations such as suspensions, elixirs and solutions; and carriers such as starches, sugars, microcrystalline cellulose, diluents, granulating agents, lubricants, binders, disintegrating agents, etc. can be used in oral solid preparations such as powders, capsules and tablets. In view of ease of administration, tablets and capsules are preferred for oral preparations, and solid pharmaceutical carriers are used here. Alternatively, standard aqueous or non-aqueous formulation techniques can be used for tablet coating.

The tablet containing the compound or pharmaceutical composition of the present invention can be compressed or molded, and optionally, can be made into a tablet together with one or more auxiliary components or adjuvants. The active ingredient is in a free-flowing form such as powder or granules, mixed with a binder, lubricant, inert diluent, surfactant or dispersant, and compressed in a suitable machine to prepare compressed tablets. The powdered compound or pharmaceutical composition is soaked with an inert liquid diluent, and then molded in a suitable machine to make a molded tablet. Preferably, each tablet contains about 0.05 mg to 5 g of active ingredient, and each cachet or capsule contains about 0.05 mg to 5 g of active ingredient. For example, a formulation intended for oral administration to humans contains about 0.5 mg to about 5 g of active ingredient, compounded with a suitable and convenient metering auxiliary material, which accounts for about 5% to 95% of the total pharmaceutical composition. The unit dosage form generally contains about 1 mg to about 2 g of the active ingredient, typically 25 mg, 50 mg, 100 mg, 200 mg, 300 mg, 400 mg, 500 mg, 600 mg, 800 mg or 1000 mg.

The pharmaceutical composition suitable for parenteral administration provided by the present invention can be prepared as an aqueous solution or suspension by adding active components into water. A suitable surfactant such as hydroxypropyl cellulose may be included. In glycerol, liquid polyethylene glycol, and their mixture in oil, dispersion systems can also be prepared. Further, a preservative may also be included in the pharmaceutical composition of the present invention to prevent the growth of harmful microorganisms.

The present invention provides pharmaceutical compositions suitable for injection, including sterile aqueous solutions or dispersion systems. Further, the above-mentioned pharmaceutical composition can be prepared into a sterile powder form for immediate preparation of sterile injection or dispersion. In any case, the final injection form must be sterile, and for easy injection, it must be easy to flow. In addition, the pharmaceutical composition must be stable during preparation and storage. Therefore, it is preferable that the pharmaceutical composition be stored under conditions of anti-microbial contamination such as bacteria and fungi. The carrier can be a solvent or dispersion medium, for example, water, ethanol, polyol (such as glycerol, propylene glycol, liquid polyethylene glycol), vegetable oil, and suitable mixtures thereof.

The pharmaceutical composition provided by the present invention may be in a form suitable for topical administration, for example, aerosol, emulsion, ointment, lotion, dusting powder or other similar dosage forms. Further, the pharmaceutical composition provided by the present invention can be in a form suitable for use in a transdermal drug delivery device. These preparations can be prepared by using the compound represented by formula (I) of the present invention, or a pharmaceutically acceptable salt thereof, through conventional processing methods. As an example, a cream or ointment is prepared by adding about 5 wt % to 10 wt % of a hydrophilic material and water to produce a cream or ointment with the desired consistency.

The pharmaceutical composition provided by the present invention may use a solid as a carrier and is suitable for rectal administration. A unit dose suppository is the most typical dosage form. Suitable auxiliary materials include cocoa butter and other materials commonly used in the art. Suppositories can be conveniently prepared by mixing the pharmaceutical composition with softened or melted auxiliary materials, then cooling and molding.

In addition to the above-mentioned adjuvant components, the above formulations may also include, as appropriate, one or more additional adjuvant components, such as diluents, buffers, flavoring agents, binders, surfactants, thickeners, lubricants and preservatives (including antioxidants), etc. Further, other adjuvants may also include penetration enhancers that regulate the isotonic pressure of the drug and blood. The pharmaceutical composition containing the compound represented by formula (I), or a pharmaceutically acceptable salt thereof, can be prepared in the form of a powder or a concentrated solution.

In general, to treat the conditions or discomforts shown above, the dose level of the drug is about 0.01 mg/kg body weight to 150 mg/kg body weight per day, or 0.5 mg to 7 g per patient per day. For example, inflammation, cancer, psoriasis, allergies/asthma, diseases and discomforts of the immune system, diseases and discomforts of the central nervous system (CNS), the effective treatment drug dosage level is 0.01 mg/kg body weight to 50 mg/kg body weight per day, or 0.5 mg to 3.5 g per patient per day.

However, it is understood that lower or higher dosages than those mentioned above may be required. The specific dosage level and treatment plan for any particular patient will depend on many factors, including the activity of the specific compound used, age, weight, overall health, gender, diet, administration time, administration route, excretion rate, and the condition of drug combination and the severity of the specific disease being treated.

EXAMPLES

In order to make the above content clearer and clearer, the present invention will use the following embodiments to further illustrate the technical solution of the present invention. The following examples are only used to illustrate specific implementations of the present invention, so that those skilled in the art can understand the present invention, but are not used to limit the protection scope of the present invention. In the specific embodiments of the present invention, technical means or methods that are not specifically described are conventional technical means or methods in the art.

Unless otherwise specified, all parts and percentages in the present invention are calculated by weight, and all temperatures refer to degrees celsius.

The following abbreviations have been used:
ATP: Adenosine triphosphate;
BINAP: Binnaphthophos;
$B_2(pin)$ or $Pin_2B_2$ or $(BPIN)_2$: pinacol diborate;
$CDCl_3$: Deuterated chloroform,
DCE: Dichloroethane;
DCM: dichloromethane;
DIBAl-H: diisobutyl aluminum hydride;
DIEA or DIPEA: N,N-diisopropylethylamine;
DMA: N,N-dimethylacetamide;
DMAP: 4-dimethylaminopyridine;
DME: ethylene glycol dimethyl ether;
DMF: N,N-dimethylformamide;
DMSO: dimethyl sulfoxide;
EA: ethyl acrylate;
EDCI.HCl: 1-(3-dimethylaminopropyl)-3-ethylcarbodiimide hydrochloride;
$Et_3N$: triethylamine;
EtOAc: ethyl acetate;
h or hrs: hours;
HATU: 2-(7-benzotriazole oxide)-N,N,N',N'-tetramethylurea hexafluorophosphate;
HOBt: 1-hydroxybenzotriazole;
KOAc: potassium acetate;
LAH: lithium aluminum tetrahydrogen;
LDA: lithium diisopropylamide;
LC-MS: liquid chromatography-mass spectrometry;
MeCN: acetonitrile,
MeI: methyl iodide;
MeOH: methanol;
min: minutes;
MOMCl: chloromethyl methyl ether;
$NEt_3$ or $Et_3N$ or TEA: triethylamine;
NMM: H-methylmorpholine;
$Pd_2(dba)_3$ or $Pd_2dba_3$: tris(dibenzylideneacetone)dipalladium,
$Pd(dppf)_2Cl_2$: 1,1'-bisdiphenylphosphinoferrocene palladium dichloride;
$Pd(PPh_3)_4$: tetrakis(triphenylphosphine)palladium;
PE: petroleum ether;
$Pin_2B_2$: pinacol diboron;
$(PPh_5)_2PdCl_2$: Bistriphenylphosphorus palladium dichloride,
RT or rt: room temperature;
TBAI: Tetrabutylammonium iodide;
TBDPSCl: tert-butyldiphenylchlorosilane;
TBSCl: tert-butyldimethylchlorosilane;
r-BuOH: tert-butanol;
TFA: trifluoroacetic acid;
THF: Tetrahydrofuran;
TLC: thin layer chromatography analysis;
xantphos: 4,5-bisdiphenylphosphine-9,9-dimethylxanthene;
XPhos or x-phos: 2-Dicyclohexylphosphorus-2,4,6-triisopropylbiphenyl.

Intermediate M1:

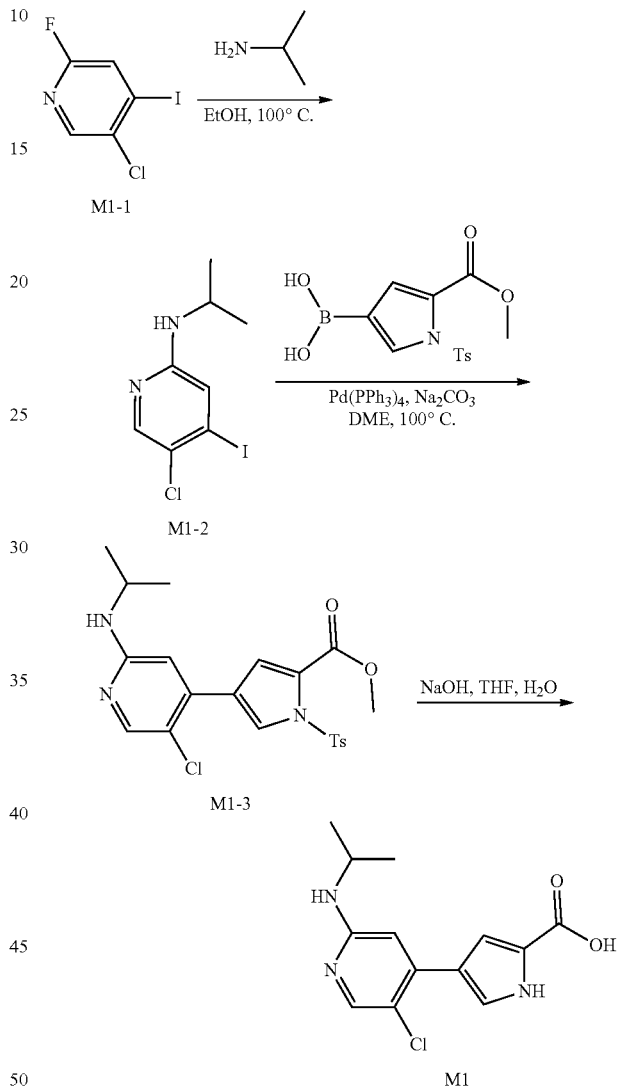

Step 1: Preparation of Compound M1-2

Compound M1-1 (4.500 g) was dissolved in ethanol (20 mL), isopropylamine (5.200 g) was added, and the reaction was stirred at 80° C. for 12 hrs. The solvent was removed under reduced pressure. The reaction mixture was quenched with $H_2O$ (50 ml), extracted with EA (50 ml), the organic phase was dried over $Na_2SO_4$, filtered and evaporated to afford a residue. The crude product was purified by flash silica chromatography. Pure fractions were evaporated to dryness to afford 3.500 g M1-2 as a light yellow oily liquid. LC-MS $[M+H]^+$=297.0.

Step 2: Preparation of Compound M1-3

Compound M1-2 (3.400 g) was dissolved in DME (20 mL), and (5-(methoxycarbonyl)-1-tosyl-1H-pyrrol-3-yl)boronic acid (5.600 g), $Pd(PPh_3)_4$ (1.300 g) and sodium carbonate (2.400 g) were dissolved in H₂O (3 mL) and added to the reaction solution under N₂, and stirred at 80° C. for 12 hrs. Filter, wash the filter cake twice with 10 mL EA. The mother liquor was quenched with H₂O (50 ml), extracted with EA (50 ml), the organic phase was dried over Na₂SO₄, filtered and evaporated to afford a residue. The crude product was purified by flash silica chromatography. Pure fractions were evaporated to dryness to afford 3.700 g M1-3 as a yellow solid. LC-MS [M+H]⁺=448.1.

Step 3: Preparation of Compound M1

Compound M1-3 (1.000 g) was dissolved in THF (20 mL), LiOH.H₂O (0.280 g) dissolved in H₂O (2 mL) was added to the reaction solution, and the reaction was stirred at 70° C. for 12 hrs. The solvent was removed under reduced pressure. And the residue was just dissolved in 2 mL water. Hydrochloric acid (6N) was slowly added to adjust the pH=6-7. A large amount of white solid precipitated out and was filtered. The filter cake was washed twice with 2 mL of H₂O, transferred to a 100 mL conical flask, added 10 mL of methanol to dissolve, added Na₂SO₄ to dry, filtered, and concentrated under reduced pressure to obtain 0.700 g M1 as an off-white solid. LC-MS [M+H]⁺=280.1.

Intermediate M2:

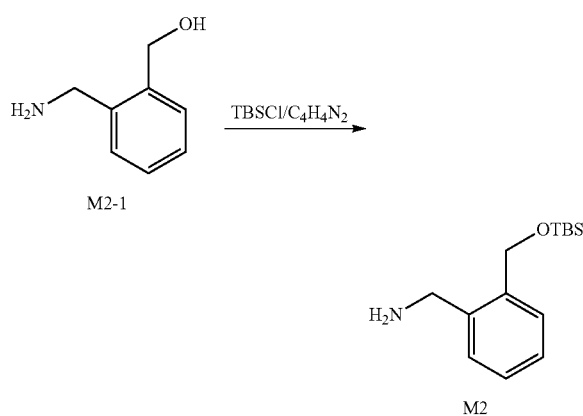

2-(Aminomethyl)benzyl alcohol (M2-1, 200 mg), TBSCl (94 mg) and imidazole (3.5 mg) were dissolved in CH₃CN (5 mL), and the reaction was stirred at room temperature for 12 hrs. The reaction solution was added with 10 mL of EtOAc and 10 mL of water, and the layers were separated. The organic phase was dried over anhydrous sodium sulfate, filtered, and concentrated under reduced pressure. The residue was separated and purified by column chromatography to obtain 210 mg of a colorless oil, namely M2. LC-MS [M+H]⁺=252.2.

Intermediate M3:

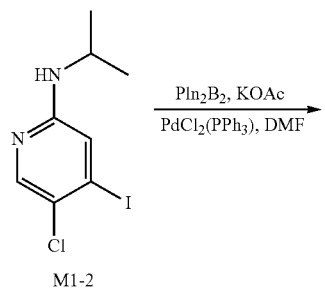

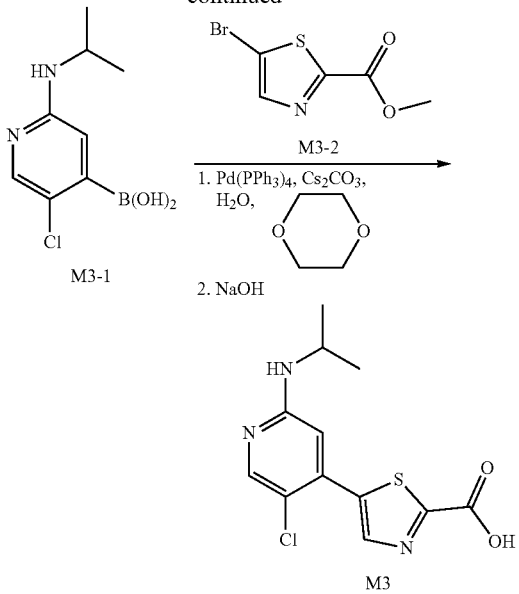

Step 1: Preparation of Compound M3-1

Dissolve 5-chloro-4-iodo-N-isopropylpyridin-2-amine (M1-2, 5.000 g) in DMF (50 mL), add Pin₂B₂ (6.500 g) and potassium acetate (3.700 g) in turn, After bubbling nitrogen for 5 min, the reaction mixture was placed in an oil bath at 105° C. for 16 hrs. After the reaction solution was cooled to room temperature, sodium hydroxide aqueous solution (1 mol/L, 100 mL) was added, the reaction mixture was extracted with ethyl acetate (2*100 mL), part of the unreacted raw materials and impurities were removed. Then the reaction mixture was diluted by hydrochloric acid (1 mol/L) and adjusted pH=7, extracted with ethyl acetate (3*100 mL), the organic phases were combined, dried with anhydrous sodium sulfate, filtered, and concentrated 4.400 g of oily yellow product. LC-MS [M+H]⁺=215.1.

Step 2: Preparation of Compound M3

The compound (5-chloro-2-(isopropylamino)pyridin-4-yl)boronic acid (M3-1, 214 mg), 5-bromothiazole-2-carboxylic acid methyl ester (M3-2, 221 mg), Pd(PPh₃)₄ (57 mg) and cesium carbonate (390 mg) were suspended in 1,4-dioxane (6 mL) and water (1 mL), after bubbling for three minutes, replaced with nitrogen three times, and reacted at 100° C. for 16 hrs. After the reaction solution was cooled, an aqueous sodium hydroxide solution (1 mol/L, 10 mL) was added, and the mixture was stirred at room temperature for 2 hrs. Part of the impurities were removed by extraction with ethyl acetate, the aqueous phase was adjusted to pH=5 with dilute hydrochloric acid (1 mol/L), the solid was precipitated and then filtered to obtain 280 mg of product LC-MS [M+H]⁺=298.0.

Intermediate M4:

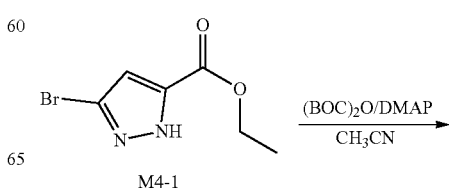

-continued

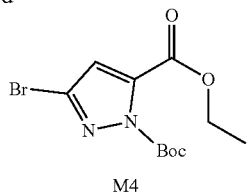

M4

The compound 5-bromo-1H-pyrazole-3-carboxylic acid ethyl ester (M4-1, 0.100 g) was dissolved in acetonitrile (2 mL), and (Boc)₂O (0.110 g) and DMAP (0.020 g) were added at room temperature. The reaction was stirred for 12 hrs. The reaction solution was directly concentrated under reduced pressure, and the residue was added with 10 mL of water and 10 mL of ethyl acetate. The layers were separated. The organic phase was added with anhydrous sodium sulfate and dried, filtered, and separated and purified by column chromatography to obtain 80 mg of light yellow oily liquid, namely M4. LC-MS [M+H]$^+$=319.0.

Intermediate M5:

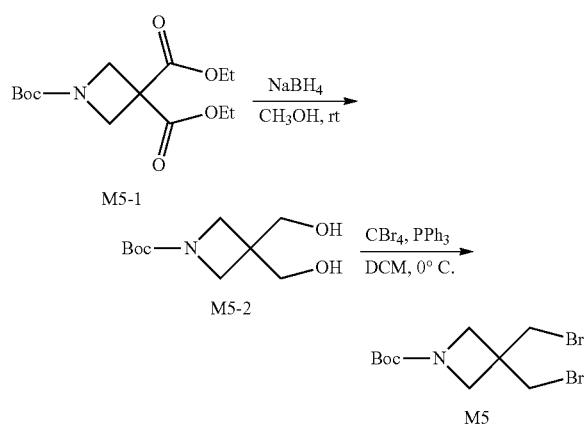

Step 1: Preparation of Compound M5-2

In a 100 mL three-necked flask, 1-(tert-butyl)-3,3-diethylazetidine-1,3,3-tricarboxylate (M2-1, 5.000 g) and 50 mL of methanol were added. After nitrogen replacement for three times, the temperature was lowered to 0° C., and sodium borohydride (1.300 g) was added in batches. After the addition, the temperature was raised to room temperature and the reaction was kept for 3 hrs. After the reaction was completed, it was concentrated under reduced pressure. The crude product was purified by flash silica chromatography (DCM:MeOH=5:1). Pure fractions were evaporated to dryness to afford 3.400 g M5-2 as a white solid. LC-MS [M+H]$^+$=218.1. $^1$H NMR (600 MHz, DMSO-d$_6$) δ 4.80 (t, J=5.5 Hz, 2H), 3.55 (s, 2H), 3.50 (s, 2H), 3.44 (s, 2H), 3.43 (s, 2H), 1.37 (s, 9H).

Step 2: Preparation of Compound M5

In a 100 ml three-necked flask, 3,3-bis(hydroxymethyl)azetidine-1-carboxylic acid tert-butyl ester (M5-2, 3.400 g) and triphenylphosphonium (9.100 g) were dissolved in 120 mL anhydrous DCM. After cooling to 0° C., carbon tetrabromide (11.500 g) was slowly added in batches under nitrogen, and the reaction was kept for 5 hrs. After the reaction was completed, it was concentrated under reduced pressure. The crude product was purified by flash silica chromatography (PE:EtOAc=9:1). Pure fractions were evaporated to dryness to afford 1.200 g M5 as a white solid.

LC-MS [M+H]$^+$=342.0. $^1$H NMR (600 MHz, CDCl$_3$) δ 3.77 (s, 4H), 3.76 (s, 4H), 1.47 (s, 9H).

Intermediate M6:

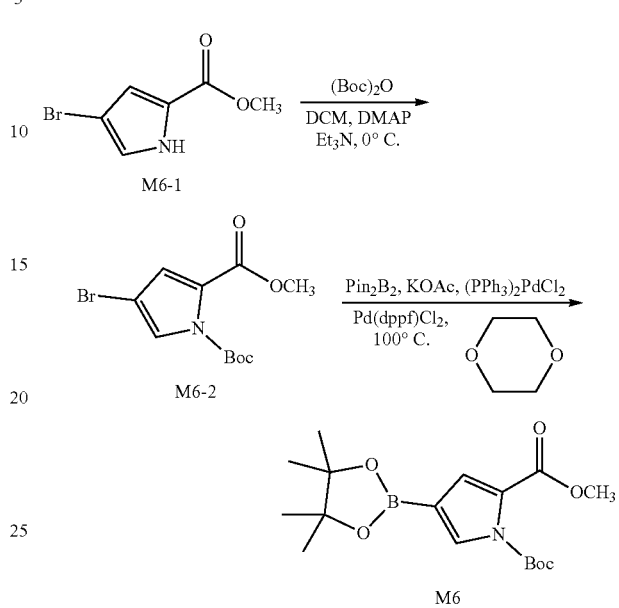

Step 1: Preparation of Compound M6-2

4-Bromo-1H-pyrrole-2-carboxylic acid methyl ester (M6-1, 50.000 g) and Boc anhydride (64.000 g) were dissolved in dichloromethane (500 mL), added triethylamine (74.400 g) and 4-dimethylaminopyridine (2.000 g), vacuum N$_2$ replacement three times, cooling to 0° C., boc anhydride (64.000 g) in dichloromethane (100 mL) solution was dropwise added during 1 h, reacting at 0° C. After 1 h, the reaction was completed, water (100 mL) was added dropwise, filtered, desolventized, and 56.200 g of the product was separated by flash column chromatography. LC-MS [M+H]$^+$=304.0.

Step 2: Preparation of Compound M6

The compound M6-2 (100.000 g) and pinacol diborate (167.000 g) were dissolved in dioxane (500 mL), potassium acetate (81.000 g), (PPh$_3$)$_2$PdCl$_2$ (5.000 g) and Pd(dppf)$_2$Cl$_2$ (5.000 g) were added, vacuum N$_2$ replacement three times, the mixture was incubated at 100° C. and reacted for 3 hrs. After the reaction was completed, cooled down to below 50° C., desolvated, added petroleum ether (500 mL), filtered, after desolventization, added petroleum ether (1000 mL) again, stirred for 45 min, filtered. The filtrated was cooled to 0-5° C., there was solid precipitation, which was filtered and dried to obtain 180.000 g of compound. LC-MS [M+H]$^+$=352.2.

Intermediate M7:

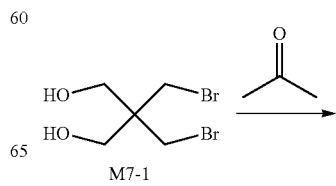

M7-1

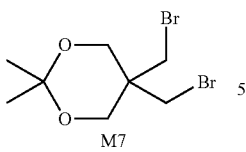

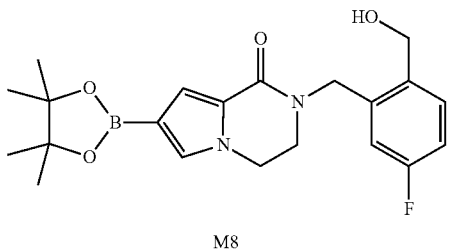

Dibromoneopentyl glycol (M7-1, 5.000 g) was dissolved in acetone (50 mL), p-toluenesulfonic acid (1.300 g) was added, and the reaction mixture was heated to reflux for 10 hrs. After cooling, the reaction mixture was concentrated under reduced pressure, H$_2$O (50 mL) and EtOAc (50 mL) were added, the pH was adjusted to 7-8 with NaHCO$_3$, the organic phase was separated, and extracted with EA (50 ml). The reaction mixture was quenched with H$_2$O (20 ml), extracted with EA (10 ml*3), the organic phase was dried over Na$_2$SO$_4$, filtered and evaporated to afford a residue. The crude product was purified by flash silica chromatography (PE:EtOAc=100:1-10:1). Pure fractions were evaporated to dryness to afford 702 mg M7 as a solid. LC-MS [M+H]$^+$=301.0. $^1$H NMR (600 MHz, CDCl$_3$) δ 3.81 (s, 4H), 3.59 (s, 4H), 1.43 (s, 6H).

Intermediate M8;

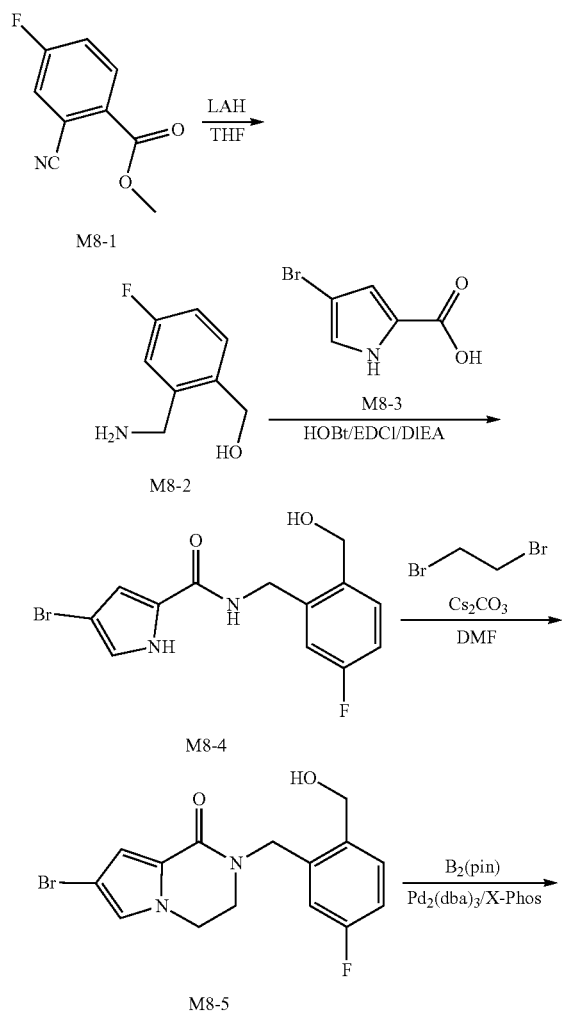

Step 1: Preparation of Compound M8-2

Methyl 2-cyano-4-fluorobenzoate (M8-1, 1.000 g) was dissolved in THF (30 mL), cooled to 0° C., lithium aluminum hydride (640 mg) was slowly added, and the reaction was carried out at room temperature for 2 hrs. The reaction solution was cooled to 0° C., and H$_2$O (0.64 mL), 15% aqueous sodium hydroxide solution (0.64 mL) and H$_2$O (1.9 mL) were slowly added in sequence, and then anhydrous sodium sulfate was added. After stirring for 10 min, it was filtered and the filtrate was concentrated. 850 mg of M8-2 was obtained, which was directly used in the next reaction. LC-MS [M+H]$^+$=156.1.

Step 2: Preparation of Compound M8-4

To the DMF (10 mL) solution of compound M8-3 (1.000 g) and M8-2 (980.06 mg) was added HOBt (1.070 g), EDCI (1.230 g) and DIEA (2.040 g, 2.83 mL), the resulting mixture was stirred at 25° C. for 12 hrs. The reaction mixture was quenched with H$_2$O (20 ml), extracted with EA (10 ml*3), the organic phase was dried over Na$_2$SO$_4$, filtered and evaporated to afford a residue. The crude product was purified by flash silica chromatography (PE:EA=5.1 to 1:1). Pure fractions were evaporated to dryness to afford 2.000 g M8-4 as a brown oil LC-MS [M+H]$^+$=327.0.

Step 3: Preparation of Compound M8-5

Dibromoethane (2.180 g) was added to the DMF (20 mL) solution of compound M8-4 (1.900 g) and cesium carbonate (4.750 g), and stirred at 100° C. for 1 h. The reaction solution was diluted with water (20 mL), extracted with ethyl acetate (10 mL*3), and the organic phases were combined. The organic phase was washed with saturated brine (30 mL), dried over anhydrous Na$_2$SO$_4$ and concentrated. The crude product was separated and purified by a column machine (PE:EA=5:1 to 1:1) to obtain compound M8-4 (1.300 g) as a brown oil. LC-MS [M+H]$^+$=353.0.

Step 4: Preparation of Compound M8

Under N$_2$ protection, the dioxane (15 mL) solution of compound M8-5 (1.300 g) and B$_2$(pin) (1120 g) was added potassium acetate (541.73 mg), Pd$_2$(dba)$_3$ (168.39 mg) and x-phos (350.87 mg), replaced with N$_2$ three times, stirred at 90° C. for 1 h. The reaction solution was diluted with water (30 mL), extracted with ethyl acetate (20 mL*3), and the organic phases were combined. The organic phase was washed with saturated brine (30 mL), dried over anhydrous Na$_2$SO$_4$ and concentrated. The crude product was separated and purified by a column machine (PE:EA=5:1 to 1:1) to (DCM:MeOH=1:0 to 20:1) to obtain compound M8 (1.100 g) as an off-white solid. LC-MS [M+H]$^+$=401.2.

Intermediate M9:

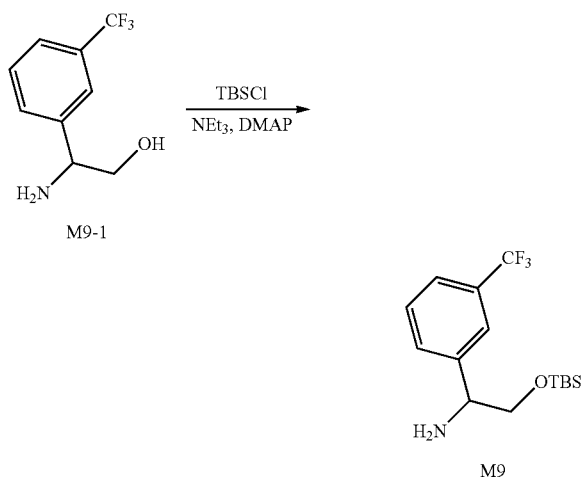

M9-1 (0.500 g) was dissolved in DCM (10 mL), DMAP (30 mg) and triethylamine (0.490 g) were added, the reaction mixture was cooled to 0° C., and TBSCl (0.550 g) in DCM was added dropwise. The reaction was stirred overnight at room temperature. The reaction mixture was diluted with DCM (10 mL), washed with water (20 mL*2), the organic phase was dried over Na$_2$SO$_4$, filtered and evaporated to afford a residue. The crude product was purified by flash silica chromatography (PE:EtOAc=100:0 to 1:1). Pure fractions were evaporated to dryness to afford 0.420 g M9 as an oily liquid. LC-MS [M+H]$^+$=320 2.

Intermediate M10:

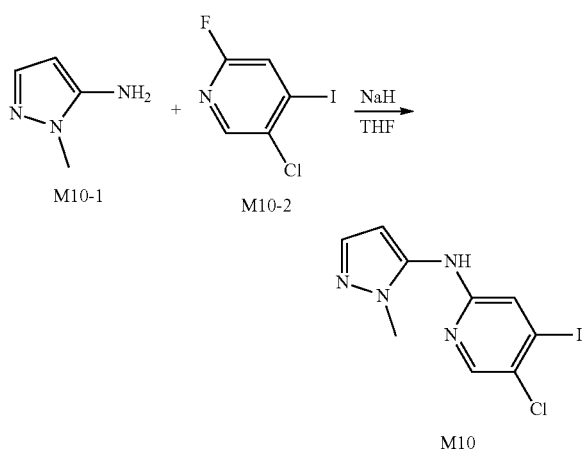

Under the protection of N$_2$ at 0° C., NaH (8.030 g) was added to the THF (400 mL) solution of compound M10-1 (15.000 g) in batches, and stirred at 0° C. for 0.5 hours. M10-2 (41.750 g) was added at −20° C., and stirred at 25° C. for 2 hours. The reaction solution was quenched with ice water (500 mL) at 0° C., extracted with ethyl acetate (200 mL*3), and the organic phase was washed with saturated brine (500 mL), dried over anhydrous Na$_2$SO$_4$ and concentrated, and the crude product was diluted with DCM (30 mL), PE (200 mL) was slowly added to the reaction solution, a solid precipitated out, the filter cake after filtration was compound M10 (18.700 g) as a yellow-brown solid. LC-MS [M+H]$^+$=335.0.

Example 1: (4-(5-chloro-2-(isopropylamino)pyridin-4-yl)-N-(2-(hydroxymethyl)benzyl)-1H-pyrrole-2-methyl amide)

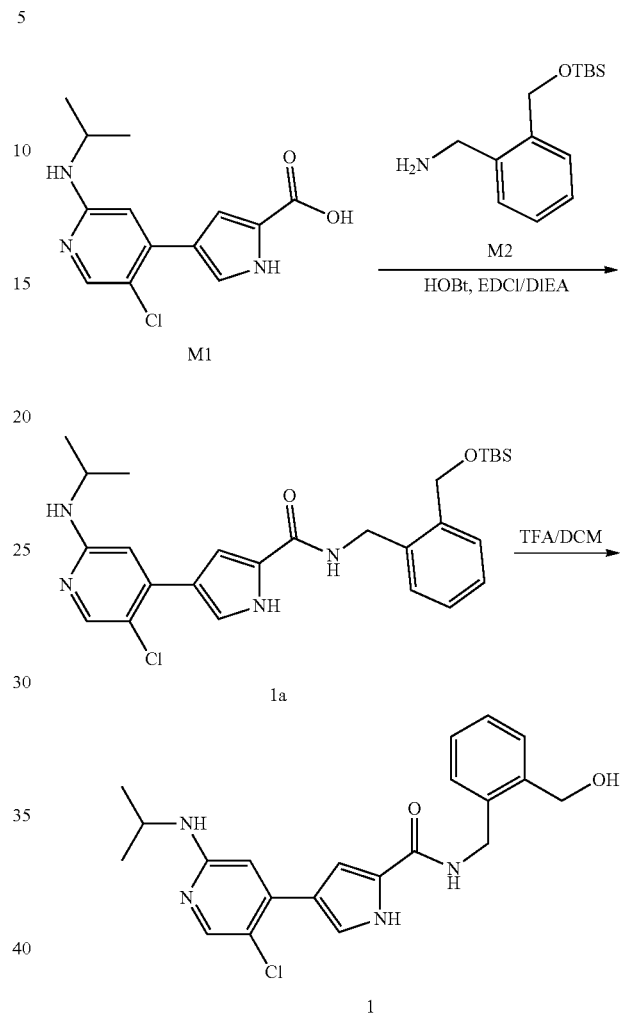

Step 1: Preparation of Compound 1a

Compounds M1 (200 mg), M2 (214 mg), HOBt (115 mg), EDCI (170 mg) and DIEA (0.35 mL) were dissolved in DMF (5 mL), and the reaction was stirred at room temperature for 12 hrs. The reaction solution was added with EtOAc (10 mL) and 10 mL of water, and the layers were separated. The organic phase was dried over anhydrous sodium sulfate, filtered, and concentrated under reduced pressure. The residue was separated and purified by column chromatography to obtain 180 mg of colorless oil, namely 1a. LC-MS [M+H]$^+$=513.2.

Step 2: Preparation of Compound 1

Compound 1a (100 mg) was dissolved in DCM (5 mL), TFA (0.5 mL) was added, and the reaction was stirred at room temperature for 2 hrs. The reaction solution was added with DCM (10 mL) and 10 mL of water, and the layers were separated. The organic phase was dried with anhydrous sodium sulfate, filtered, and concentrated under reduced pressure. The residue was separated and purified by column chromatography to obtain 7.4 mg of yellow oil, namely compound 1. LC-MS [M+H]$^+$=399.2.

Example 2: (5-(5-Chloro-2-(isopropylamino)pyridin-4-yl)-N-(5-fluoro-2-(hydroxymethyl)benzyl)thiazole-2-formamide)

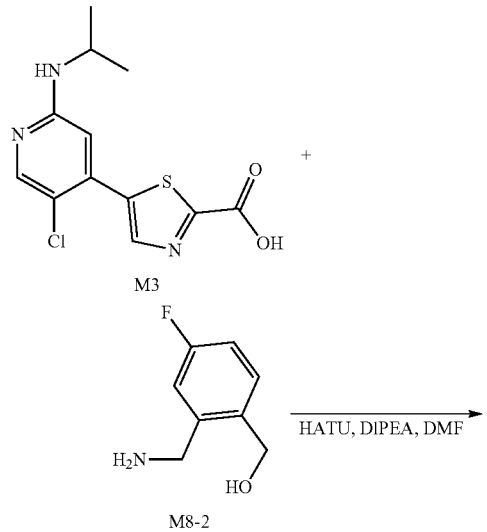

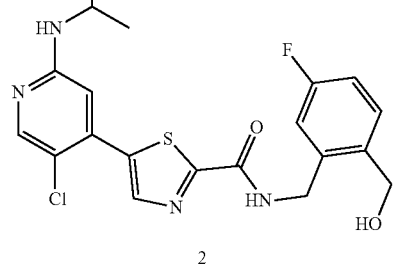

Step 2: Preparation of Compound 2

Compound M3 (700 mg) was dissolved in DMF (10 mL), DIPEA (1.2 mL) and HATU (1.100 g) were added sequentially, and after stirring at room temperature for 5 min, M8-2 (437 mg) was added, and stirring was continued at room temperature for 30 min. The reaction mixture was diluted with ethyl acetate (50 mL), the organic phase was washed with 5% lithium chloride aqueous solution (3*30 mL), separated, dried, concentrated, and passed the column to obtain 566 mg of product. LC-MS [M+H]$^+$=435.1.

The example compounds 3-5 were synthesized by referring to the synthetic procedures of similar compounds in the example compounds using commercially available raw materials.

TABLE 1

| Example | Structure | Chemical Name | LC-MS [M + H]$^+$ |
|---|---|---|---|
| 3 | 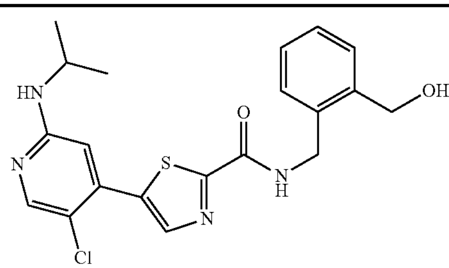 | 5-(5-chloro-2-(isopropylamino)pyridin-4-yl)-N-(2-(hydroxymethyl)benzyl)thiazole-2-formamide | 417.1 |
| 4 | 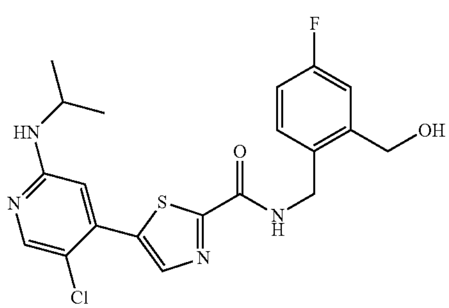 [SMILES: CC(C)Nc1cc(-c2cnc(C(=O)NCc3ccc(F)cc3CO)s2)c(Cl)cn1] | 5-(5-chloro-2-(isopropylamino)pyridin-4-yl)-N-(4-fluoro-2-(hydroxymethyl)benzyl)thiazole-2-formamide | 435.1 |
| 5 | 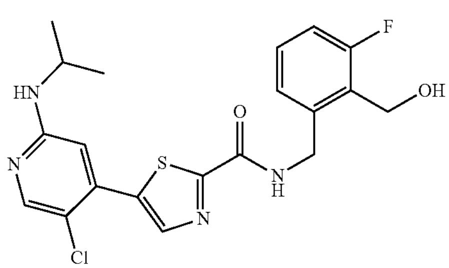 [SMILES: CC(C)Nc1cc(-c2cnc(C(=O)NCc3cccc(F)c3CO)s2)c(Cl)cn1] | 5-(5-chloro-2-(isopropylamino)pyridin-4-yl)-N-(3-fluoro-2-(hydroxymethyl)benzyl)thiazole-2-formamide | 435.1 |

Example 6: (8'-(5-Chloro-2-(isopropylamino)pyridin-4-yl)-2'-(2-(hydroxymethyl)benzyl)-2',3-dihydro-1'H,5'H-spiro[oxetane-3,4'-pyrrolo[1,2-a][1,4]diazepine]-1'-one)

Example 7: (2'-(5-Chloro-2-(isopropylamino)pyridin-4-yl)-5'-(2-(hydroxymethyl)benzyl)-5',6-dihydro-4'H,8'H-spiro[oxetane-3,7'-pyrazolo[1,5-a][1,4]diazepine]-4'-one)

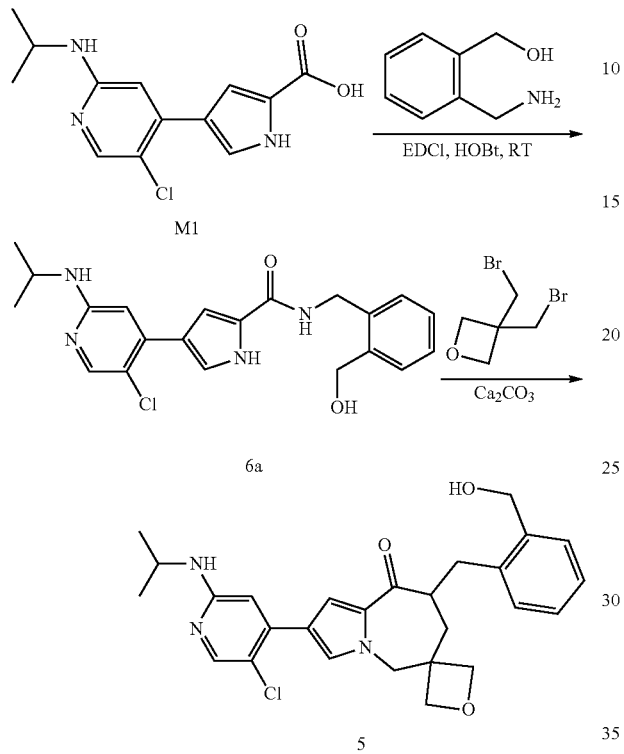

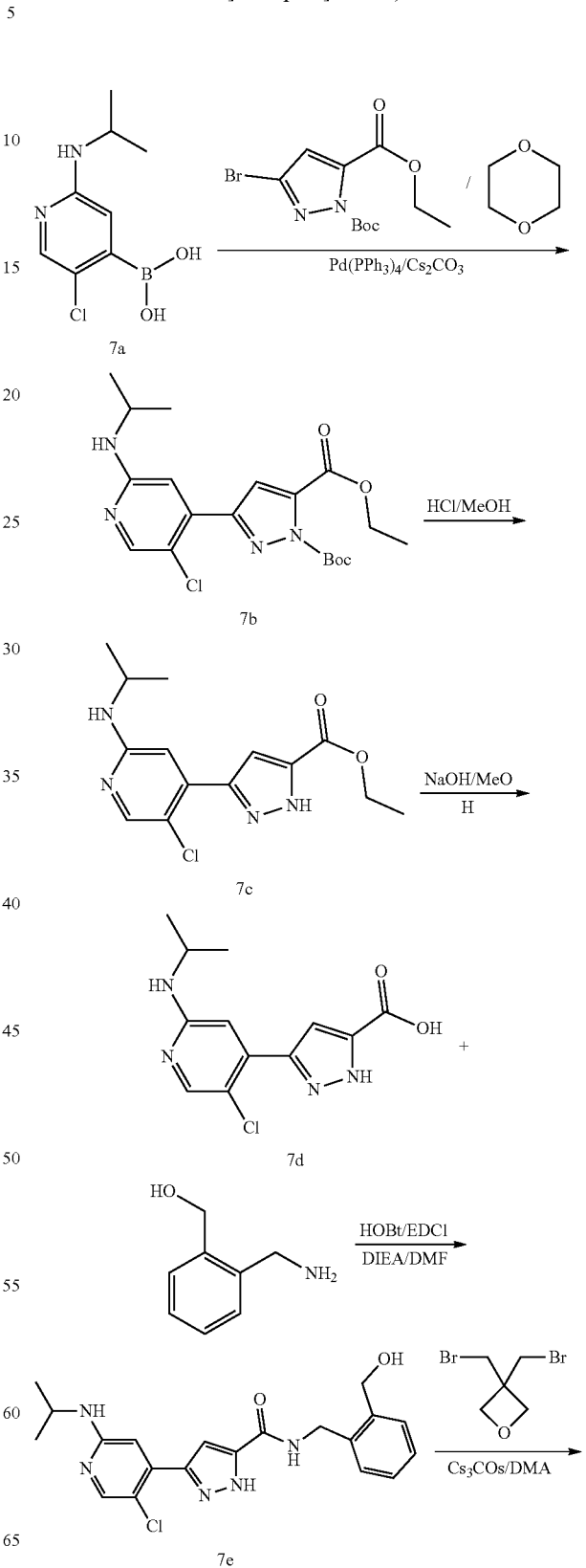

Step 1: Preparation of Compound 6a

M1 (1.500 g) was dissolved in DMF, HOBt (869 mg), EDCl.HCl (2.049 g), DIEA (2.078 g) and 2-(aminomethyl)benzyl alcohol (883 mg) were added, the above mixture was stirred and reacted overnight. Water was added to the reaction mixture and extracted with EtOAc (100 mL*3). The organic phase was washed with brine (30 mL*4), dried over anhydrous $Na_2SO_4$, concentrated under reduced pressure, and the residue was purified by column chromatography to obtain 1.456 g of compound 6a LC-MS [M+H]$^+$=399.2.

$^1$H NMR (600 MHz, DMSO-d$_4$): 12.04-11.59 (m, 1H), 8.61 (t, J=5.9 Hz, 1H), 7.97 (s, 1H), 7.44-7.39 (m, 1H), 7.36 (br.s., 1H), 7.31-7.26 (m, 2H), 7.26-7.21 (m, 2H), 6.57 (s, 1H), 6.41 (d, J=7.7 Hz, 1H), 5.20 (t, J=5.3 Hz, 1H), 4.62 (d, J=5.1 Hz, 2H), 4.50 (d, J=5.9 Hz, 2H), 3.94 (qd, J=6.6, 13.5 Hz, 1H), 1.14 (d, J=6.2 Hz, 6H).

Step 2: Preparation of Compound 6

Under nitrogen protection, the compound 6a (1.456 g) was dissolved in DMA (40 mL), 3,3-bisbromomethyl-1-oxetane (890 mg) and cesium carbonate (3.568 g) were added, and the reaction was heated for 100° C. for 1 h. LC-MS detected the completion of the reaction, the mixture was poured into ice water after cooling down, extracted with EtOAc (100 mL*3), the organic phases was combined, washed with saturated brine (30 mL*4), dried over anhydrous $Na_2SO_4$, concentrated under reduced pressure, and the residue was purified by column (PE:EtOAc=1:1), 706 mg of compound 6 was obtained. LC-MS [M+H]$^+$=481.2.

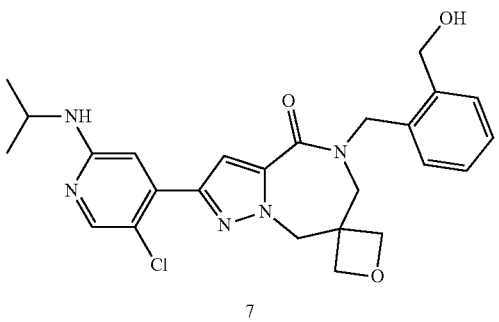

7

Step 1: Preparation of Compound 7b

Dissolve 7a (200 mg) and M4 (356 mg) in dioxane (5 mL), dissolve cesium carbonate (606 mg) in 1 mL of water and add to the reaction solution, add Pd(PPh$_3$)$_4$ (107 mg) under nitrogen protection. The temperature of the reaction solution was raised to 100° C. and the reaction was stirred for 12 hrs. The reaction solution was filtered with celite, and the filter cake was washed once with EtOAc (50 mL). After the mother liquor was directly concentrated under reduced pressure, the residue was purified by column chromatography to obtain 210 mg of a colorless oily liquid, namely compound 7b. LC-MS [M+H]$^+$=409.2.

Step 2: Preparation of Compound 7c 7b (210 mg) was dissolved in methanol (10 mL), concentrated hydrochloric acid (1 mL) was added, and the reaction was stirred at room temperature for 2 hrs. The reaction solution was directly concentrated under reduced pressure to obtain 320 mg of the residue, namely 7c. LC-MS [M+H]$^+$=309.1.

Step 3: Preparation of Compound 7d

Compound 7c (320 mg) was dissolved in methanol (5 mL), NaOH (208 mg) was added, and the reaction was refluxed for 12 hrs. The reaction solution was directly concentrated under reduced pressure. The residue was added with 1 mL of water, and the pH was adjusted to 6-7 with concentrated hydrochloric acid. There was a white solid after precipitation, filtration, the filter cake was washed twice with 1 mL of water and transferred to a 100 mL erlenmeyer flask, dissolved in methanol and then dried with sodium sulfate, filtered, and concentrated under reduced pressure to obtain 200 mg of white solid, that was 7d. LC-MS [M+H]$^+$=281.1.

Step 4: Preparation of Compound 7e

Compound 7d (200 mg), 2-(aminomethyl)benzyl alcohol (117 mg), HOBt (116 mg), EDCI.HCl (165 mg) and DIEA (0.38 mL) were dissolved in DMF (10 mL), and the reaction was stirred at room temperature for 12 hrs. The reaction solution was added with EtOAc (10 mL) and 10 mL of water. The layers were separated. The organic phase was dried over anhydrous sodium sulfate, filtered, and concentrated under reduced pressure. The residue was separated and purified by column chromatography to obtain 180 mg of anhydrous oily compound, namely 7e. LC-MS [M+H]$^+$= 400.2.

Step 5: Preparation of Compound 7

Compound 7e (180 mg) was dissolved in DMA (5 mL), 3,3-bisbromomethyl-1-oxetane (107 mg), cesium carbonate (440 mg) were added, and the reaction was stirred at 100° C. for 2 hrs. Add 10 mL of ethyl acetate to the solution, the organic phase was separated, washed with 10 mL of water again, dried with anhydrous sodium sulfate, filtered, and concentrated under reduced pressure. The residue was separated and purified by column chromatography to obtain 85 mg of white solid compound 7. LC-MS [M+H]$^+$=482.2.

Example 8: (2-(5-Chloro-2-(isopropylamino)pyridin-4-yl)-7-(chloromethyl)-7-(hydroxy methyl)-5-(2-(hydroxymethyl)benzyl)-5,6,7,8-tetrahydro-4H-pyrazolo[1,5-a][1,4]diazepine-4-one)

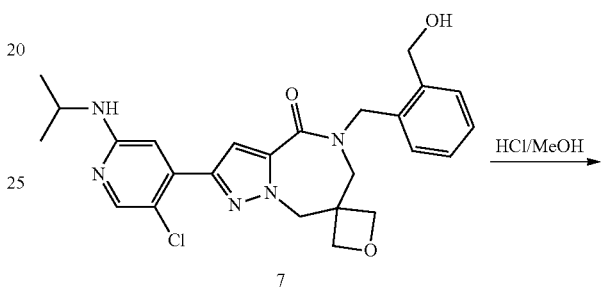

7

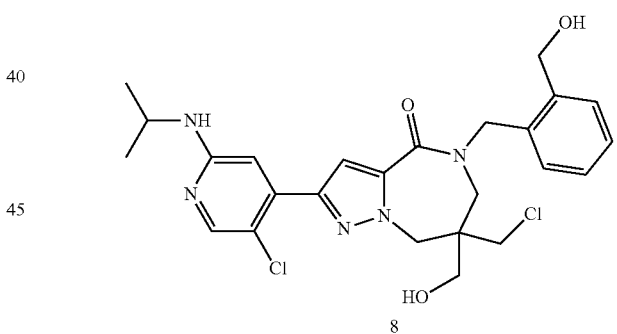

8

Compound 7 (50 mg) was dissolved in methanol (3 mL), concentrated hydrochloric acid (1 mL) was added, and the reaction was stirred at room temperature for 2 hrs. After the reaction solution was directly concentrated under reduced pressure, the residue was added with saturated sodium carbonate solution to adjust pH=7-8, and then add 10 mL of ethyl acetate, the organic phase was separated, washed with 10 mL of water again, dried with anhydrous sodium sulfate, filtered, and concentrated under reduced pressure. The residue was separated and purified by column chromatography to obtain 15 mg of white solid compound 8. LC-MS [M+H]$^+$= 518.2.

Using commercially available raw materials, referring to the synthesis steps of similar compounds in the example compounds, the example compounds 9-21 in Table 2 were synthesized.

TABLE 2

| Example | Structure | Chemical Name | LC-MS [M + H]+ |
|---|---|---|---|
| 9 | 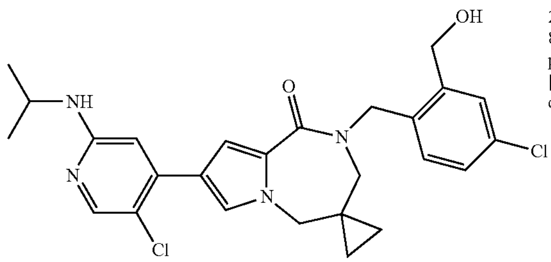 [SMILES: CC(C)Nc1cc(-c2cc3n(c2)CC2(CC2)CN(Cc2ccc(Cl)cc2CO)C3=O)c(Cl)cn1] | 2'-(4-chloro-2-(hydroxymethyl)benzyl)-8'-(5-chloro-2-(isopropylamino)pyridin-4-yl)-2',3'-dihydro-1'h,5'h-spiro[cyclopropane-1,4'-pyrrolo[1,2-a][1,4]diazepine]-1'-one | 499.2 |
| 10 | 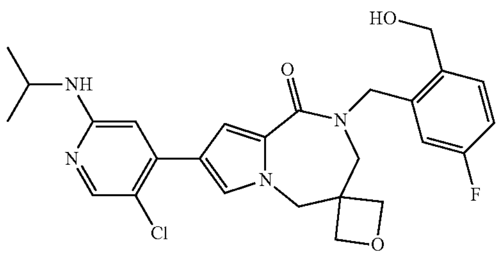 [SMILES: CC(C)Nc1cc(-c2cc3n(c2)CC2(COC2)CN(Cc2cc(F)ccc2CO)C3=O)c(Cl)cn1] | 8'-(5-chloro-2-(isopropylamino)pyridin-4-yl)-2'-(5-fluoro-2-(hydroxymethyl)benzyl)-2',3'-dihydro-1'h,5'h-spiro[oxacyclobutane-3,4'-pyrrolo[1,2-a][1,4]diazepine]-1'-one | 499.2 |
| 11 | 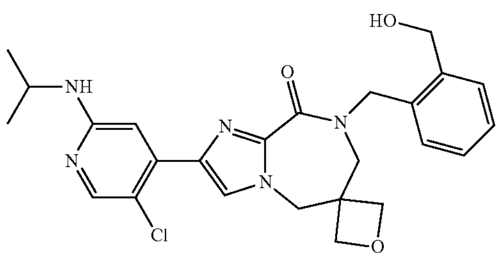 [SMILES: CC(C)Nc1cc(-c2cn3c(n2)C(=O)N(Cc2ccccc2CO)CC2(COC2)C3)c(Cl)cn1] | 2-(5-chloro-2-(isopropylamino)pyridin-4-yl)-8-(2-(hydroxymethyl)benzyl)-7,8-dihydro-5h,9h-spiro[imidazo[1,2-a][1,4]diaza-6,3'-oxacyclobutane]-9-one | 482.2 |
| 12 | 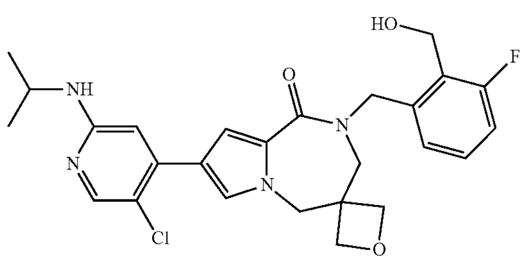 [SMILES: CC(C)Nc1cc(-c2cc3n(c2)CC2(COC2)CN(Cc2cccc(F)c2CO)C3=O)c(Cl)cn1] | 8'-(5-chloro-2-(isopropylamino)pyridin-4-yl)-2'-(3-fluoro-2-(hydroxymethyl)benzyl)-2',3'-dihydro-1'h,5'h-spiro[oxacyclobutane-3,4'-pyrrolo[1,2-a][1,4]diazepine]-1'-one | 499.2 |
| 13 | 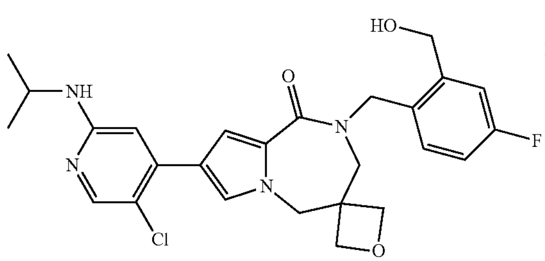 [SMILES: CC(C)Nc1cc(-c2cc3n(c2)CC2(COC2)CN(Cc2ccc(F)cc2CO)C3=O)c(Cl)cn1] | 8'-(5-chloro-2-(isopropylamino)pyridin-4-yl)-2'-(2-(hydroxymethyl)benzyl)-2',3'-dihydro-1'h,5'h-spiro[azacyclobutane-3,4'-pyrrolo[1,2-a][1,4]diazepine]-1'-one | 499.2 |
| 14 | 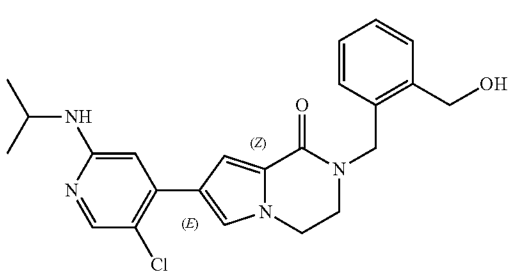 [SMILES: CC(C)Nc1cc(-c2cc3n(c2)CCN(Cc2ccccc2CO)C3=O)c(Cl)cn1] | 7-(5-chloro-2-(isopropylamino)pyridin-4-yl)-2-(2-(hydroxymethyl)benzyl)-3,4-dihydropyrrolo[1,2-a]pyrazine-1(2H)-one | 425.2 |

TABLE 2-continued

| Example | Structure | Chemical Name | LC-MS [M + H]+ |
|---|---|---|---|
| 15 | 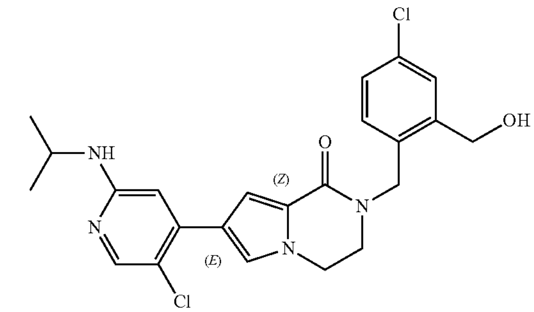 [SMILES: CC(C)Nc1cc(-c2cc3n(c2)CCN(Cc2ccc(Cl)cc2CO)C3=O)c(Cl)cn1] | 2-(4-chloro-2-(hydroxymethyl)benzyl)-7-(5-chloro-2-(isopropylamino)pyridin-4-yl)-3,4-dihydropyrrolo[1,2-a]pyrazine-1(2H)-one | 459.1 |
| 16 | 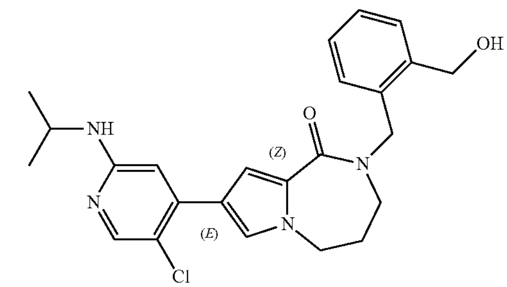 [SMILES: CC(C)Nc1cc(-c2cc3n(c2)CCCN(Cc2ccccc2CO)C3=O)c(Cl)cn1] | 8-(5-chloro-2-(isopropylamino)pyridin-4-yl)-2-(2-(hydroxylmethyl)benzyl)-2,3,4,5-tetrahydro-1h-pyrrolo[1,2-a][1,4]diazepine-1-one | 439.2 |
| 17 | 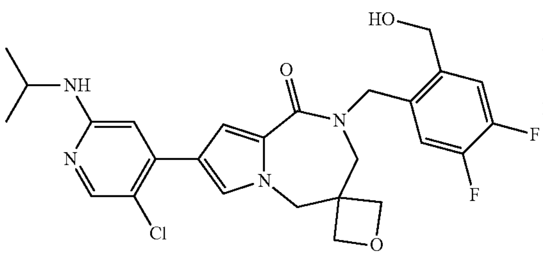 [SMILES: CC(C)Nc1cc(-c2cc3n(c2)CC2(COC2)CN(Cc2cc(F)c(F)cc2CO)C3=O)c(Cl)cn1] | 8'-(5-chloro-2-(isopropylamino)pyridin-4-yl)-2'-(4,5-difluoro-2-(hydroxymethyl)benzyl)-2',3'-dihydro-1'h,5'h-spiro[oxacyclobutane-3,4'-pyrrolo[1,2-a][1,4]diazepine]-1'-one | 517.2 |
| 18 | 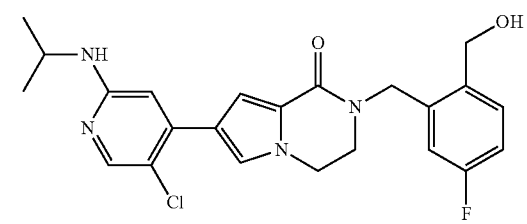 [SMILES: CC(C)Nc1cc(-c2cc3n(c2)CCN(Cc2cc(F)ccc2CO)C3=O)c(Cl)cn1] | 7-(5-chloro-2-(isopropylamino)pyridin-4-yl)-2-(5-fluoro-2-(hydroxymethyl)benzyl)-3,4-dihydropyrrolo[1,2-a]pyrazine-1(2H)-one | 443.2 |
| 19 | 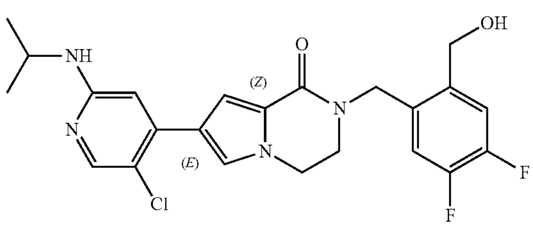 [SMILES: CC(C)Nc1cc(-c2cc3n(c2)CCN(Cc2cc(F)c(F)cc2CO)C3=O)c(Cl)cn1] | 7-(5-chloro-2-(isopropylamino)pyridine-4-yl)-2-(4,5-difluoro-2-(hydroxymethyl)benzyl)-3,4-dihydropyrrolo[1,2-a]pyrazine-1(2H)-one | 461.2 |
| 20 | 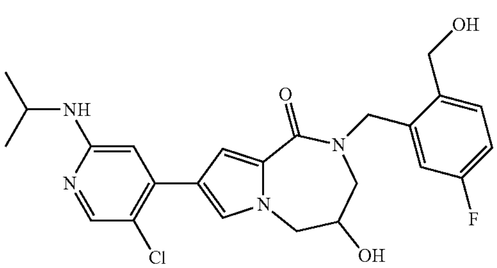 [SMILES: CC(C)Nc1cc(-c2cc3n(c2)CC(O)CN(Cc2cc(F)ccc2CO)C3=O)c(Cl)cn1] | 8-(5-chloro-2-(isopropylamino)pyridin-4-yl)-2-(5-fluoro-2-(hydroxymethyl)benzyl)-4-hydroxy-2,3,4,5-tetrahydro-1h-pyrrolo[1,2-a][1,4]diazepine-1-one | 473.2 |

TABLE 2-continued

| Example | Structure | Chemical Name | LC-MS [M + H]+ |
|---|---|---|---|
| 21 | 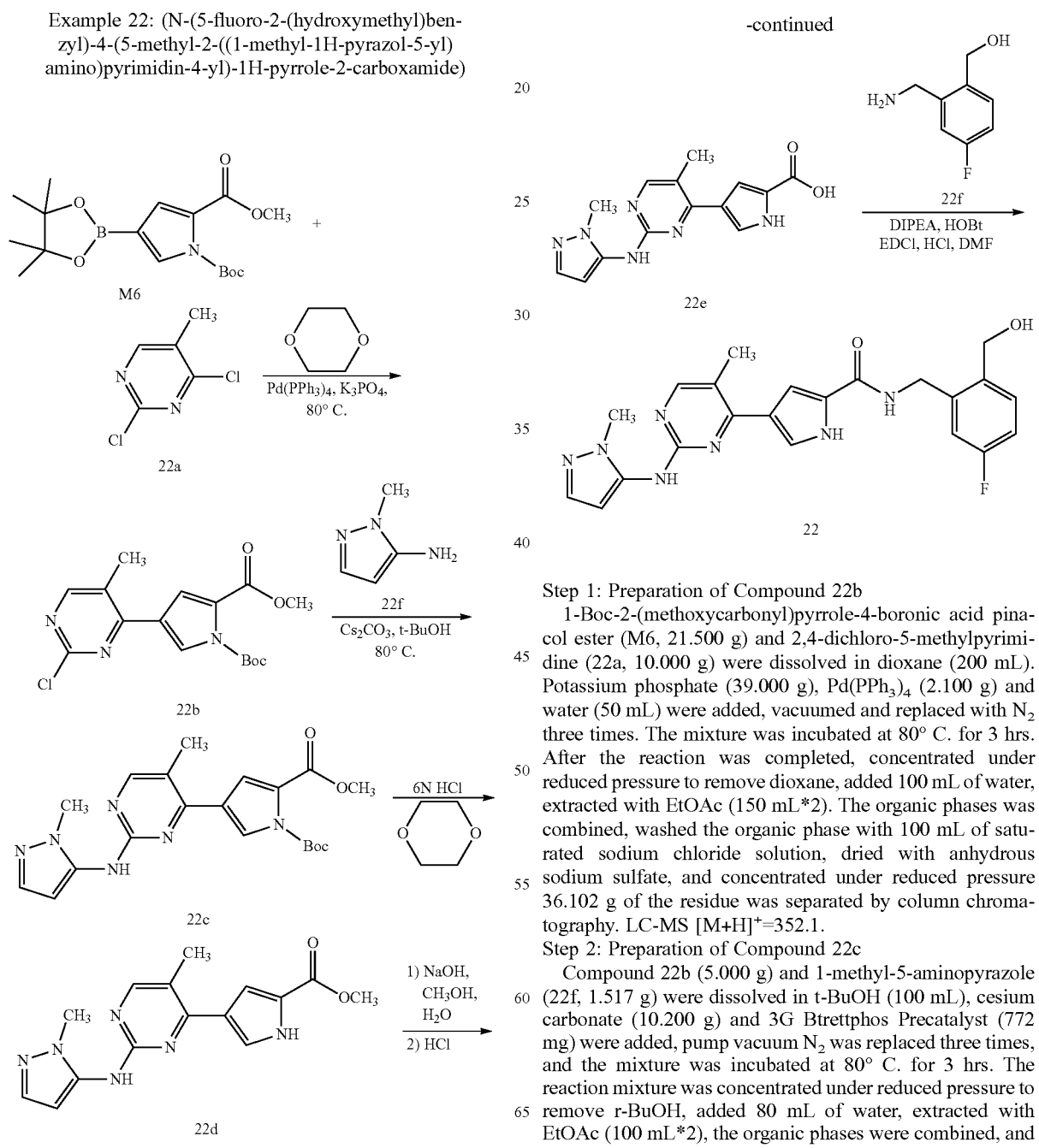 | 8-(5-chloro-2-(isopropylamino)pyridin-4-yl)-2-(4,5-difluoro-2-(hydroxymethyl)benzyl)-2,3,4,5-tetrahydro-1h-pyrrolo[1,2-a][1,4]diazepine-1-one | 475.2 |

Example 22: (N-(5-fluoro-2-(hydroxymethyl)benzyl)-4-(5-methyl-2-((1-methyl-1H-pyrazol-5-yl)amino)pyrimidin-4-yl)-1H-pyrrole-2-carboxamide)

Step 1: Preparation of Compound 22b

1-Boc-2-(methoxycarbonyl)pyrrole-4-boronic acid pinacol ester (M6, 21.500 g) and 2,4-dichloro-5-methylpyrimidine (22a, 10.000 g) were dissolved in dioxane (200 mL). Potassium phosphate (39.000 g), Pd(PPh$_3$)$_4$ (2.100 g) and water (50 mL) were added, vacuumed and replaced with N$_2$ three times. The mixture was incubated at 80° C. for 3 hrs. After the reaction was completed, concentrated under reduced pressure to remove dioxane, added 100 mL of water, extracted with EtOAc (150 mL*2). The organic phases was combined, washed the organic phase with 100 mL of saturated sodium chloride solution, dried with anhydrous sodium sulfate, and concentrated under reduced pressure 36.102 g of the residue was separated by column chromatography. LC-MS [M+H]$^+$=352.1.

Step 2: Preparation of Compound 22c

Compound 22b (5.000 g) and 1-methyl-5-aminopyrazole (22f, 1.517 g) were dissolved in t-BuOH (100 mL), cesium carbonate (10.200 g) and 3G Btrettphos Precatalyst (772 mg) were added, pump vacuum N$_2$ was replaced three times, and the mixture was incubated at 80° C. for 3 hrs. The reaction mixture was concentrated under reduced pressure to remove r-BuOH, added 80 mL of water, extracted with EtOAc (100 mL*2), the organic phases were combined, and washed with 80 mL of saturated sodium chloride solution, dried over anhydrous sodium sulfate, concentrated under reduced pressure, and the residue 44.100 g of the product was separated by chromatography. LC-MS [M+H]⁺=413.2.

Step 3: Preparation of Compound 22d

Compound 22c (3.000 g) was dissolved in dioxane (50 mL), 10 mL 6N HCl was added and stirred at room temperature for 5 hrs. After the reaction was completed, adjusted the pH to 7-8 with saturated aqueous sodium bicarbonate solution, extracted with EtOAc (50 mL*3), the organic phases were combined, washed with 50 mL saturated sodium chloride solution, dried with anhydrous sodium sulfate, concentrated under reduced pressure, and the residue chromatographic purification yielded 2.200 g of compound 22d. LC-MS [M+H]⁺=313.1.

Step 4: Preparation of Compound 22e

Compound 22d (2.200 g) was dissolved in MeOH (50 mL), sodium hydroxide (3.000 g) and water (50 mL) were added, and the mixture was stirred at 60° C. for 2 hrs. After the reaction was completed, the methanol was removed by concentration under reduced pressure, and extracted with PE:EA=2:1. The pH of the aqueous phase was adjusted to 5-6 with hydrochloric acid. A light yellow solid precipitated out and filtered with suction to obtain 61.8 g of the target compound. LC-MS [M+H]⁺=299.1.

Step 5: Preparation of Compound 22

Compound 22e (500 mg) and compound 2b (466 mg) were dissolved in DMF (15 mL), HOBt (405 mg) and EDCI.HCl (850 mg) were added, finally DIPEA (970 mg) was added. The reaction was reacted at room temperature for 3 hrs. The reaction mixture was added 30 mL water, and extracted with EA (20 mL*3), the organic phases were combined, washed with saturated brine (20 mL*3), dried over anhydrous sodium sulfate, concentrated under reduced pressure, and the residue was purified by column chromatography to obtain 268 mg. LC-MS [M+H]⁺=436 2.

Example 23: (2-(5-Fluoro-2-(hydroxymethyl)benzyl)-7-(5-methyl-2-((1-methyl-1H-pyrazol-5-yl)amino)pyrimidin-4-yl)-3,4-dihydropyrrolo[1,2-a]pyrazine-1(2H)-one) preparation

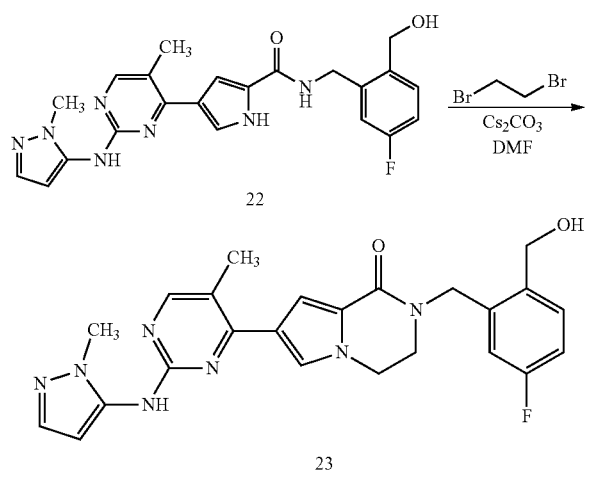

Compound 22 (100 mg) and 1,2-dibromoethane (128 mg) were dissolved in DMF (5 mL), cesium carbonate (225 mg) was added, and the reaction was carried out at 80° C. for 3 hrs. After the reaction was completed, water (20 mL) was added, EA extraction (20 mL*3), the organic phases were combined, washed with saturated brine (30 mL*3), dried over anhydrous sodium sulfate, concentrated under reduced pressure, and the residue was purified by column chromatography to obtain 28 mg. LC-MS [M+H]⁺=462.2.

Example 24: (8'-(5-Chloro-2-(isopropylamino)pyridin-4-yl)-2'-(2-(hydroxymethyl)benzyl)-2',3'-dihydro-1'H,5'H-spiro[azetidine-3,4'-pyrrolo[1,2-a][1,4]diazepine]-1'-one)

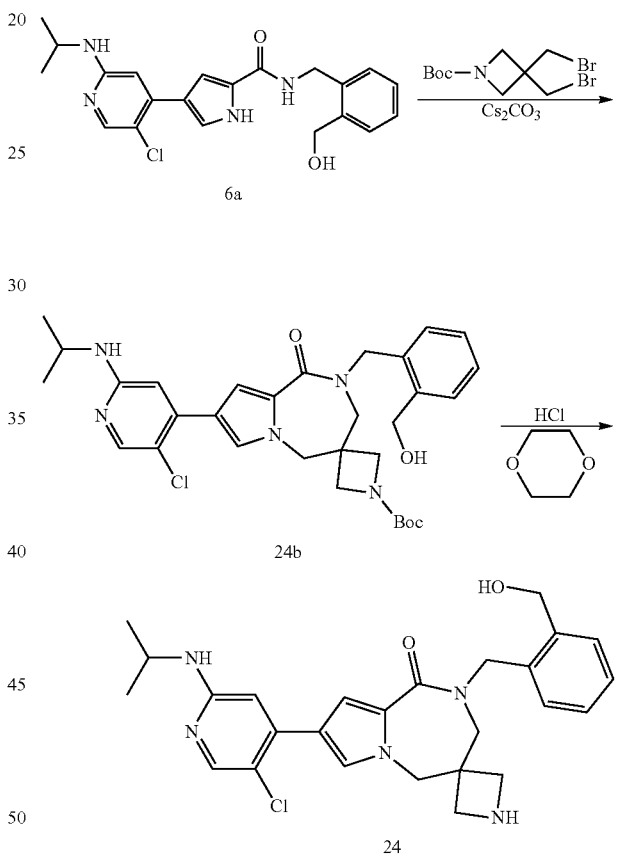

Step 1: Preparation of Compound 24b

Compound 6a (1.000 g) and compound M5 (928 mg) were dissolved in DMA (30 mL), cesium carbonate (2.400 g) was added, and the reaction was heated at 100° C. for 1 h. TLC detected the completion of the reaction, the reaction mixture was cooled to room temperature, added with ice water (60 mL), extracted with EtOAc (50 mL*2), the organic phases were combined, washed with saturated brine (100 mL*4), dried with anhydrous Na₂SO₄, concentrated under reduced pressure, and the residue was purified by column chromatography (PE:EtOAc=1:1) to obtain 880 mg of compound 24b. LC-MS [M+H]⁺=580.3.

Step 2: Preparation of Compound 24

Compound 24b (880 mg) was added to 1,4-dioxane (18 mL), 6N HCl (2 mL) was added, and the reaction was stirred overnight at room temperature. TLC detected the completion of the reaction. The reaction mixture was concentrated under reduced pressure with half of the solvent, added EtOAc (40 mL), adjusted pH=7-8 with saturated NaHCO$_3$, the organic phases were separated, and continued to use EtOAc:THF=1:1 (50 mL*4) for the aqueous phase. After extraction, the organic phases were combined, dried over anhydrous Na$_2$SO$_4$, and concentrated under reduced pressure. The residue was beaten with EA to obtain 700 mg of compound 24. LC-MS [M+H]$^+$=480.2.

Example 25: (8'-(5-Chloro-2-(isopropylamino)pyridin-4-yl)-2'-(2-hydroxymethyl)benzyl)-1-methyl-2',3'-dihydro-1'H,5'H-spiro[azetidine-3,4'-pyrrolo[1,2-a][1,4]diazepine]-1'-ketone

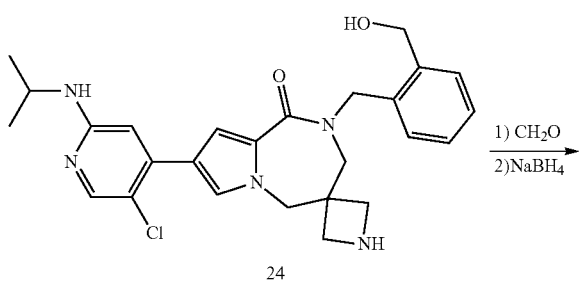

Compound 24 (200 mg) was dissolved in 6 mL dichloromethane, 35% aqueous formaldehyde solution (288 mg) and acetic acid (60 mg) were added, the reaction was stirred at room temperature for 2 hrs. After the reaction was completed, cooled to 0° C. and added sodium borohydride (100 mg) in batches, after the addition, the temperature was raised to room temperature and stirred for 2 hrs. The reaction solution was directly mixed with sample column chromatography (DCM:MeOH=10:1), and 10 mg of the product was isolated. LC-MS [M+H]$^+$=494.2.

Examples 26 and 27: (8-(5-Chloro-2-(isopropylamino)pyridin-4-yl)-2-(2-(hydroxymethyl)benzyl)-2',2'-dimethyl-2,3-dihydro-1H,5H-spiro[pyrrolo[1,2-a][1,4]diazepine-4,5'-[1,3]dioxane]-1-one) and (8-(5-chloro-2-(isopropylamino)pyridin-4-yl)-4,4-bis(hydroxymethyl)-2-(2-(hydroxyl(methyl)benzyl)-2,3,4,5-tetrahydro-1H pyrrolo[1,2-a][1,4]diazepine-1-one)

Step 1: Preparation of Compound 26

Compound 6a (100 mg) was dissolved in DMF (5 mL), M7 (80 mg) and cesium carbonate (244 mg) were added, and the reaction was heated at 80° C. for 1.5 hrs. TLC detected the completion of the reaction, the reaction mixture was cooled to room temperature, added with ice water (10 mL), extracted with EtOAc (15 mL*2), the organic phases were combined, washed with saturated brine (3 mL*4), dried with anhydrous Na$_2$SO$_4$, concentrated under reduced pressure, and the residue column chromatography yielded 65 mg of crude product of compound 26. LC-MS [M+H]$^+$=539.2.

Step 2: Preparation of Compound 27

The crude compound 26 (65 mg) was dissolved in ethyl acetate (5 mL), 1N HCl (2 mL) was added, and the reaction was heated at 30° C. for 1 h. The reaction mixture was added with NaHCO$_3$ to adjust pH=7-8, extracted with EtOAc (5 mL*3), the organic phase was dried with anhydrous Na$_2$SO$_4$, concentrated under reduced pressure, and the residue was purified by column chromatography (EtOAc) to obtain a solid 18 mg, namely compound 27. LC-MS [M+H]$^+$= 499.3. The example compounds 28 and 29 in Table 3 were synthesized by referring to the synthetic steps of similar compounds in the example compounds with commercially available raw materials

TABLE 3

| Example | Structure | Chemical Name | LC-MS [M + H]+ |
|---|---|---|---|
| 28 | 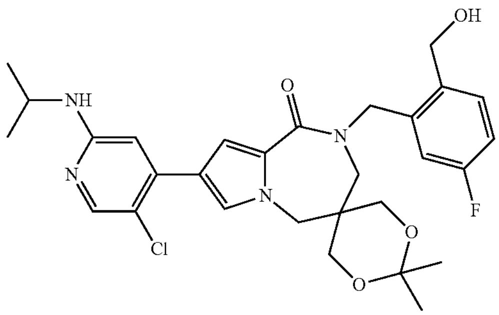 [SMILES: CC(C)Nc1cc(-c2cc3n(c2)CC2(COC(C)(C)OC2)CN(Cc2cc(F)ccc2CO)C3=O)c(Cl)cn1] | 8-(5-chloro-2-(isopropylamino)pyridin-4-yl)-2-(5-fluoro-2-(hydroxymethyl)benzyl)-2',2'-dimethyl-2,3-dihydro-1h,5h-spiro[pyrrolo[1,2-a][1,4]diazepine-4,5'-[1,3]dioxane]-1-one | 557.2 |
| 29 | 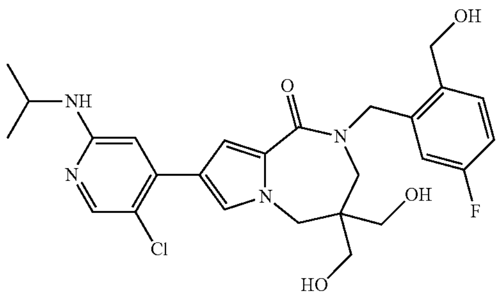 [SMILES: CC(C)Nc1cc(-c2cc3n(c2)CC(CO)(CO)CN(Cc2cc(F)ccc2CO)C3=O)c(Cl)cn1] | 8-(5-chloro-2-(isopropylamino)pyridin-4-yl)-2-(5-fluoro-2-(hydroxymethyl)benzyl)-4,4-bis(hydroxymethyl)-2,3,4,5-tetrahydro-1h-pyrrolo[1,2-a][1,4]diazepine-1-one | 517.2 |

Example 30: (7-(5-Chloro-2-(oxetan-3-ylamino)pyridin-4-yl)-2-(5-fluoro-2-(hydroxymethyl)benzyl)-3,4-dihydropyrrolo[1,2-a]pyrazine-1(2H)-one)

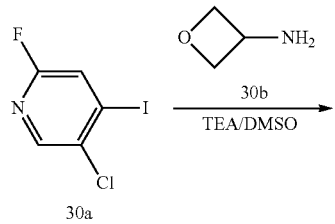

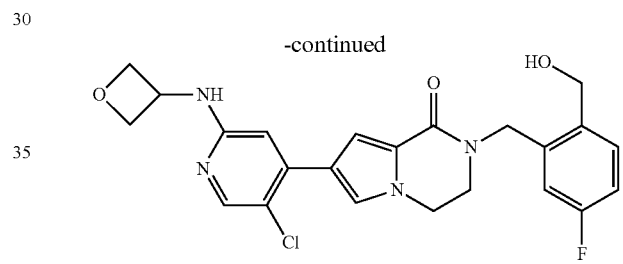

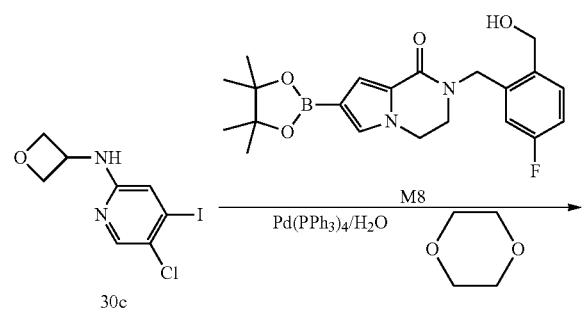

Step 1: Preparation of Compound 30c

Triethylamine (5.500 g, 7.58 mL) was added to the DMSO (20 mL) solution of compounds 30a (2.000 g) and 30b (1.140 g), and stirred at 90° C. for 4 hrs. The reaction solution was diluted with water (20 mL), extracted with ethyl acetate (10 mL*3), and the organic phases were combined. The organic phase was washed with saturated brine (20 mL), dried over anhydrous $Na_2SO_4$ and concentrated. The crude product was separated and purified by a column machine (PE:EA=1.0 to 10.1) to obtain compound 30c (800 mg) as a yellow solid. LC-MS [M+H]+=311.0.

Step 2: Preparation of Compound 30

Under $N_2$ protection, to a mixed solution of compound 30c (300 mg) and compound M8 (502.71 mg) in dioxane (5 mL) and water (1 mL) was added potassium carbonate (400.57 mg) and Pd(pph3)4 (111.58 mg)), $N_2$ replacement three times, stirring at 80° C. for 1 h. The reaction solution was diluted with water (20 mL), extracted with ethyl acetate (20 mL*3), and the organic phases were combined. The organic phase was washed with saturated brine (30 mL), dried over anhydrous $Na_2SO_4$ and concentrated. The crude product was separated and purified by preparative TLC (DCM:MeOH=20:1) to obtain compound 30 (134 mg) as a yellow-white solid. LC-MS [M+H]+=457.1.

Example 31: (7-(5-Chloro-2-((tetrahydrofuran-3-yl)amino)pyridin-4-yl)-2-(5-fluoro-2-(hydroxymethyl)benzyl)-3,4-dihydropyrrolo[1,2-a]pyrazine-1(2H)-one)

Example 32: (2-(5-Fluoro-2-(hydroxymethyl)benzyl)-7-(5-methyl-2-(oxetan-3-ylamino)pyrimidine-4-yl)-3,4-dihydropyrrolo[1,2-a]pyrazine-1(2H)-one)

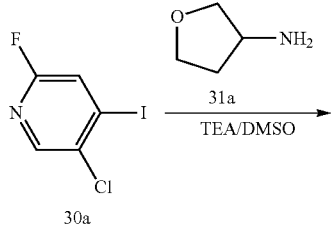

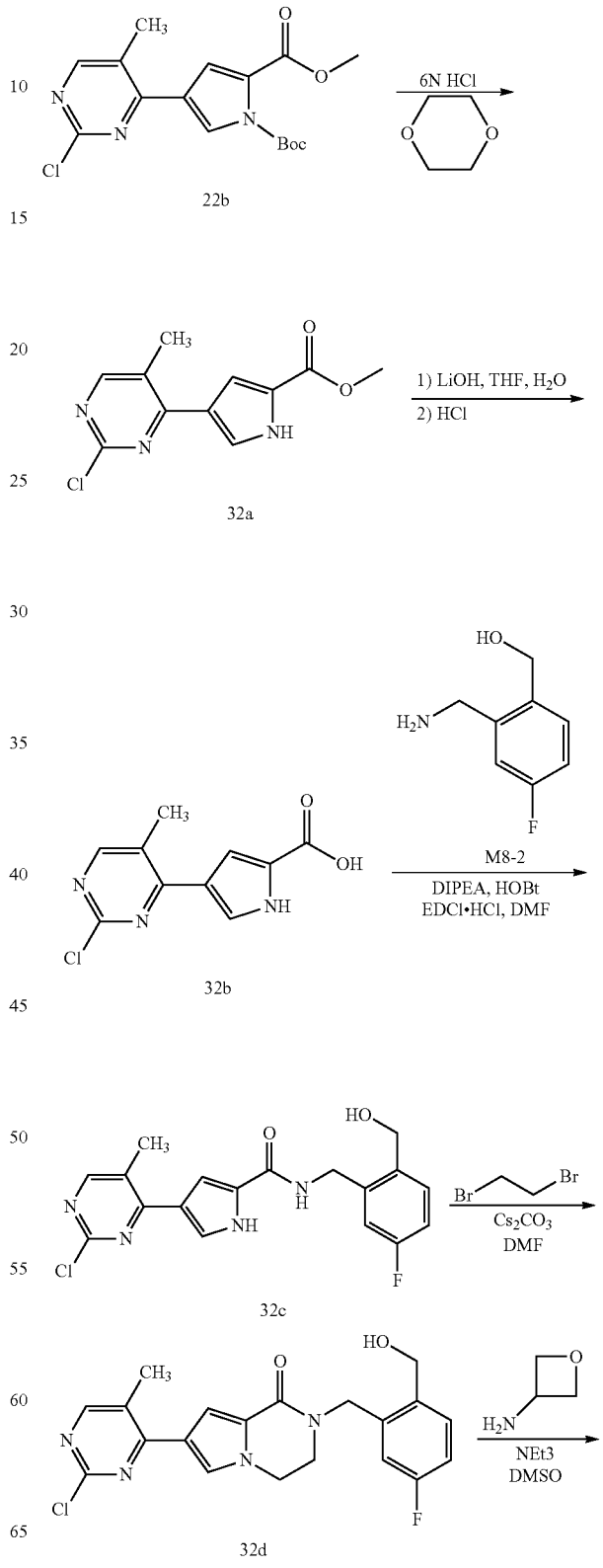

Step 1: Preparation of Compound 31b

Triethylamine (1.970 g, 2.71 mL) was added to the DMSO (10 mL) solution of compound 30a (1.000 g) and 31a (954.87 mg), and stirred at 90° C. for 4 hrs. The reaction solution was diluted with water (20 mL), extracted with ethyl acetate (10 mL*3), and the organic phases were combined. The organic phase was washed with saturated brine (20 mL), dried over anhydrous $Na_2SO_4$ and concentrated. The crude product was separated and purified by a column machine (PE:EA=1.0 to 10:1) to obtain compound 31b (650 mg) as a yellow solid LC-MS $[M+H]^+=325.0$.

Step 2: Preparation of Compound 31

Under $N_2$ protection, to a mixed solution of compound 31b (300 mg) and compound M8 (443.98 mg) in dioxane (5 mL) and water (1 mL) was added potassium carbonate (383.26 mg) and Pd(pph$_3$)$_4$ (106.76 mg)), $N_2$ replacement three times, stirring at 80° C. for 1 h. The reaction solution was diluted with water (20 mL), extracted with ethyl acetate (20 mL*3), and the organic phases were combined. The organic phase was washed with saturated brine (30 mL), dried over anhydrous $Na_2SO_4$ and concentrated. The crude product was separated and purified by preparative TLC (DCM:MeOH=20:1) to obtain compound 31 (145 mg) as an off-white solid. LC-MS $[M+H]^+=471.1$.

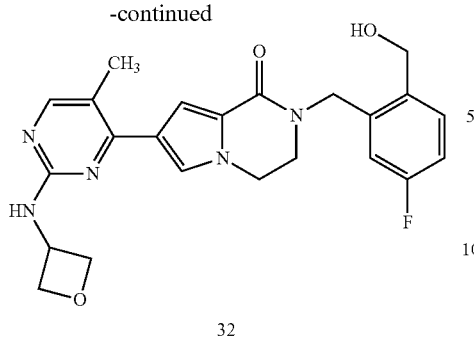

32

Step 1: Preparation of Compound 32a

Compound 22b (5.000 g) was dissolved in dioxane (80 mL), 6N hydrochloric acid (20 mL) was added, and the reaction was stirred at room temperature for 2 hrs, and then heated at 60'C' for 12 hrs. TLC detected the completion of the reaction. The reaction mixture was concentrated under reduced pressure, 50 mL of water was added, and the white solid compound 32a was obtained by direct filtration, which was directly used in the next step. LC-MS $[M+H]^+$=252.1.

Step 2: Preparation of Compound 32b

The above compound 32a (crude product) was dissolved in THF (100 mL), and then LiOH (8.000 g) in water (100 mL) was added, and the mixture was heated and refluxed for 5 hrs. Concentrate under reduced pressure to remove organic solvent, 4N HCl was added to adjust pH=6-7, the mixture was filtered and filter cake was washed with water, and dried to obtain 2.955 g of white solid LC-MS $[M+H]^+$=238.0.

Step 3: Preparation of Compound 32c

Compound 32b (2.955 g) was dissolved in DMF (60 mL), HOBt (2.013 g), EDCI.HCl (4.739 g), compound M8-2 (2.312 g) and DIEA (4.808 g) were added, the above mixture was stirred and reacted overnight. The reaction mixture was poured into ice water (50 mL), and EtOAc (30 mL) was added to precipitate a solid. The mixture was filtered and filter cake was washed with water and PE:EA (1:1) and dried to obtain 4.025 g of compound 32c. LC-MS $[M+H]^+$=375.1.

Step 4: Preparation of Compound 32d

Compound 32c (1.000 g) and 1,2-dibromoethane (752 mg) were dissolved in DMA (20 mL), cesium carbonate (2.600 g) was added, and the reaction was carried out at 80° C. for 1.5 hrs. After the reaction, water (40 mL) was added dropwise to precipitate a solid. The mixture was filtered and filter cake was washed with water and PE EA (2.1) and dried to obtain 0.855 g of compound 32d. LC-MS $[M+H]^+$=401.1.

Step 5: Preparation of Compound 32

Compound 32d (200 mg) and 3-oxetanamine (365 mg) were dissolved in DMSO (3 mL), triethylamine (404 mg) was added, and the tube was sealed and heated at 130° C. to react for 7 hrs. The reaction mixture was cooled to room temperature, water (10 mL) was added, extracted with EA (20 mL*3), the organic phases were combined, washed with saturated brine (10 mL*4), dried over anhydrous sodium sulfate, concentrated under reduced pressure, and the residue was purified by column chromatography. 49.8 mg. LC-MS $[M+H]^+$=438.4.

Example 33: (2-(5-fluoro-2-(hydroxymethyl)ben-zyl)-7-(5-methyl-2-((tetrahydrofuran-3-yl)amino)pyrimidin-4-yl)-3,4-dihydropyrrolo[1,2-a]pyrazine-1(2H)-one)

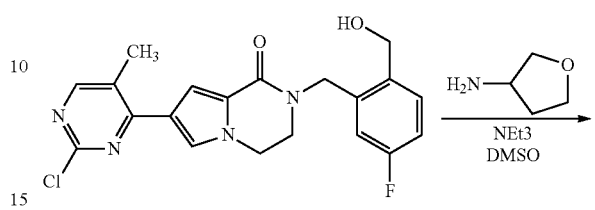

32d

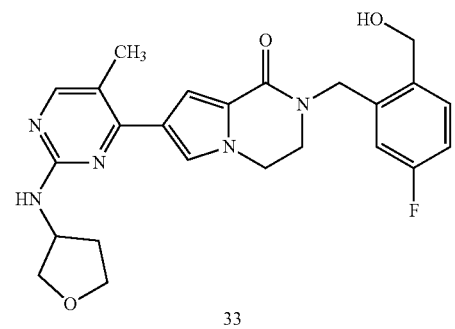

33

Compound 32d (250 mg) and 3-aminotetrahydrofuran hydrochloride (540 mg) were dissolved in DMSO (10 mL), triethylamine (1.134 g) was added, and the tube was sealed and heated at 130° C. for 8 hrs. The reaction mixture was cooled to room temperature, water (20 mL) was added, EA extraction (30 mL*3), the organic phases were combined, washed with saturated brine (10 mL*4), dried over anhydrous sodium sulfate, concentrated under reduced pressure, and the residue was purified by column chromatography to obtain 71.9 mg of compound 33. LC-MS $[M+H]^+$=452.4.

Example 34: ((R)-7-(5-chloro-2-(isopropylamino)pyridin-4-yl)-2-(5-fluoro-2-(hydroxymethyl)benzyl)-3-(methoxymethyl)-3,4-dihydropyrrolo[1,2-a]pyrazine-1(2H)-one)

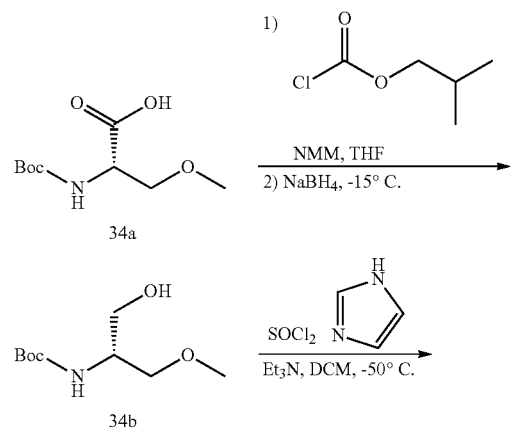

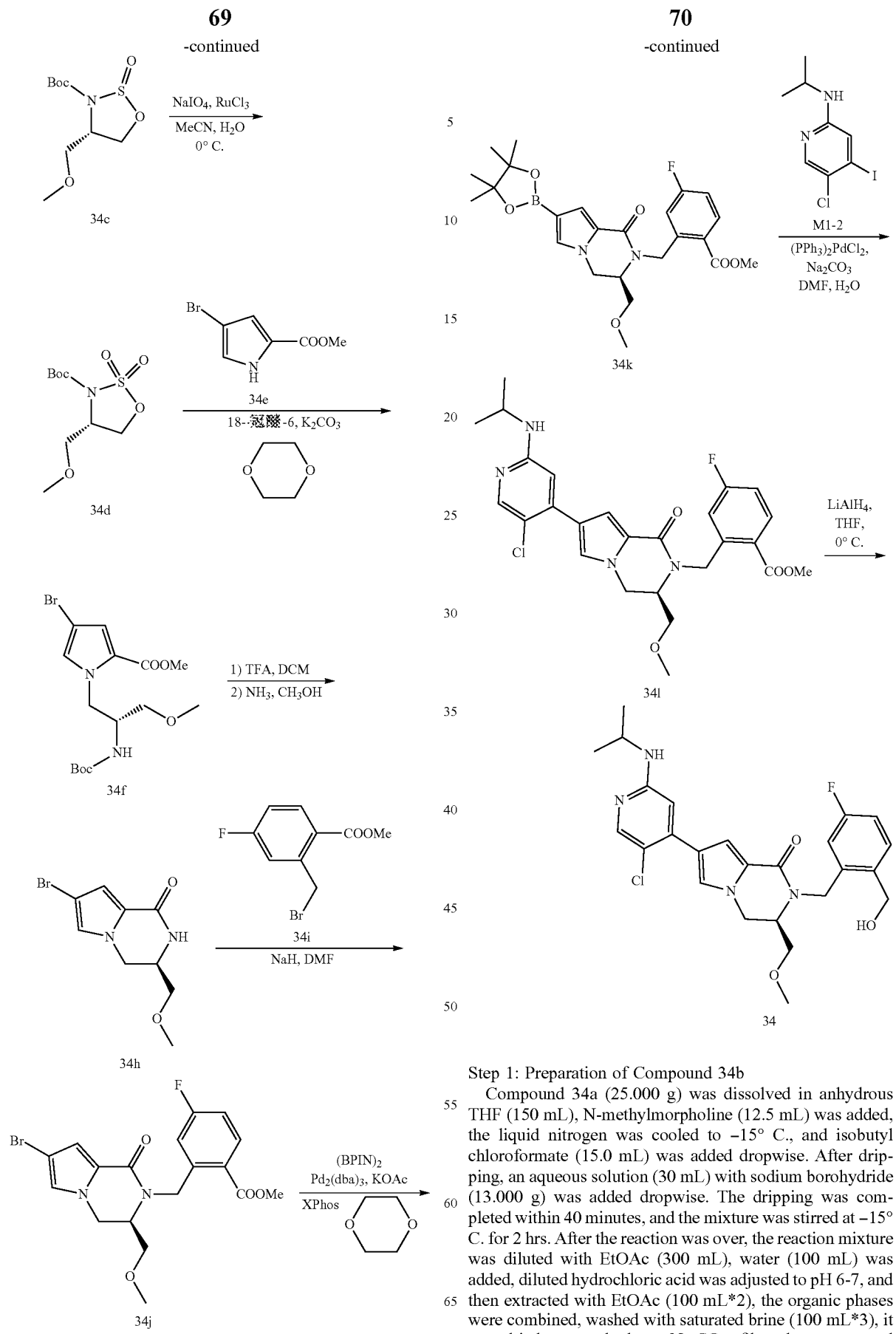

Step 1: Preparation of Compound 34b

Compound 34a (25.000 g) was dissolved in anhydrous THF (150 mL), N-methylmorpholine (12.5 mL) was added, the liquid nitrogen was cooled to −15° C., and isobutyl chloroformate (15.0 mL) was added dropwise. After dripping, an aqueous solution (30 mL) with sodium borohydride (13.000 g) was added dropwise. The dripping was completed within 40 minutes, and the mixture was stirred at −15° C. for 2 hrs. After the reaction was over, the reaction mixture was diluted with EtOAc (300 mL), water (100 mL) was added, diluted hydrochloric acid was adjusted to pH 6-7, and then extracted with EtOAc (100 mL*2), the organic phases were combined, washed with saturated brine (100 mL*3), it was dried over anhydrous Na$_2$SO$_4$, filtered, concentrated under reduced pressure, and the residue was purified by column chromatography (PE:EtOAc=1:1) to obtain 21.000 g, namely compound 34b. LC-MS [M+H]$^+$=206.1.

Step 2: Preparation of Compound 34c

Imidazole (27.300 g), triethylamine (23.100 g) and dichloromethane (500 mL) were added into a 1000 mL three-necked flask, the reaction was vacuumized, protected with $N_2$, and cooled the liquid nitrogen to −50° C., thionyl chloride (15.900 g) was added dropwise. After dripping, dissolve compound 34b (21.000 g) in dichloromethane (150 mL), which was added dropwise to the above reaction system at −50° C., finishing the dripping within 40 min, keeping the temperature for 2 hrs. After the reaction, the reaction solution w as added to ice water (300 mL), separated, the aqueous phase was extracted with dichloromethane (150 mL), the organic phases were combined, washed with saturated brine (150 mL), dried with anhydrous $Na_2SO_4$, filtered, and reduced pressure after concentration, the residue was purified by column chromatography (DCM) to obtain 21.300 g, namely compound 34c. LC-MS [M+H]$^+$= 252.1.

Step 3: Preparation of Compound 34d

Add compound 34c (21.300 g), acetonitrile (185 mL), water (100 mL) and ruthenium trichloride into a 500 mL three-necked flask, the reaction was cooled to 0° C., sodium periodate (22.400 g) was added in batches, stirring at 0° C. for 3 hrs. After the reaction was completed, the reaction mixture was added EtOAc (500 mL) and water (300 mL), separated the layers, the aqueous phase was extracted with EtOAc (300 mL), the organic phases were combined, washed with saturated brine (300 mL*2), and dried with anhydrous $Na_2SO_4$, filtered and concentrated under reduced pressure to obtain 21.900 g of brown liquid, namely compound 34d. LC-MS [M+H]$^+$=268.1.

Step 4: Preparation of Compound 34f

Compound 34d (10.000 g) and 4-bromo-1H-pyrrole-2-carboxylic acid methyl ester (34e, 5.100 g) were dissolved in dioxane (150 mL), and 18-crown-6 was added under nitrogen protection. Potassium carbonate (31.000 g) w as added, and the reaction was incubated at 60° C. for 5 hrs. After the reaction was completed, after cooling to room temperature, the reaction mixture was filtered, the filtrate was concentrated, and the concentrated residue was stirred with water (150 mL) and extracted with EtOAc (100 mL*2). The organic phases were combined, washed with saturated brine (100 mL*2), dried with anhydrous $Na_2SO_4$, filtered, and concentrated under reduced pressure to obtain 10.100 g of light brown solid, namely compound 34f. LC-MS [M+H]$^+$=391.1.

Step 5: Preparation of Compound 34h

Dissolve compound 34f (5.100 g) in dichloromethane (100 mL), add 15% trifluoroacetic acid in dichloromethane solution (100 mL) at 0° C. under nitrogen protection, the reaction was stirred at room temperature for 1 h, after the reaction was completed, concentrated and removed the solution. Then, 7N ammonia methanol solution (40 mL) was added, and the mixture was stirred at room temperature for 6 hrs. After the reaction solution was concentrated, dichloromethane (200 mL) was added, the reaction mixture was washed with water (100 mL*2), washed with saturated brine (100 mL), dried with anhydrous $Na_2SO_4$, filtered, and concentrated under reduced pressure to obtain a solid 3.000 g, namely compound 34h. LC-MS [M+H]$^+$=259.0.

Step 6: Preparation of Compound 34j

Compound 34h (3.000 g) was dissolved in dichloromethane (50 mL), NaH (510 mg) was added under nitrogen protection, stirred at room temperature for 0.5 h, and then 2-bromomethyl-4-fluorobenzoic acid methyl ester (34i, 2.900 g) was added in batches, stirred at room temperature for 0.5 h. After the reaction was completed, added saturated ammonium chloride solution (100 mL), extracted with EtOAc (100 mL*2). The organic phases were combined, washed with water (100 mL), washed with saturated brine (100 mL), dried over $Na_2SO_4$, filtered, and concentrated under reduced pressure to obtain a solid 4.5 g, namely compound 34j. LC-MS [M+H]$^+$=425.0.

Step 7: Preparation of Compound 34k

Compound 34j (3.500 g), pinacol diborate (5.200 g), potassium acetate (1.300 g) and x-phos (0.800 g) was dissolved in 1,4-dioxane (50 mL) and under nitrogen protection, $Pd_2(dba)_3$ (380 mg) was added, the reaction was incubated at 90° C. and reacted for 2 hrs. After the reaction was completed, the reaction mixture was filtered, the filtrate was concentrated, the concentrated residue was added to water (100 mL) and stirred, extracted with EtOAc (50 mL*3), and the organic phases are combined. It was washed with saturated brine (50 mL), dried over anhydrous $Na_2SO_4$, filtered, and concentrated under reduced pressure. The residue was purified by column chromatography (PE:EtOAc=2:1) to obtain 3.600 g, namely compound 34k. LC-MS [M+H]$^+$=473.2.

Step 8: Preparation of Compound 34l

Compound 34k (3.600 g), 5-chloro-4-iodo-N-isopropylpyridin-2-amine (M1-2, 2700 g), sodium carbonate (2.000 g) were dissolved in DMF (36 mL) and $(PPh_3)_2PdCl_2$ (380 mg) was added to the mixture of water (30 mL), under the protection of nitrogen, incubated at 80° C. and reacted for 2 hrs. After the reaction was completed, added EtOAc (50 mL) and water (50 mL) and stirred, separated the liquids and used EtOAc for the aqueous phase to extract (50 mL*2). The organic phases are combined, washed with water (50 mL*2), saturated brine (50 mL), dried with anhydrous $Na_2SO_4$, filtered, concentrated under reduced pressure, and purified by columned chromatography (PE:EtOAc=1:1) to obtain 2.200 g of compound 34l. LC-MS [M+H]$^+$=515.2.

Step 9: Preparation of Compound 34

Compound 34l (2.200 g) was dissolved in tetrahydrofuran (30 mL), the reaction was replaced with nitrogen three times, cooled to 0° C., lithium aluminum tetrahydrogen (327 mg) was added in batches, kept at 0° C. and reacted for 1 h. After the reaction was completed, water was slowly added (0.3 mL) to quench the reaction, then 15% sodium hydroxide aqueous solution (0.3 mL) was added, finally added water (0.9 mL), stirred for 5 min, and dried over anhydrous $Na_2SO_4$ for 30 min, filtered, the filter cake was washed with tetrahydrofuran. After concentration of the filtrate, the residue was purified by column chromatography (DCM:MeOH=50:1) to obtain 768 mg, namely compound 34. LC-MS [M+H]$^+$=487.3.

Example 35: ((R)-2-(5-fluoro-2-(hydroxymethyl) benzyl)-3-(methoxymethyl)-7-(5-methyl-2-((1-methyl-1H-pyrazol-5-yl)amino)pyrimidin-4-yl)-3,4-dihydropyrrolo[1,2-a]pyrazine-1(2H)-one)

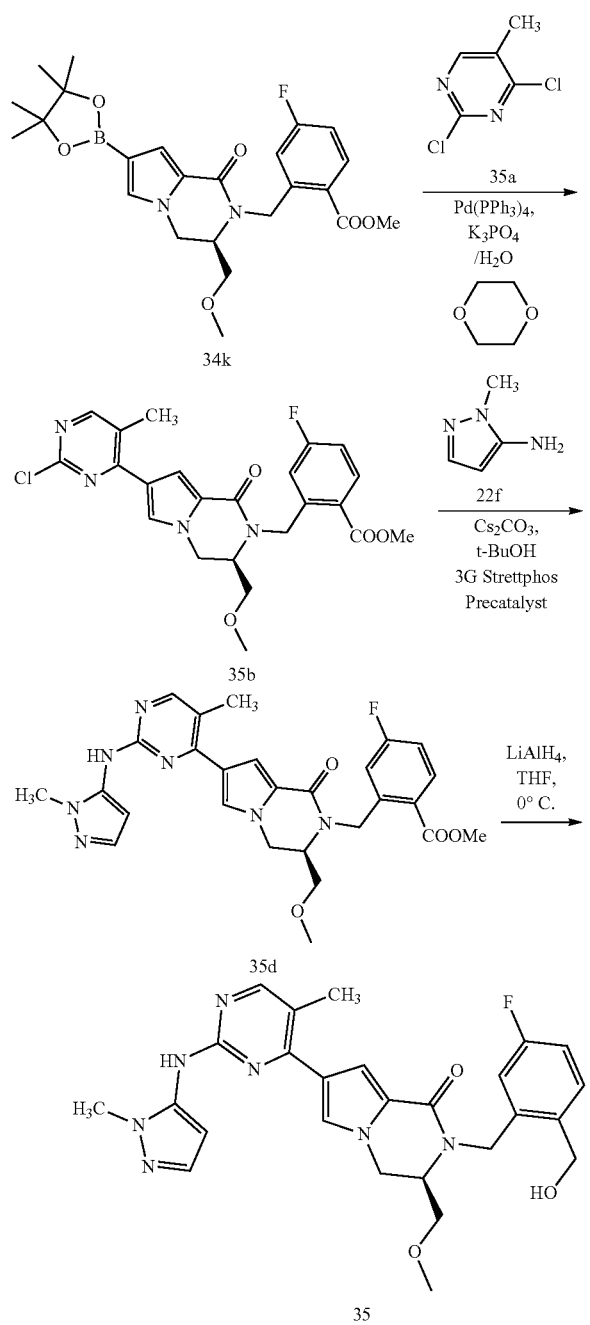

Step 1: Preparation of Compound 35b

Compound 34k (1.900 g) and 2,4-dichloro-5-methylpyrimidine (35a, 648 mg) were dissolved in dioxane (20 mL). Potassium phosphate (2.500 g). Pd(PPh3)4 (139 mg) and water (5 mL) were added, then reaction was evacuated and replaced with N2 three times, and incubated at 80° C. for 3 hrs. After the reaction was completed, concentrated under reduced pressure to remove dioxane, added 50 mL of water, extracted with EtOAc (50 mL*2). The organic phases are combined, and washed with 50 mL of saturated sodium chloride solution, dried the organic phase with anhydrous Na2SO4, and concentrated under reduced pressure. The product 35b separated by column chromatography from the residue was 1.800 g. LC-MS [M+H]+=473.1.

Step 2: Preparation of Compound 35d

Compound 35b (1.800 g) and 1-methyl-5-aminopyrazole (22f, 407 mg) was dissolved in t-BuOH (20 mL), cesium carbonate (2.700 g) and 3G Btrettphos Precatalyst (207 mg) were added, and vacuum N2 was replaced three times, and the mixture was incubated at 80° C. for 3 hrs. Concentrate under reduced pressure to remove t-BuOH, the residue was added 30 mL water, extracted with EtOAc (30 mL*2), the organic phases are combined, and washed with 30 mL saturated sodium chloride solution, dried over anhydrous sodium sulfate, concentrated under reduced pressure, and the residue was columned the chromatographic separation product 35d of 1,200 g. LC-MS [M+H]+=534.2.

Step 3: Preparation of Compound 35

Dissolve compound 35d (1.200 g) in tetrahydrofuran (30 mL), replace with nitrogen three times, cool to 0° C., add lithium aluminum tetrahydrogen (171 mg) in batches, keep at 0° C. and react for 1 h. After the reaction was completed, water (0.2 mL) was slowly added to quench the reaction, then 15% sodium hydroxide aqueous solution (0.2 mL) was added, finally added water (0.6 mL), stirred for 5 min, and dried over anhydrous Na2SO4 for 30 min, filtered, the filter cake was washed with tetrahydrofuran. After concentration of the filtrate, the residue was purified by column chromatography to obtain 500 mg of compound 35. LC-MS [M+H]+=506.2.

Example 36: ((R)-2-(5-fluoro-2-(hydroxymethyl) benzyl)-7-(2-(isopropylamino)-5-methylpyrimidin-4-yl)-3-(Methoxymethyl)-3,4-dihydropyrrolo[1,2-a] pyrazine-1(2H)-one)

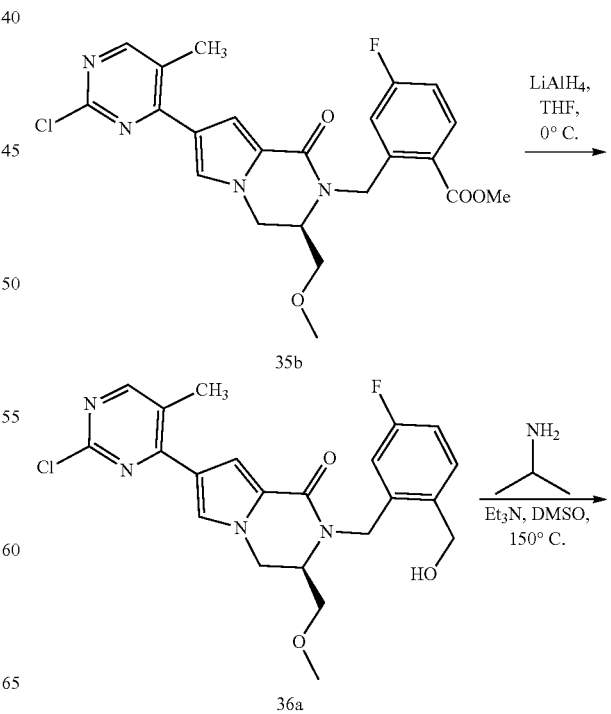

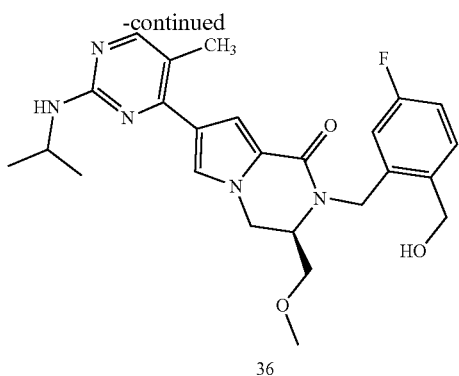

36

Step 1: Preparation of Compound 36a

Compound 35b (1.500 g) was dissolved in tetrahydrofuran (30 mL), replaced with nitrogen three times, cooled to 0° C., lithium aluminum tetrahydrogen (243 mg) was added in batches, keeping at 0° C. for 1 h. After the reaction was completed, water (0.3 mL) was slowly added to quench the reaction, then added 15% sodium hydroxide aqueous solution (0.3 mL), finally added water (0.9 mL) stirring for 5 min, the organic phases was dried over anhydrous $Na_2SO_4$ for 30 min, filtered, the filter cake was washed with tetrahydrofuran. After concentration of the filtrate, the residue was purified by column chromatography to obtain 800 mg, namely compound 36a. LC-MS [M+H]$^+$=445.1.

Step 2: Preparation of Compound 36

Compound 36a (800 mg) was dissolved in DMSO (10 mL), isopropylamine (1.100 g) and triethylamine (1.800 g) were added, and the reaction was carried out in microwave at 150° C. for 1 h. After the reaction was completed, added water (20 mL), extracted with EA (20 mL*3), the organic phases was combined, washed with saturated brine (20 mL*3), dried with anhydrous sodium sulfate, concentrated under reduced pressure, and purified the residue by column chromatography to obtain 350 mg. Namely compound 36. LC-MS [M+H]$^+$=468.3.

The example compounds 37-41 in Table 4 were synthesized by referring to the synthetic steps of similar compounds in the example compounds using commercially available raw materials.

TABLE 4

| Example | Structure | Chemical Name | LC-MS [M + H]$^+$ |
|---|---|---|---|
| 37 | 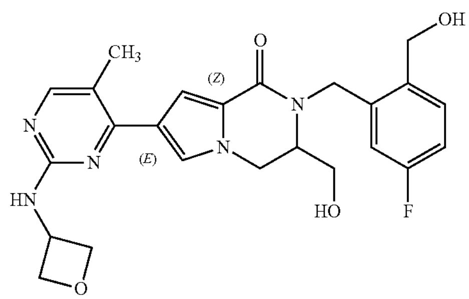 [SMILES: Cc1cnc(NC2COC2)nc1-c1cc2n(c1)CC(CO)N(Cc1cc(F)ccc1CO)C2=O] | 2-(5-fluoro-2-(hydroxymethyl)benzyl)-3-(hydroxymethyl)-7-(5-methyl-2-(oxacyclobutane-3-ylamino)pyrimidin-4-yl)-3,4-dihydropyrrolo[1,2-a]pyrazine-1(2H)-one | 468.2 |
| 38 | 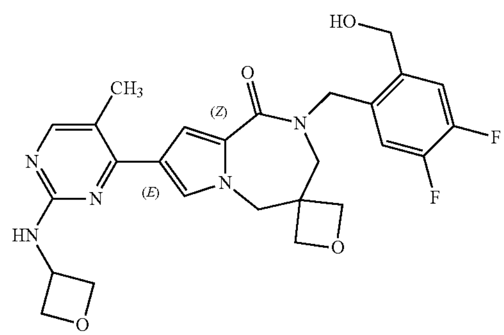 [SMILES: Cc1cnc(NC2COC2)nc1-c1cc2n(c1)CC1(COC1)CN(Cc1cc(F)c(F)cc1CO)C2=O] | 2'-(4,5-difluoro-2-(hydroxymethyl)benzyl)-8'-(5-methyl-2-(oxacyclobutane-3-yl amino)pyrimidin-4-yl)-2',3'-dihydro-1'h,5'H spiro[oxacyclobutane-3,4'-pyrrolo[1,2-a][1,4]diazepine]-1'-one | 512.2 |
| 39 | 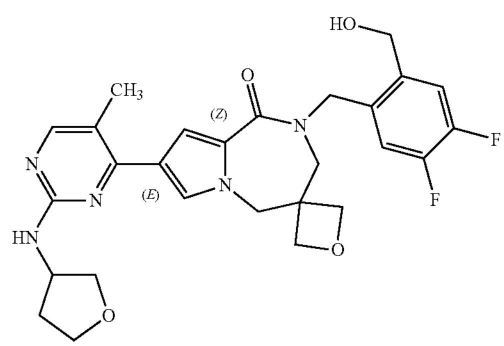 [SMILES: Cc1cnc(NC2CCOC2)nc1-c1cc2n(c1)CC1(COC1)CN(Cc1cc(F)c(F)cc1CO)C2=O] | 2'-(4,5-difluoro-2-(hydromethyl)benzyl)-8'-(5-methyl-2-((tetrahydrofuran-3-yl)amino)pyrimidin-4-yl)-2',3' dihydro-1'h,5'H spiro[oxacyclobutane-3,4'-pyrrolo[1,2-a][1,4]diazepine]-1'-one | 526.2 |

TABLE 4-continued

| Example | Structure | Chemical Name | LC-MS [M + H]+ |
|---|---|---|---|
| 40 | 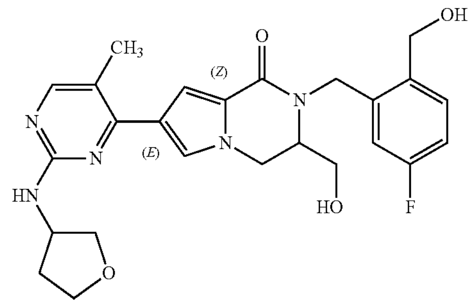 [SMILES: Cc1cnc(NC2CCOC2)nc1-c1cc2n(c1)CC(CO)N(Cc1cc(F)ccc1CO)C2=O] | 2-(5-fluoro-2-(hydroxymethyl)benzyl)-3-(hydroxymethyl)-7-(5-methyl-2-((tetrahydrofuran-3-yl)amino)pyrimidin-4-yl)-3,4-dihydropyrrolo[1,2-a]pyrazine-1(2H)-one | 482.2 |
| 41 | 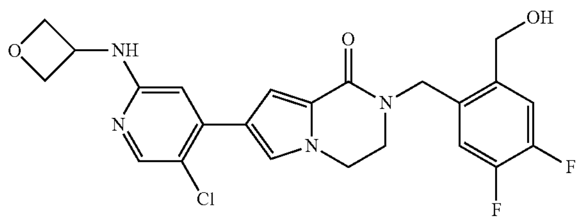 [SMILES: O=C1c2cc(-c3cc(NC4COC4)ncc3Cl)cn2CCN1Cc1cc(F)c(F)cc1CO] | 7-(5-chloro-2-(oxacyclobutane-3-yl amino)pyridine-4-yl)-2-(4,5-difluoro-2-(hydroxymethyl)benzyl)-3,4-dihydropyrrolo[1,2-a]pyrazine-1(2H)-one | 475.1 |

Example 42: (8-(5-chloro-2-(isopropylamino)pyridin-4-yl)-2-(5-fluoro-2-(hydroxymethyl)benzyl)-4-(hydroxymethyl)-2,3,4,5-tetrahydro-1H-pyrrolo[1,2-a][1,4]diazepine-1-one)

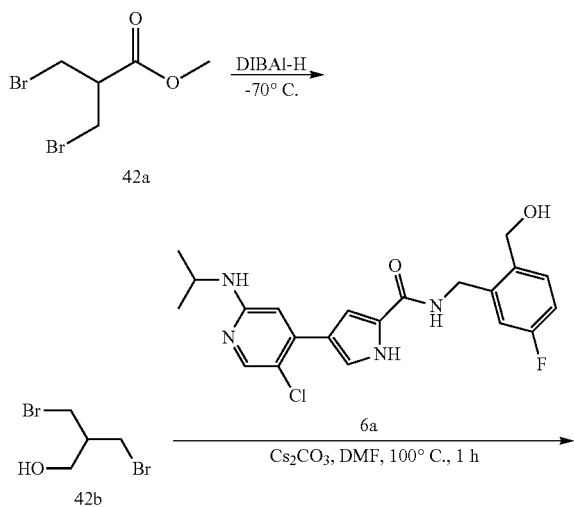

Step 1: Preparation of Compound 42b

Methyl 3-bromo-2-(bromomethyl)propionate (42a, 1.000 g) was dissolved in anhydrous THF (20 mL), under the protection of nitrogen, reduced the temperature to −70° C., and DIBAl-H was added (8.08 mL) dropwise, after dripping, the temperature was naturally raised to CC and reacted for 45 minutes. 1N HCl (20 mL) was added dropwise to quench the reaction, and then extracted with MTBE (20 mL), the organic phase was washed with water (20 mL*2), dried with anhydrous Na$_2$SO$_4$, concentrated under reduced pressure, and the residue was column chromatographed to obtain an oily substance of 753 mg, namely compound 42b. LC-MS [M+H]$^+$=231.0

Step 2: Preparation of Compound 42

Compound 42b (620 mg) and compound 6a (350 mg) were dissolved in DMF (18 mL), cesium carbonate (820 mg) was added, and the reaction was carried out at 100° C. for 1 h. After the reaction was completed, water (20 mL) was added drop wise, extracted with EA (30 mL*3), the organic phases were combined, washed with saturated brine, dried with anhydrous Na$_2$SO$_4$, concentrated under reduced pressure, and the residue was column chromatographed to obtain 32 mg of pale yellow solid, namely compound 42. LC-MS [M+H]$^+$=487.2.

Example 43: (8-(5-Chloro-2-(isopropylamino)pyridin-4-yl)-2-(5-fluoro-2-(hydroxymethyl)benzyl)-2,3-dihydro-1H,5H-spiro[pyrrolo[1,2-a][1,4]diazepine-4,5'-[1,3]dioxane]-1-one)

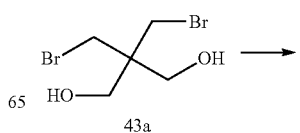

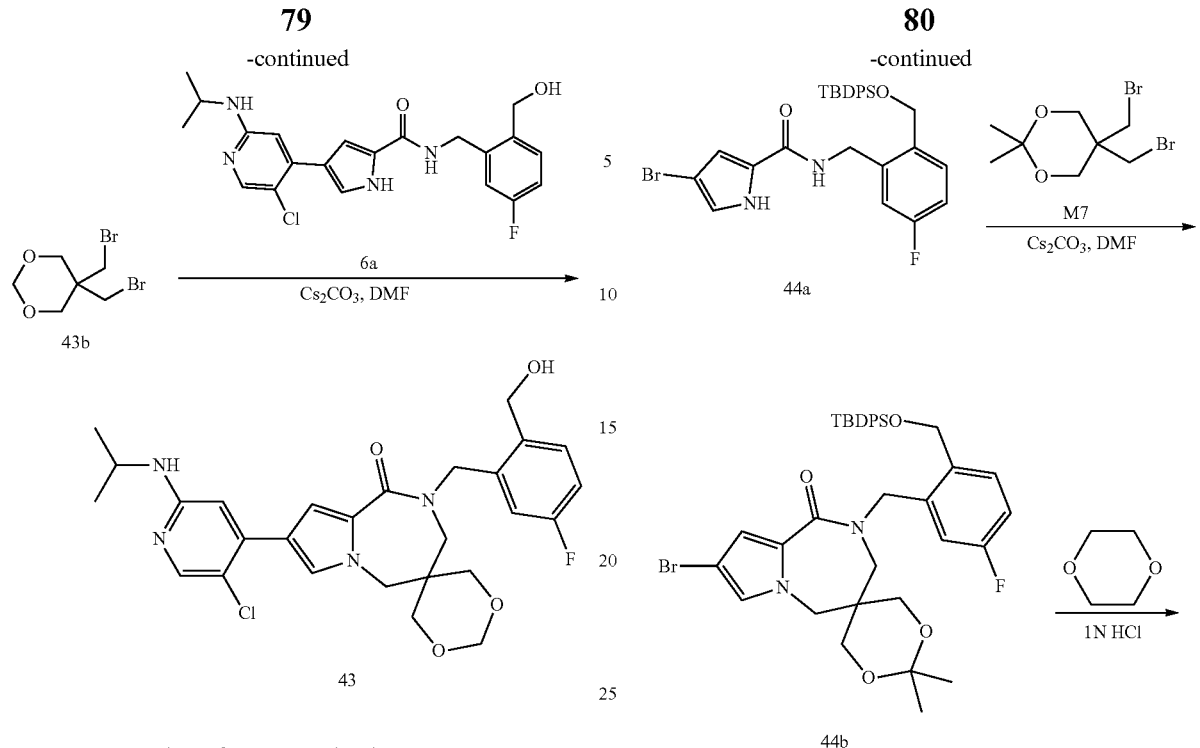

Step 1: Preparation of Compound 43b

Dibromoneopentyl glycol (43a, 2.500 g) was added to the formaldehyde solution (3.5 mL), con HCl (2 mL) was added, then the reaction was heated and refluxed for 12 hrs. After completion, the reaction was cooled, added water (25 mL) and extracted with DCM (25 mL*2), the organic phases was combined, washed with saturated NaHCO$_3$ (20 mL*2), dried with anhydrous Na$_2$SO$_4$, concentrated under reduced pressure to obtain an oil 2.544 g, namely compound 43b. LC-MS [M+H]$^+$=272.9.

Step 2: Preparation of Compound 43

Compound 43b (66 mg) and compound 6a (100 mg) were dissolved in DMF (5 mL), cesium carbonate (235 mg) was added, and the reaction was carried out at 100° C. for 1 h. After the reaction was completed, water (20 mL) was added dropwise, extracted with EA (30 mL), washed with saturated brine (10 mL*4), dried with anhydrous Na$_2$SO$_4$, concentrated under reduced pressure, and the residue was column chromatographed to obtain 83 mg of a white solid, namely compound 43. LC-MS [M+H]$^+$=529.2.

Example 44: (8-(5-Chloro-2-(isopropylamino)pyridin-4-yl)-2-(5-fluoro-2-(hydroxymethyl)benzyl)-4,4-bis(methoxymethyl)-2,3,4,5-tetrahydro-1H-pyrrolo[1,2-a][1,4]diazepine-1-one)

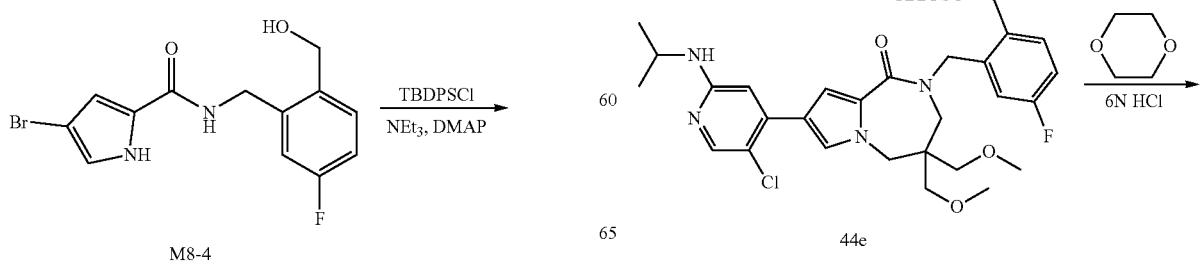

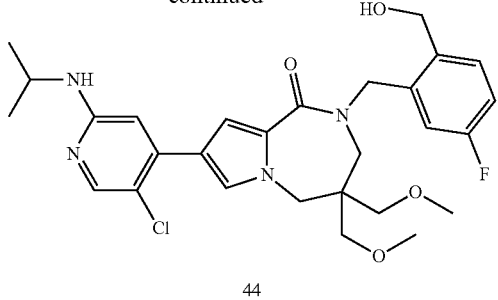

44

Step 1: Preparation of Compound 44a

Compound M8-4 (2.322 g), triethylamine (2.151 g) and DMAP (173 mg) were dissolved in DCM (35 mL), and TBDPSCl (2.789 g) was added dropwise at 0° C. After dripping, the reaction was stirred at room temperature for 12 hrs. The reaction solution was diluted with 35 mL of DCM, 40 mL of water was added, and the layers were separated. The organic phase was dried with anhydrous sodium sulfate, filtered, and concentrated under reduced pressure. The residue was separated and purified by column chromatography to obtain 2.950 g of colorless oil, namely compound 44a. LC-MS [M+H]$^+$=565.1.

Step 2: Preparation of Compound 44b

Under the protection of nitrogen, compound 44a (2.950 g) was dissolved in DMF (60 mL), compound M7 (1.575 g) and cesium carbonate (5.083 g) were added, and the reaction was heated at 90° C. for 1 h LC-MS detected the completion of the reaction. After cooling, the mixture was poured into ice water, extracted with EtOAc (100 mL*2), the organic phases was combined, washed with saturated brine (30 mL*4), dried over anhydrous Na$_2$SO$_4$, concentrated under reduced pressure, and the residue was purified by column chromatography (PE:EtOAc=1:1) to obtain 1.767 g of compound 44b. LC-MS [M+H]$^+$=705.2.

Step 3: Preparation of Compound 44c

Compound 44b (1.567 g) was dissolved in dioxane (75 mL), 1N HCl (30 mL) was added, rt reaction was performed for 2.5 hrs, TLC showed that the reaction was completed. H$_2$O (50 mL) and EA (50 mL) was added, NaHCO$_3$ was added to adjust PH=7-8, the organic phase was separated, washed with water (50 mL*2), dried with anhydrous Na$_2$SO$_4$, concentrated under reduced pressure, and purified by column chromatography to obtain 1.100 g compound 44c. LC-MS [M+H]$^+$=665.2.

Step 4: Preparation of Compound 44d

Under the protection of nitrogen, compound 44c (300 mg) was dissolved in anhydrous THF (10 mL), the temperature was lowered to 0° C., NaH (54 mg) was added in batches, and the reaction was stirred for 30 minutes. CH$_3$I (192 mg) was added dropwise to complete the RT reaction for 2 hrs.

Treatment, water (20 mL) was added dropwise under ice bath conditions, EA (20 mL*2) was added for extraction, washed with water (10 mL), dried with anhydrous Na$_2$SO$_4$, concentrated under reduced pressure, and the residue was purified by column chromatography to obtain 130 mg of compound 44d. LC-MS [M+H]$^+$=693.2.

Step 5: Preparation of Compound 44e

Compound 7a (80 mg) and compound 44d (130 mg) was dissolved in dioxane (5 mL), sodium carbonate (60 mg) was dissolved in 0.5 mL water which was added to the reaction solution, then Pd(dppf)$_2$Cl$_2$ (8 mg) was added under nitrogen protection. The reaction solution was heated to 80° C. and stirred for 12 hrs. The reaction solution was filtered with celite, the filter cake was washed once with EtOAc (10 mL), the mother liquor was directly concentrated under reduced pressure, and the residue was purified by column chromatography to obtain 60 mg of solid, namely compound 44e. LC-MS [M+H]$^+$=783.3.

Step 6: Preparation of Compound 44

Compound 44e (60 mg) was dissolved in dioxane (2 mL), 6N HCl (1 mL) was added, and the reaction was carried out at RT for 12 hrs. TLC showed that the reaction was completed. H$_2$O (10 mL) and EA (10 mL) was added, NaHCO$_3$ was added to adjust PH=7-8, the organic phase was separated, washed with water (5 mL), dried with anhydrous Na$_2$SO$_4$, concentrated under reduced pressure, and purified by column chromatography to obtain 14.6 mg of white solid. Namely compound 44. LC-MS [M+H]$^+$=545.2.

Example 45: ((R)-7-(5-chloro-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazin-1(2H)-one)

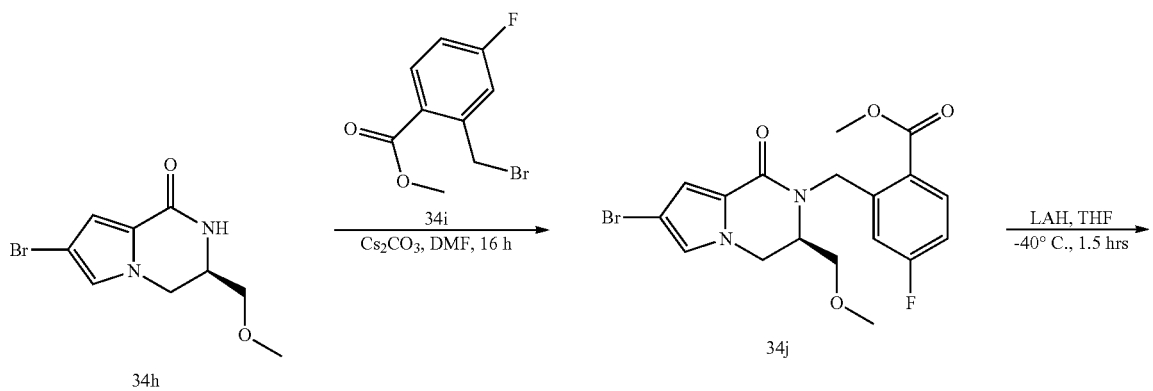

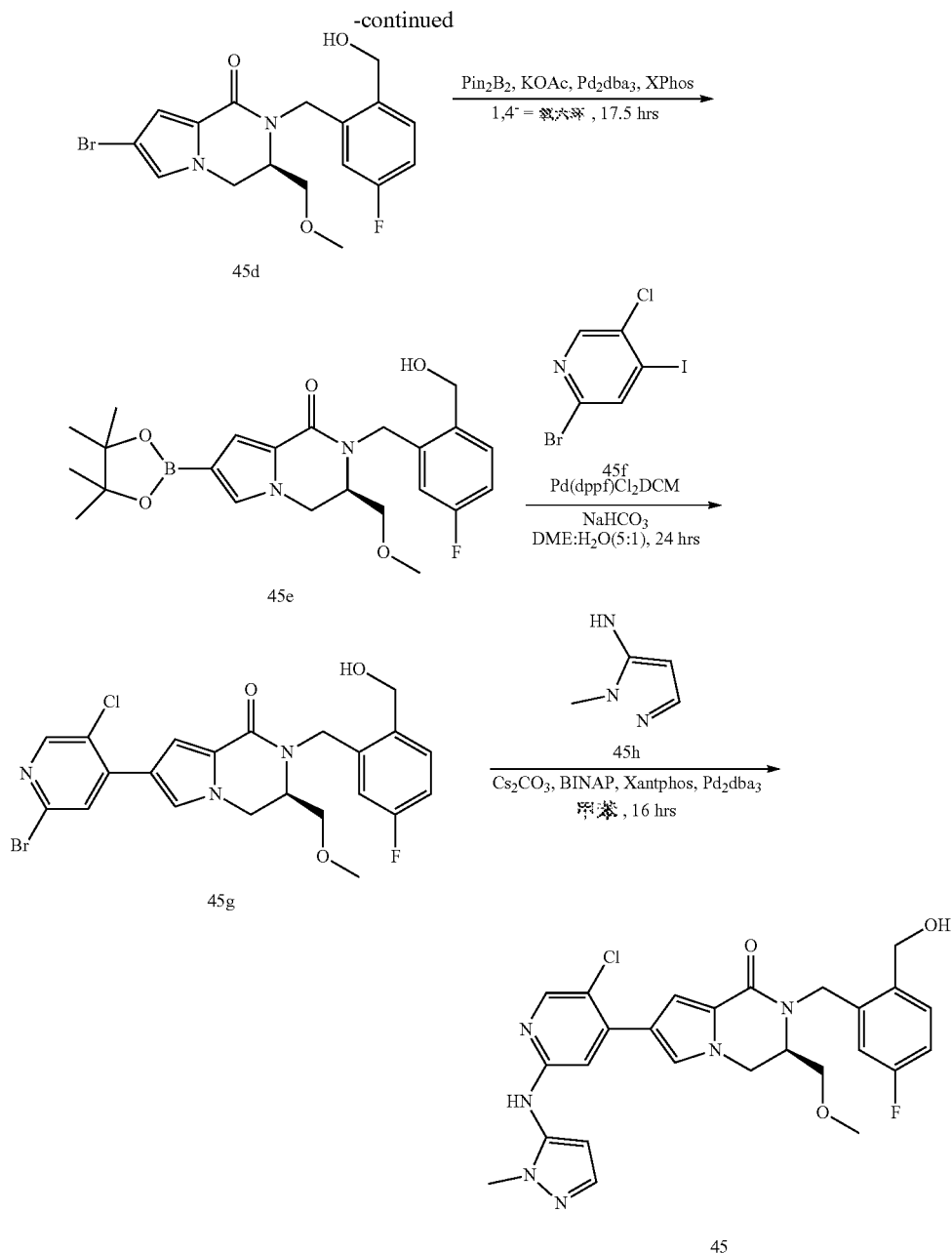

Step 1: Preparation of Compound 34j

The raw material (R)-7-bromo-3-(methoxymethyl)-3,4-dihydropyrrolo[1,2-a]pyrazine-1(2H)-one (34 h, 12.0 g) was dissolved in DMF (23 mL), added cesium carbonate (37.7 g) and 2-(bromomethyl)-4-fluorobenzoic acid methyl ester (34i, 37.7 g), the reaction was reacted at room temperature for 16 hours, and LC-MS monitored the reaction to be completed. Quench with water (200 mL), ethyl acetate (2*200 mL) diluted the solution. The organic phases were separated and combined and washed with 5% aqueous lithium chloride solution (3*200 mL). The organic phases were separated and dried with anhydrous sodium sulfate, filtered, and concentrated 20.0 g of crude product. The crude product was slurried with petroleum ether and methyl tert-butyl ether (4:1) in volume ratio to obtain 14.7 g of pure solid. The mother liquor was concentrated through the column (petroleum ether:ethyl acetate=3:1) to obtain 4.2 g of pure product. The product was 18.9 g, namely compound 34j. LC-MS [M+H]$^+$=425.0.

Step 2: Preparation of Compound 45d

The compound (R)-2-((7-bromo-3-(methoxymethyl)-1-oxo-3,4-dihydropyrrolo[1,2-a]pyrazine-2(1H)-yl)methyl)-4-fluorobenzoic acid methyl ester (45c, 14.7 g) was dissolved in THF (220 mL), cooled to −50° C. under nitrogen protection, and slowly added in batches of lithium tetrahydroaluminum (1.3 g)), controlling the temperature between −30° C. and −40° C. After one and a half hours, TLC detected that the reaction was completed. Water (1.3 mL), 15% aqueous sodium hydroxide solution (1.3 mL), water (3.9 mL), and anhydrous sodium sulfate (70 g) were added to the reaction solution in turn. The reaction was reacted at room temperature for 10 minutes, filtered, and concentrated to obtain 13.7 g of the product, namely compound 45d. LC-MS [M+H]$^+$=397.1.

Step 3: Preparation of Compound 45e

The (R)-7-bromo-2-(5-fluoro-2-(hydroxymethyl)benzyl)-3-(methoxymethyl)-3,4-dihydropyrrolo[1,2-a]pyrazine-1(2H)-one (45d, 13.7 g) was dissolved in 1,4-dioxane, and pinacol diboron (22.0 g) tris(dibenzylideneacetone)dipalladium (1.5 g), X-Phos (3.3 g) and potassium acetate (5.4 g) were added at room temperature, degas with nitrogen for three times, then the reaction was placed in 70° C. oil bath for 18 hrs. After the reaction was completed, it was cooled to room temperature, the reaction solution was filtered with celite, the filter cake was washed with ethyl acetate (100 mL*3), the filtrate was washed with water (100 mL*3), the organic phase was separated, dried, concentrated, and passed through the column (first pure dichloromethane was used to wash off the pigment, and then petroleum ether was used to ratio ethyl acetate 2:1 to 1:2) to obtain 16.5 g of the product, namely compound 45e. LC-MS [M+H]$^+$=445.2.

Step 4: Preparation of Compound 45g ((R)-2-(5-Fluoro-2-(hydroxymethyl)benzyl)-3-(methoxymethyl)-7-(4,4,5,5-tetramethyl-1,3,2-dioxaborolan-2-yl)-3,4-dihydropyrrolo[1,2-a]pyrazine-1(2H)-one (45e, 15.5 g) was dissolved in ethylene dimethyl ether and water (300 mL:60 mL), 2-bromo-5-chloro-4-iodopyridine (45f, 11.1 g), sodium bicarbonate (8.8 g), Pd(dppf)$_2$Cl$_2$DCM (1.5 g) were added in turn. After degassing with nitrogen three times, the reaction was placed in an oil bath at 60° C. for 18 hrs. LC-MS detected that about 20% of the raw materials were unreacted, and Pd(dppf)$_2$Cl$_2$DCM (0.75 g) was added to continue the reaction for 3 hrs. After the reaction was completed, it was cooled to room temperature, the reaction solution was filtered with celite, the filter cake was washed with ethyl acetate (100 mL*2), the filtrate was washed with water (100 mL*3), the organic phase was separated, dried, concentrated, and passed through the column (dichloromethane:methanol=25:1). After obtaining the crude product, it was slurried with methyl tert-butyl ether (50 mL), filtered to obtain 6.0 g of solid product, and the mother liquor was concentrated to obtain 5.0 g of crude product, namely compound 45 g. LC-MS [M+H]$^+$=508.0.

Step 5: Preparation of Compound 45

(R)-7-(2-bromo-5-chloropyridin-4-yl)-2-(5-fluoro-2-(hydroxymethyl)benzyl)-3-(methoxy methyl)-3,4-dihydropyrrolo[1,2-a]pyrazine-1(2H)-one (45 g, 4.3 g) was dissolved in toluene (70 mL), and 1-methyl-5-amino pyrazole (45 h, 1.0 g), cesium carbonate (8.3 g), BINAP (1.6 g) and tris(dibenzylideneacetone)dipalladium (0.8 g) were added sequentially at room temperature, degassed with nitrogen for three times, then placed in 70° C. oil bath for 18 hrs. After the reaction was completed, it was cooled to room temperature, the reaction solution was filtered with diatomaceous earth, the filter cake was washed with ethyl acetate (50 mL*2), the filtrate was concentrated, and passed through the column (dichloromethane:methanol=25:1) to obtain 4.0 g of crude product which was purified by Pre-TLC (dichloromethane: isopropanol=10:1), 2.28 g of compound 45 was obtained. $^1$HNMR (600 MHz, DMSO) δ 8.84 (s, 1H), 8.16 (s, 1H), 7.68 (d, J=1.5 Hz, 1H), 7.45 (dd, J=8.5, 6.3 Hz, 1H), 7.35 (d, J=1.7 Hz, 1H), 7.10 (m, 3H), 6.95 (s, 1H), 6.25 (d, J=1.7 Hz, 1H), 5.20 (m, 2H), 4.59-4.47 (m, 2H), 4.42-4.26 (m, 3H), 3.88 (m, 1H), 3.68 (s, 3H), 3.42 (m, 1H), 3.31-3.25 (m, 1H), 3.22 (s, 3H). LC-MS [M+H]$^+$=525.2.

Example 46: ((R)-2-(5-chloro-2-(isopropylamino)pyridin-4-yl)-7-(5-fluoro-2-(hydroxymethyl)benzyl)-6-(methoxymethyl)-6,7-dihydroimidazo[1,2-a]pyrazine-8-(5H)-one)

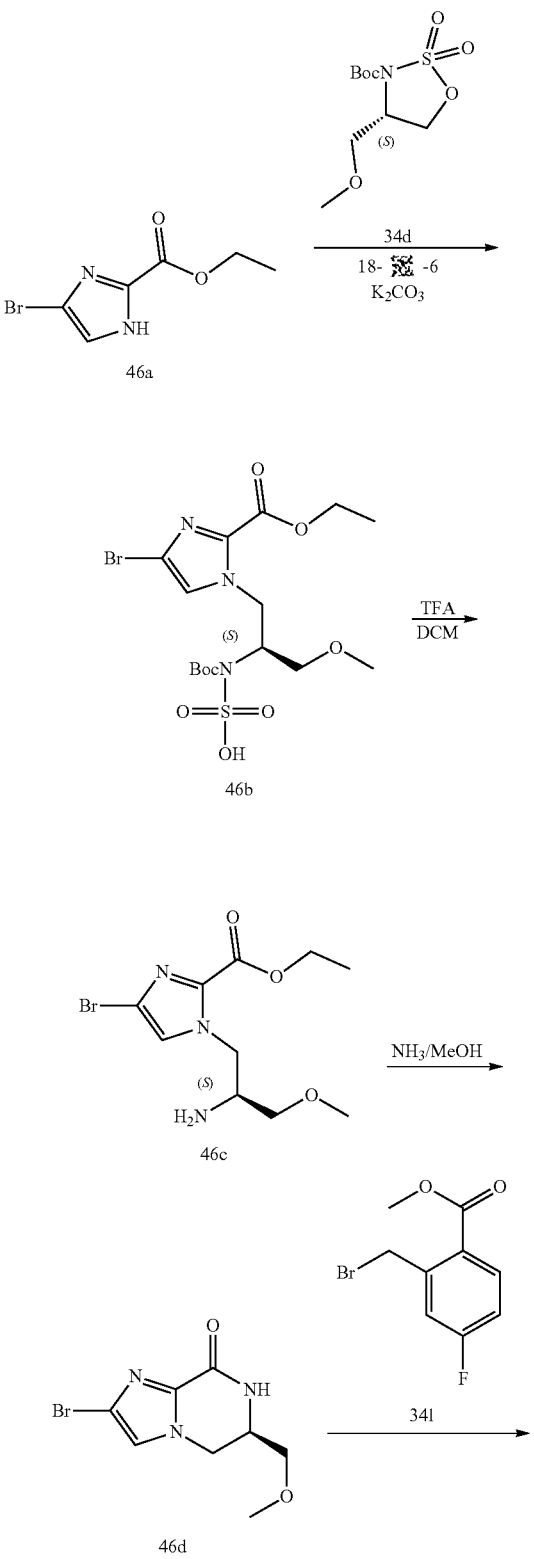

87

-continued

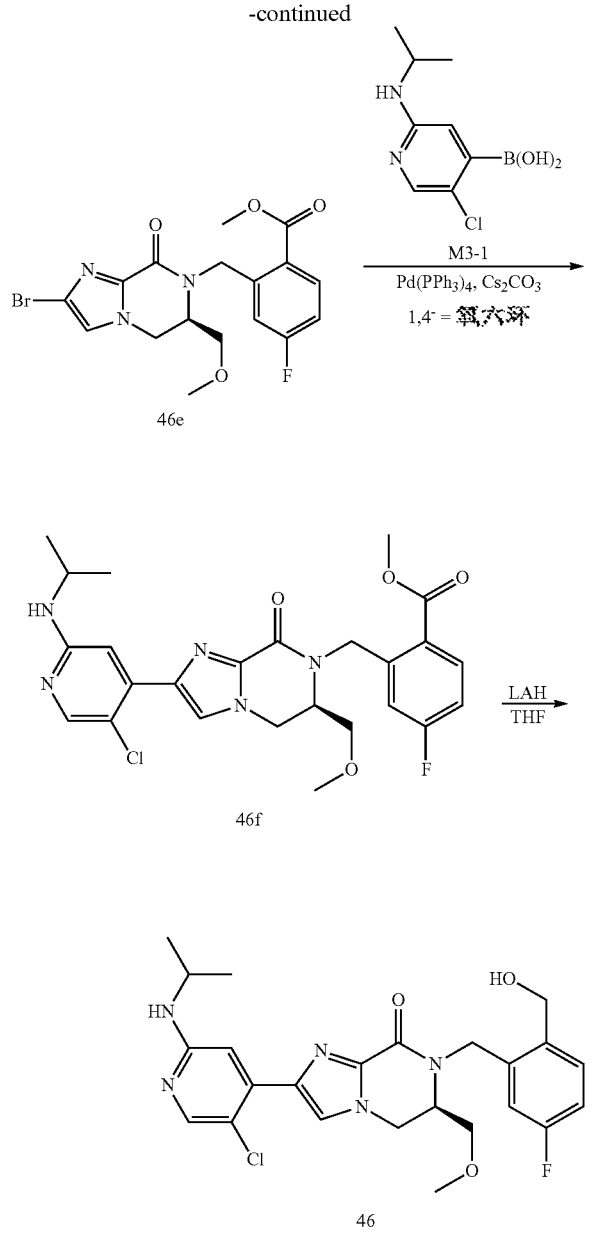

46e

46f

46

Preparation of Compound 46f (R)-2-((2-Bromo-6-(methoxymethyl)-8-oxo-5,6-dihydroimidazo[1,2-a]pyrazine-7(8H)-yl)methyl)-4-fluorobenzoic acid methyl ester (46e, 180 mg), (5-chloro-2-(isopropylamino)pyridin-4-yl)boronic acid (M3-1, 180 mg), Pd(PPh$_3$)$_4$ (25 mg) and sodium carbonate (136 mg) were mixed in 1,4-dioxane (5 mL) and water (1 mL), the reaction was replaced with nitrogen three times, and placed in an oil bath at 90° C. for 16 hrs. The reaction solution was cooled to room temperature, diluted with ethyl acetate (10 mL), washed with water (3*10 mL), the organic phase was separated, dried, and concentrated on a chromatography column (dichloromethane/methanol=97/3) to obtain 120 mg of product, namely Compound 46f. LC-MS [M+H]$^+$=516.2.

The synthesis of compounds 46b, 46c, 46d, 46e and 46 was synthesized according to the synthetic procedures of similar compounds in the example compounds.

88

Example 47: ((H)-7-(5-chloro-3-fluoro-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-ketone)

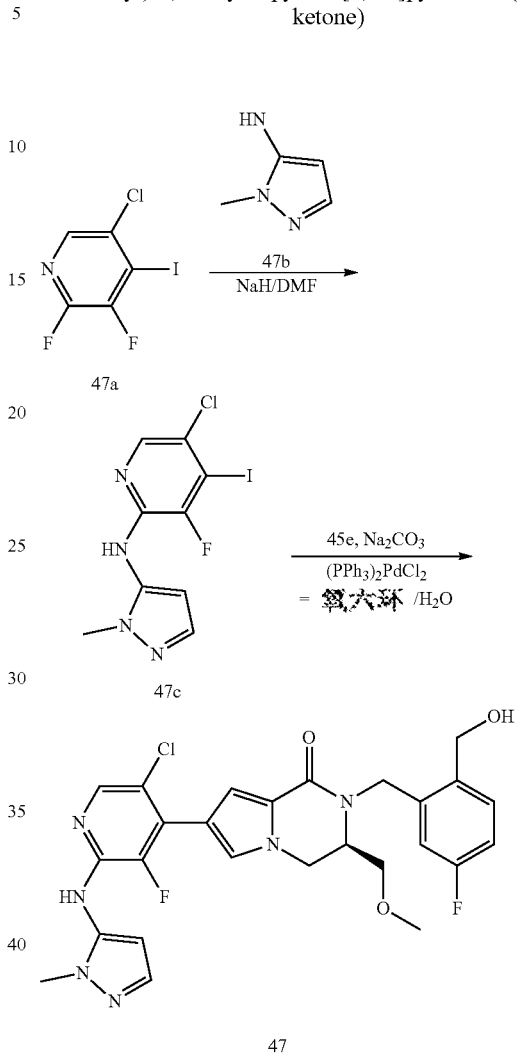

47

Step 1: Preparation of Compound 47c

The raw material 1-methyl-5-aminopyrazole (47b, 566 mg) was dissolved in DMF, cooled to 0° C., sodium hydrogen (348 mg) was added, and after stirring for 30 minutes, 5-chloro-2,3-bis fluoro-4-iodopyridine (47a, 1.600 g) was reacted for 30 minutes at room temperature. The reaction solution was quenched with water (1 mL), diluted with ethyl acetate (50 mL), washed with 5% lithium chloride aqueous solution (20 mL*3), the organic phase was separated, dried, concentrated, and passed through a column (petroleum ether:ethyl acetate=1:1), 940 mg of the product was obtained, namely compound 47c. LC-MS [M+H]$^+$=352.9.

Step 2: Preparation of Compound 47

5-Chloro-3-fluoro-4-iodo-1H-(1-methyl-1H-pyrazol-5-yl)pyridin-2-amine (47c, 352 mg), (R)-2-(5-fluoro-2-(hydroxymethyl)benzyl)-3-(methoxymethyl)-7-(4,4,5,5-tetramethyl-1,3,2-dioxaborolane-2-yl)-3,4-dihydropyrrolo[1,2-a]pyrazine-1(2H)-one (40e, 444 mg), sodium carbonate (318 mg) and (PPh$_3$)$_2$PdCl$_2$ (35 mg) were mixed in 1,4-dioxane and water (V:V=8 mL:2 mL). The reaction was replaced with nitrogen three times and placed at 70° C. to react for 3 hours. After the completion of the reaction, it was diluted with ethyl acetate (20 mL), washed with water (10 mL*3), the organic phase was separated, dried, concentrated, and passed through a column (petroleum ether:ethyl acetate=1:2) to obtain 113.5 mg of the product, namely compound 47. LC-MS [M+H]$^+$=543 2.

Example 48: ((R)-7-(5-chloro-3-methyl-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-ketone)

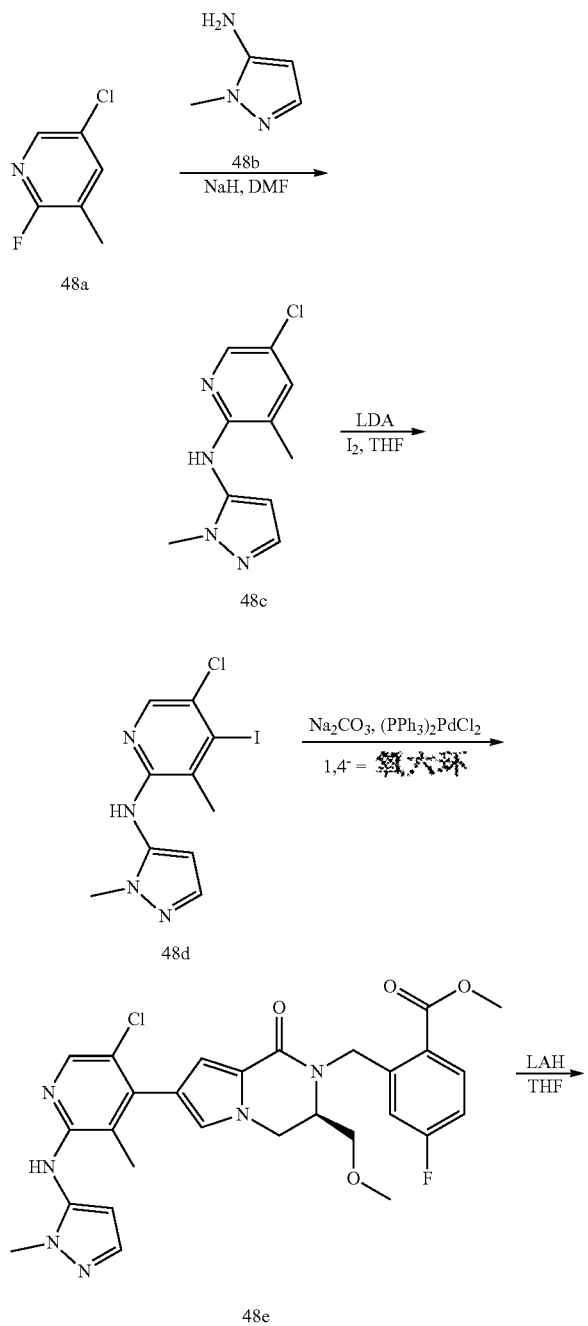

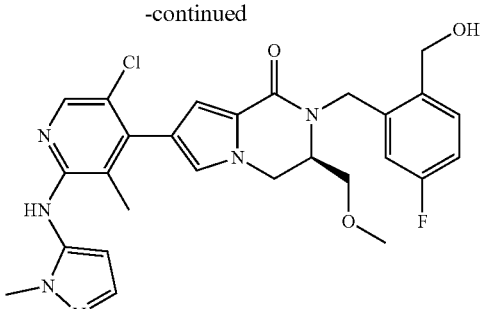

Step 1: Preparation of Compound 48c

The compound 5-chloro-2-fluoro-3-methylpyridine (48a, 1.000 g) was dissolved in DMF, cooled to 0° C., sodium hydrogen was slowly added in batches, and stirred at low temperature for 30 minutes, then 1-methyl was added 5-aminopyrazole (48b, 0.700 g), the reaction was slowly warmed to room temperature and then heated to 45° C. to react for 16 hrs. After the reaction solution was quenched with water, it was extracted with ethyl acetate (20 mL*2), washed with 5% lithium chloride aqueous solution (10 mL*3), the organic phase was separated, concentrated, and passed through the column to obtain 230 mg of the product, namely compound 48c. LC-MS [M+H]$^+$=223.1.

Step 2: Preparation of Compound 48d

The starting material 5-chloro-3-methyl-N-(1-methyl-1H-pyrazol-5-yl)pyridin-2-amine (48c, 230 mg) was dissolved in THF and cooled to −75° C., the solution was slowly added LDA dropwise, and reacted at −78° C. for 2 hours. The elemental iodine (320 mg) was dissolved in THF, and after cooling to −78° C., the above reaction solution was added dropwise. After 1 hours, it was quenched with saturated aqueous ammonium chloride (10 mL), extracted with ethyl acetate (20 mL*2), the organic phase was washed with sodium thiosulfate (20 mL*2), the organic phase was separated, dried, concentrated, and passed through the column (Petroleum ether:ethyl acetate=2:1) to obtain 200 mg of product, namely compound 48d. LC-MS [M+H]$^+$=349.0.

Step 3: Preparation of Compound 48e

The 5-chloro-4-iodo-3-methyl JV-(1-methyl-1H-pyrazol-5-yl)pyri din-2-amine (48d, 180 mg), (R)-4-fluoro-2-((3-(methoxymethyl)-1-oxo-7-(4,4,5,5-tetramethyl-1,3,2-dioxaborolane-2-yl)-3-(-3),4-dihydropyrrolo[1,2-a]pyrazine-2 (1H)-yl)methyl)methyl)benzoate (272 mg), sodium carbonate (165 mg) and (PPh$_3$)$_2$PdCl$_2$ (18 mg), mixed with 1,4-dioxane and water (V:V=8 mL:2 mL), replaced with nitrogen three times, placed at 70° C. for 3 hours. After the completion of the reaction, ethyl acetate was diluted (20 mL), washed with water (10 mL*3), the organic phase was separated, dried, concentrated, and passed through a column (petroleum ether, ethyl acetate=1.2) to obtain 20 mg of the product, namely compound 48e. LC-MS [M+H]$^+$=567.2

Step 4: Preparation of Compound 48

The compound (R)-2-((7-(5-chloro-3-methyl-2-((1-methyl-1H-pyrazol-5-yl)amino)pyridin-4-yl)-3-(methoxymethyl)-1-oxo-3,4-dihydropyrrolo[1,2-a]pyrazine-2(1H)-yl)methyl)-4-fluorobenzoic acid methyl ester (48e, 20 mg) was dissolved in anhydrous THF, after cooling to 0° C., lithium aluminum hydride (8 mg) was added, and the mixture was stirred at room temperature overnight. After

Example 49: (2-<5-Fluoro-2-(hydroxymethyl)benzyl)-7-(5-methyl-2-(o-tolylamino)pyrimidin-4-yl)-3,4-dihydropyrrolo[1,2-a]pyrazine-1(2H)-one)

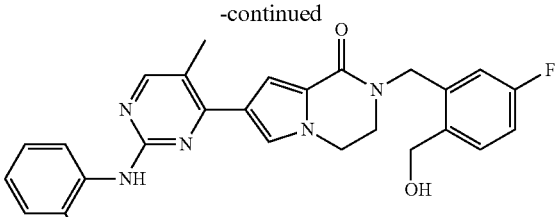

49

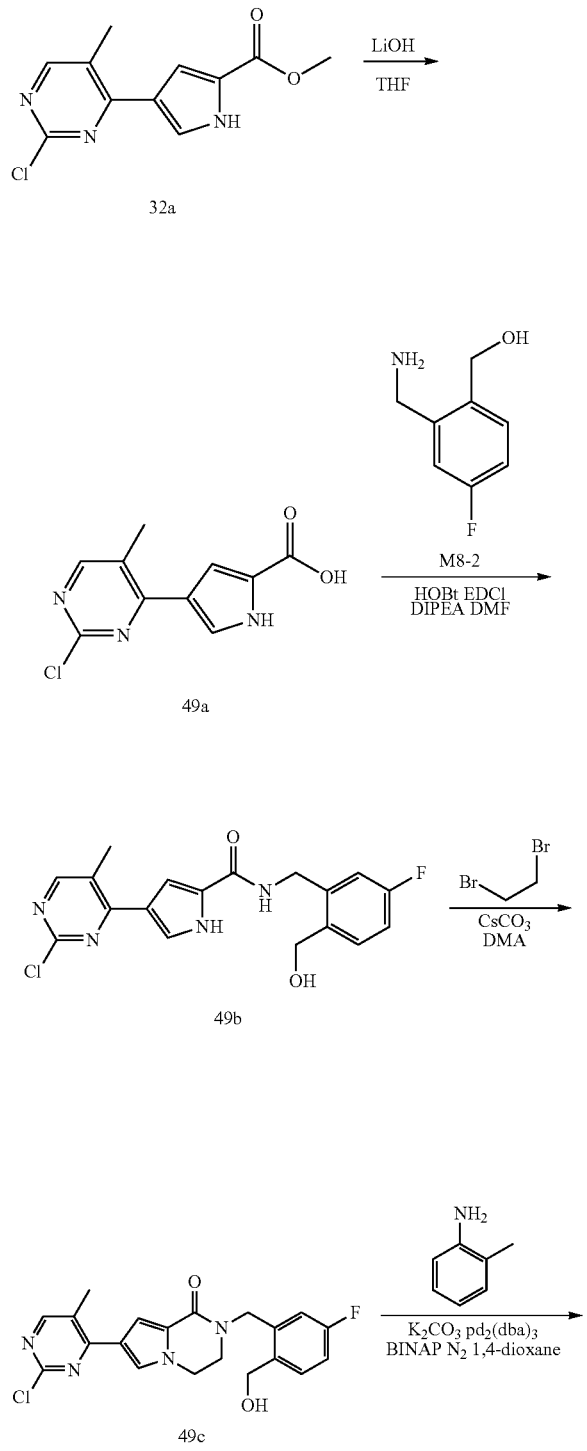

Step 1: Preparation of Compound 49a

Compound 32a (5.010 g) and lithium hydroxide (6.000 g) were added to a 250 mL reaction flask, THF (50 mL) and 6 mL water were added, heated to reflux for 6 hrs, 6 mL water and 3.310 g lithium hydroxide were added, and heating was continued for 12 hrs. 800 mL of water was added to the reaction solution to a clear state, concentrated hydrochloric acid was added dropwise to adjust the pH=7, a large amount of white solids appeared, which was filtered, the filter cake was collected, stirred with methanol, and desolvated at 45-68° C. to obtain 3.020 g of white solid powder, which was the compound 49a. LC-MS [M+H]$^+$=238.0.

Step 2: Preparation of Compound 49b

Compound 49a (3.000 g), compound M8-2 (4.010 g), HOBT (2.050 g), EDCI (2.940 g) and DIPEA (4.890 g) were added to a 250 mL reaction flask respectively, 50 mL DMF was added to dissolve, and stirred at room temperature for 12 hrs. 200 mL of water and 150 mL of ethyl acetate was added to the reaction solution and stirred thoroughly and separated the layers. Add 100 mL of ethyl acetate to extract the aqueous layer twice, the organic layers was combined, dried over anhydrous sodium sulfate, filtered, and desolvated to obtain a red-brown viscous liquid. The red-brown viscous liquid was slurried by ethyl acetate:petroleum ether=2:1, filtered, the filter cake was dried to obtain 1.490 g of yellowish solid powder, namely compound 49b. LC-MS [M+H]$^+$=375.1.

Step 3: Preparation of Compound 49c

Compound 49b (1.490 g), 1,2-dibromoethane (3.730 g), cesium carbonate (3.890 g) and N,N-dimethylacetamide (18 mL) were added to a 100 mL reaction flask for 1.5 hrs at 98° C. oil bath temperature. 50 mL of water and 100 mL of ethyl acetate were added to the reaction solution, stirred well, let stand and separate the layers, 50 mL of ethyl acetate was added to the aqueous layer and extracted once. The organic layers was combined and washed mice with 30 mL of saturated sodium chloride aqueous solution. The organic layer was dried over anhydrous sodium sulfate, filtered, and the filtrate was desolventized to obtain a pale yellow solid. Ethyl acetate:petroleum ether=5.1 was beaten, filtered, and the filter cake was dried to obtain 750 mg of white solid powder, namely compound 49c. LC-MS [M+H]$^+$=401.1.

Step 4: Preparation of Compound 49 Add compound 49c (0.100 g), o-methylaniline (0.320 g), potassium carbonate (0.050 g), pd$_2$(dba)$_3$ (0.020 g) and BINAP (0.020 g) into a 25 mL reaction flask, 1,4-dioxane (4 mL) was dissolved, N$_2$ balloon was replaced and protected, and the reaction was heated in an oil bath at 100° C. for 12 hrs. The reaction solution was filtered with diatomaceous earth, the filtrate was desolventized, 3 mL of water and 5 mL of ethyl acetate were added, and after full shaking, the layers were separated, the organic layer was dried with anhydrous sodium sulfate, filtered, and the filtrate was desolvated and mixed with a silica gel column to obtain 21.80 mg purple powder. Namely compound 49. LC-MS [M+H]$^+$=472.2.

Example 50: (7-(5-Chloro-2-((1-methyl-1H-pyrazol-5-yl)amino)pyridin-4-yl)-2-(5-fluoro-2-(hydroxymethyl)benzyl)-3,4-dihydropyrrolo[1,2-a]pyrazine-1(2H)-one)
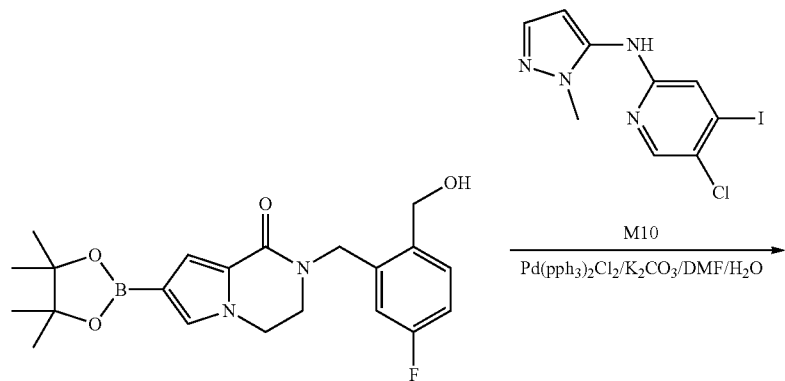
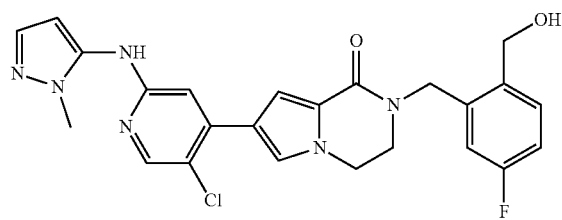
50

Under the protection of $N_2$, potassium carbonate (7.440 g) and $Pd(PPh_3)_2Cl_2$ (1.260 g) were added to the mixed solution of compound M10 (6.000 g) and compound M8 (7.540 g) in DMF (80 mL) and water (20 mL). Replace with $N_2$ three times and stir at 90° C. for 4 hours. The reaction solution was filtered through celite, the filtrate was diluted with water (200 mL), extracted with ethyl acetate (100 mL*3), the organic phases were combined, washed with saturated brine (300 mL), dried over anhydrous $Na_2SO_4$ and concentrated, and the crude product was passed through a column machine separation and purification (DCM: MeOH=20:1) to obtain compound 50 (4.250 g) as a white solid. $^1$HNMR (600 MHz, DMSO-$d_6$): 8.86 (s, 1H), 8.16 (s, 1H), 7.65 (d, J=1.7 Hz, 1H), 7.45 (dd, J=6.1, 8.4 Hz, 1H), 7.35 (d, J=1.8 Hz, 1H), 7.12-7.07 (m, 2H), 7.03 (dd, J=2.7, 10.0 Hz, 1H), 6.94 (s, 1H), 6.24 (d, J=1.8 Hz, 1H), 5.22 (t, J=5.3 Hz, 1H), 4.73 (s, 2H), 4.55 (d, J=5.3 Hz, 2H), 4.32-4.22 (m, 2H), 3.69-3.65 (m, 5H). LC-MS [M+H]$^+$=481.2.

Example 51: ((R)-7-(5-chloro-2-((4-fluoro-1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-ketone)

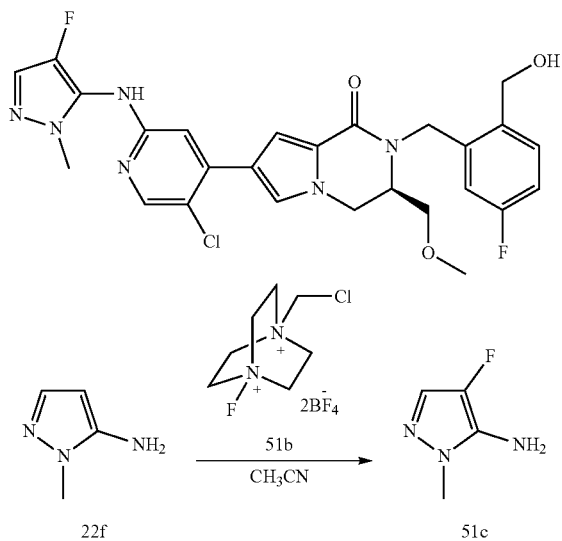

51

Preparation of Compound 51c

Compound 22f (1000 mg) was dissolved in dichloromethane, and the system was reduced to 0° C. with ice water. Compound 51b (3649 mg) was added to the reaction system at 0° C., and after stirring for 30 minutes, the temperature was raised to room temperature and stirred for 2 hours. The reaction was stopped, the solvent was removed under reduced pressure, washed with saturated brine (200 mL), extracted with ethyl acetate (150 mL*2), the organic phases were combined, dried over anhydrous sodium sulfate, filtered, and separated by column chromatography to obtain 302 mg of light yellow liquid. Namely compound 51c. LC-MS [M+H]$^+$=116.1.

The synthesis of compound 51 was synthesized by referring to the synthetic procedures of similar compounds in the example compounds.

Example 52: ((R)-7-(5-chloro-2-((1-ethyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one)

52

(R)-7-(2-bromo-5-chloropyridin-4-yl)-2-(5-fluoro-2-(hydroxymethyl)benzyl)-3-(methoxy methyl)-3,4-dihydropyrrolo[1,2-a]pyrazine-1(2H)-one (45 g, 50 mg) was dissolved in toluene (70 mL), and 1-ethyl-5-aminopyridine azole (33 mg), cesium carbonate (98 mg), BINAP (18 mg) and tris (dibenzylideneacetone)dipalladium (9 mg) were added sequentially at room temperature. The reaction was degassed with nitrogen three times and placed in an oil bath at 70° C. for 6 hrs. After the reaction was completed, it was cooled to room temperature, the reaction solution was filtered with celite, the filter cake was washed with ethyl acetate (5 mL*2), the filtrate was concentrated, and the product was purified by climbing to obtain 29 mg of compound 52. LC-MS [M+H]$^+$=539.2.

Example 53: ((R)-7-(5-chloro-2-((1-methyl-1H-pyrazol-5-yl)amino)pyridin-4-yl)-2-(5-fluoro-2-(hydroxymethyl)benzyl)-3-((methoxymethoxy)methyl)-3,4-dihydropyrrolo[1,2-a]pyrazine-1(2H)-ketone)

53

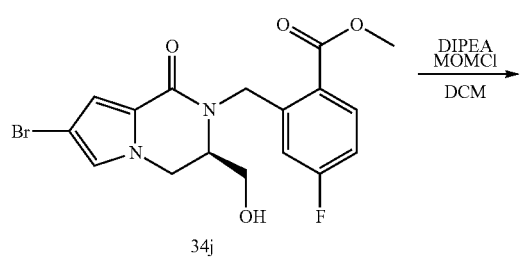

34j

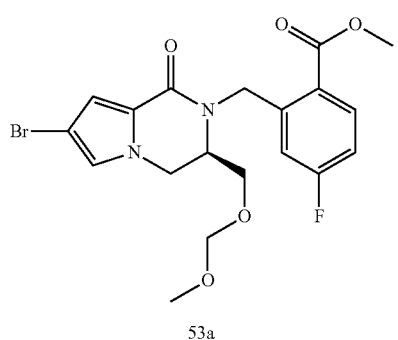

53a

Step 1: Preparation of Compound 53a

Compound 34j (220 mg) and DIPEA (274 mg) were dissolved in anhydrous DCM (4 mL), MOMCl (128 mg) was added to the reaction solution under ice-water bath cooling, and then the reaction was stirred at room temperature for 16 hours. The reaction solution was added with DCM (10 mL) and 10 mL of water, and the layers were separated. The organic phase was dried with anhydrous sodium sulfate, filtered, and concentrated under reduced pressure. The residue was separated and purified by column chromatography to obtain 80 mg of a colorless oily compound, namely compound 53a LC-MS [M+H]$^+$=455.1.

The synthesis of compound 53 was synthesized by referring to the synthetic procedures of similar compounds in the example compounds.

Example 54: ((R)-7-(5-chloro-2-((1-(difluoromethyl)-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-ketone)

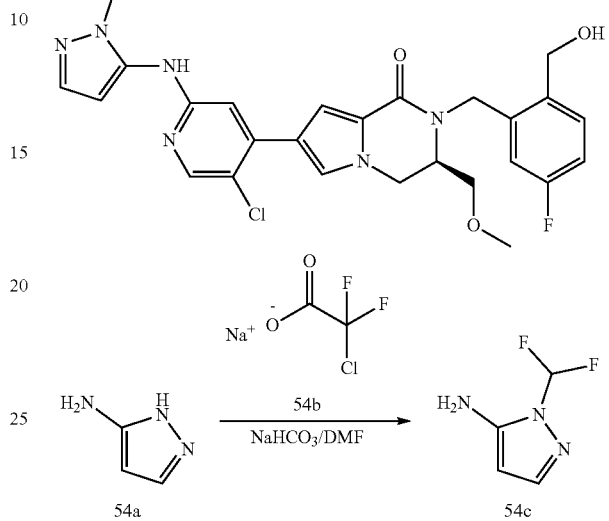

Under the protection of nitrogen, compound 54a (3000 mg), compound 54b (8300 mg) and sodium bicarbonate (6000 mg) were dissolved in DMF (120 mL), heated to 90° C. and stirred overnight. Stop heating, saturated brine (200 mL) was added to the system after cooling to room temperature, and then extracted with ethyl acetate (150 mL*2). The organic phases was combined, dried with anhydrous sodium sulfate, filtered, and separated by column chromatography to obtain 445 mg yellow liquid, which was compound 54c. LC-MS [M+H]$^+$=134.1.

The synthesis of compound 54 was synthesized with reference to the synthetic procedures of similar compounds in the example compounds.

The example compounds 55-167 in Table 5 were synthesized by referring to the synthetic steps of similar compounds in the above example compounds using commercially available raw materials.

TABLE 5

| Example | Structure | Chemical Name | LC-MS [M + H]$^+$ |
|---|---|---|---|
| 55 | (structure shown) | 8-(5-chloro-2-(isopropylamino)pyridin-4-yl)-2-(5-fluoro-2-(hydroxymethyl)benzyl)-4-methoxy-2,3,4,5-tetrahydro-1h-pyrrolo[1,2-a][1,4]diazepine-1-one | 487.2 |

TABLE 5-continued

| Example | Chemical Name | LC-MS [M + H]+ |
|---|---|---|
| 56 | 8-(5-chloro-2-(isopropylamino) pyridin-4-yl)-2-(5-fluoro-2-(hydroxymethyl)benzyl)-4-(hydroxymethyl)-4-(methoxymethyl)-2,3,4,5-4,5-tetrahydro-1h-pyrrolo[1,2-a][1,4]diazepine-1-one | 531.2 |
| 57 | Methyl 7-(5-chloro-2-(isopropylamino)pyridin-4-yl)-2-(5-fluoro-2-(hydroxymethyl)benzyl)-1-oxo-1,2,3,4-tetrahydropyrrolo[1,2-a]pyrazine-3-carboxylic acid ethyl ester | 502.0 |
| 58 | 8-(5-chloro-2-(isopropylamino) pyridin-4-yl)-2-(4-chloro-5-fluoro-2-(hydroxymethyl)benzyl)-4,4-bis(hydroxymethyl)-2,3,4,5-tetrahydro-1h-pyrrolo[1,2-a][1,4]diazepine-1-one | 551.2 |
| 59 | (R)-7-(5-chloro-2-(isopropylamino)pyridin-4-yl)-2-(5-fluoro-2-(hydroxymethyl)benzyl)-3-(hydroxymethyl)-3,4-dihydropyrrolo[1,2-a]pyrazine-1(2H)-one | 473.2 |
| 60 | (R)-7-(5-chloro-2-(oxacyclobutane-3-ylamino)pyridine-4-yl)-2-(5-fluoro-2-(hydroxymethyl)benzyl)-3-(methoxymethyl)-3,4-dihydropyrrolo[1,2-a]pyrazine-1(2H)-one | 502.0 |

TABLE 5-continued

| Example | Chemical Name | LC-MS [M + H]+ |
|---|---|---|
| 61 | (3R)-7-(5-chloro-2-((tetrahydrofuran-3-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 516.0 |
| 62 | (R)-7-(5-chloro-2-((tetrahydro-2h-pyran-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 530.0 |
| 63 | (R)-7-(5-chloro-2-((3,3-difluorocyclobutyl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 536.0 |
| 64 | (R)-7-(2-(TERT butylamino)-5-chloropyridine-4-yl)-2-(5-fluoro-2-(hydroxymethyl)benzyl)-3-(methoxymethyl)-3,4-dihydropyrrolo[1,2-a]pyrazine-1(2H)-one | 502.0 |
| 65 | (R)-7-(5-chloro-2-((2-hydroxy-2-methylpropyl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 518.0 |
| 66 | (R)-7-(5-chloro-2-((1-methylpiperidin-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 542.2 |

TABLE 5-continued

| Example | Structure | Chemical Name | LC-MS [M + H]⁺ |
|---|---|---|---|
| 67 | 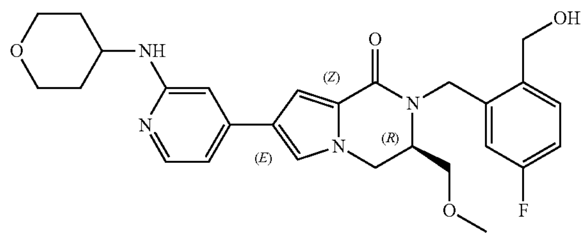 | (R)-2-(5-fluoro-2-(hydroxymethyl)benzyl)-3-(methoxymethyl)-7-(2-((tetrahydro-2h-pyran-4-yl)amino)pyridine-4-yl)-3,4-dihydropyrrolo[1,2-a]pyrazine-1(2H)-one | 495.2 |
| 68 | 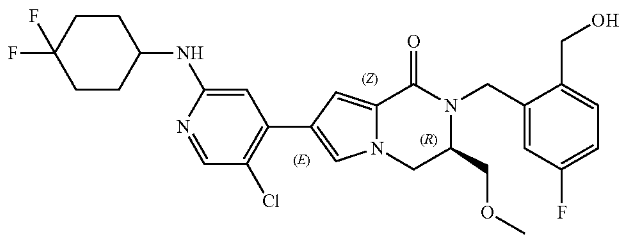 | (R)-7-(5-chloro-2-((4,4-difluorocyclohexyl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 563.2 |
| 69 | 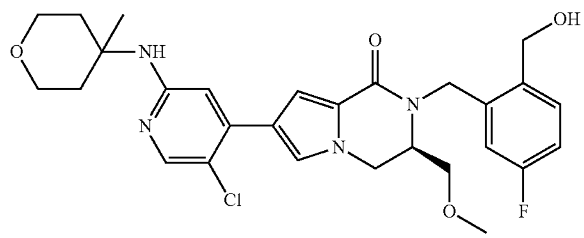 [SMILES: COC[C@H]1Cn2cc(-c3cc(NC4(C)CCOCC4)ncc3Cl)cc2C(=O)N1Cc1cc(F)ccc1CO] | (R)-7-(5-chloro-2-((4-methyltetrahydro-2h-pyran-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 544.0 |
| 70 | 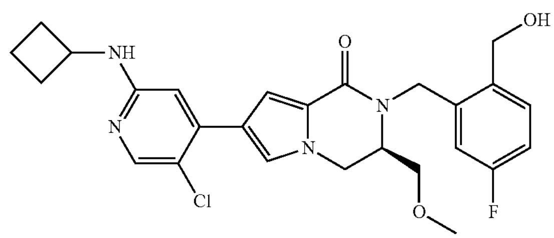 [SMILES: COC[C@H]1Cn2cc(-c3cc(NC4CCC4)ncc3Cl)cc2C(=O)N1Cc1cc(F)ccc1CO] | (R)-7-(5-chloro-2-(cyclobutylamino)pyridin-4-yl)-2-(5-fluoro-2-(hydroxymethyl)benzyl)-3-(methoxymethyl)-3,4-dihydropyrrolo[1,2-a]pyrazine-1(2H)-one | 500.0 |
| 71 | 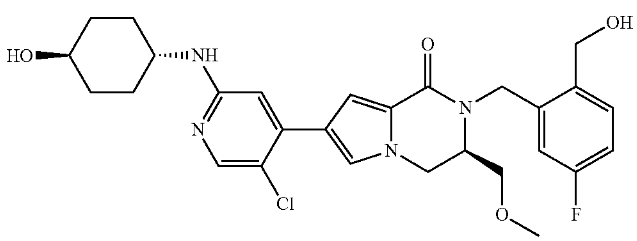 [SMILES: COC[C@H]1Cn2cc(-c3cc(N[C@H]4CC[C@H](O)CC4)ncc3Cl)cc2C(=O)N1Cc1cc(F)ccc1CO] | (R)-7-(5-chloro-2-(((1R,4R)-4-hydroxycyclohexyl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 544.0 |
| 72 | 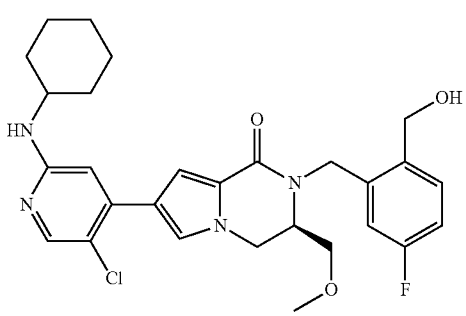 [SMILES: COC[C@H]1Cn2cc(-c3cc(NC4CCCCC4)ncc3Cl)cc2C(=O)N1Cc1cc(F)ccc1CO] | (R)-7-(5-chloro-2-(cyclohexylamino)pyridin-4-yl)-2-(5-fluoro-2-(hydroxymethyl)benzyl)-3-(methoxymethyl)-3,4-dihydropyrrolo[1,2-a]pyrazine-1(2H)-one | 528.0 |

TABLE 5-continued

| Example | Structure | Chemical Name | LC-MS [M + H]+ |
|---|---|---|---|
| 73 | 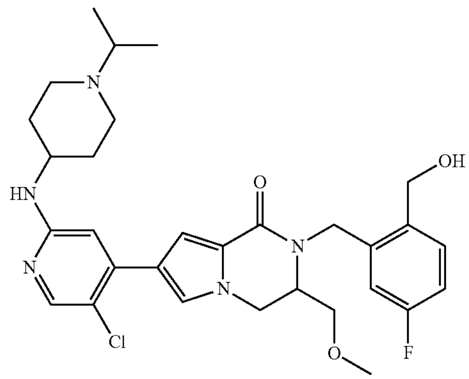 [SMILES: COCC1Cn2cc(-c3cc(NC4CCN(C(C)C)CC4)ncc3Cl)cc2C(=O)N1Cc1cc(F)ccc1CO] | 7-(5-chloro-2-((1-isopropylpiperidin-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 570.3 |
| 74 | 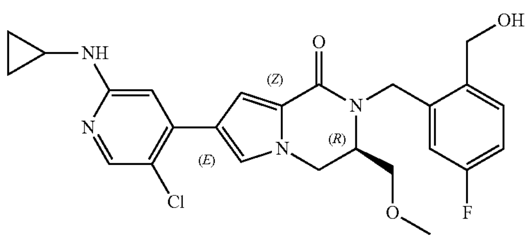 | (R)-7-(5-chloro-2-(cyclopropylamino)pyridin-4-yl)-2-(5-fluoro-2-(hydroxymethyl)benzyl)-3-(methoxymethyl)-3,4-dihydropyrrolo[1,2-a]pyrazine-1(2H)-one | 485.2 |
| 75 | 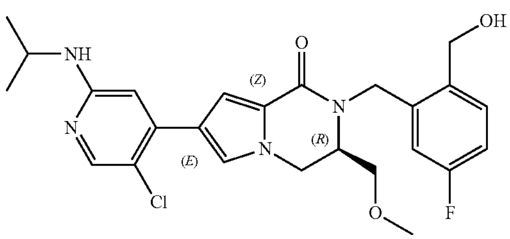 | (R)-2-(5-fluoro-2-(hydroxymethyl)benzyl)-7-(5-fluoro-2-(isopropylamino)pyridin-4-yl)-3-(methoxymethyl)-3,4-dihydropyrrolo[1,2-a]pyrazine-1(2H)-one | 471.2 |
| 76 | 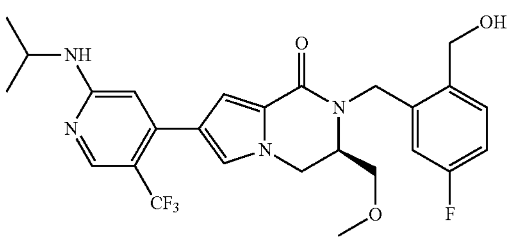 [SMILES: COC[C@H]1Cn2cc(-c3cc(NC(C)C)ncc3C(F)(F)F)cc2C(=O)N1Cc1cc(F)ccc1CO] | (R)-2-(5-fluoro-2-(hydroxymethyl)benzyl)-7-(2-(isopropylamino)-5-(trifluoromethyl)pyridin-4-yl)-3-(methoxymethyl)-3,4-dihydropyrrolo[1,2-a]pyrazine-1(2H)-one | 521.5 |
| 77 | 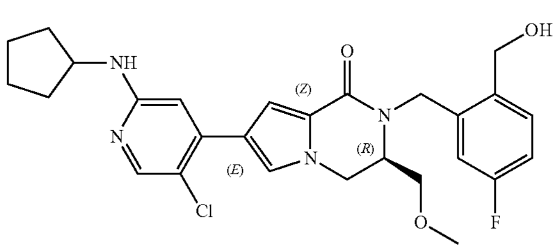 | (R)-7-(5-chloro-2-(cyclopentylamino)pyridin-4-yl)-2-(5-fluoro-2-(hydroxymethyl)benzyl)-3-(methoxymethyl)-3,4-dihydropyrrolo[1,2-a]pyrazine-1(2H)-one | 513.2 |

TABLE 5-continued

| Example | Structure | Chemical Name | LC-MS [M + H]+ |
|---|---|---|---|
| 78 | 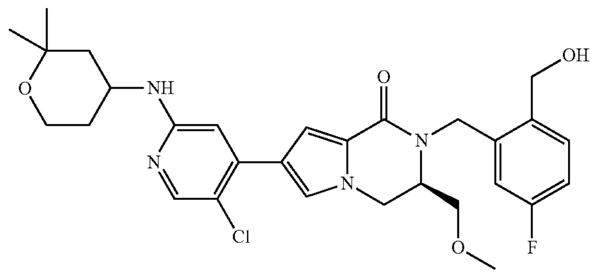 [SMILES: COC[C@H]1Cn2cc(-c3cc(NC4CCOC(C)(C)C4)ncc3Cl)cc2C(=O)N1Cc1cc(F)ccc1CO] | (3R)-7-(5-chloro-2-((2,2-dimethyltetrahydro-2h-pyran-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 557.2 |
| 79 | 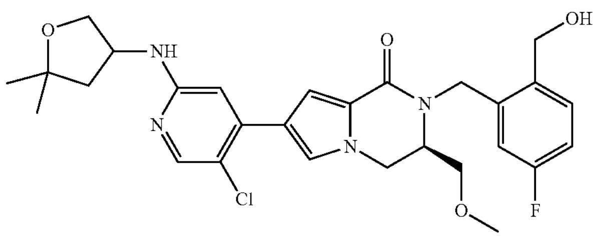 [SMILES: COC[C@H]1Cn2cc(-c3cc(NC4COC(C)(C)C4)ncc3Cl)cc2C(=O)N1Cc1cc(F)ccc1CO] | (3R)-7-(5-chloro-2-((5,5-dimethyltetrahydrofuran-3-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 543.2 |
| 80 | 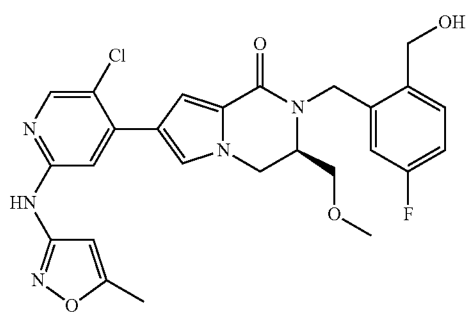 [SMILES: COC[C@H]1Cn2cc(-c3cc(Nc4cc(C)on4)ncc3Cl)cc2C(=O)N1Cc1cc(F)ccc1CO] | (R)-7-(5-chloro-2-((5-Methylisoxazole-3-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 526.2 |
| 81 | 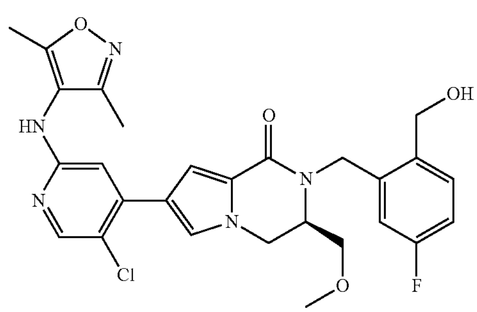 [SMILES: COC[C@H]1Cn2cc(-c3cc(Nc4c(C)noc4C)ncc3Cl)cc2C(=O)N1Cc1cc(F)ccc1CO] | (R)-7-(5-chloro-2-((3,5-dimethyl-isoxazole-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 541.0 |
| 82 | 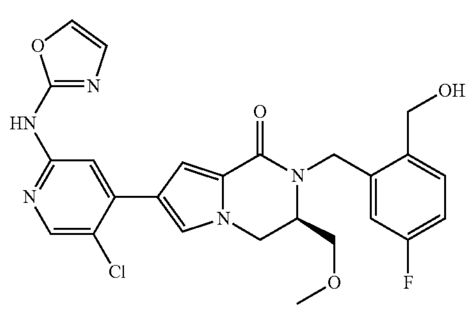 [SMILES: COC[C@H]1Cn2cc(-c3cc(Nc4ncco4)ncc3Cl)cc2C(=O)N1Cc1cc(F)ccc1CO] | (R)-7-(5-chloro-2-(oxazol-yl amino)pyridin4-yl)-2-(5-fluoro-2-(hydroxymethyl)benzyl)-3-(methoxymethyl)-3,4 dihydropyrrolo[1,2-a]pyrazine-1(2H)-one | 513.0 |

TABLE 5-continued

| Example | Structure | Chemical Name | LC-MS [M + H]+ |
|---|---|---|---|
| 83 | 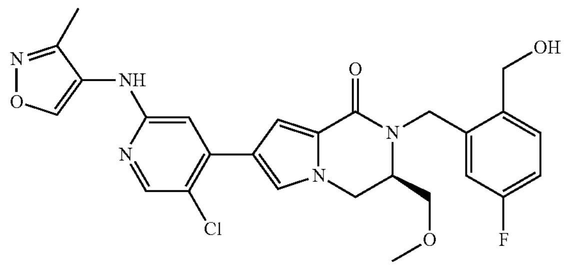 [SMILES: COC[C@H]1Cn2cc(-c3cc(Nc4conc4C)ncc3Cl)cc2C(=O)N1Cc1cc(F)ccc1CO] | (R)-7-(5-chloro-2-((3-methylisoxazole-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 527.0 |
| 84 | 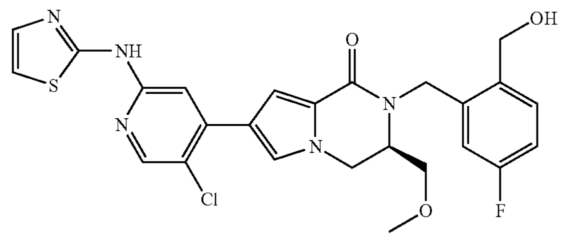 [SMILES: COC[C@H]1Cn2cc(-c3cc(Nc4nccs4)ncc3Cl)cc2C(=O)N1Cc1cc(F)ccc1CO] | (R)-7-(5-chloro-2-(thiazol-2-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one | 529.0 |
| 85 | 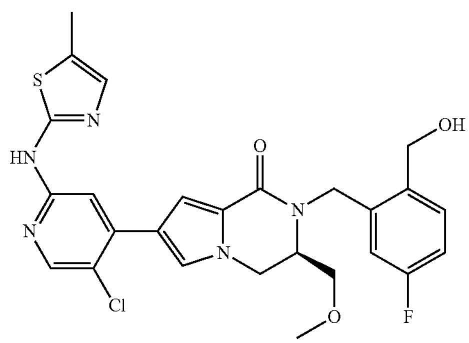 [SMILES: COC[C@H]1Cn2cc(-c3cc(Nc4ncc(C)s4)ncc3Cl)cc2C(=O)N1Cc1cc(F)ccc1CO] | (R)-7-(5-chloro-2-((5-methylthiazol-2-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 543.0 |
| 86 | 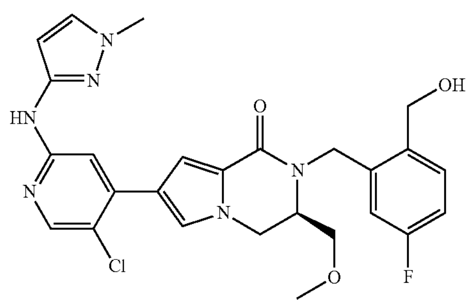 [SMILES: COC[C@H]1Cn2cc(-c3cc(Nc4ccn(C)n4)ncc3Cl)cc2C(=O)N1Cc1cc(F)ccc1CO] | (R)-7-(5-chloro-2-((1-methyl-1h-pyrazole-3-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 526.0 |
| 87 | 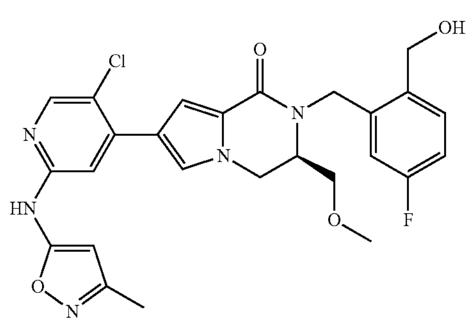 [SMILES: COC[C@H]1Cn2cc(-c3cc(Nc4cc(C)no4)ncc3Cl)cc2C(=O)N1Cc1cc(F)ccc1CO] | (R)-7-(5-chloro-2-((3-methylisoxazole-5-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 526.2 |

TABLE 5-continued

| Example | Structure | Chemical Name | LC-MS [M + H]+ |
|---|---|---|---|
| 88 | 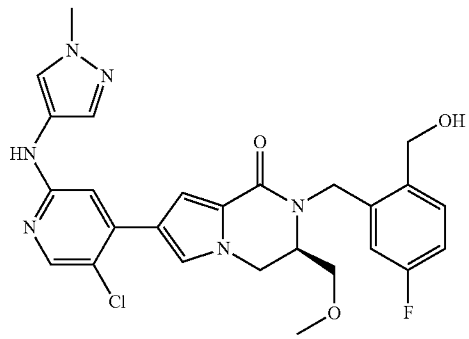 [SMILES: COC[C@H]1Cn2cc(-c3cc(Nc4cnn(C)c4)ncc3Cl)cc2C(=O)N1Cc1cc(F)ccc1CO] | (R)-7-(5-chloro-2-((1-methyl-1h-pyrazole-4-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 526.0 |
| 89 | 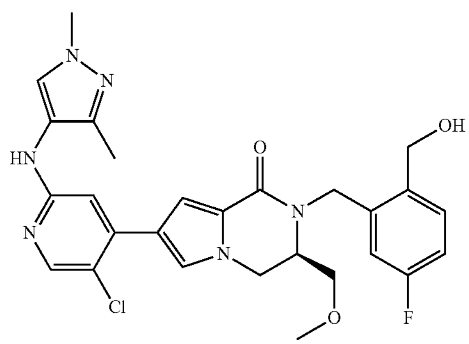 [SMILES: COC[C@H]1Cn2cc(-c3cc(Nc4cn(C)nc4C)ncc3Cl)cc2C(=O)N1Cc1cc(F)ccc1CO] | (R)-7-(5-chloro-2-((1,3-dimethyl-1h-pyrazole-4-yl)amino)pyridine-4-yl)-2-(5-fluoro-2-(hydroxymethyl)benzyl)-3-(methoxymethyl)-3,4-dihydropyrrolo[1,2-a]pyrazin-1(2H)-one | 540.0 |
| 90 | 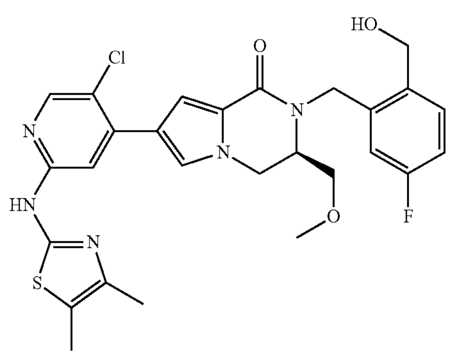 [SMILES: COC[C@H]1Cn2cc(-c3cc(Nc4nc(C)c(C)s4)ncc3Cl)cc2C(=O)N1Cc1cc(F)ccc1CO] | (R)-7-(5-chloro-2-((4,5-dimethylthiazol-2-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 556.2 |
| 91 | 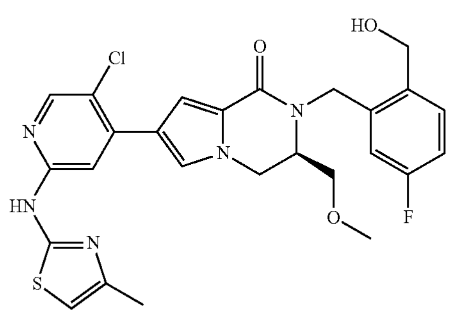 [SMILES: COC[C@H]1Cn2cc(-c3cc(Nc4nc(C)cs4)ncc3Cl)cc2C(=O)N1Cc1cc(F)ccc1CO] | (R)-7-(5-chloro-2-((4-methylthiazol-2-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 542.1 |

TABLE 5-continued

| Example | Structure | Chemical Name | LC-MS [M + H]+ |
| --- | --- | --- | --- |
| 92 | 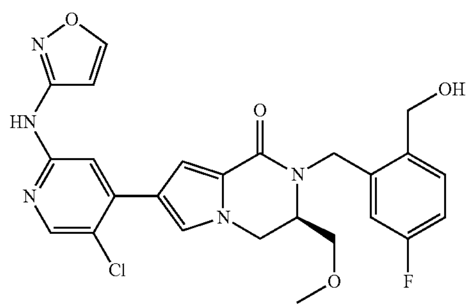 [SMILES: COC[C@H]1Cn2cc(-c3cc(Nc4ccon4)ncc3Cl)cc2C(=O)N1Cc1cc(F)ccc1CO] | (R)-7-(5-chloro-2-(isoxazol-3-yl-amino)pyridine-4-yl)-2-(5-fluoro-2-(hydroxyethyl)benzyl)-3-(methoxymethyl)-3,4-dihydropyrrolo[1,2-a]pyrazine-1(2H)-one | 513.0 |
| 93 | 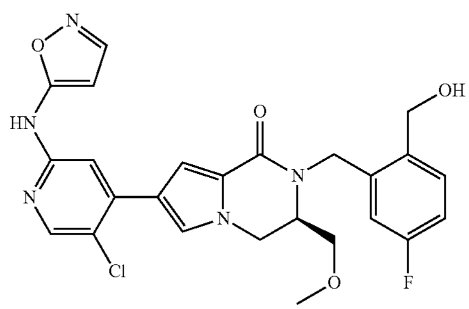 [SMILES: COC[C@H]1Cn2cc(-c3cc(Nc4ccno4)ncc3Cl)cc2C(=O)N1Cc1cc(F)ccc1CO] | (R)-7-(5-chloro-2-(isoxazol-5-yl amino)pyridine-4-yl)-2-(5-fluoro-2-(hydroxymethyl)benzyl)-3-(methoxymethyl)-3,4-dihydropyrrolo[1,2-a]pyrazine-1(2H)-one | 513.0 |
| 94 | 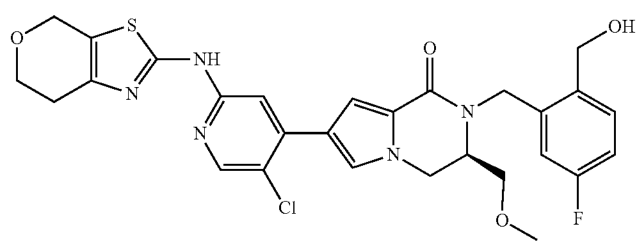 [SMILES: COC[C@H]1Cn2cc(-c3cc(Nc4nc5c(s4)COCC5)ncc3Cl)cc2C(=O)N1Cc1cc(F)ccc1CO] | (R)-7-(5-chloro-2-((6,7-dihydro-4h-pyrano[4,3-d]thiazol-2-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 585.1 |
| 95 | 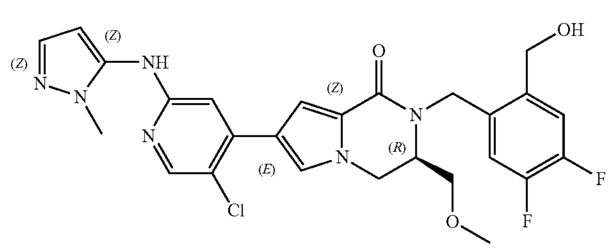 | (R)-7-(5-chloro-2-((1-methyl-1h-pyrazole-5-yl)amino)pyridine-4-yl)-2-(4,5-difluoro-2-(hydroxymethyl)benzyl)-3-(methoxymethyl)-3,4-dihydropyrrolo[1,2-a]pyrazine-1(2H)-one | 543.2 |
| 96 | 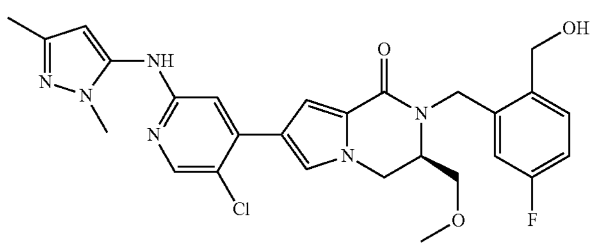 [SMILES: COC[C@H]1Cn2cc(-c3cc(Nc4cc(C)nn4C)ncc3Cl)cc2C(=O)N1Cc1cc(F)ccc1CO] | (R)-7-(5-chloro-2-((1,3-dimethyl-1h-pyrazole-5-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 540.0 |

TABLE 5-continued

| Example | Structure | Chemical Name | LC-MS [M + H]+ |
|---|---|---|---|
| 97 | 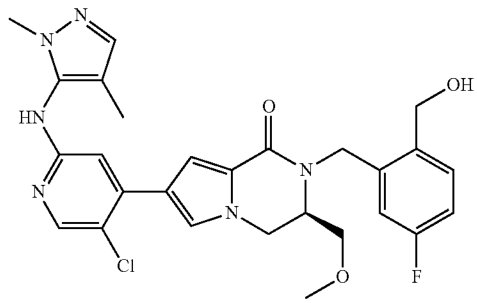 [SMILES: COC[C@H]1Cn2cc(-c3cc(Nc4c(C)cnn4C)ncc3Cl)cc2C(=O)N1Cc1cc(F)ccc1CO] | (R)-7-(5-chloro-2-((1,4-dimethyl-1h-pyrazole-5-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 540.0 |
| 98 | 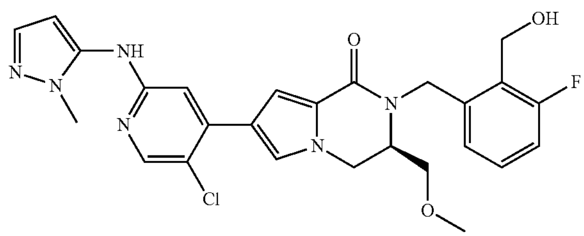 [SMILES: COC[C@H]1Cn2cc(-c3cc(Nc4ccnn4C)ncc3Cl)cc2C(=O)N1Cc1cccc(F)c1CO] | (R)-7-(5-chloro-2-((1-methyl-1h-pyrazole-5-yl)amino)pyridine-4-yl)-2-(3-fluoro-2-(hydroxymethyl)benzyl)-3-(methoxymethyl)-3,4-dihydropyrrolo[1,2-a]pyrazine-1(2H)-one | 525.2 |
| 99 | 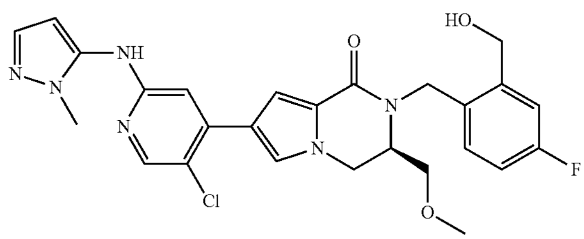 [SMILES: COC[C@H]1Cn2cc(-c3cc(Nc4ccnn4C)ncc3Cl)cc2C(=O)N1Cc1ccc(F)cc1CO] | (R)-7-(5-chloro-2-((1-methyl-1h-pyrazole-5-yl)amino)pyridine-4-yl)-2-(4-fluoro-2-(hydroxymethyl)benzyl)-3-(methoxymethyl)-3,4-dihydropyrrolo[1,2-a]pyrazine-1(2H)-one | 525.2 |
| 100 | 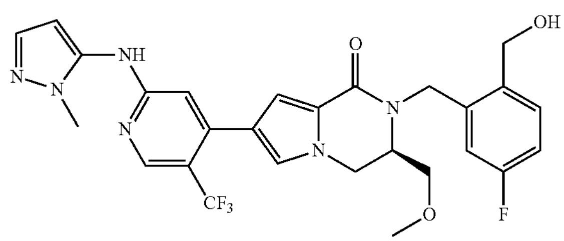 [SMILES: COC[C@H]1Cn2cc(-c3cc(Nc4ccnn4C)ncc3C(F)(F)F)cc2C(=O)N1Cc1cc(F)ccc1CO] | (R)-2-(5-fluoro-2-(hydroxymethyl)benzyl)-3-(methoxymethyl)-7-(2-((1-methyl-1h-pyrazole-5-yl)amino)-5-(trifluoromethyl)pyridin-4-yl)-3,4-dihydropyrrolo[1,2-a]pyrazine-1(2H)-one | 559.2 |
| 101 | 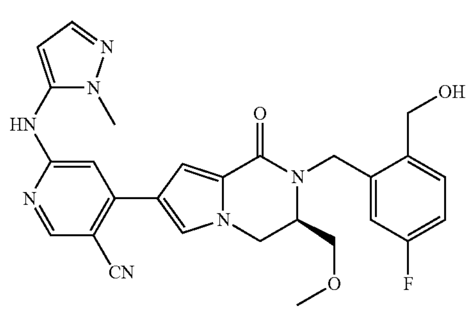 [SMILES: COC[C@H]1Cn2cc(-c3cc(Nc4ccnn4C)ncc3C#N)cc2C(=O)N1Cc1cc(F)ccc1CO] | (R)-4-(2-(5-fluoro-2-(hydroxymethyl)benzyl)-3-(methoxymethyl)-1-oxo-1,2,3,4-tetrahydropyrrolo[1,2-a]pyrazin-7-yl)-6-((1-methyl-1h-pyrazole-5-yl)amino)nicotinic acid | 516.6 |

TABLE 5-continued

| Example | Structure | Chemical Name | LC-MS [M + H]+ |
|---|---|---|---|
| 102 | 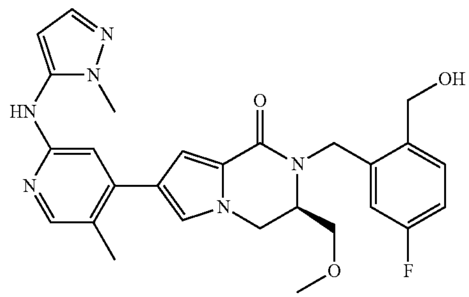 [SMILES: COC[C@H]1Cn2cc(-c3cc(Nc4ccnn4C)ncc3C)cc2C(=O)N1Cc1cc(F)ccc1CO] | (R)-2-(5-fluoro-2-(hydroxymethyl)benzyl)-3-(methoxymethyl)-7-(5-methyl-2-((1-methyl-1h-pyrazole-5-yl)amino)pyridine-4-yl)-3,4-dihydropyrrolo[1,2-a]pyrazine-1(2H)-one | 506.3 |
| 103 | 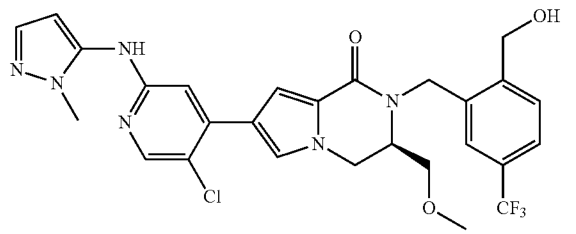 [SMILES: COC[C@H]1Cn2cc(-c3cc(Nc4ccnn4C)ncc3Cl)cc2C(=O)N1Cc1cc(C(F)(F)F)ccc1CO] | (R)-7-(5-chloro-2-((1-methyl-1h-pyrazole-5-yl)amino)pyridine-4-yl)-2-(2-(hydroxymethyl)-5-(trifluoromethyl)benzyl)-3-(methoxymethyl)-3,4-dihydropyrrolo[1,2-a]pyrazine-1(2H)-one | 575.2 |
| 104 | 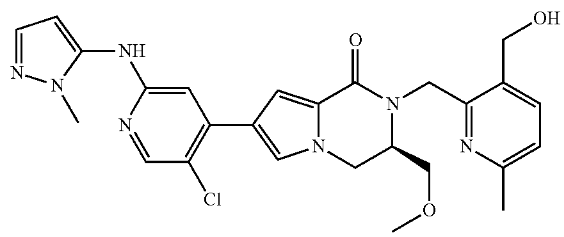 [SMILES: COC[C@H]1Cn2cc(-c3cc(Nc4ccnn4C)ncc3Cl)cc2C(=O)N1Cc1nc(C)ccc1CO] | (R)-7-(5-chloro-2-((1-methyl-1h-pyrazole-5-yl)amino)pyridine-4-yl)-2-((3-(hydroxymethyl)-6-methylpyridin-2-yl)methyl)-3-(methoxymethyl)-3,4-dihydropyrrolo[1,2-a]pyrazine-1(2H)-one | 522.2 |
| 105 | 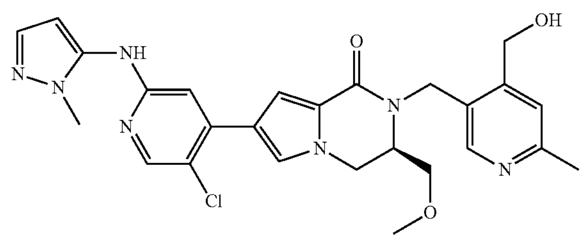 [SMILES: COC[C@H]1Cn2cc(-c3cc(Nc4ccnn4C)ncc3Cl)cc2C(=O)N1Cc1cnc(C)cc1CO] | (R)-7-(5-chloro-2-((1-methyl-1h-pyrazole-5-yl)amino)pyridine-4-yl)-2-((4-(hydroxymethyl)-6-methylpyridin-3-yl)methyl)-3-(methoxymethyl)-3,4-dihydropyrrolo[1,2-a]pyrazine-1(2H)-one | 522.2 |
| 106 | 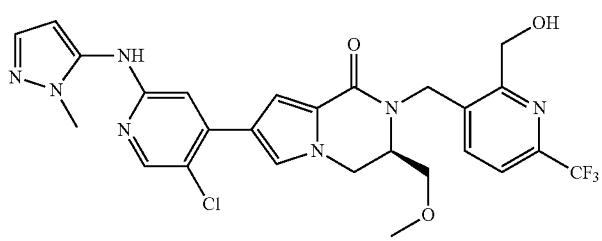 [SMILES: COC[C@H]1Cn2cc(-c3cc(Nc4ccnn4C)ncc3Cl)cc2C(=O)N1Cc1ccc(C(F)(F)F)nc1CO] | (R)-7-(5-chloro-2-((1-methyl-1h-pyrazole-5-yl)amino)pyridine-4-yl)-2-((2-(hydroxymethyl)-6-(trifluoromethyl)pyridin-3-yl)methyl)-3-(methoxymethyl)-3,4-dihydropyrrolo[1,2-a]pyrazine-1(2H)-one | 576.2 |
| 107 | 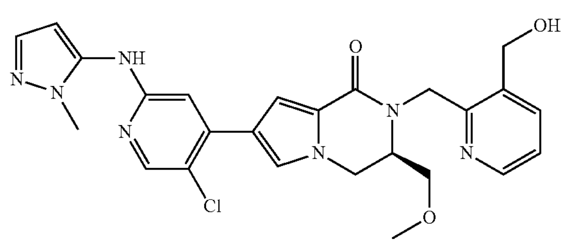 [SMILES: COC[C@H]1Cn2cc(-c3cc(Nc4ccnn4C)ncc3Cl)cc2C(=O)N1Cc1ncccc1CO] | (R)-7-(5-chloro-2-((1-methyl-1h-pyrazole-5-yl)amino)pyridine-4-yl)-2-((3-(hydroxymethyl)pyridin-2-yl)methyl)-3-(methoxymethyl)-3,4-dihydropyrrolo[1,2-a]pyrazine-1(2H)-one | 508.2 |

TABLE 5-continued

| Example | Structure | Chemical Name | LC-MS [M + H]+ |
|---|---|---|---|
| 108 | 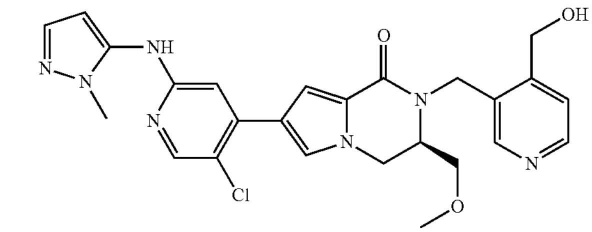 [SMILES: COC[C@H]1Cn2cc(-c3cc(Nc4ccnn4C)ncc3Cl)cc2C(=O)N1Cc1cnccc1CO] | (R)-7-(5-chloro-2-((1-methyl-1h-pyrazole-5-yl)amino)pyridine-4-yl)-2-((4-(hydroxymethyl)pyridin-3-yl)methyl)-3-(methoxymethyl)-3,4-dihydropyrrolo[1,2-a]pyrazine-1(2H)-one | 508.2 |
| 109 | 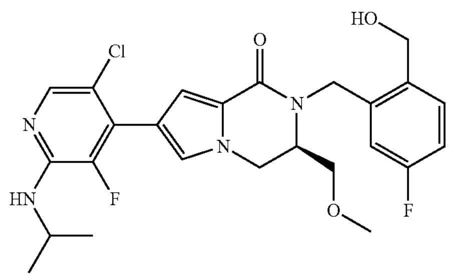 [SMILES: COC[C@H]1Cn2cc(-c3c(Cl)cnc(NC(C)C)c3F)cc2C(=O)N1Cc1cc(F)ccc1CO] | (R)-7-(5-chloro-3-fluoro-2-(isopropylamino)pyridin-4-yl)-2-(5-fluoro-2-(hydroxymethyl)benzyl)-3-(methoxymethyl)-3,4-dihydropyrrolo[1,2-a]pyrazine-1(2H)-one | 506.0 |
| 110 | 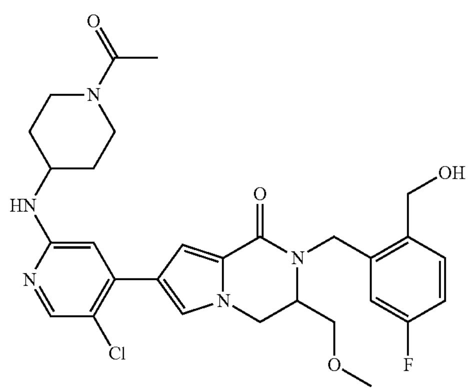 [SMILES: COCC1Cn2cc(-c3cc(NC4CCN(C(C)=O)CC4)ncc3Cl)cc2C(=O)N1Cc1cc(F)ccc1CO] | 7-(2-((1-acetylpiperidin-4-yl)amino)-5-chloropyridine-4-yl)-2-(5-fluoro-2-(hydroxymethyl)benzyl)-3-(methoxymethyl)-3,4-dihydropyrrolo[1,2-a]pyrazine-1(2H)-one | 570.2 |
| 111 | 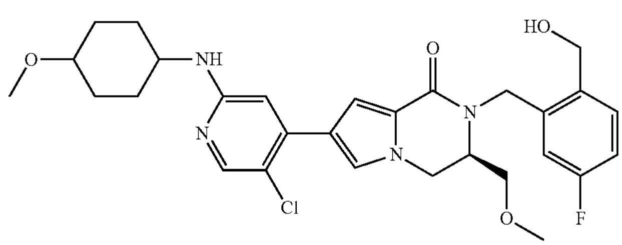 [SMILES: COC[C@H]1Cn2cc(-c3cc(NC4CCC(OC)CC4)ncc3Cl)cc2C(=O)N1Cc1cc(F)ccc1CO] | (R)-7-(5-chloro-2-((4-methoxycyclohexyl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 557.2 |
| 112 | 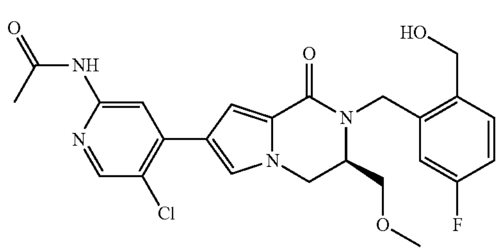 [SMILES: COC[C@H]1Cn2cc(-c3cc(NC(C)=O)ncc3Cl)cc2C(=O)N1Cc1cc(F)ccc1CO] | (R)-N-(5-chloro-4-(2-(5-fluoro-2-(hydroxymethyl)benzyl)-3-(methoxymethyl)-1-oxo-1,2,3,4-tetrahydropyrrolo[1,2-a]pyrazin-7-yl)pyridine-2-yl)acetamide | 487.2 |

TABLE 5-continued

| Example | Structure | Chemical Name | LC-MS [M + H]+ |
|---|---|---|---|
| 113 | 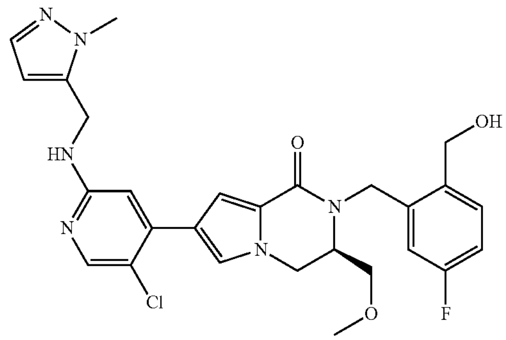 [SMILES: COC[C@H]1Cn2cc(-c3cc(NCc4ccnn4C)ncc3Cl)cc2C(=O)N1Cc1cc(F)ccc1CO] | (R)-7-(5-chloro-2-(((1-methyl-1h-pyrazole-5-yl)methyl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 540.0 |
| 114 | 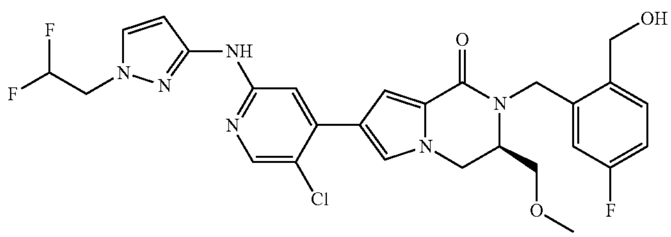 [SMILES: COC[C@H]1Cn2cc(-c3cc(Nc4ccn(CC(F)F)n4)ncc3Cl)cc2C(=O)N1Cc1cc(F)ccc1CO] | (R)-7-(5-chloro-2-((1-(2,2-difluoroethyl)-1h-pyrazole-3-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 576.0 |
| 115 | 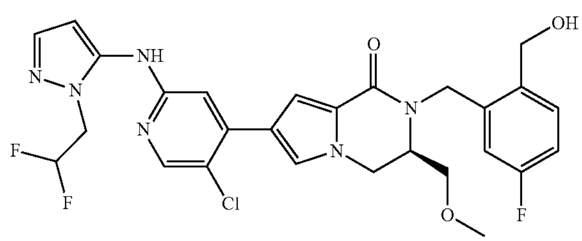 [SMILES: COC[C@H]1Cn2cc(-c3cc(Nc4ccnn4CC(F)F)ncc3Cl)cc2C(=O)N1Cc1cc(F)ccc1CO] | (R)-7-(5-chloro-2-((1-(2,2-difluoroethyl)-1h-pyrazole-5-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 576.0 |
| 116 | 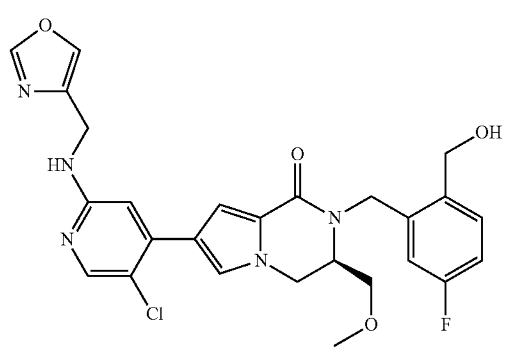 [SMILES: COC[C@H]1Cn2cc(-c3cc(NCc4cocn4)ncc3Cl)cc2C(=O)N1Cc1cc(F)ccc1CO] | (R)-7-(5-chloro-2-((oxazol-4-methylene)amino)pyridine-4-yl)-2-(5-fluoro-2-(hydroxymethyl)benzyl)-3-(methoxymethyl)-3,4-dihydropyrrole[1,2-a]pyrazine-1(2H)-one | 527.0 |
| 117 | 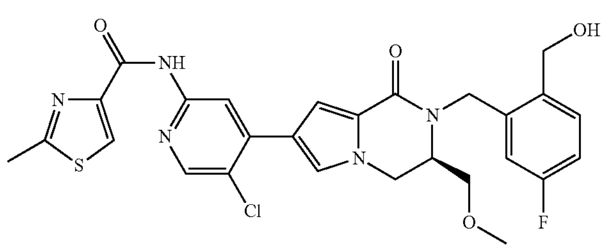 [SMILES: COC[C@H]1Cn2cc(-c3cc(NC(=O)c4csc(C)n4)ncc3Cl)cc2C(=O)N1Cc1cc(F)ccc1CO] | (R)-N-(5-chloro-4-(2-(5-fluoro-2-(hydroxymethyl)benzyl)-3-(methoxymethyl)-1-oxo-1,2,3,4-tetrahydropyrrolo[1,2-a]pyrazin-7-yl)pyridine-2-yl)-2-methylthiazol-4-formamide | 571.0 |

TABLE 5-continued

| Example | Structure | Chemical Name | LC-MS [M + H]+ |
|---|---|---|---|
| 118 | 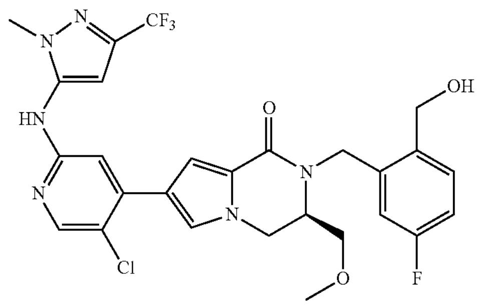 [SMILES: COC[C@H]1Cn2cc(-c3cc(Nc4cc(C(F)(F)F)nn4C)ncc3Cl)cc2C(=O)N1Cc1cc(F)ccc1CO] | (R)-7-(5-chloro-2-((1-methyl-3-(trifluoromethyl)-1h-pyrazole-5-yl)amino)pyridine-4-yl)-2-(5-fluoro-2-(hydroxymethyl)benzyl)-3-(methoxymethyl)-3,4-dihydropyrrolo[1,2-a]pyrazine-1(2H)-one | 594.0 |
| 119 | 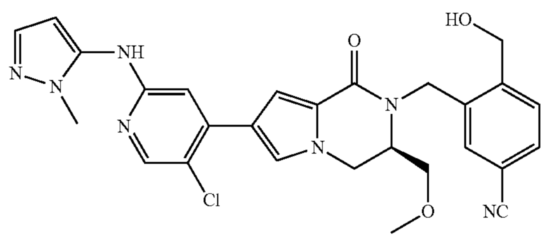 [SMILES: COC[C@H]1Cn2cc(-c3cc(Nc4ccnn4C)ncc3Cl)cc2C(=O)N1Cc1cc(C#N)ccc1CO] | (R)-3-((7-(5-chloro-2-((1-methyl-1h-pyrazole-5-yl)amino)pyridine-4-yl)-3-(methoxymethyl)-1-oxo-3,4-dihydropyrrolo[1,2-a]pyrazin-2(1H)-yl)methyl)-4-(hydroxymethyl)benzylnitrile | 537.7 |
| 120 | 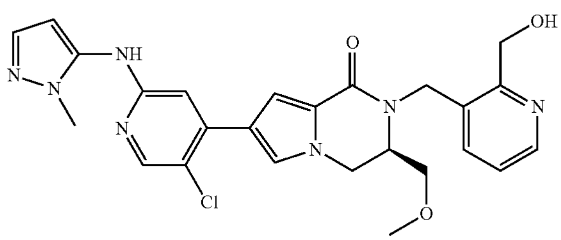 | (R)-7-(5-chloro-2-((1-methyl-1h-pyrazole-5-yl)amino)pyridine-4-yl)-2-((2-(hydroxymethyl)pyridin-3-yl)methyl)-3-(methoxymethyl)-3,4-dihydropyrrolo[1,2-a]pyrazine-1(2H)-one | 508.2 |
| 121 | 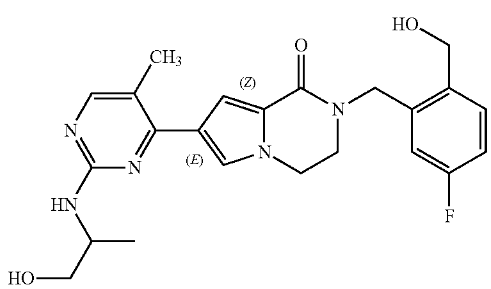 [SMILES: Cc1cnc(NC(C)CO)nc1-c1cc2n(c1)CCN(Cc1cc(F)ccc1CO)C2=O] | 2-(5-fluoro-2-(hydroxymethyl)benzyl)-7-(2-((1-hydroxypropyl-2-yl)amino)-5-methylpyrimidin-4-yl)-3,4-dihydropyrrolo[1,2-a]pyrazine-1(2H)-one | 440.2 |
| 122 | 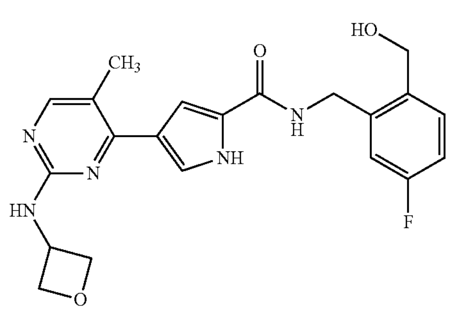 [SMILES: Cc1cnc(NC2COC2)nc1-c1c[nH]c(C(=O)NCc2cc(F)ccc2CO)c1] | N-(5-fluoro-2-(hydroxymethyl)benzyl)-4-(5-methyl-2-(oxacyclobutane-3-ylamino)pyrimidin-4-yl)-1h-pyrrole-2-formamide | 412.2 |

TABLE 5-continued

| Example | Structure | Chemical Name | LC-MS [M + H]+ |
|---|---|---|---|
| 123 | 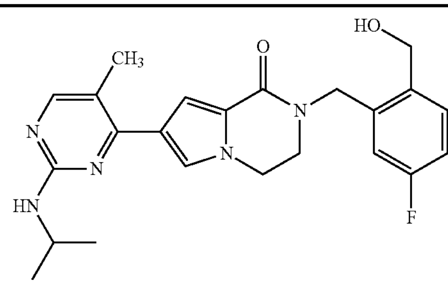 | 2-(5-fluoro-2-(hydroxymethyl)benzyl)-7-(2-(isopropylamino)-5-methylpyrimidin-4-yl)-3,4-dihydropyrrolo[1,2-a]pyrazine-1(2H)-one | 424.7 |
| 124 | 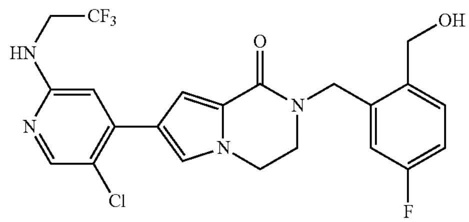 [SMILES: O=C1c2cc(-c3cc(NCC(F)(F)F)ncc3Cl)cn2CCN1Cc1cc(F)ccc1CO] | 7-(5-chloro-2-((2,2,2-trifluoroethyl)amino)pyridine-4-yl)-2-(5-fluoro-2-(hydroxymethyl)benzyl)-3,4-dihydropyrrolo[1,2-a]pyrazine-1(2H)-one | 483.1 |
| 125 | 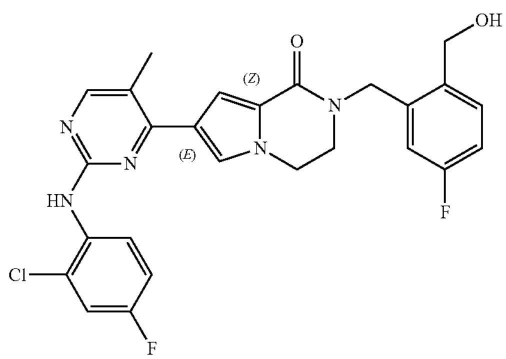 [SMILES: Cc1cnc(Nc2ccc(F)cc2Cl)nc1-c1cc2n(c1)CCN(Cc1cc(F)ccc1CO)C2=O] | 7-(2-((2-chloro-4-fluorophenyl)amino)-5-methylpyrimidin-4-yl)-2-(5-fluoro-2-(hydroxymethyl)benzyl)-3,4-dihydropyrrolo[1,2-a]pyrazine-1(2H)-one | 510.1 |
| 126 | 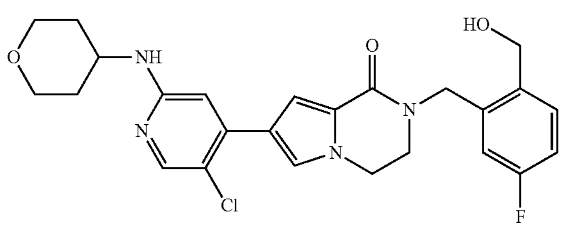 [SMILES: O=C1c2cc(-c3cc(NC4CCOCC4)ncc3Cl)cn2CCN1Cc1cc(F)ccc1CO] | 7-(5-chloro-2-((tetrahydro-2h-pyran-4-yl)amino)pyridine-4-yl)-2-(5-fluoro-2-(hydroxymethyl)benzyl)-3,4-dihydropyrrolo[1,2-a]pyrazine-1(2H)-one | 485.2 |
| 127 | 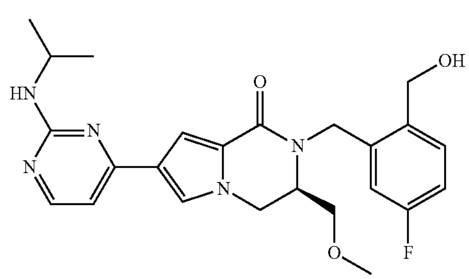 [SMILES: COC[C@H]1Cn2cc(-c3ccnc(NC(C)C)n3)cc2C(=O)N1Cc1cc(F)ccc1CO] | (R)-2-(5-fluoro-2-(hydroxymethyl)benzyl)-7-(2-(isopropylamino)pyrimidin-4-yl)-3-(methoxymethyl)-3,4-dihydropyrrolo[1,2-a]pyrazine-1(2H)-one | 454.5 |
| 128 | 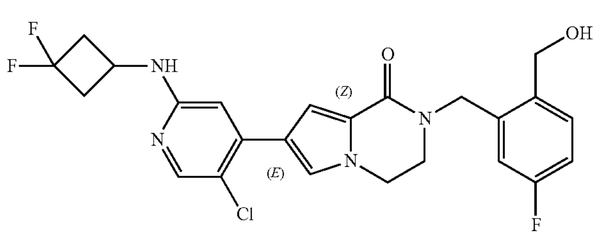 [SMILES: O=C1c2cc(-c3cc(NC4CC(F)(F)C4)ncc3Cl)cn2CCN1Cc1cc(F)ccc1CO] | 7-(5-chloro-2-((3,3-difluorocyclobutyl)amino)pyridine-4-yl)-2-(5-fluoro-2-(hydroxymethyl)benzyl)-3,4-dihydropyrrolo[1,2-a]pyrazine-1(2H)-one | 491.1 |

TABLE 5-continued

| Example | Structure | Chemical Name | LC-MS [M + H]+ |
|---|---|---|---|
| 129 | 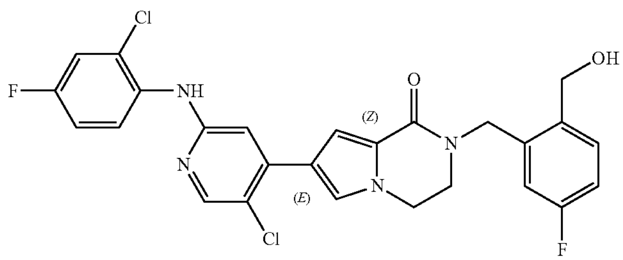 [SMILES: O=C1c2cc(-c3cc(Nc4ccc(F)cc4Cl)ncc3Cl)cn2CCN1Cc1cc(F)ccc1CO] | 7-(5-chloro-2-((2-chloro-4-fluorophenyl)amino)pyridine-4-yl)-2-(5-fluoro-2-(hydroxymethyl)benzyl)-3,4-dihydropyrrolo[1,2-a]pyrazine-1(2H)-one | 529.1 |
| 130 | 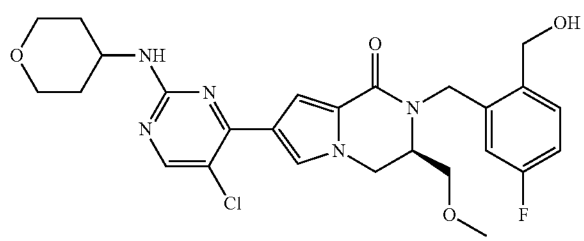 [SMILES: COC[C@H]1Cn2cc(-c3nc(NC4CCOCC4)ncc3Cl)cc2C(=O)N1Cc1cc(F)ccc1CO] | (R)-7-(5-chloro-2-((tetrahydro-2h-pyran-4-yl)amino)pyrimidin-4-yl)-2-(5-fluoro-2-(hydroxymethyl)benzyl)-3-(methoxymethyl)-3,4-dihydropyrrolo[1,2-a]pyrazine-1(2H)-one | 531.0 |
| 131 | 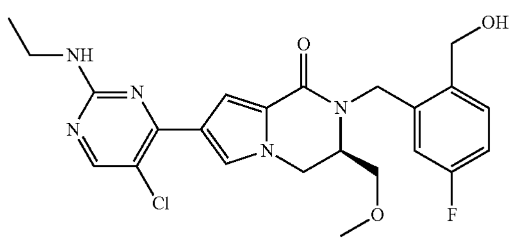 [SMILES: CCNc1ncc(Cl)c(-c2cc3n(c2)C[C@H](COC)N(Cc2cc(F)ccc2CO)C3=O)n1] | (R)-7-(5-chloro-2-(ethylamino)pyrimidin-4-yl)-2-(5-fluoro-2-(hydroxymethyl)benzyl)-3-(methoxymethyl)-3,4-dihydropyrrolo[1,2-a]pyrazine-1(2H)-one | 475.0 |
| 132 | 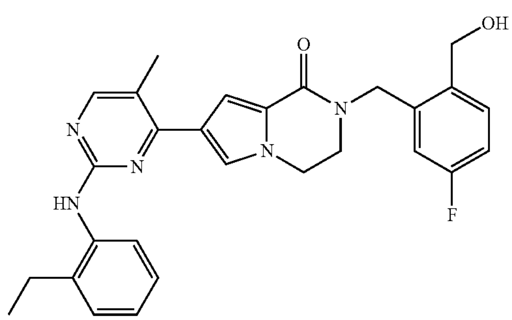 [SMILES: CCc1ccccc1Nc1ncc(C)c(-c2cc3n(c2)CCN(Cc2cc(F)ccc2CO)C3=O)n1] | 7-(2-((2-Ethylphenyl)amino)-5-methylpyrimidin-4-yl)-2-(5-fluoro-2-(hydroxymethyl)benzyl)-3,4-dihydropyrrolo[1,2-a]pyrazine-1(2H)-one | 459.2 |
| 133 | 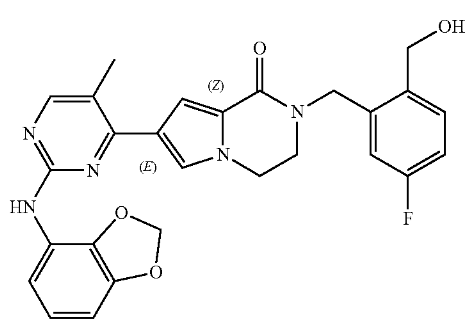 [SMILES: Cc1cnc(Nc2cccc3c2OCO3)nc1-c1cc2n(c1)CCN(Cc1cc(F)ccc1CO)C2=O] | 7-(2-(benzo[D][1,3]dioxocyclopentene-4-ylamino)-5-methylpyrimidin-4-yl)-2-(5-fluoro-2-(hydroxymethyl)benzyl)-3,4-dihydropyrrolo[1,2-a]pyrazine-1(2H)-one | 502.2 |

TABLE 5-continued

| Example | Structure | Chemical Name | LC-MS [M + H]+ |
|---|---|---|---|
| 134 | 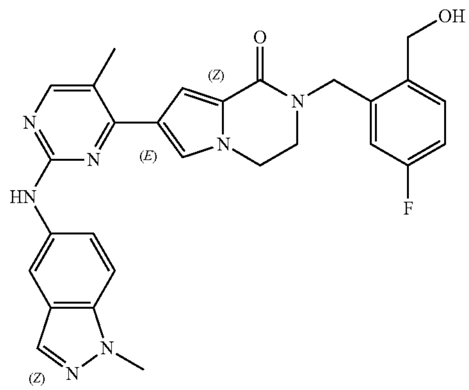 [SMILES: Cc1cnc(Nc2ccc3c(cnn3C)c2)nc1-c1cc2n(c1)CCN(Cc1cc(F)ccc1CO)C2=O] | 2-(5-fluoro-2-(hydroxymethyl) benzyl)-7-(5-methyl-2-((1-methyl-1h-indazole-5-yl) amino)pyrimidin-4-yl)-3,4-dihydropyrrolo[1,2-a] pyrazine-1(2H)-one | 512.2 |
| 135 | 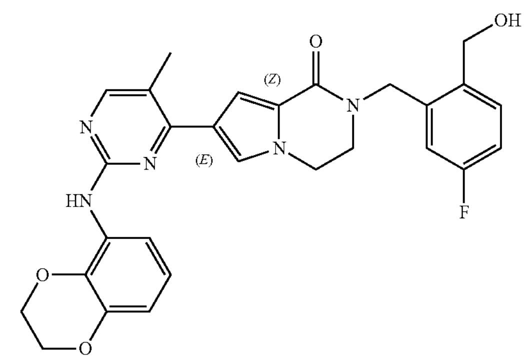 [SMILES: Cc1cnc(Nc2cccc3c2OCCO3)nc1-c1cc2n(c1)CCN(Cc1cc(F)ccc1CO)C2=O] | 7-(2-((2,3-dihydrobenzo[b][1,4] dioxane-5-yl)amino)-5-methylpyrimidin-4-yl)-2-(5-fluoro-2-(hydroxymethyl) benzyl)-3,4-dihydropyrrolo[1,2-a] pyrazine-1(2H)-one | 516.2 |
| 136 | 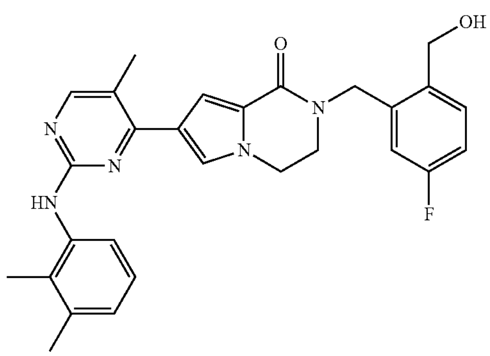 [SMILES: Cc1cnc(Nc2cccc(C)c2C)nc1-c1cc2n(c1)CCN(Cc1cc(F)ccc1CO)C2=O] | 7-(2-((2,3-dimethylphenyl) amino)-5-methylpyrimidin-4-yl)-2-(5-fluoro-2-(hydroxymethyl) benzyl)-3,4-dihydropyrrolo[1,2-a] pyrazine-1(2H)-one | 486.2 |
| 137 | 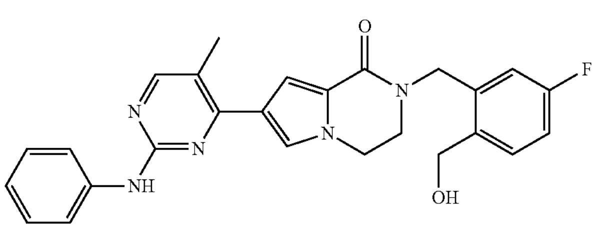 [SMILES: Cc1cnc(Nc2ccccc2)nc1-c1cc2n(c1)CCN(Cc1cc(F)ccc1CO)C2=O] | 2-(5-fluoro-2-(hydroxymethyl) benzyl)-7-(5-methyl-2-(phenylamino)pyrimidin-4-yl)-3,4-dihydropyrrolo[1,2-a] pyrazine-1(2H)-one | 458.2 |

TABLE 5-continued

| Example | Structure | Chemical Name | LC-MS [M + H]+ |
|---------|-----------|---------------|----------------|
| 138 | 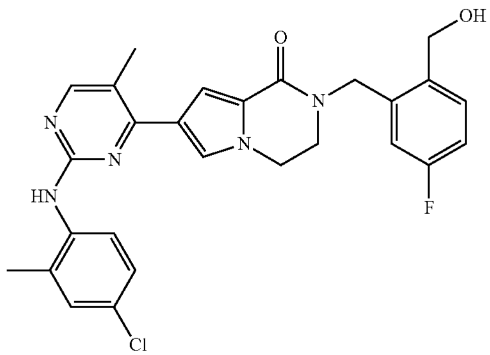 [SMILES: Cc1cc(Cl)ccc1Nc1ncc(C)c(-c2cc3n(c2)CCN(Cc2cc(F)ccc2CO)C3=O)n1] | 7-(2-((4-chloro-2-methylphenyl)amino)-5-methylpyrimidin-4-yl)-2-(5-fluoro-2-(hydroxymethyl)benzyl)-3,4-dihydropyrrolo[1,2-a]pyrazine-1(2H)-one | 506.2 |
| 139 | 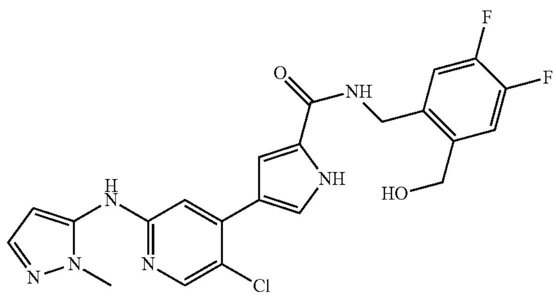 [SMILES: Cn1nccc1Nc1cc(-c2c[nH]c(C(=O)NCc3cc(F)c(F)cc3CO)c2)c(Cl)cn1] | 4-(5-chloro-2-((1-methyl-1h-pyrazole-5-yl)amino)pyridine-4-yl)-N-(4,5-difluoro-2-(hydroxymethyl)benzyl)-1h-pyrrole-2-formamide | 473.9 |
| 140 | 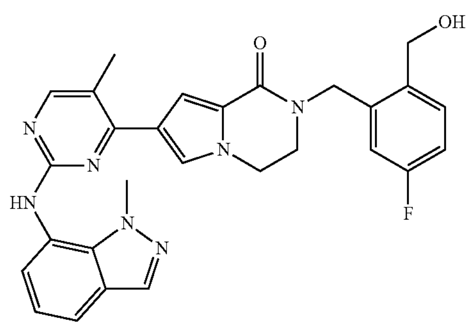 [SMILES: Cc1cnc(Nc2cccc3cnn(C)c23)nc1-c1cc2n(c1)CCN(Cc1cc(F)ccc1CO)C2=O] | 2-(5-fluoro-2-(hydroxymethyl)benzyl)-7-(5-methyl-2-((1-methyl-1h-indazole-7-yl)amino)pyrimidin-4-yl)-3,4-dihydropylrolo[1,2-a]pyrazine-1(2H)-one | 512.2 |
| 141 | 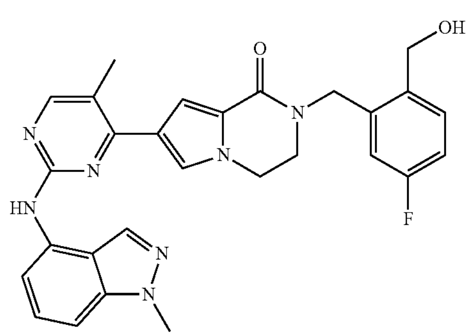 [SMILES: Cc1cnc(Nc2cccc3c2cnn3C)nc1-c1cc2n(c1)CCN(Cc1cc(F)ccc1CO)C2=O] | 2-(5-fluoro-2-(hydroxymethyl)benzyl)-7-(5-methyl-2-((1-methyl-1h-indazole-4-yl)amino)pyrimidin-4-yl)-3,4-dihydropyrrolo[1,2-a]pyrazine-1(2H)-one | 512.2 |

TABLE 5-continued

| Example | Structure | Chemical Name | LC-MS [M + H]+ |
|---|---|---|---|
| 142 | 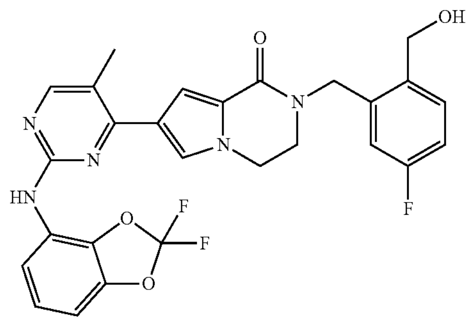 [SMILES: Cc1cnc(Nc2cccc3c2OC(F)(F)O3)nc1-c1cc2n(c1)CCN(Cc1cc(F)ccc1CO)C2=O] | 7-(2-((2,2-difluorobenzo[D][1,3]dioxocyclopentene-4-yl)amino)-5-methylpyrimidin-4-yl)-2-(5-fluoro-2-(hydroxymethyl)benzyl)-3,4-dihydropyrrolo[1,2-a]pyrazine-1(2H)-one | 538.2 |
| 143 | 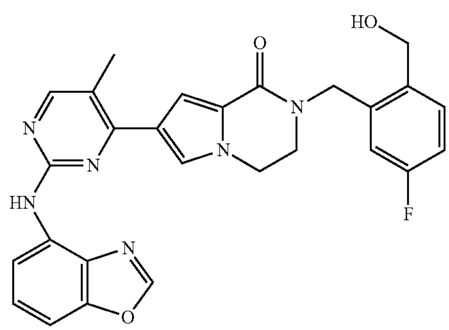 [SMILES: Cc1cnc(Nc2cccc3ocnc23)nc1-c1cc2n(c1)CCN(Cc1cc(F)ccc1CO)C2=O] | 7-(2-(benzo[d]oxazol-4-ylamino)-5-methylpyrimidin-4-yl)-2-(5-fluoro-2-(hydroxymethyl)benzyl)-3,4-dihydropyrrolo[1,2-a]pyrazine-1(2H)-one | 499.2 |
| 144 | 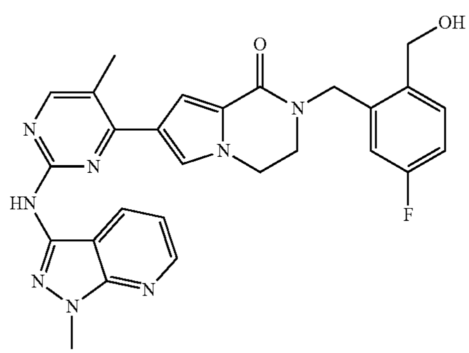 [SMILES: Cc1cnc(Nc2nn(C)c3ncccc23)nc1-c1cc2n(c1)CCN(Cc1cc(F)ccc1CO)C2=O] | 2-(5-fluoro-2-(hydroxymethyl)benzyl)-7-(5-methyl-2-((1-methyl-1h-pyrazolo[3,4-b]pyridin-3-yl)amino)pyrimidine-4-yl)-3,4-dihydropyrrolo[1,2-a]pyrazine-1(2H)-one | 513.2 |
| 145 | 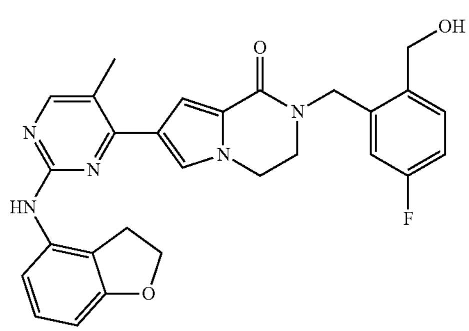 [SMILES: Cc1cnc(Nc2cccc3c2CCO3)nc1-c1cc2n(c1)CCN(Cc1cc(F)ccc1CO)C2=O] | 7-(2-((2,3-dihydrobenzofuran-4-yl)amino)-5-methylpyrimidin-4-yl)-2-(5-fluoro-2-(hydroxymethyl)benzyl)-3,4-dihydropyrrolo[1,2-a]pyrazine-1(2H)-one | 500.2 |

TABLE 5-continued

| Example | Structure | Chemical Name | LC-MS [M + H]+ |
|---|---|---|---|
| 146 | 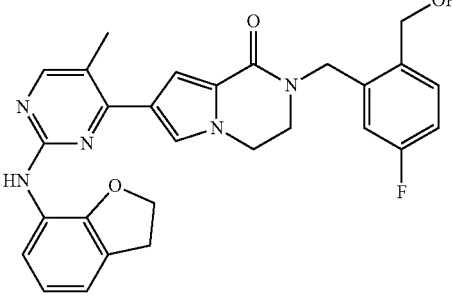 | 7-(2-((2,3-dihydrobenzofuran-7-yl)amino)-5-methylpyrimidin-4-yl)-2-(5-fluoro-2-(hydroxymethyl)benzyl)-3,4-dihydropyrrolo[1,2-a]pyrazine-1(2H)-one | 500.2 |
| 147 | 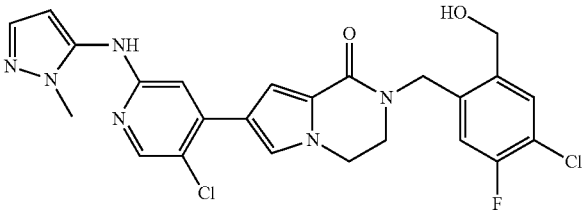 [SMILES: Cn1nccc1Nc1cc(-c2cc3n(c2)CCN(Cc2cc(F)c(Cl)cc2CO)C3=O)c(Cl)cn1] | 7-(5-chloro-2-((1-methyl-1h-pyrazole-5-yl)amino)pyridine-4-yl)-2-(4-chloro-5-fluoro-2-(hydroxymethyl)benzyl)-3,4-dihydropyrrolo[1,2-a]pyrazine-1(2H)-one | 515.1 |
| 148 | 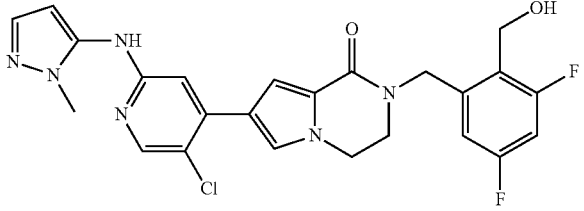 [SMILES: Cn1nccc1Nc1cc(-c2cc3n(c2)CCN(Cc2cc(F)cc(F)c2CO)C3=O)c(Cl)cn1] | 7-(5-chloro-2-((1-methyl-1h-pyrazole-5-yl)amino)pyridine-4-yl)-2-(3,5-difluoro-2-(hydroxymethyl)benzyl)-3,4-dihydropyrrolo[1,2-a]pyrazine-1(2H)-one | 499.1 |
| 149 | 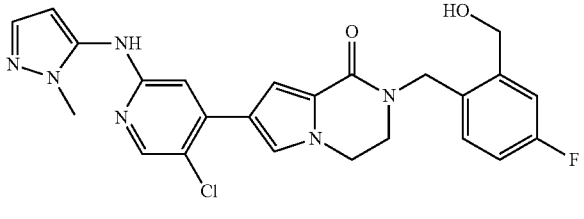 [SMILES: Cn1nccc1Nc1cc(-c2cc3n(c2)CCN(Cc2ccc(F)cc2CO)C3=O)c(Cl)cn1] | 7-(5-chloro-2-((1-methyl-1h-pyrazole-5-yl)amino)pyridine-4-yl)-2-(4-fluoro-2-(hydroxymethyl)benzyl)-3,4-dihydropyrrolo[1,2-a]pyrazine-1(2H)-one | 481.2 |
| 150 | 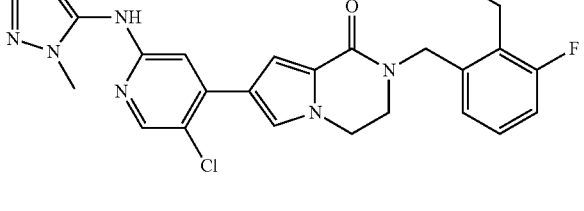 | 7-(5-chloro-2-((1-methyl-1h-pyrazole-5-yl)amino)pyridine-4-yl)-2-(3-fluoro-2-(hydroxymethyl)benzyl)-3,4-dihydropyrrolo[1,2-a]pyrazine-1(2H)-one | 481.2 |
| 151 | 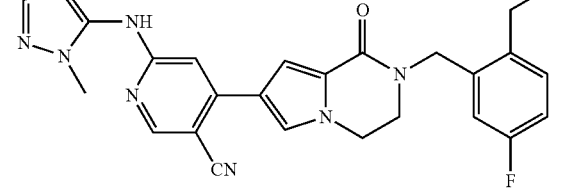 | 4-(2-(5-fluoro-2-(hydroxymethyl)benzyl)-1-oxo-1,2,3,4-tetrahydropyrrolo[1,2-a]pyrazin-7-yl)-6-((1-methyl-1h-pyrazole-5-yl)amino)nicotinic acid | 472.2 |

TABLE 5-continued

| Example | Structure | Chemical Name | LC-MS [M + H]+ |
|---|---|---|---|
| 152 | 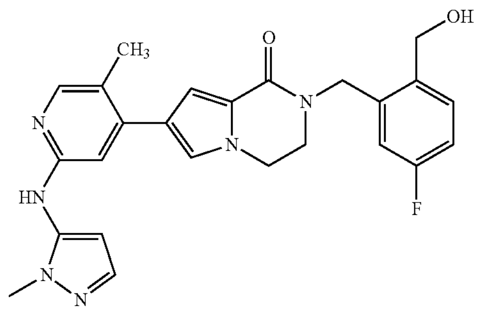 | 2-(5-fluoro-2-(hydroxymethyl)benzyl)-7-(5-methyl-2-((1-methyl-1h-pyrazole-5-yl)amino)pyridine-4-yl)-3,4-dihydropyrrolo[1,2-a]pyrazine-1(2H)-one | 461.2 |
| 153 | 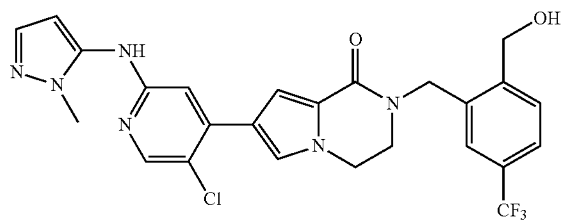 [SMILES: Cn1nccc1Nc1cc(-c2cc3n(c2)CCN(Cc2cc(C(F)(F)F)ccc2CO)C3=O)c(Cl)cn1] | 7-(5-chloro-2-((1-methyl-1h-pyrazole-5-yl)amino)pyridine-4-yl)-2-(2-(hydroxymethyl)-5-(trifluoromethyl)benzyl)-3,4-dihydropyrrolo[1,2-a]pyrazine-1(2H)-one | 531.1 |
| 154 | 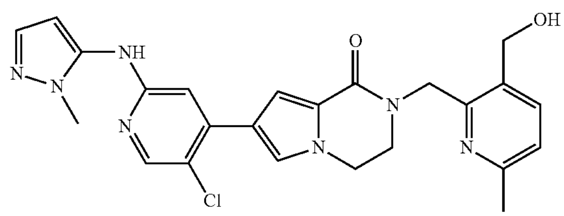 [SMILES: Cc1ccc(CO)c(CN2CCn3cc(-c4cc(Nc5ccnn5C)ncc4Cl)cc3C2=O)n1] | 7-(5-chloro-2-((1-methyl-1h-pyrazole-5-yl)amino)pyridine-4-yl)-2-((3-(hydroxymethyl)-6-methylpyridin-2-yl)methyl)-3,4-dihydropyrrolo[1,2-a]pyrazine-1(2H)-one | 478.2 |
| 155 | 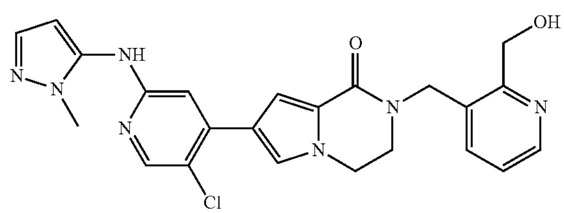 [SMILES: Cn1nccc1Nc1cc(-c2cc3n(c2)CCN(Cc2cccnc2CO)C3=O)c(Cl)cn1] | 7-(5-chloro-2-((1-methyl-1h-pyrazole-5-yl)amino)pyridine-4-yl)-2-((2-(hydroxymethyl)pyridin-3-yl)methyl)-3,4-dihydropyrrolo[1,2-a]pyrazine-1(2H)-one | 464.2 |
| 156 | 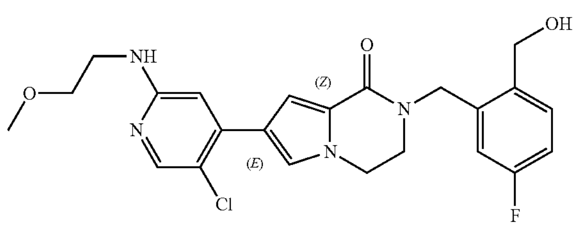 [SMILES: COCCNc1cc(-c2cc3n(c2)CCN(Cc2cc(F)ccc2CO)C3=O)c(Cl)cn1] | 7-(5-chloro-2-((2-Methoxyethyl)amino)pyridine-4-yl)-2-(5-fluoro-2-(hydroxymethyl)benzyl)-3,4-dihydropyrrolo[1,2-a]pyrazine-1(2H)-one | 458.2 |
| 157 | 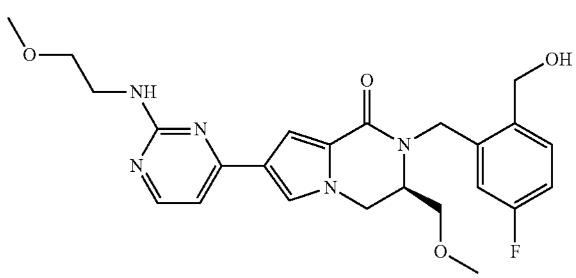 [SMILES: COCCNc1nccc(-c2cc3n(c2)C[C@H](COC)N(Cc2cc(F)ccc2CO)C3=O)n1] | (R)-2-(5-fluoro-2-(hydroxymethyl)benzyl)-7-(2-((2-Methoxyethyl)amino)pyrimidin-4-yl)-3-(methoxymethyl)-3,4-dihydropyrrolo[1,2-a]pyrazine-1(2H)-one | 470.5 |

TABLE 5-continued

| Example | Structure | Chemical Name | LC-MS [M + H]+ |
|---|---|---|---|
| 158 | 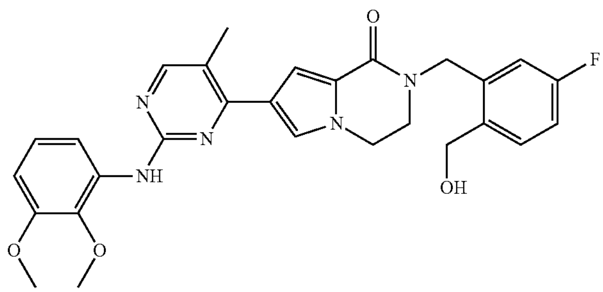 [SMILES: COc1cccc(Nc2ncc(C)c(-c3cc4n(c3)CCN(Cc3cc(F)ccc3CO)C4=O)n2)c1OC] | 7-(2-((2,3-dimethoxyphenyl)amino)-5-methylpyrimidin-4-yl)-2-(5-fluoro-2-(hydroxymethyl)benzyl)-3,4-dihydropyrrolo[1,2-a]pyrazine-1(2H)-one | 518.2 |
| 159 | 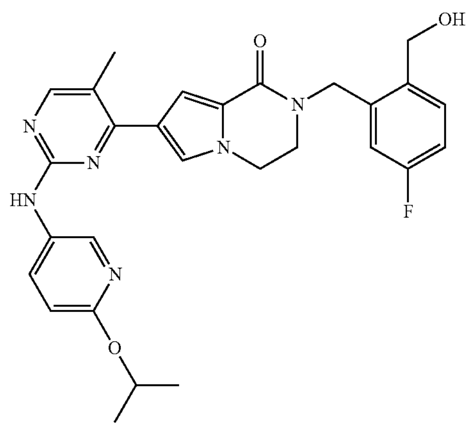 [SMILES: Cc1cnc(Nc2ccc(OC(C)C)nc2)nc1-c1cc2n(c1)CCN(Cc1cc(F)ccc1CO)C2=O] | 2-(5-fluoro-2-(hydroxymethyl)benzyl)-7-(2-((6-isopropoxypyridin-3-yl)amino)5-methylpyrimidin-4-yl)-3,4-dihydropyrrolo[1,2-a]pyrazine-1(2H)-one | 517.2 |
| 160 | 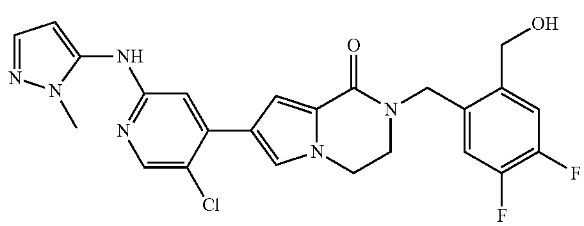 [SMILES: Cn1nccc1Nc1cc(-c2cc3n(c2)CCN(Cc2cc(F)c(F)cc2CO)C3=O)c(Cl)cn1] | 7-(5-chloro-2-((1-methyl-1h-pyrazole-5-yl)amino)pyridine-4-yl)-2-(4,5-difluoro-2-(hydroxymethyl)benzyl)-3,4-dihydropyrrolo[1,2-a]pyrazine-1(2H)-one | 499.1 |
| 161 | 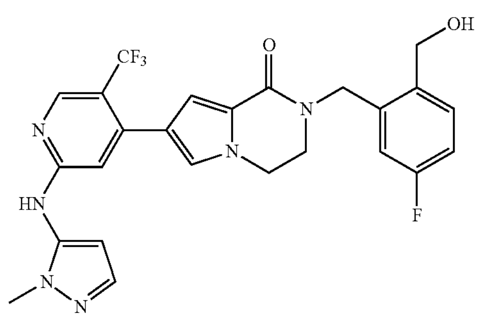 [SMILES: Cn1nccc1Nc1cc(-c2cc3n(c2)CCN(Cc2cc(F)ccc2CO)C3=O)c(C(F)(F)F)cn1] | (5-fluoro-2-(hydroxylmethyl)benzyl)-7-(2-((1-methyl-1h-pyrazole-5-yl)amino)-5-(trifluoromethyl)pyridin-4-yl)-3,4-dihydropyrrolo[1,2-a]pyrazine-1(2H)-one | 515.2 |
| 162 | 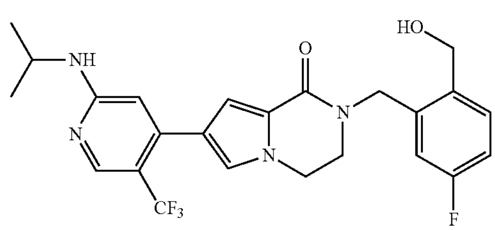 [SMILES: CC(C)Nc1cc(-c2cc3n(c2)CCN(Cc2cc(F)ccc2CO)C3=O)c(C(F)(F)F)cn1] | 2-(5-fluoro-2-(hydroxymethyl)benzyl)-7-(2-(isopropylamino)-5-(trifluoromethyl)pyridin-4-yl)-3,4-dihydropyrrolo[1,2-a]pyrazine-1(2H)-one | 477.2 |

TABLE 5-continued

| Example | Structure | Chemical Name | LC-MS [M + H]+ |
|---|---|---|---|
| 163 | 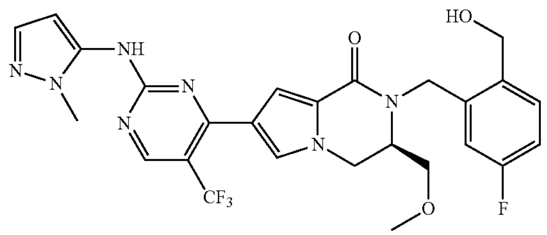 [SMILES: COC[C@H]1Cn2cc(-c3nc(Nc4ccnn4C)ncc3C(F)(F)F)cc2C(=O)N1Cc1cc(F)ccc1CO] | (R)-2-(5-fluoro-2-(hydroxymethyl)benzyl)-3-(methoxymethyl)-7-(2-((1-methyl-1h-pyrazole-5-yl)amino)-5-(trifluoromethyl)pyrimidin-4-yl)-3,4-dihydropyrrolo[1,2-a]pyrazine-1(2H)-one | 560.2 |
| 164 | 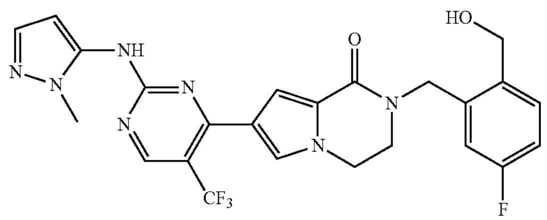 [SMILES: Cn1nccc1Nc1ncc(C(F)(F)F)c(-c2cc3n(c2)CCN(Cc2cc(F)ccc2CO)C3=O)n1] | 2-(5-fluoro-2-(hydroxymethyl)benzyl)-7-(2-((1-methyl-1h-pyrazole-5-yl)amino)-5-(trifluoromethyl)pyrimidin-4-yl)-3,4-dihydropyrrolo[1,2-a]pyrazine-1(2H)-one | 516.2 |
| 165 | 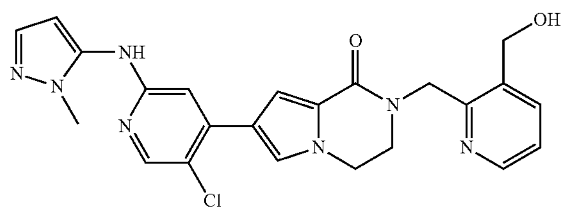 [SMILES: Cn1nccc1Nc1cc(-c2cc3n(c2)CCN(Cc2ncccc2CO)C3=O)c(Cl)cn1] | 7-(5-chloro-2-((1-methyl-1h-pyrazole-5-yl)amino)pyridine-4-yl)-2-((3-(hydroxymethyl)pyridin-2-yl)methyl)-3,4-dihydropyrrolo[1,2-a]pyrazine-1(2H)-one | 464.2 |
| 166 | 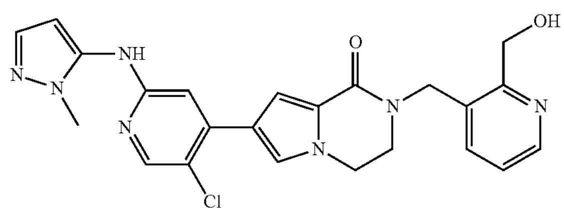 [SMILES: Cn1nccc1Nc1cc(-c2cc3n(c2)CCN(Cc2cccnc2CO)C3=O)c(Cl)cn1] | 7-(5-chloro-2-((1-methyl-1h-pyrazole-5-yl)amino)pyridine-4-yl)-2-((2-(hydroxymethyl)pyridin-3-yl)methyl)-3,4-dihydropyrrolo[1,2-a]pyrazine-1(2H)-one | 464.2 |
| 167 | 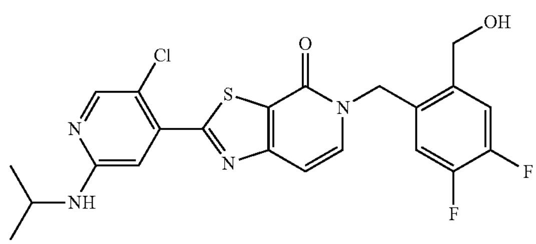 [SMILES: CC(C)Nc1cc(-c2nc3ccn(Cc4cc(F)c(F)cc4CO)c(=O)c3s2)c(Cl)cn1] | 2-(5-chloro-2-(isopropylamino)pyridin-4-yl)-5-(4,5-difluoro-2-(hydroxymethyl)benzyl)thiazolo[5,4-c]pyridine-4(5H)-one | 477.1 |
| 168 | 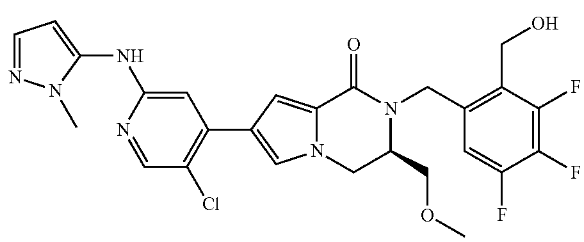 [SMILES: COC[C@H]1Cn2cc(-c3cc(Nc4ccnn4C)ncc3Cl)cc2C(=O)N1Cc1cc(F)c(F)c(F)c1CO] | (R)-7-(5-chloro-2-((1-methyl-1h-pyrazole-5-yl)amino)pyridine-4-yl)-3-(methoxymethyl)-2-(3,4,5-fluoro-2-(hydroxymethyl)benzyl)-3,4-dihydropyrrolo[1,2-a]pyrazine-1(2H)-one | 561.16 |

¹H NMR (600 MHz, DMSO-d₆) of compound 57: 8.05-7.92 (m, 1H), 7.66-7.57 (m, 1H), 7.43 (dd, J=6.4, 7.9 Hz, 1H), 7.21-7.13 (m, 1H), 7.11-6.96 (m, 2H), 6.62 (s, 1H), 6.40 (d, J=7.3 Hz, 1H), 5.35-5.23 (m, 1H), 5.19 (t, J=5.1 Hz, 1H), 4.76-4.64 (m, 2H), 4.61-4.43 (m, 3H), 4.23-4.12 (m, 1H), 3.99-3.90 (m, 1H), 3.37-3.25 (m, 3H), 1.14 (d, J=6.2 Hz, 6H).

¹H NMR (600 MHz, DMSO-d₆) of compound 115: 8.92 (s, 1H), 8.18 (s, 1H), 7.68 (d, J=1.7 Hz, 1H), 7.51-7.41 (m, 2H), 7.13-7.07 (m, 3H), 7.00 (s, 1H), 6.44 (t, J=4.0 Hz, 1H), 6.37 (d, J=1.8 Hz, 1H), 6.34 (t, J=4.0 Hz, 1H), 6.25 (t, J=4.1 Hz, 1H), 5.76 (s, 1H), 5.23-5.16 (m, 2H), 4.58-4.48 (m, 3H), 4.40-4.30 (m, 3H), 3.92-3.86 (m, 1H), 3.48-3.39 (m, 1H), 3.29 (dd, J=8.2, 9.8 Hz, 1H), 3.22 (s, 3H), 1.99 (s, 1H), 1.20-1.14 (m, 1H).

¹H NMR (600 MHz, CHLOROFORM-d) of compound 120: 8.55 (d, J=4.4 Hz, 1H), 8.17 (s, 1H), 7.71 (d, J=7.7 Hz, 1H), 7.52 (d, J=1.8 Hz, 1H), 7.44 (s, 1H), 7.33 (d, J=1.7 Hz, 1H), 7.30 (dd, J=5.0, 7.7 Hz, 1H), 7.24 (d, J=1.7 Hz, 1H), 7.09 (s, 1H), 6.62 (s, 1H), 6.40 (br.s., 1H), 6.19-6.14 (m, 1H), 5.56 (d, J=1.8 Hz, 1H), 5.42 (d, J=15.6 Hz, 1H), 4.90-4.77 (m, 1H), 4.30-4.13 (m, 1H), 3.79 (s, 1H), 3.73-3.66 (m, 1H), 3.49-3.42 (m, 1H), 3.41-3.35 (m, 1H), 3.34-3.29 (m, 1H), 1.62-1.55 (m, 1H), 1.51-1.46 (m, 1H), 1.31-1.23 (m, 1H), 0.92-0.82 (m, 1H), 0.09-0.06 (m, 7H).

¹H NMR (500 MHz, DMSO-d₆) of compound 148 8.85 (s, 1H), 8.15 (s, 1H), 7.64 (s, 1H), 7.35 (s, 1H), 7.21-7.06 (m, 2H), 6.99-6.81 (m, 2H), 6.33-6.11 (m, 1H), 5.16 (brs, 1H), 4.85 (s, 2H), 4.57 (brs, 2H), 4.30 (brs, 2H), 3.70 (br.s., 2H), 3.68 (s, 3H).

COMPARATIVE EXAMPLE

Comparative Example 1: (7-(5-chloro-2-(isopropylamino)pyridin-4-yl)-2-(2-hydroxy-1-(3-(trifluoromethyl)benzene(yl)ethyl)-3,4-dihydropyrrolo[1,2-a]pyrazine-1(2H)-one)

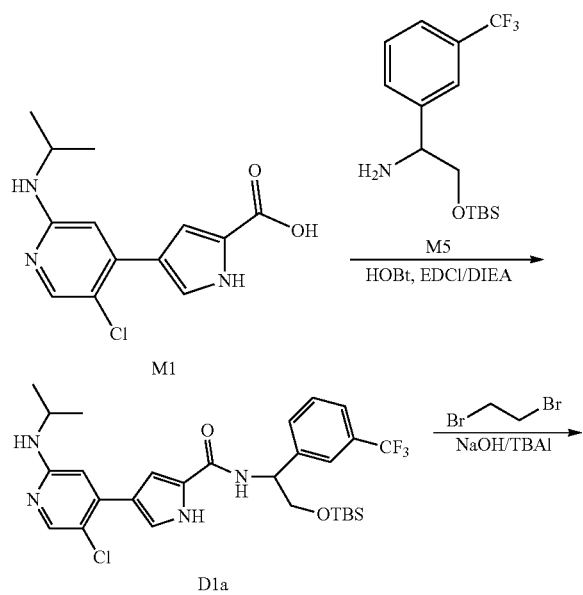

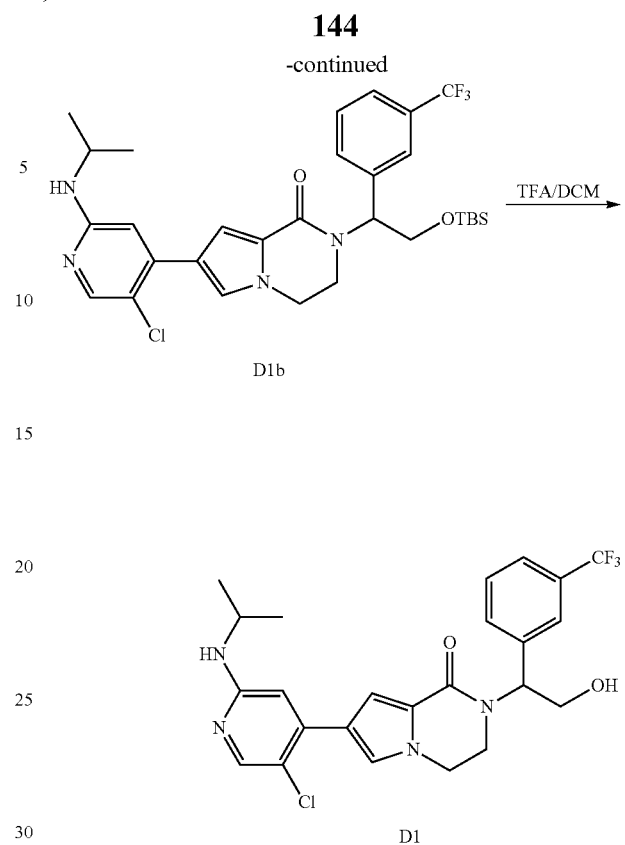

Step 1: Preparation of Compound D1a

Compound M1 (200 mg), M5 (271 mg), HOBt (115 mg), EDCI (170 mg) and DIEA (0.35 mL) were dissolved in DMF (5 mL), and the reaction was stirred at room temperature for 12 hrs. The reaction solution was added with EtOAc (10 mL) and 10 mL of water, and the layers were separated. The organic phase was dried with anhydrous sodium sulfate, filtered, and concentrated under reduced pressure. The residue was separated and purified by column chromatography to obtain 180 mg of colorless oil, namely D1a. LC-MS [M+H]⁺=581.2.

Step 2: Preparation of Compound D1b

Compound D1a (180 mg) and 1,2-dibromoethane (651 mg) were dissolved in DCE (5 mL), NaOH (3.5 mL, 1M) aqueous solution, TBAI (13 mg) were added, and the reaction was stirred at 80° C. for 12 hrs. The reaction solution was added with DCM (10 mL) and 10 mL of water, and the layers were separated. The organic phase was dried over anhydrous sodium sulfate, filtered, and concentrated under reduced pressure. The residue was separated and purified by column chromatography to obtain 120 mg of colorless oil, namely D1b. LC-MS [M+H]⁺=607.2.

Step 3: Preparation of Comparative Compound D1

Compound D1b (120 mg) was dissolved in DCM (5 mL), TFA (0.5 mL) was added, and the reaction was stirred at room temperature for 2 hrs. The reaction solution was added with DCM (10 mL) and 10 mL of water, and the layers were separated. The organic phase w as dried over anhydrous sodium sulfate, filtered, and concentrated under reduced pressure. The residue was separated and purified by column chromatography to obtain 5.3 mg of light yellow oil, namely D1. LC-MS [M+H]⁺=493.2.

Comparative Example D2: (S)-4-(5-chloro-2-(iso-propylamino)pyridin-4-yl)-N'-(1-(3-chloro phenyl)-2-hydroxyethyl)-1H-pyrazole-1-carboxamide Comparative Example D3: (S)-4-(5-chloro-2-(iso-propylamino)pyridin-4-yl)-1H-(1-(3-chloro phenyl)-2-hydroxyethyl)-1-methyl-1H-imidazole-2-carboxamide) preparation

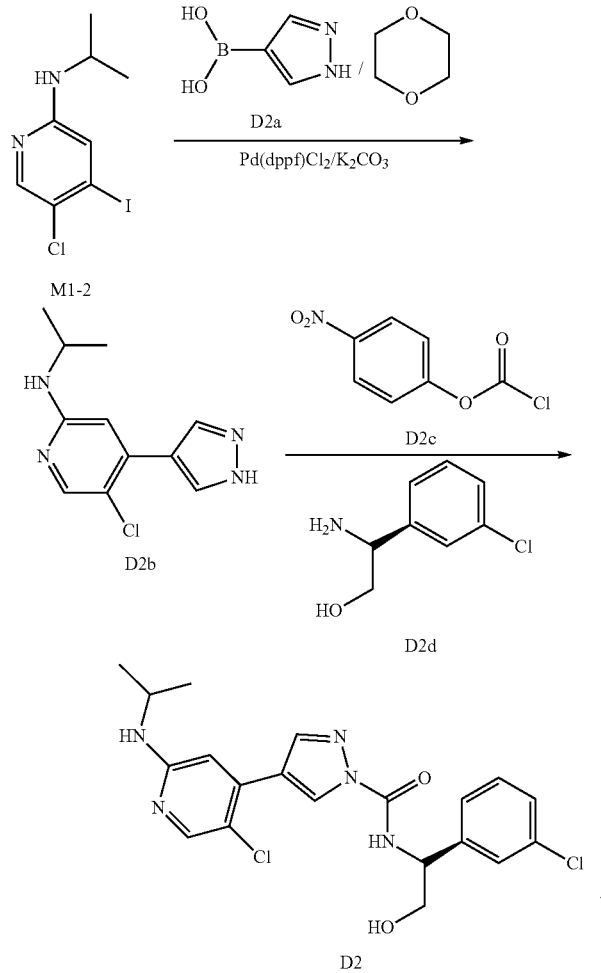

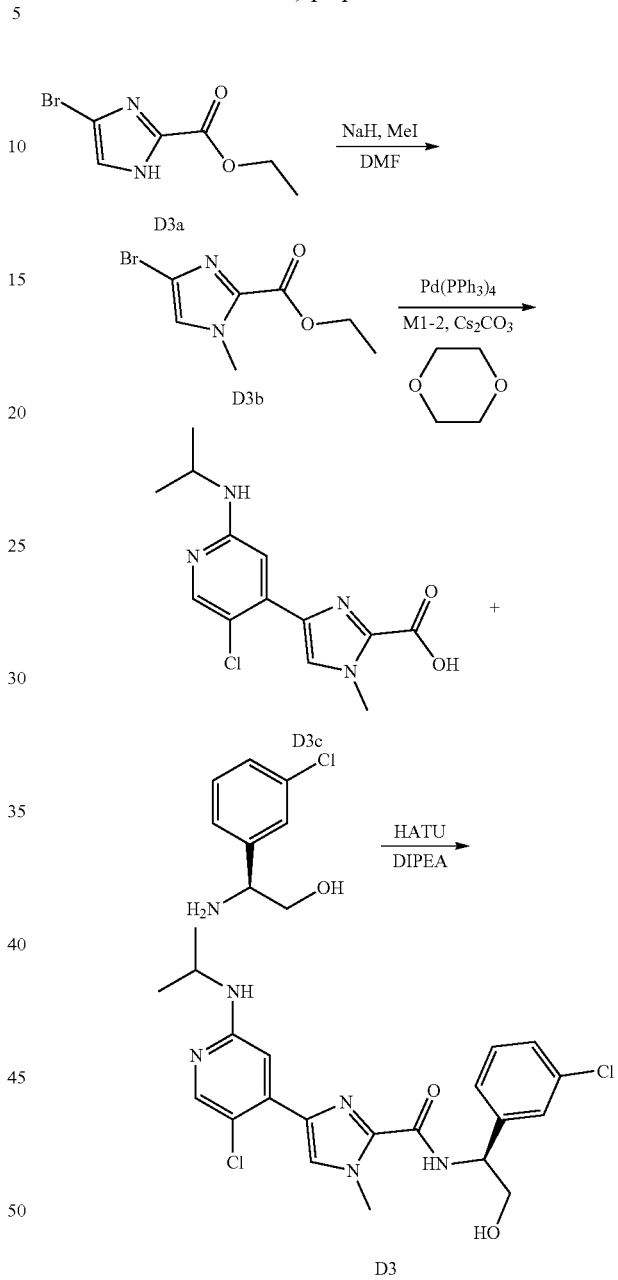

Step 1: Preparation of Compound D2b

M1-2 (300 mg), D2a (270 mg), Pd(dppf)$_2$Cl$_2$ (170 mg), K$_2$CO$_3$ (480 mg) were dissolved in dioxane (10 mL), protected by nitrogen, and stirred at 100° C. for 12 hrs. The reaction solution was added with EtOAc (10 mL) and 10 mL of water, and the layers were separated. The organic phase was dried over anhydrous sodium sulfate, filtered, and concentrated under reduced pressure. The residue was separated and purified by column chromatography to separate and purify 100 mg of a colorless oil, namely D2b. LC-MS [M+H]$^+$=237.1.

Step 2: Preparation of Comparative Compound D2

D2b (100 mg) was dissolved in THF (10 mL), under ice bath, NaHCO$_3$ (130 mg) and D2c (150 mg) were slowly added to the above reaction, and the reaction was stirred under ice bath for 1 h, then Et$_3$N (0.35 mL) and D2d (170 mg) were added and stirred under ice bath for 2 hrs. The reaction solution was added with EtOAc (10 mL) and 10 mL of water, and the layers were separated. The organic phase was dried with anhydrous sodium sulfate, filtered, and concentrated under reduced pressure. The residue was separated and purified by column chromatography to obtain 40 mg of white solid, namely D2. LC-MS [M+H]$^+$=434.1.

Step 1: Preparation of Compound D3b 4-bromo-1H-imidazole-2-carboxylic acid ethyl ester (D3a, 218 mg) was dissolved in DMF (10 mL), cooled to 0° C., sodium hydrogen (60 mg) was slowly added, and after reacting for 30 min, methyl iodide was added, stirring at room temperature overnight. After quenching with water (20 ml), ethyl acetate (3*20 mL) was extracted, the organic phases were combined and washed with saturated aqueous ammonium chloride solution (3*20 mL), the organic phases were separated, dried over anhydrous sodium sulfate, filtered, and concentrated. The residue was purified by column chromatography (petroleum ether:ethyl acetate=3:1) to obtain 148 mg of compound D3b LC-MS [M+H]$^+$=233.0.

Step 2: Preparation of Compound D3c

D3b (148 mg), M1-2 (133 mg), cesium carbonate (240 mg) and Pd(PPh$_3$)$_4$ (37 mg) were dissolved in 1,4-dioxane (8 mL) and water (2 mL), and the reaction was replaced with nitrogen three times, it was placed in an oil bath at 100° C. for 16 hrs. The reaction solution was cooled to room temperature, diluted with ethyl acetate, washed with water (3*10 mL), the product was dissolved in the aqueous phase, and the aqueous phase was adjusted to pH=6 with dilute hydrochloric acid, extracted with ethyl acetate (8*10 mL), and the organic phases were combined, dried with anhydrous sodium sulfate and passed through the column to obtain 60 mg of product. LC-MS [M+H]$^+$=295.1.

Step 3: Preparation of Comparative Compound D3

D3c (60 mg), HATU (91 mg) and DIPEA (0.1 mL) was dissolved in DMF (4 mL), stirring for 2 min, (S)-2-amino-2-(3-chlorophenyl)ethyl-1-alcohol (42 mg) was added, the reaction was stirred at room temperature for 4 hrs. After the reaction solution was diluted with ethyl acetate, washed with saturated ammonium chloride (3*10 mL), the organic phase was dried, concentrated, and purified to obtain 2.6 mg of product. LC-MS [M+H]$^+$=448.1.

The comparative example compound 4-10 (D4-D10) in Table 6 was synthesized by referring to the synthetic method of the similar compound in the example compound and the comparative example compound with the commercially available raw materials.

TABLE 6

| Comparative Example | Structure | Chemical Name | LC-MS [M + H]$^+$ |
|---|---|---|---|
| D4 | 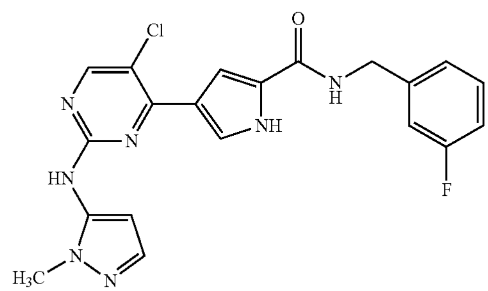 [SMILES: Cn1nccc1Nc1ncc(Cl)c(-c2c[nH]c(C(=O)NCc3cccc(F)c3)c2)n1] | N-(3-fluorobenzyl)-4-(5-methyl-2-((1-methyl-1h-pyrazole-5-yl)amino)pyrimidin-4-yl)-1h-pyrrole-2-formamide | 406.2 |
| D5 | 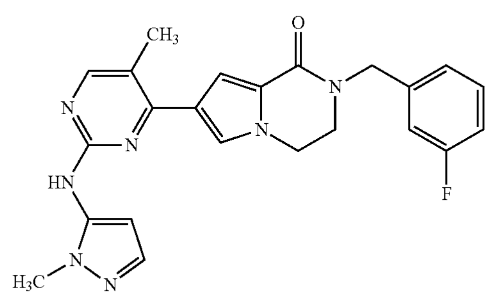 [SMILES: Cc1cnc(Nc2ccnn2C)nc1-c1cc2n(c1)CCN(Cc1cccc(F)c1)C2=O] | 2-(3-fluorobenzyl)-7-(5-methyl-2-((1-methyl-1h-pyrazole-5-yl)amino)pyrimidin-4-yl)-3,4-dihydropyrrolo[1,2-a]pyrazine-1(2H)-one | 432.2 |
| D6 | 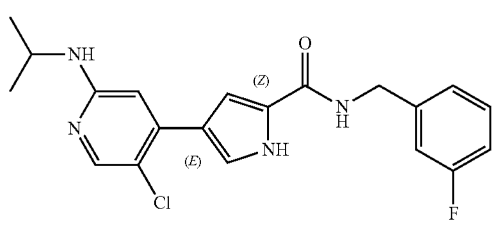 [SMILES: CC(C)Nc1cc(-c2c[nH]c(C(=O)NCc3cccc(F)c3)c2)c(Cl)cn1] | 4-(5-chloro-2-(isopropylamino)pyridine-4-yl)-N-(3-fluorobenzyl)-1h-pyrrole-2-formamide | 387.1 |
| D7 | 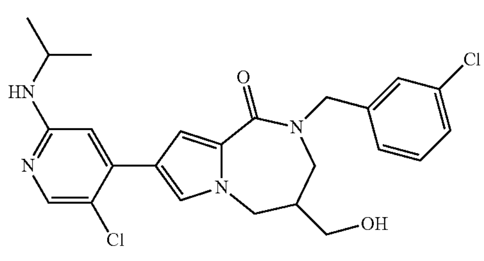 [SMILES: CC(C)Nc1cc(-c2cc3n(c2)CC(CO)CN(Cc2cccc(Cl)c2)C3=O)c(Cl)cn1] | 8-(5-chloro-2-(isopropylamino)pyridin-4-yl)-2-(3-chlorophenylmethyl)-4-(hydroxymethyl)-2,3,4,5-tetrahydro-1h-pyrrolo[1,2-a][1,4]diazepine-1-one | 473.1 |

TABLE 6-continued

| Comparative Example | Structure | Chemical Name | LC-MS [M + H]+ |
|---|---|---|---|
| D8 | 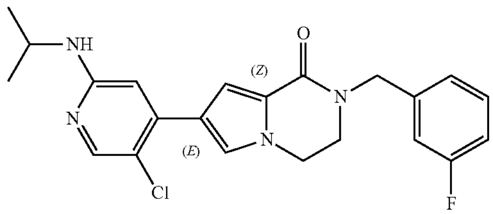 [SMILES: CC(C)Nc1cc(-c2cc3n(c2)CCN(Cc2cccc(F)c2)C3=O)c(Cl)cn1] | 7-(5-chloro-2-(isopropylamino) pyridin-4-yl)-2-(3-fluorobenzyl)- 3,4-dihydropyrrolo[1,2-a] pyrazine-1(2H)-one | 413.2 |
| D9 | 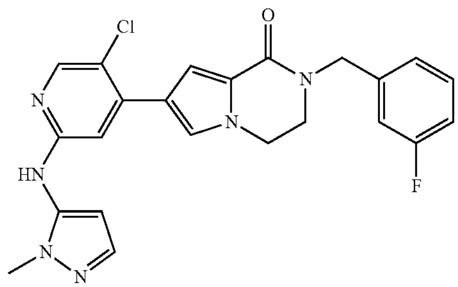 [SMILES: Cn1nccc1Nc1cc(-c2cc3n(c2)CCN(Cc2cccc(F)c2)C3=O)c(Cl)cn1] | 7-(5-chloro-2- ((1-methyl-1h-pyrazole-5-yl) amino)pyridine-4-yl)-2- (3-fluorobenzyl)- 3,4-dihydropyrrolo[1,2-a] pyrazine-1(2H)-one | 451.1 |
| D10 | 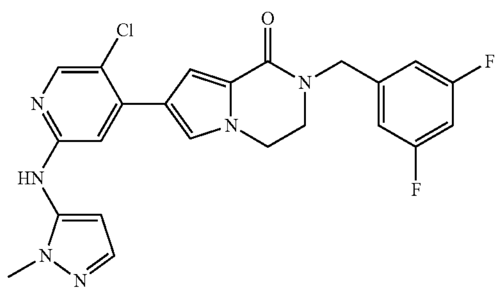 [SMILES: Cn1nccc1Nc1cc(-c2cc3n(c2)CCN(Cc2cc(F)cc(F)c2)C3=O)c(Cl)cn1] | 7-(5-chloro-2- ((1-methyl-1h-pyrazole-5-yl) amino)pyridine-4-yl)-2- (3,5-difluorobenzyl)- 3,4-dihydropyrrolo[1,2-a] pyrazine-1(2H)-one | 469.1 |

Biological Assay

Example A: Kinase Assay

The compound was diluted to the desired concentration with DMSO, transferred 100 μL to a 96-well plate, and performed a gradient dilution 10 μL of compound from each well was taken and mixed with 90 μL of kinase buffer, and then transferred 5 μL from each well to a 384-well plate. Kinase and FAM-labeled peptide and ATP were added to 1× kinase alkaline buffer to obtain 2.5× enzyme solution and 2.5× peptide solution, 10 μL of 2.5× enzyme solution was added to the 384-well assay plate. After incubating for 10 minutes at room temperature, 10 μL of 2.5× peptide solution was added to the 384-well plate. After reacting for a specific time at 28*0, 25 μL of termination buffer was added to stop reaction. After reading the collected data on Caliper, the data was converted to inhibition percentage.

Inhibition percentage=(maximum value−conversion value)/(maximum value−minimum value)*100.

The "maximum" is the DMSO control, the "minimum" indicates the low control.

Graphpad Prism software was used to perform curve fitting and obtain $IC_{50}$ value.

All the compounds in the examples have good inhibition on ERK1 and ERK2, most of the compounds inhibit ERK1 and ERK2 with $IC_{50}$<10 nM. The $IC_{50}$ data that some of the example compounds and comparative compounds 3, 6 and 7 (D3, D6, D7) inhibit ERK1 and ERK2 is shown in Table 7.

TABLE 7

| Example | $IC_{50}$(nM) ERK1 | $IC_{50}$(nM) ERK2 |
|---|---|---|
| D3 | 163.4 | 115.5 |
| D6 | 44 | 26 |
| D7 | >300 | >300 |
| 1 | 3.0 | 3.4 |
| 2 | 1.0 | 0.9 |
| 3 | 0.9 | 0.7 |
| 4 | 1.8 | 1.8 |
| 5 | 1.5 | 1.2 |
| 6 | 0.8 | 0.5 |
| 8 | 1.3 | 1.4 |
| 10 | 0.89 | 0.87 |
| 13 | 0.74 | 0.89 |
| 14 | 0.7 | 0.6 |
| 16 | 0.9 | 0.6 |
| 17 | 0.47 | 0.40 |
| 18 | 0.4 | 0.49 |
| 19 | 0.3 | 0.6 |
| 20 | 0.34 | 0.56 |
| 21 | 0.73 | 0.76 |
| 22 | 0.43 | 0.34 |
| 23 | 0.42 | 0.48 |
| 24 | 0.65 | 0.53 |
| 25 | 1.3 | 0.84 |
| 26 | 1.3 | 1.4 |
| 27 | 0.96 | 0.59 |
| 28 | 0.90 | 1.6 |
| 29 | 0.68 | 0.83 |
| 30 | 0.31 | 0.20 |
| 31 | 0.30 | 0.32 |

TABLE 7-continued

| Example | IC$_{50}$(nM) ERK1 | ERK2 |
|---|---|---|
| 32 | 0.44 | 0.27 |
| 33 | 0.45 | 0.40 |
| 34 | 0.2 | 0.4 |
| 35 | 0.84 | 0.48 |
| 42 | 2.5 | 1.6 |
| 43 | 0.6 | 0.5 |
| 45 | 0.9 | 1.2 |
| 46 | 2.8 | 1.4 |
| 47 | / | 0.9 |
| 49 | 0.9 | 0.8 |
| 50 | 0.72 | 0.89 |
| 56 | 0.95 | 0.64 |
| 57 | 0.9 | 0.5 |
| 59 | 0.51 | 0.49 |
| 60 | 0.54 | 0.46 |
| 61 | 0.38 | 0.41 |
| 62 | 0.93 | 0.39 |
| 63 | 1.5 | 1.6 |
| 65 | 0.97 | 1.6 |
| 67 | 1.6 | 1.2 |
| 70 | 1.8 | 2.0 |
| 71 | 1.1 | 1.4 |
| 73 | 3.1 | 0.9 |
| 74 | 1.2 | 1.3 |
| 75 | 0.76 | 0.87 |
| 77 | 1.1 | 1.5 |
| 78 | 0.87 | 1.5 |
| 79 | 0.36 | 0.39 |
| 80 | 0.73 | 0.68 |
| 81 | 1.1 | 1.5 |
| 86 | 0.91 | 0.80 |
| 88 | / | 1.0 |
| 89 | / | 1.1 |
| 95 | / | 0.9 |
| 96 | / | 1.8 |
| 97 | / | 0.97 |
| 110 | 0.6 | 0.7 |
| 111 | 0.9 | 0.9 |
| 112 | 0.4 | 1.0 |
| 114 | 1.3 | 1.3 |
| 115 | 1.6 | 1.2 |
| 117 | 1.2 | 1.0 |
| 121 | 0.2 | 0.2 |
| 122 | 0.65 | 0.71 |
| 123 | 0.53 | 0.44 |
| 124 | 0.79 | 0.98 |
| 126 | 0.57 | 0.32 |
| 127 | 1.6 | 0.35 |
| 128 | 0.65 | 0.89 |
| 131 | 0.83 | 1.4 |
| 132 | 0.8 | 0.9 |
| 133 | 0.7 | 0.7 |
| 134 | 0.5 | 0.5 |
| 135 | 1.6 | 0.7 |
| 136 | 0.9 | 0.4 |
| 137 | 2.7 | 0.6 |
| 140 | 1.3 | 1.1 |
| 141 | 0.93 | 0.87 |
| 148 | / | 0.7 |
| 151 | / | 0.2 |
| 152 | / | 0.3 |
| 159 | 1.9 | 1.7 |
| 160 | / | 0.89 |
| 163 | / | 0.62 |
| 164 | / | 0.66 |
| 168 | / | 0.59 |

Note:
"/" means not tested.

Example B: Cell Proliferation Assay (COLO205)

COLO205 cells were spread into a 96-well plate at 135 μL/well at 2000 cells. After incubating overnight, compound solutions of gradient concentration was prepared, and added 15 μL of DMSO solution of the test compound of each concentration to the cells of each well. The final concentration of the compound was 30000, 10000, 3333.3, 1111.1, 370.4, 123.5, 41.2, 13.7, 4.6, 0 nM (the final concentration of DMSO was 0.5%). 5% $CO_2$ was incubated for 120 h at 37° C. 50 μL of Cell-titer Glo working solution was added to each well, shaked and mixed, and incubated at room temperature for 10 minutes. The multi-functional microplate reader read the luminescence value, and converted the luminescence value reading into inhibition percentage.

Inhibition percentage=(maximum value−reading)/(maximum value−minimum value)*100.

The "maximum value" was the DMSO control, the "minimum value" indicates the cell-free control group.

Graphpad Prism software was used to perform curve fitting and obtain IC$_{50}$ value.

All the example compounds have good inhibition on COLO205 cells, most of the compounds inhibited COLO205 cells with IC$_{50}$<100 nM. Refer to table 8 for the IC$_{50}$ data of some of the example compounds and comparative example compounds 1-8 (D1-D8) and AZD0364 on COLO205 cells.

TABLE 8

| Example | COLO205 Cell IC$_{50}$(nM) |
|---|---|
| D1 | 7332 |
| D2 | 12192 |
| D3 | >10000 |
| D4 | 252.1 |
| D5 | 93.7 |
| D6 | >10000 |
| D7 | >10000 |
| D8 | 1627 |
| 2 | 77.5 |
| 6 | 9 |
| 8 | 36.08 |
| 10 | 16.67 |
| 13 | 50.8 |
| 16 | 56 |
| 17 | 25 |
| 18 | 56.6 |
| 20 | 76.7 |
| 21 | 73.3 |
| 22 | 35.3 |
| 23 | 18.7 |
| 24 | 50 |
| 27 | 9.6 |
| 29 | 7.6 |
| 33 | 76 |
| 35 | 16.64 |
| 45 | 3.3 |
| AZD0364 | 72.42 |
| 50 | 11.3 |
| 51 | 24.4 |
| 52 | 13.6 |
| 53 | 3.9 |
| 62 | 17.52 |
| 86 | 29.4 |
| 88 | 28.8 |
| 89 | 12 |
| 95 | 6.9 |
| 96 | 11 |
| 98 | 10.7 |
| 99 | 21.7 |
| 100 | 19 |
| 102 | 6.4 |
| 115 | 16.7 |
| 126 | 30.31 |
| 130 | 20.4 |
| 148 | 12.9 |
| 150 | 17.8 |
| 152 | 14.3 |

TABLE 8-continued

| Example | COLO205 Cell IC$_{50}$(nM) |
|---|---|
| 160 | 11.36 |
| 163 | 15.4 |
| 164 | 28.9 |
| 168 | 11 |

Example C: Cell Proliferation Assay (HCT 116)

The HCT 116 cells were paved in a 96-well plate at 1200 cells, 160 μL/well. After incubating overnight, the compound solutions of gradient concentration was prepared, and 40 μL of DMSO solution of the test compound of each concentration was added to the cells of each well. The final concentration of the compound was 30000, 10000, 3333.3, 1111.1, 370.4, 123.5, 41.2, 13.7, 4.6, 0 nM (the final concentration of DMSO was 0.5%). 5% $CO_2$ was incubated for 120 h at 37° C. 50 μL of Cell-titer Glo working solution was added to each well, shaked and mixed, and incubated at room temperature for 10 minutes. The multi-functional microplate reader read the luminescence value, and converted the luminescence value reading into inhibition percentage.

Inhibition percentage=(maximum value−reading)/(maximum value−minimum value)*100.

The "maximum value" was the DMSO control, the "minimum value" indicated the cell-free control group.

Graphpad Prism software was used to perform curve fitting and obtain IC$_{50}$ value.

All the compounds in the examples have good inhibition on HCT116 cells. Most of the compounds inhibit HCT116 cells with IC$_{50}$<100 nM. Refer to Table 9 for the IC$_{50}$ data of some of the compounds in the examples and comparative compounds 9-10 (D9-D10) and AZD0364 on HCT116 cells.

TABLE 9

| Example | HCT 116 Cell IC$_{50}$(nM) |
|---|---|
| D9 | 53.6 |
| D10 | 52.3 |
| 29 | 6.3 |
| 35 | 10.41 |
| 45 | 6.2 |
| 50 | 6.5 |
| 52 | 10.7 |
| 54 | 16.2 |
| 62 | 7.99 |
| 71 | 27 |
| 83 | 23 |
| 95 | 6.9 |
| 98 | 9 |
| 99 | 18 |
| AZD0364 | 83 |
| 100 | 19.9 |
| 102 | 11.6 |
| 126 | 14.3 |
| 130 | 5.3 |
| 148 | 6.3 |
| 149 | 21.2 |
| 150 | 9.5 |
| 152 | 7.6 |
| 160 | 10.7 |
| 161 | 24.6 |
| 163 | 18.8 |
| 168 | 8.4 |

Although the present invention has been comprehensively described through its embodiments, it is worth noting that various changes and modifications are obvious to those skilled in the art. Such changes and modifications should be included in the scope of the appended claims of the present invention.

The invention claimed is:

1. A compound of the Formula (I) or a pharmaceutically-acceptable salt, solvate, or prodrug thereof,

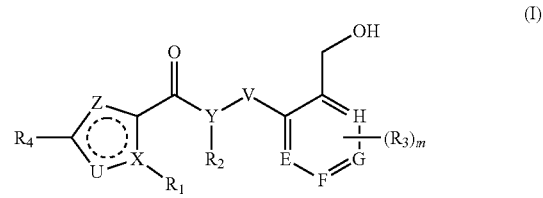

(I)

wherein,
⸺ stands for a single or double bond;
X and Y are N;
Z and U are independently selected from the group consisting of O, S, $NR_{10}$ and $C(R_{10})_2$, wherein $R_{10}$ is independently H, or unsubstituted or substituted $C_{1-8}$ alkyl;
V is $(CH_2)_n$;
E, F, G and H are independently N or CH;
$R_1$ and $R_2$ are independently absent or are selected from the group consisting of H, halogen, hydroxyl, CN, $C_{1-8}$ alkyl, $C_{1-8}$ alkoxy, $C_{2-8}$ alkenyl, $C_{2-8}$ alkynyl, $C_{3-10}$ cycloalkyl, $C_{6-10}$ aryl, $C_{5-10}$ heteroaryl and $C_{3-10}$ heterocyclyl, wherein any of the $C_{1-8}$ alkyl, $C_{1-8}$ alkoxy, $C_{2-8}$ alkenyl, $C_{2-8}$ alkynyl, $C_{3-10}$ Cycloalkyl, $C_{6-10}$ aryl, $C_{5-10}$ heteroaryl or $C_{3-10}$ heterocyclyl is unsubstituted or substituted with halogen, hydroxy or $C_{1-8}$ alkyl; or
$R_1$ and $R_2$ together with the atoms to which they are attached form a $C_{5-10}$ cycloalkyl, $C_{5-10}$ heterocyclyl or $C_{5-10}$ heteroaryl group, wherein any of the $C_{5-10}$ cycloalkyl, $C_{5-10}$ heterocyclyl or $C_{5-10}$ heteroaryl is unsubstituted or substituted with halogen, hydroxy, CN, $C_{1-8}$ alkyl, —$C_{1-8}$ alkyl-hydroxy, —$C_{1-8}$ alkyl-halogen, —$C_{1-8}$ alkyl-$C_{1-8}$ alkoxy, —$C_{1-8}$ alkyl-$C_{1-8}$ alkoxy-$C_{1-8}$ alkoxy, —(C=O)O$C_{1-8}$ alkyl, $C_{1-8}$ alkoxy, $C_{2-8}$ alkenyl, $C_{2-8}$ alkynyl, $C_{3-10}$ cycloalkyl, $C_{6-10}$ aryl, $C_{5-10}$ heteroaryl or $C_{3-10}$ heterocyclyl; or any of the $C_{5-10}$ cycloalkyl, $C_{5-10}$ heterocyclyl or $C_{5-10}$ heteroaryl group and an additional $C_{3-10}$ cycloalkyl group, $C_{3-10}$ heterocyclyl, $C_{6-10}$ aryl group or $C_{5-10}$ heteroaryl group form a spiro ring, wherein any of the additional $C_{3-10}$ cycloalkyl group, $C_{3-10}$ heterocyclyl, $C_{6-10}$ aryl or $C_{5-10}$ heteroaryl is unsubstituted or substituted with $C_{1-8}$ alkyl;
$R_3$ is selected from the group consisting of halogen, hydroxy, CN, $C_{1-8}$ alkyl, $C_{1-8}$ alkoxy, $C_{2-8}$ alkenyl, $C_{2-8}$ alkynyl, $C_{3-10}$ cycloalkyl, $C_{6-10}$ aryl, $C_{5-10}$ heteroaryl and $C_{3-10}$ heterocyclyl, wherein any of the $C_{1-8}$ alkyl, $C_{1-8}$ alkoxy, $C_{2-8}$ alkenyl, $C_{2-8}$ alkynyl, $C_{3-10}$ cycloalkyl, $C_{6-10}$ aryl, $C_{5-10}$ heteroaryl or $C_{3-10}$ heterocyclyl is unsubstituted or substituted with halogen, hydroxy or $C_{1-8}$ alkyl;
$R_4$ is selected from the group consisting of $C_{5-10}$ cycloalkyl, $C_{6-10}$ aryl, $C_{5-10}$ heteroaryl and $C_{5-10}$ heterocyclyl, wherein any of the $C_{5-10}$ cycloalkyl, $C_{6-10}$ aryl, $C_{5-10}$ heteroaryl or $C_{5-10}$ heterocyclyl is unsubstituted or substituted with halogen, hydroxy, amino, CN, $C_{1-8}$ alkyl, $C_{1-8}$ haloalkyl or $NR_5R_6$, wherein $R_5$ and $R_6$ are independently selected from the group consisting of H, halogen, hydroxyl, CN, $C_{1-8}$ alkyl, —(C=O)$C_{1-8}$ alkyl, $C_{3-10}$ cycloalkyl, $C_{6-10}$ aryl, $C_{5-10}$ heteroaryl, $C_{3-10}$ heterocyclyl, —(C=O)$C_{5-10}$ heteroaryl or —(C=O)$C_{3-10}$ heterocyclyl, wherein any of the $C_{1-8}$ alkyl, —(C=O) $C_{1-8}$ alkyl, $C_{3-10}$ cycloalkyl, $C_{6-10}$ aryl, $C_{5-10}$ heteroaryl, $C_{3-10}$ heterocyclyl, —(C=O)$C_{5-10}$ heteroaryl or —(C=O)$C_{3-10}$ heterocyclyl is unsubstituted or substituted with halogen, hydroxy, amino, CN, $C_{1-8}$ alkyl, $C_{1-8}$ haloalkyl, —(C=O)$C_{1-8}$ alkyl, $C_{1-8}$ alkoxy, $C_{5-10}$ heteroaryl or $C_{3-10}$ heterocyclyl;

each heterocyclyl or heteroaryl contains 1, 2 or 3 heteroatoms independently selected from the group consisting of N, O and S;

m and n are independently 0, 1, 2, 3, or 4.

2. The compound of the Formula (I) or a pharmaceutically-acceptable salt, solvate, or prodrug thereof as claimed in claim 1, wherein both Z and U are CH.

3. The compound of the Formula (I) or a pharmaceutically-acceptable salt, solvate, or prodrug thereof as claimed in claim 1, wherein Z is S, and U is CH; Z is CH, and U is N; or Z is N, and U is CH.

4. The compound of the Formula (I) or a pharmaceutically-acceptable salt, solvate, or prodrug thereof as claimed in claim 1, wherein X is C, Z is S, and U is N.

5. The compound of the Formula (I) or a pharmaceutically-acceptable salt, solvate, or prodrug thereof as claimed in claim 1, wherein both $R_1$ and $R_2$ are H.

6. The compound of the Formula (I) or a pharmaceutically-acceptable salt, solvate, or prodrug thereof as claimed in claim 1, wherein $R_1$ is absent, and $R_2$ is H.

7. The compound of the Formula (I) or a pharmaceutically-acceptable salt, solvate, or prodrug thereof as claimed in claim 1, wherein $R_1$ and $R_2$ together with the atoms to which they are attached form $C_{5-8}$ cycloalkyl or $C_{5-8}$ heterocyclyl, wherein any of the $C_{5-8}$ cycloalkyl or $C_{5-8}$ heterocyclyl is unsubstituted or substituted with F, Cl, hydroxy, CN, $C_{1-6}$ alkyl, —$C_{1-6}$ alkyl-hydroxy, —$C_{1-6}$ alkyl-chloro, —$C_{1-6}$ alkyl-$C_{1-6}$ alkoxy, —(C=O)O$C_{1-6}$ alkyl, $C_{1-6}$ alkoxy, $C_{3-6}$ cycloalkyl, phenyl, $C_{5-8}$ heteroaryl or $C_{3-6}$ heterocyclyl; or any of the $C_{5-8}$ cycloalkyl or $C_{5-8}$ heterocyclyl and an additional $C_{3-7}$ cycloalkyl, $C_{3-7}$ heterocyclyl, phenyl or $C_{5-8}$ heteroaryl group forms a spiro ring, wherein any of the additional $C_{3-7}$ cycloalkyl, $C_{3-7}$ heterocyclyl, phenyl or $C_{5-8}$ heteroaryl is unsubstituted or substituted with $C_{1-6}$ alkyl, and each heterocyclyl or heteroaryl contains 1 or 2 heteroatoms independently selected from the group consisting of N, O and S.

8. The compound of the Formula (I) or a pharmaceutically-acceptable salt, solvate, or prodrug thereof as claimed in claim 1, wherein

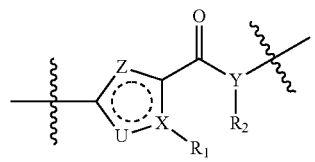

is selected from the group consisting of

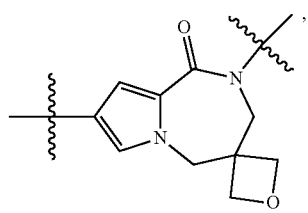

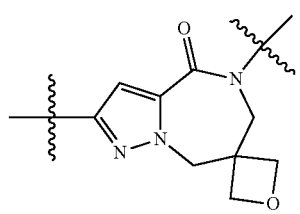

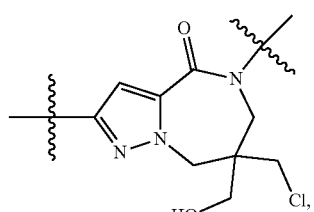

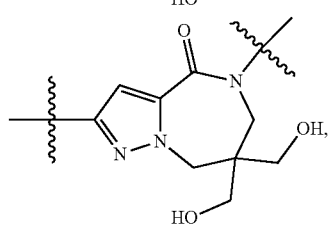

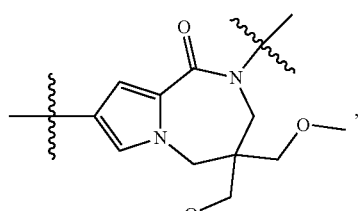

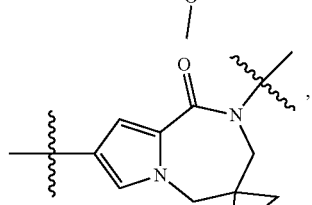

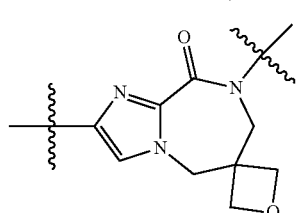

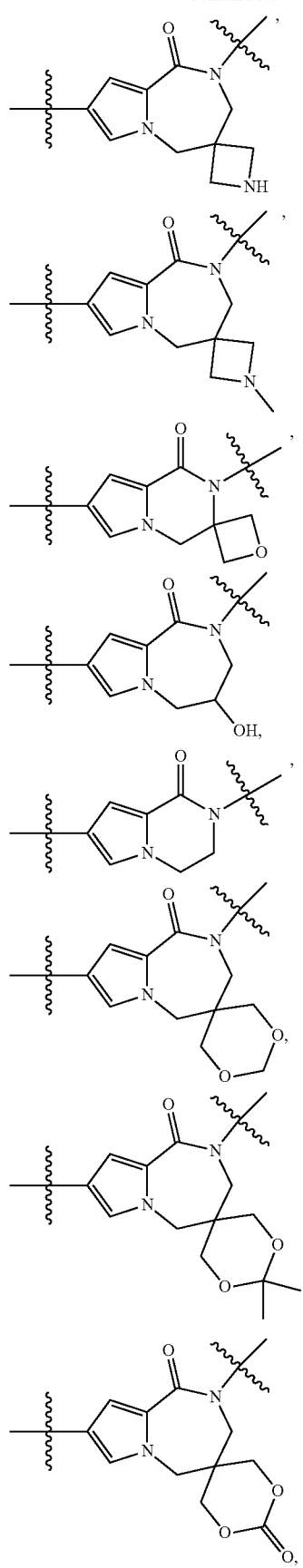
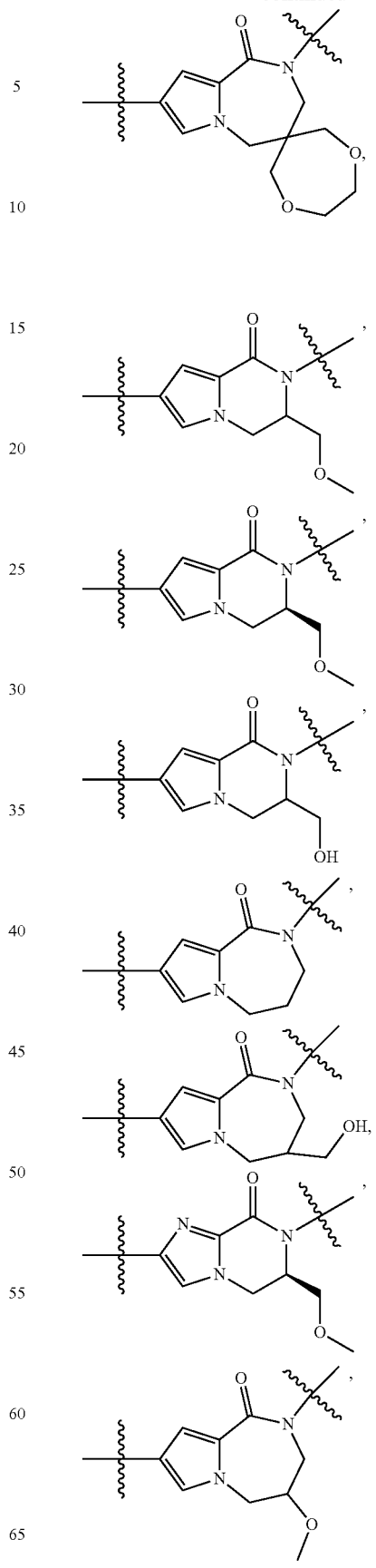

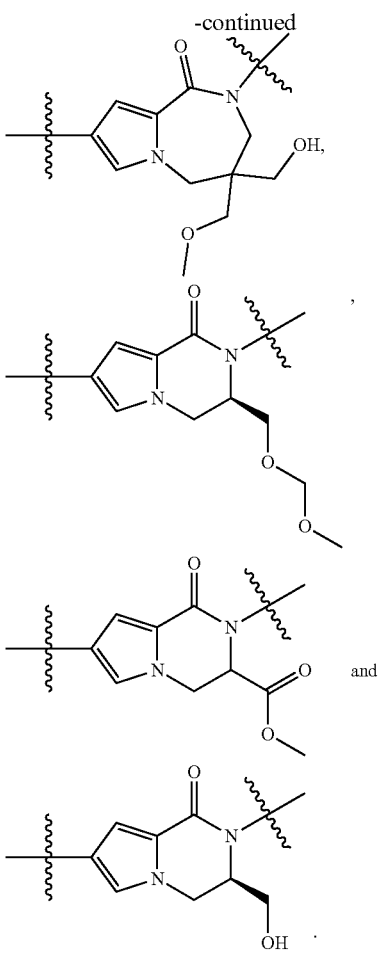

9. The compound of the Formula (I) or a pharmaceutically-acceptable salt, solvate, or prodrug thereof as claimed in claim 8, wherein

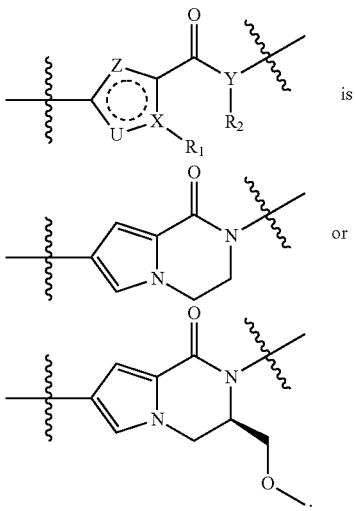

10. The compound of the Formula (I) or a pharmaceutically-acceptable salt, solvate, or prodrug thereof as claimed in claim 1, wherein n is 1.

11. The compound of the Formula (I) or a pharmaceutically-acceptable salt, solvate, or prodrug thereof as claimed in claim 1, wherein E, F, G, and H are defined in the following groups:
(v) E, F, G and H are all CH;
(vi) E, F, G are CH, and H is N;
(vii) E is N, and F, G, and H are CH; or
(viii) F is N, and E, G, and H are CH.

12. The compound of the Formula (I) or a pharmaceutically-acceptable salt, solvate, or prodrug thereof as claimed in claim 11, wherein E, F, G and H are all CH.

13. The compound of the Formula (I) or a pharmaceutically-acceptable salt, solvate, or prodrug thereof as claimed in claim 1, wherein $R_3$ is independently selected from the group consisting of hydroxy, CN, halogen, $C_{1-6}$ alkyl and $C_{1-6}$ haloalkyl.

14. The compound of the Formula (I) or a pharmaceutically-acceptable salt, solvate, or prodrug thereof as claimed in claim 13, wherein $R_3$ is independently selected from the group consisting of hydroxyl, CN, F, C, methyl and trifluoromethyl.

15. The compound of the Formula (I) or a pharmaceutically-acceptable salt, solvate, or prodrug thereof as claimed in claim 1, wherein $R_4$ is selected from the group consisting of $C_{5-6}$ cycloalkyl, phenyl, $C_{5-6}$ heteroaryl and $C_{5-6}$ heterocyclyl, wherein any of the $C_{5-6}$ cycloalkyl, phenyl, $C_{5-6}$ heteroaryl or $C_{5-6}$ heterocyclyl is unsubstituted or substituted with halogen, hydroxy, amino, CN, $C_{1-6}$ alkyl, $C_{1-6}$ haloalkyl or $NR_5R_6$.

16. The compound of the Formula (I) or a pharmaceutically-acceptable salt, solvate, or prodrug thereof as claimed in claim 15, wherein $R_4$ is selected from the group consisting of phenyl, pyridyl or pyrimidinyl, wherein any of the phenyl, pyridyl or pyrimidinyl is unsubstituted or is substituted with F, Cl, CN, methyl, trifluoromethyl or $NR_5R_6$.

17. The compound of the Formula (I) or a pharmaceutically-acceptable salt, solvate, or prodrug thereof as claimed in claim 1, wherein $R_5$ and $R_6$ are independently selected from the group consisting of H, halogen, hydroxyl, $C_{1-6}$ alkyl, —(C=O)$C_{1-6}$ alkyl, $C_{3-7}$ cycloalkyl, phenyl, $C_{5-10}$ heteroaryl and $C_{3-10}$ heterocyclyl, wherein any of the $C_{1-6}$ alkyl, —(C=O)$C_{1-6}$ alkyl, $C_{3-7}$ cycloalkyl, phenyl, $C_{5-10}$ heteroaryl or $C_{3-10}$ heterocyclyl is unsubstituted or substituted with F, Cl, hydroxy, amino, CN, $C_{1-6}$alkoxy, $C_{1-6}$ alkyl, —(C=O)$C_{1-6}$ alkyl, $C_{1-6}$ haloalkyl, —$C_{5-6}$ heterocyclyl, —$C_{5-6}$ heteroaryl, —$C_{5-6}$ heterocyclyl-$C_{1-6}$ alkyl or —$C_{5-6}$ heteroaryl-$C_{1-6}$ alkyl.

18. The compound of the Formula (I) or a pharmaceutically-acceptable salt, solvate, or prodrug thereof as claimed in claim 17, wherein $R_5$ and $R_6$ are independently selected from the group consisting of H, methyl, ethyl, propyl, isopropyl,

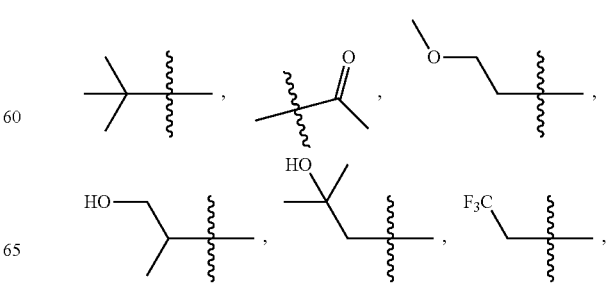

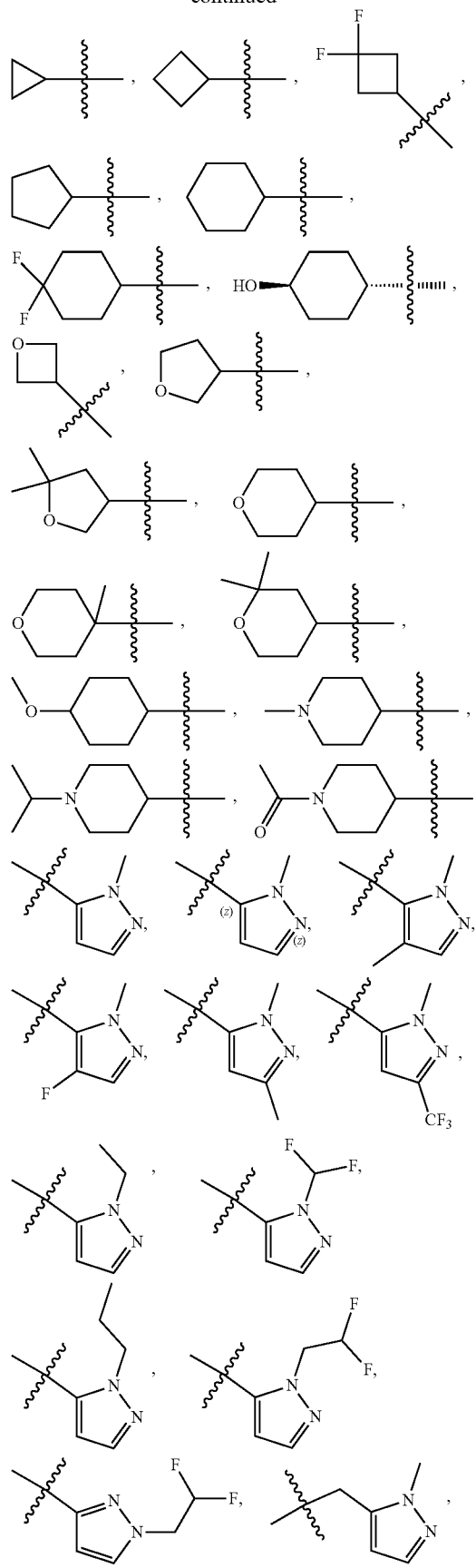
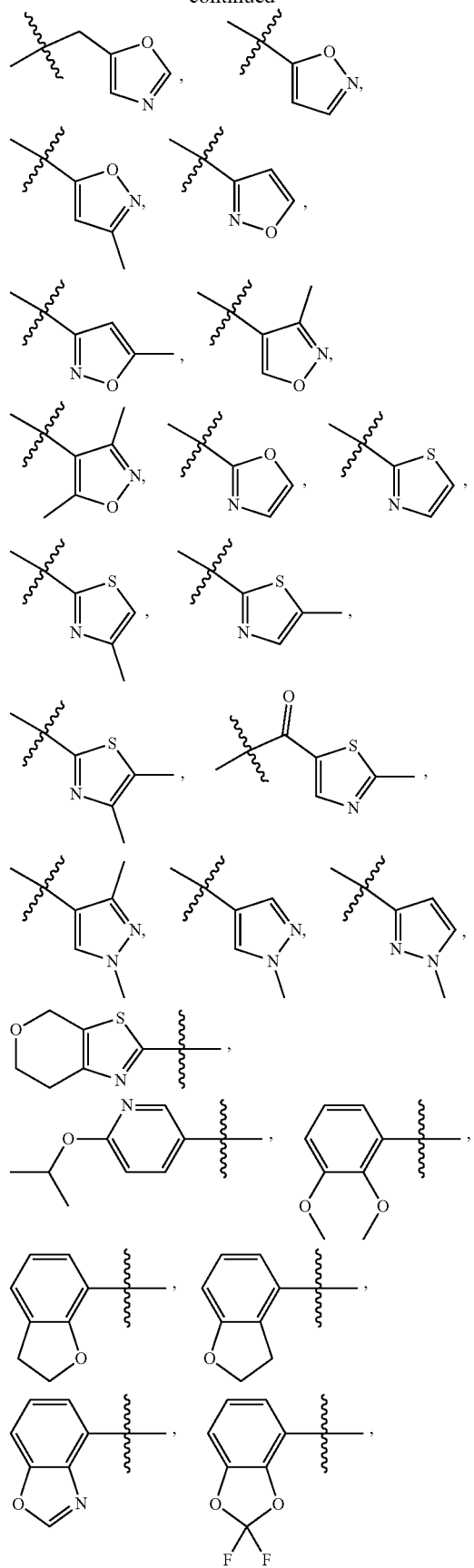

-continued
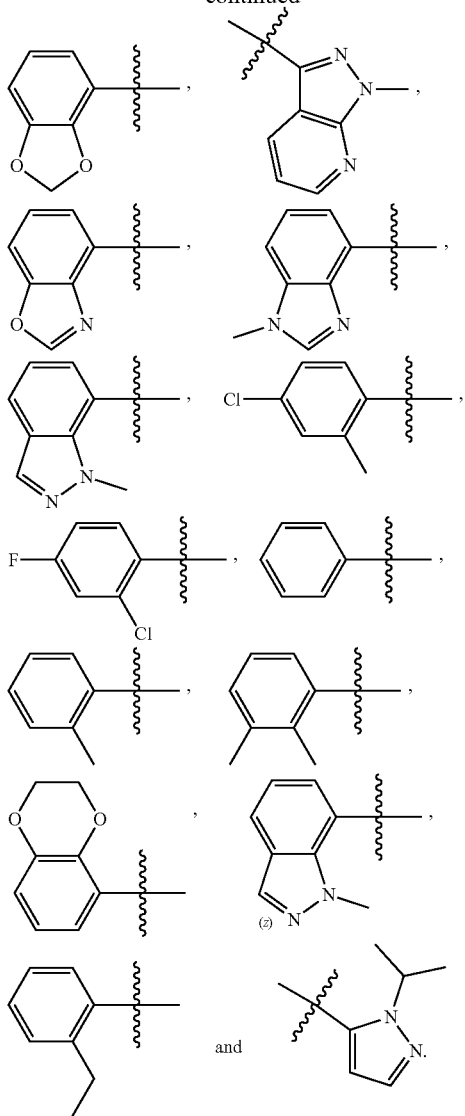
19. The compound of the Formula (I) or a pharmaceutically-acceptable salt, solvate, or prodrug thereof as claimed in claim 1, wherein R$_4$ is selected from the group consisting of
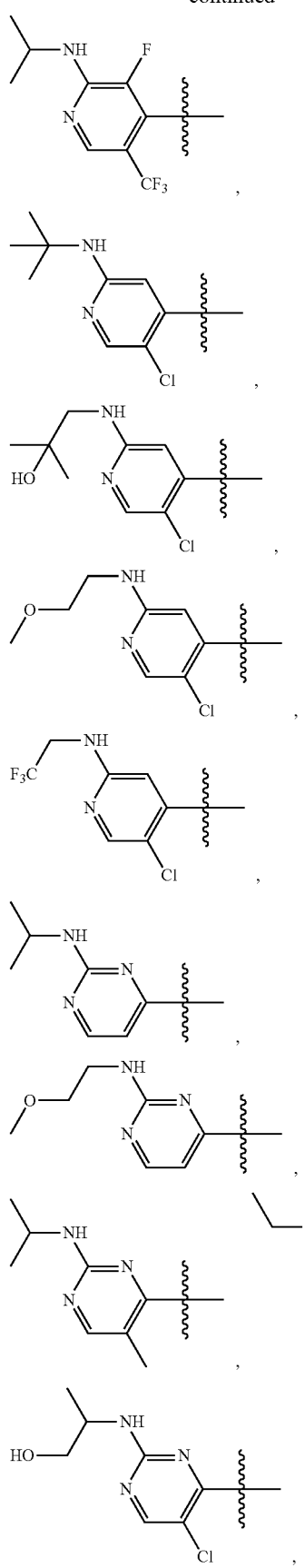

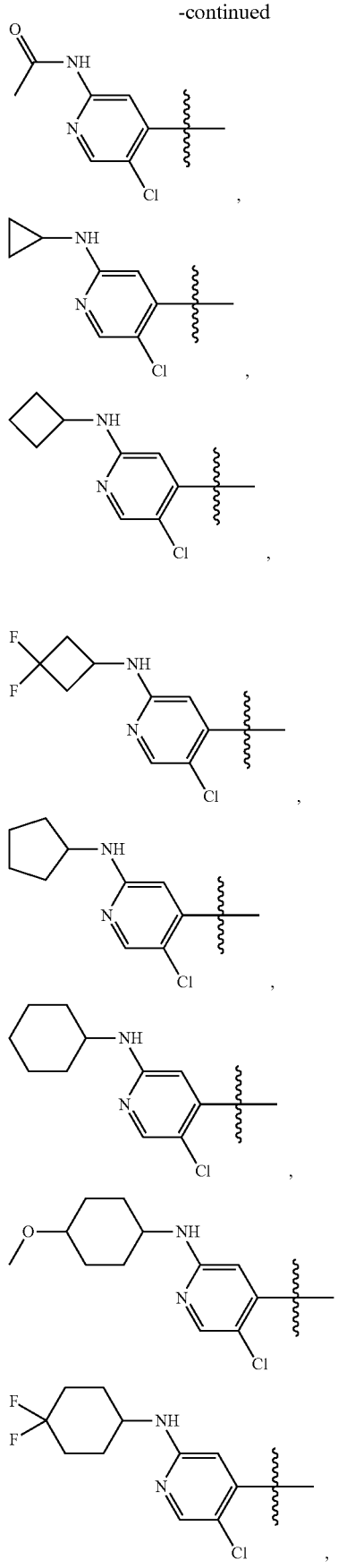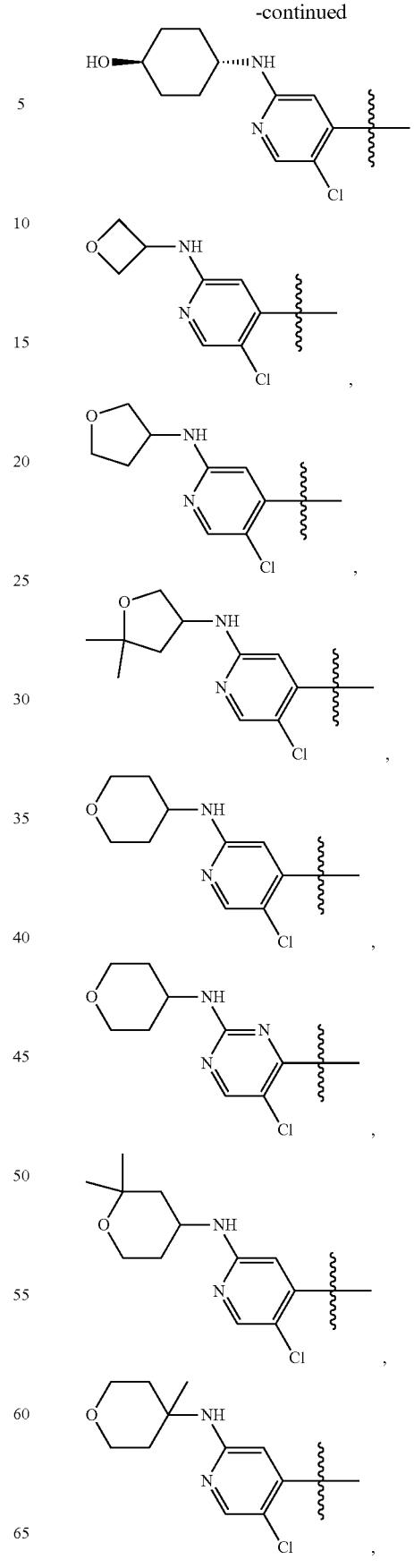

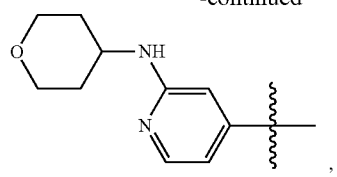,
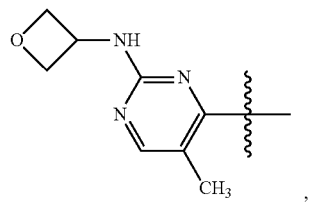,
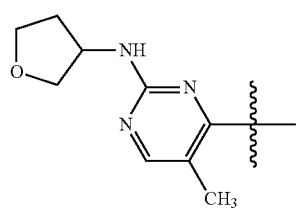,
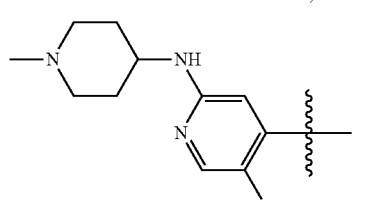,
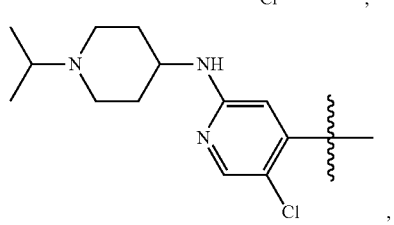,
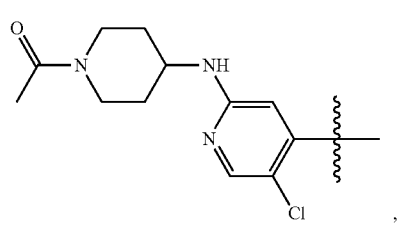,
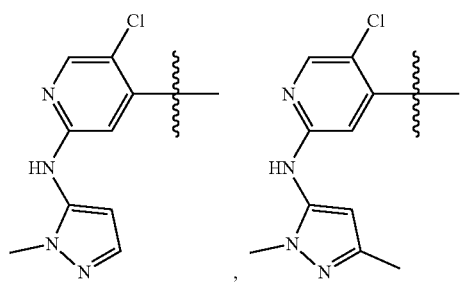,
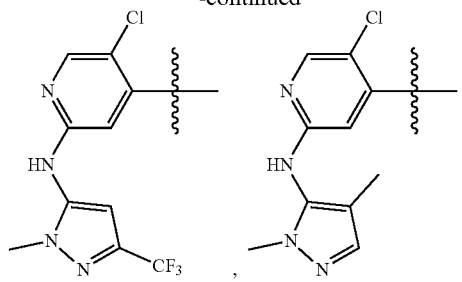,
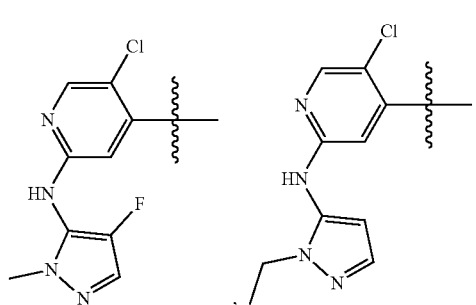,
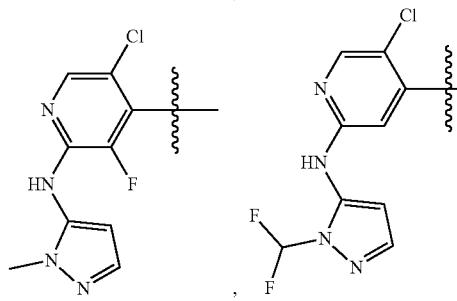,
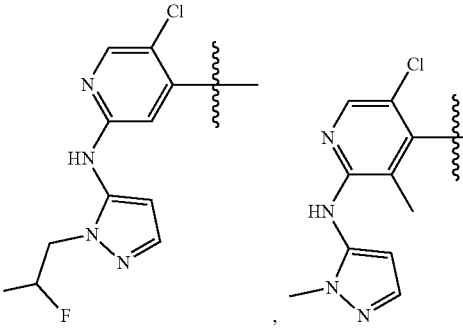,
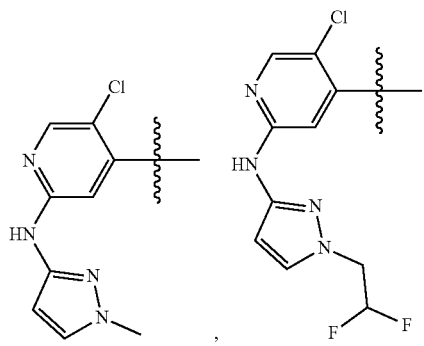,

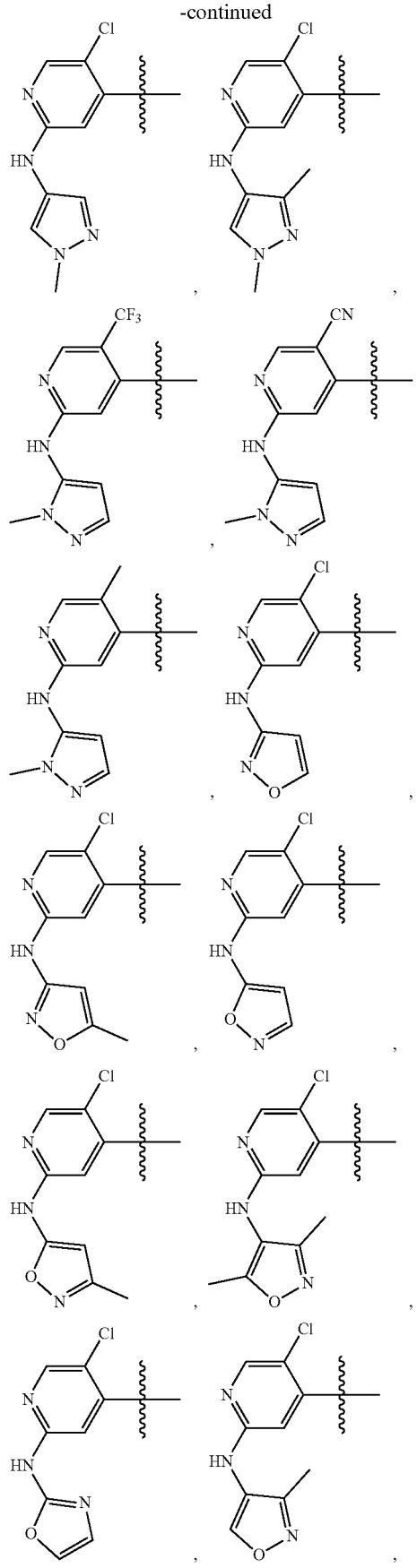
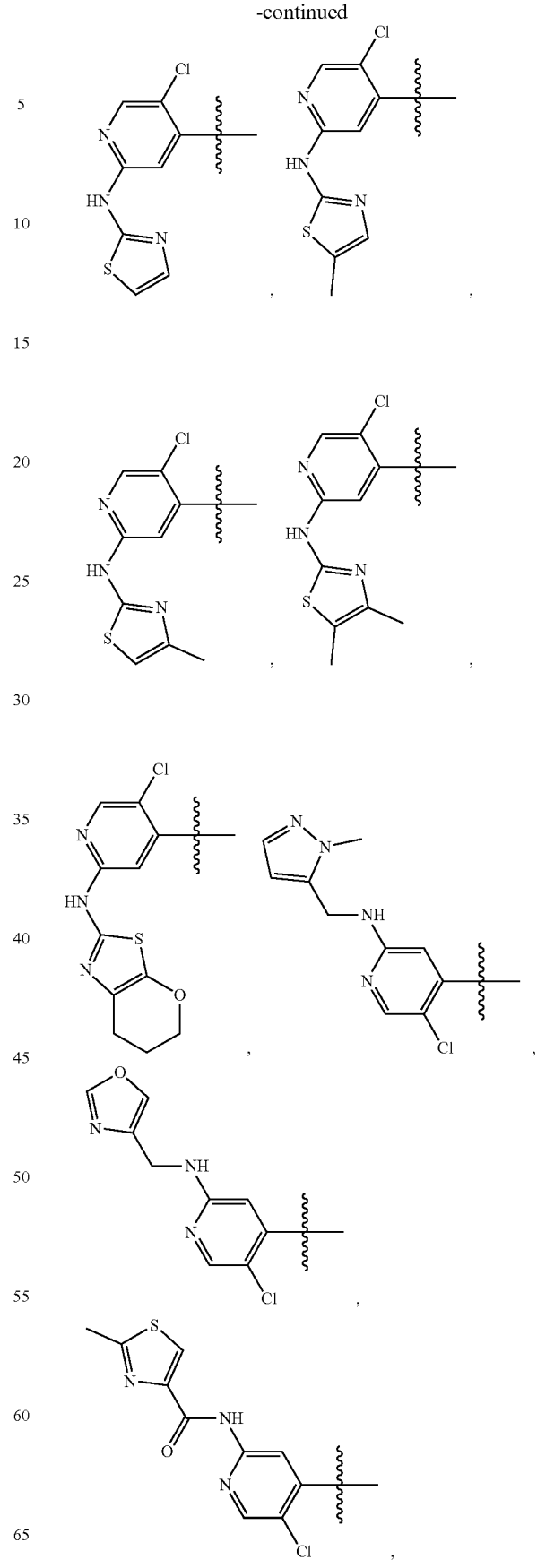

-continued
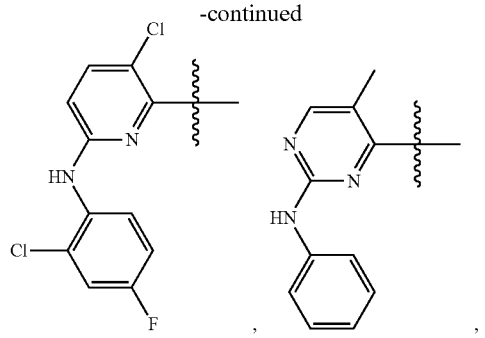
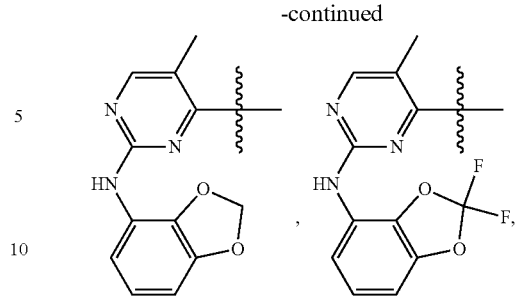
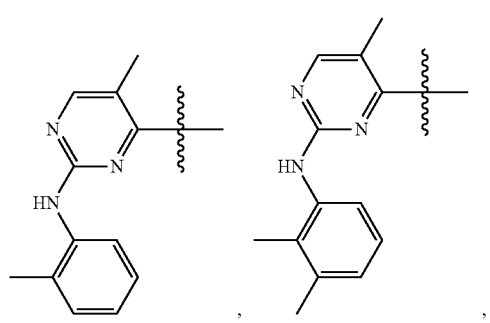
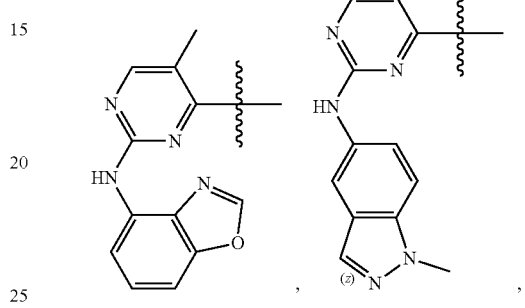
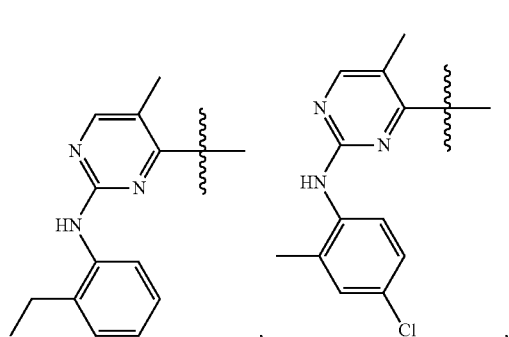
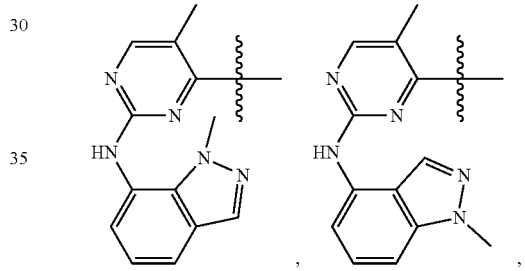
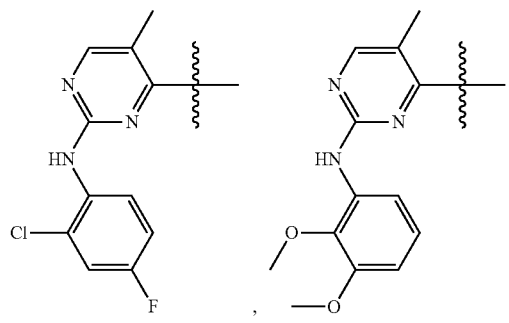
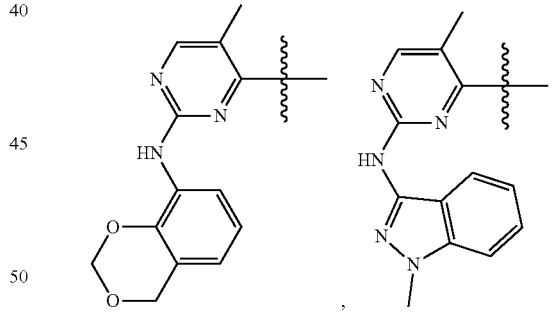
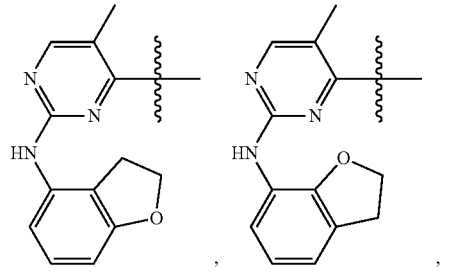
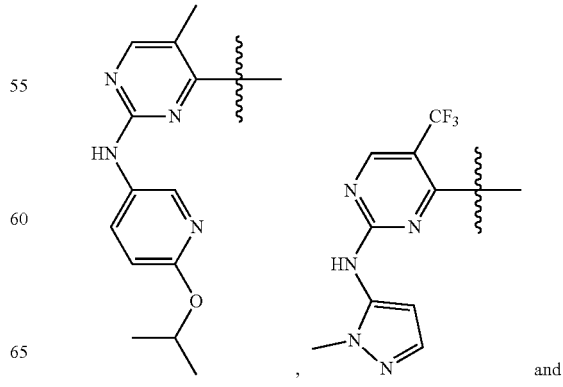
and

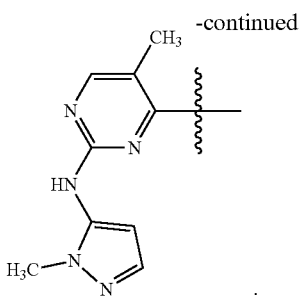

20. The compound of the Formula (I) or a pharmaceutically-acceptable salt, solvate, or prodrug thereof as claimed in claim 19, wherein R₄ is

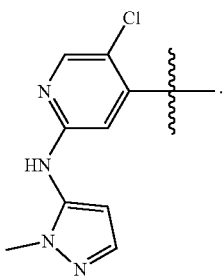 [SMILES: *c1cc(Nc2ccnn2C)ncc1Cl]

21. The compound of the Formula (I) or a pharmaceutically-acceptable salt, solvate, or prodrug thereof as claimed in claim 1, wherein m is 0, 1, or 2.

22. A compound or a pharmaceutically acceptable salt thereof, wherein the compound is selected from the group consisting of:
1) 4-(5-Chloro-2-(isopropylamino)pyridin-4-yl)-N-(2-(hydroxymethyl)benzyl)-1H-pyrrole-2-carboxamide;
2) 5-(5-Chloro-2-(isopropylamino)pyridin-4-yl)-N-(5-fluoro-2-(hydroxymethyl)benzyl)thiazole-2-carboxamide;
3) 5-(5-Chloro-2-(isopropylamino)pyridin-4-yl)-N-(2-(hydroxymethyl)benzyl)thiazole-2-carboxamide;
4) 5-(5-Chloro-2-(isopropylamino)pyridin-4-yl)-N-(4-fluoro-2-(hydroxymethyl)benzyl)thiazole-2-carboxamide;
5) 5-(5-Chloro-2-(isopropylamino)pyridin-4-yl)-N-(3-fluoro-2-(hydroxymethyl)benzyl)thiazole-2-carboxamide;
6) 8'-(5-Chloro-2-(isopropylamino)pyridin-4-yl)-2'-(2-(hydroxymethyl)benzyl)-2',3'-dihydro-1'H,5'H-spiro[oxetane-3,4'-pyrrolo[1,2-a][1,4]diazepine]-1'-one;
7) 2'-(5-Chloro-2-(isopropylamino)pyridin-4-yl)-5'-(2-(hydroxymethyl)benzyl)-5',6-dihydro-4'H,8'H-spiro[oxetane-3,7'-pyrazolo[1,5-a][1,4]diazepine]-4'-one;
8) 2-(5-Chloro-2-(isopropylamino)pyridin-4-yl)-7-(chloromethyl)-7-(hydroxymethyl)-5-(2-(hydroxymethyl)benzyl)-5,6,7,8-Tetrahydro-4H-pyrazolo[1,5-a][1,4]diazepine-4-one;
9) 2'-(4-Chloro-2-(hydroxymethyl)benzyl)-8'-(5-chloro-2-(isopropylamino)pyridin-4-yl)-2',3'-dihydro-1'H,5'H-spiro[cyclopropane-1,4'-pyrrolo[1,2-a][1,4]diazepine]-1'-one;
10) 8'-(5-Chloro-2-(isopropylamino)pyridin-4-yl)-2'-(5-fluoro-2-(hydroxymethyl)benzyl)-2',3'-dihydro-1'H,5'H-spiro[oxetane-3,4'-pyrrolo[1,2-a][1,4]diazepine]-1'-one;
11) 2-(5-Chloro-2-(isopropylamino)pyridin-4-yl)-8-(2-(hydroxymethyl)benzyl)-7,8-dihydro-5H,9H-spiro[imidazo[1,2-a][1,4]diazepine-6,3'-oxetane]-9-one;
12) 8'-(5-Chloro-2-(isopropylamino)pyridin-4-yl)-2'-(3-fluoro-2-(hydroxymethyl)benzyl)-2',3'-dihydro-1'H,5'H-spiro[oxetane-3,4'-pyrrolo[1,2-a][1,4]diazepine]-1'-one;
13) 8'-(5-Chloro-2-(isopropylamino)pyridin-4-yl)-2'-(2-(hydroxymethyl)benzyl)-2',3'-dihydro-1'H,5'H-spiro[azetidine-3,4'-pyrrolo[1,2-a][1,4]diazepine]-1'-one;
14) 7-(5-Chloro-2-(isopropylamino)pyridin-4-yl)-2-(2-(hydroxymethyl)benzyl)-3,4-dihydro pyrrolo[1,2-a]pyrazine-1(2H)-one;
15) 2-(4-Chloro-2-(hydroxymethyl)benzyl)-7-(5-chloro-2-(isopropylamino)pyridin-4-yl)-3,4-dihydropyrrolo[1,2-a]pyrazine-1(2H)-one;
16) 8-(5-Chloro-2-(isopropylamino)pyridin-4-yl)-2-(2-(hydroxymethyl)benzyl)-2,3,4,5-tetrahydro-1H-pyrrolo[1,2-a][1,4]diazepine-1-one;
17) 8'-(5-Chloro-2-(isopropylamino)pyridin-4-yl)-2'-(4,5-difluoro-2-(hydroxymethyl)benzyl)-2',3'-dihydrogen-1'H,5'H-spiro[oxetane-3,4'-pyrrolo[1,2-a][1,4]diazepine-1'-one;
18) 7-(5-Chloro-2-(isopropylamino)pyridin-4-yl)-2-(5-fluoro-2-(hydroxymethyl)benzyl)-3,4-dihydropyrrolo[1,2-a]pyrazine-1(2H)-one;
19) 7-(5-Chloro-2-(isopropylamino)pyridin-4-yl)-2-(4,5-difluoro-2-(hydroxymethyl)benzyl)-3,4-dihydropyrrolo[1,2-a]pyrazine 1(2H)-one;
20) 8-(5-Chloro-2-(isopropylamino)pyridin-4-yl)-2-(5-fluoro-2-(hydroxymethyl)benzyl)-4-hydroxy-2,3,4,5-tetrahydro-1H-pyrrolo[1,2-a][1,4]diazepine-1-one;
21) 8-(5-Chloro-2-(isopropylamino)pyridin-4-yl)-2-(4,5-difluoro-2-(hydroxymethyl)benzyl)-2,3,4,5-tetrahydro-1H-pyrrolo[1,2-a][1,4]diazepine-1-one;
22) N-(5-Fluoro-2-(hydroxymethyl)benzyl)-4-(5-methyl-2-((1-methyl-1H-pyrazol-5-yl)amino)pyrimidine-4-yl)-1H-pyrrole-2-carboxamide;
23) 2-(5-Fluoro-2-(hydroxymethyl)benzyl)-7-(5-methyl-2-((1-methyl-1H-pyrazol-5-yl)amino)pyrimidin-4-yl)-3,4-dihydropyrrolo[1,2-a]pyrazine-1(2H)-one: or
24) 8'-(5-Chloro-2-(isopropylamino)pyridin-4-yl)-2'-(2-(hydroxymethyl)benzyl)-1-methyl-2',3'-dihydro-1'H,5'H-spiro[azetidine-3,4'-pyrrolo[1,2-a][1,4]diazepine]-1'-one
25) 8'-(5-Chloro-2-(isopropylamino)pyridin-4-yl)-2'-(2-(hydroxymethyl)benzyl)-2',3'-dihydro-1'H,5'H-spiro[azetidine-3,4'-pyrrolo[1,2-a][1,4]diazepine]-1'-one;
26) 8-(5-Chloro-2-(isopropylamino)pyridin-4-yl)-2-(2-(hydroxymethyl)benzyl)-2',2'-dimethyl-2,3-dihydrogen-1H,5H-spiro[pyrrolo[1,2-a][1,4]diazepine-4,5'-[1,3]dioxane]-1-one;
27) 8-(5-Chloro-2-(isopropylamino)pyridin-4-yl)-4,4-bis(hydroxymethyl)-2-(2-(hydroxymethyl)benzyl)-2,3,4,5-tetrahydro-1H pyrrolo[1,2-a][1,4]diazepine-1-one;
28) 8-(5-Chloro-2-(isopropylamino)pyridin-4-yl)-2-(5-fluoro-2-(hydroxymethyl)benzyl)-2',2'-dimethyl-2,3-dihydro-1H,5H-spiro[pyrrolo[1,2-a][1,4]diazepine-4,5'-[1,3]dioxane]-1-one;
29) 8-(5-Chloro-2-(isopropylamino)pyridin-4-yl)-2-(5-fluoro-2-(hydroxymethyl)benzyl)-4,4-bis(hydroxymethyl)-2,3,4,5-tetrahydro-1H-pyrrolo[1,2-a][1,4]diazepine-1-one;
30) 7-(5-Chloro-2-(oxetan-3-yl)amino)pyridin-4-yl)-2-(5-fluoro-2-(hydroxymethyl)benzyl)-3,4-dihydropyrrolo[1,2-a]pyrazine-1(2H)-one;

31) 7-(5-Chloro-2-((tetrahydrofuran-3-yl)amino)pyridin-4-yl)-2-(5-fluoro-2-(hydroxymethyl)benzyl)-3,4-dihydropyrrole[1,2-a]pyrazine-1(2H)-one;
32) 2-(5-Fluoro-2-(hydroxymethyl)benzyl)-7-(5-methyl-2-(oxetan-3-ylamino)pyrimidin-4-yl)-3,4-dihydropyrrolo[1,2-a]pyrazine-1(2H)-one;
33) 2-(5-Fluoro-2-(hydroxymethyl)benzyl)-7-(5-methyl-2-((tetrahydrofuran-3-yl)amino)pyrimidin-4-yl)-3,4-dihydropyrrolo[1,2-a]pyrazine-1(2H)-one;
34) (R)-7-(5-chloro-2-(isopropylamino)pyridin-4-yl)-2-(5-fluoro-2-(hydroxymethyl)benzyl)-3-(methoxy(methyl)-3,4-dihydropyrrolo[1,2-a]pyrazine-1(2H)-one;
35) (R)-2-(5-Fluoro-2-(hydroxymethyl)benzyl)-3-(methoxymethyl)-7-(5-methyl-2-((1-methyl-1H-pyrazol-5-yl)amino)pyrimidin-4-yl)-3,4-dihydropyrrolo[1,2-a]pyrazine-1(2H)-one;
36) (R)-2-(5-Fluoro-2-(hydroxymethyl)benzyl)-7-(2-(isopropylamino)-5-methylpyrimidin-4-yl)-3-(methoxymethyl)-3,4-dihydropyrrolo[1,2-a]pyrazine-1(2H)-one;
37) 2-(5-Fluoro-2-(hydroxymethyl)benzyl)-3-(hydroxymethyl)-7-(5-methyl-2-(oxetan-3-ylamino)pyrimidine-4-yl)-3,4-dihydropyrrolo[1,2-a]pyrazine-1(2H)-one;
38) 2'-(4,5-Difluoro-2-(hydroxymethyl)benzyl)-8'-(5-methyl-2-(oxetan-3-ylamino)pyrimidin-4-yl)-2',3'-dihydro-1'H,5'H spiro[oxetane-3,4'-pyrrolo[1,2-a][1,4]diazepine]-1'-ketone;
39) 2'-(4,5-Difluoro-2-(hydroxymethyl)benzyl)-8'-(5-methyl-2-((tetrahydrofuran-3-yl)amino)pyrimidin-4-yl)-2',3'dihydro-1'H,5'H spiro[oxetane-3,4'-pyrrolo[1,2-a][1,4]diazepine]-1'-one; or
40) 2-(5-Fluoro-2-(hydroxymethyl)benzyl)-3-(hydroxymethyl)-7-(5-methyl-2-((tetrahydrofuran-3-yl)amino)pyrimidin-4-yl)-3,4-dihydropyrrolo[1,2-a]pyrazine-1(2H)-one;
41) 7-(5-Chloro-2-(oxetan-3-ylamino)pyridin-4-yl)-2-(4,5-difluoro-2-(hydroxymethyl)benzyl)-3,4-dihydropyrrolo[1,2-a]pyrazine-1(2H)-one;
42) 8-(5-Chloro-2-(isopropylamino)pyridin-4-yl)-2-(5-fluoro-2-(hydroxymethyl)benzyl)-4-(hydroxymethyl)-2,3,4,5-tetrahydro-1H-pyrrolo[1,2-a][1,4]diazepine-1-one;
43) 8-(5-Chloro-2-(isopropylamino)pyridin-4-yl)-2-(5-fluoro-2-(hydroxymethyl)benzyl)-2,3-dihydro-1H,5H-Spiro[pyrrolo[1,2-a][1,4]diazepine-4,5'-[1,3]dioxane]-1-one;
44) 8-(5-Chloro-2-(isopropylamino)pyridin-4-yl)-2-(5-fluoro-2-(hydroxymethyl)benzyl)-4,4-bis(methoxymethyl))-2,3,4,5-tetrahydro-1H-pyrrolo[1,2-a][1,4]diazepine-1-one;
45) (R)-7-(5-chloro-2-((1-methyl-1H-pyrazol-5-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;
46) (R)-2-(5-Chloro-2-(isopropylamino)pyridin-4-yl)-7-(5-fluoro-2-(hydroxymethyl)benzyl)-6-(methoxy(methyl)-6,7-dihydroimidazo[1,2-a]pyrazine-8-(5H)-one;
47) (R)-7-(5-chloro-3-fluoro-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
48) (R)-7-(5-chloro-3-methyl-2-((1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
49) 2-(5-Fluoro-2-(hydroxymethyl)benzyl)-7-(5-methyl-2-(o-tolylamino)pyrimidin-4-yl)-3,4-dihydropyrrolo[1,2-a]pyrazine-1(2H)-one;
50) 7-(5-chloro-2-((1-methyl-1H-pyrazol-5-yl)amino)pyridin-4-yl)-2-(5-fluoro-2-(hydroxymethyl)benzyl)-3,4-Dihydropyrrolo[1,2-a]pyrazine-1(2H)-one;
51) (R)-7-(5-chloro-2-((4-fluoro-1-methyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
52) (R)-7-(5-chloro-2-((1-ethyl-1H-pyrazol-5-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;
53) (R)-7-(5-chloro-2-((1-methyl-1H-pyrazol-5-yl)amino)pyridin-4-yl)-2-(5-fluoro-2-(hydroxymethyl)benzyl)-3-((methoxymethoxy)methyl)-3,4-dihydropyrrolo[1,2-a]pyrazine-1(2H)-one;
54) (R)-7-(5-chloro-2-((1-(difluoromethyl)-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
55) 8-(5-Chloro-2-(isopropylamino)pyridin-4-yl)-2-(5-fluoro-2-(hydroxymethyl)benzyl)-4-methoxy-2,3,4,5-tetrahydro-1H-pyrrolo[1,2-a][1,4]diazepine-1-one;
56) 8-(5-Chloro-2-(isopropylamino)pyridin-4-yl)-2-(5-fluoro-2-(hydroxymethyl)benzyl)-4-(hydroxymethyl)-4-(methoxymethyl)-2,3,4,5-4,5-tetrahydro-1H-pyrrolo[1,2-a][1,4]diazepine-1-one;
57) Methyl 7-(5-chloro-2-(isopropylamino)pyridin-4-yl)-2-(5-fluoro-2-(hydroxymethyl)benzyl)-1-oxo-1,2,3,4-tetrahydropyrrolo[1,2-a]pyrazine-3-carboxylic acid ethyl ester;
58) 8-(5-Chloro-2-(isopropylamino)pyridin-4-yl)-2-(4-chloro-5-fluoro-2-(hydroxymethyl)benzyl)-4,4-bis(hydroxy(methyl)-2,3,4,5-tetrahydro-1H-pyrrolo[1,2-a][1,4]diazepine-1-one;
59) (R)-7-(5-chloro-2-(isopropylamino)pyridin-4-yl)-2-(5-fluoro-2-(hydroxymethyl)benzyl)-3-(hydroxymethyl)-3,4-dihydropyrrolo[1,2-a]pyrazine-1(2H)-one;
60) (R)-7-(5-chloro-2-(oxetan-3-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;
61) (3R)-7-(5-chloro-2-((tetrahydrofuran-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
62) (R)-7-(5-chloro-2-((tetrahydro-2H-pyran-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
63) (R)-7-(5-chloro-2-((3,3-difluorocyclobutyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
64) (R)-7-(2-(tert-butylamino)-5-chloropyridin-4-yl)-2-(5-fluoro-2-(hydroxymethyl)benzyl)-3-(methoxy(methyl)-3,4-dihydropyrrolo[1,2-a]pyrazine-1(2H)-one;
65) (R)-7-(5-chloro-2-((2-hydroxy-2-methylpropyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
66) (R)-7-(5-Chloro-2-((1-methylpiperidin-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

67) (R)-2-(5-Fluoro-2-(hydroxymethyl)benzyl)-3-(methoxymethyl)-7-(2-((tetrahydro-2H-pyran-4-yl)amino)pyridin-4-yl)-3,4-dihydropyrrolo[1,2-a]pyrazine-1(2H)-one;
68) (R)-7-(5-chloro-2-((4,4-difluorocyclohexyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
69) (R)-7-(5-chloro-2-((4-methyltetrahydro-2H-pyran-4-yl)amino)pyridin-4-yl)-2-(5-fluoro-2-((hydroxymethyl)benzyl)-3-(methoxymethyl)-3,4-dihydropyrrolo[1,2-a]pyrazine-1(2H)-one;
70) (R)-7-(5-chloro-2-(cyclobutylamino)pyridin-4-yl)-2-(5-fluoro-2-(hydroxymethyl)benzyl)-3-(methoxy(methyl))-3,4-dihydropyrrolo[1,2-a]pyrazine-1(2H)-one;
71) (R)-7-(5-chloro-2-(((1R,4R)-4-hydroxycyclohexyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
72) (R)-7-(5-chloro-2-(cyclohexylamino)pyridin-4-yl)-2-(5-fluoro-2-(hydroxymethyl)benzyl)-3-(methoxymethylyl)-3,4-dihydropyrrolo[1,2-a]pyrazine-1(2H)-one;
73) 7-(5-Chloro-2-((1-isopropylpiperidin-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
74) (R)-7-(5-chloro-2-(cyclopropylamino)pyridin-4-yl)-2-(5-fluoro-2-(hydroxymethyl)benzyl)-3-(methoxy(methyl))-3,4-dihydropyrrolo[1,2-a]pyrazine-1(2H)-one;
75) (R)-2-(5-Fluoro-2-(hydroxymethyl)benzyl)-7-(5-fluoro-2-(isopropylamino)pyridin-4-yl)-3-(methoxy(methyl))-3,4-dihydropyrrolo[1,2-a]pyrazine-1(2H)-one;
76) (R)-2-(5-Fluoro-2-(hydroxymethyl)benzyl)-7-(2-(isopropylamino)-5-(trifluoromethyl)pyridin-4-yl)-3-(methoxymethyl)-3,4-dihydropyrrolo[1,2-a]pyrazine-1(2H)-one;
77) (R)-7-(5-chloro-2-(cyclopentylamino)pyridin-4-yl)-2-(5-fluoro-2-(hydroxymethyl)benzyl)-3-(methoxy(methyl))-3,4-dihydropyrrolo[1,2-a]pyrazine-1(2H)-one;
78) (3R)-7-(5-chloro-2-((2,2-dimethyltetrahydro-2H-pyran-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
79) (3R)-7-(5-chloro-2-((5,5-dimethyltetrahydrofuran-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
80) (R)-7-(5-chloro-2-((5-methylisoxazol-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
81) (R)-7-(5-Chloro-2-((3,5-dimethylisoxazol-4-yl)amino)pyridin-4-yl)-2-(5-fluoro-2-(hydroxy(methyl))benzyl)-3-(methoxymethyl)-3,4-dihydropyrrolo[1,2-a]pyrazine-1(2H)-one;
82) (R)-7-(5-chloro-2-(oxazol-2-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;
83) (R)-7-(5-chloro-2-((3-methylisoxazol-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
84) (R)-7-(5-chloro-2-(thiazol-2-ylamino)pyridin-4-yl)-2-(5-fluoro-2-(hydroxymethyl)benzyl)-3-(methyl(oxymethyl))-3,4-dihydropyrrolo[1,2-a]pyrazine-1(2H)-one;
85) (R)-7-(5-chloro-2-((5-methylthiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
86) (R)-7-(5-chloro-2-((1-methyl-1H-pyrazol-3-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;
87) (R)-7-(5-chloro-2-((3-methylisoxazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
88) (R)-7-(5-chloro-2-((1-methyl-1H-pyrazol-4-yl)amino)pyridin-4-yl)-2-(5-fluoro-2-(hydroxymethyl(yl)benzyl)-3-(methoxymethyl)-3,4-dihydropyrrolo[1,2-a]pyrazine-1(2H)-one;
89) (R)-7-(5-chloro-2-((1,3-dimethyl-1H-pyrazol-4-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
90) (R)-7-(5-chloro-2-((4,5-dimethylthiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
91) (R)-7-(5-chloro-2-((4-methylthiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
92) (R)-7-(5-Chloro-2-(isoxazol-3-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;
93) (R)-7-(5-Chloro-2-(isoxazol-5-ylamino)pyridin-4-yl)-2-(5-fluoro-2-(hydroxymethyl)benzyl)-3-(methoxymethyl)-3,4-dihydropyrrolo[1,2-a]pyrazine-1(2H)-one;
94) (R)-7-(5-Chloro-2-((6,7-dihydro-4H-pyrano[4,3-d]thiazol-2-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-ketone;
95) (R)-7-(5-Chloro-2-((1-methyl-1H-pyrazol-5-yl)amino)pyridin-4-yl)-2-(4,5-difluoro-2-(hydroxymethyl)benzyl)-3-(methoxymethyl)-3,4-dihydropyrrolo[1,2-a]pyrazine-1(2H)-one;
96) (R)-7-(5-chloro-2-((1,3-dimethyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
97) (R)-7-(5-chloro-2-((1,4-dimethyl-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;
98) (R)-7-(5-chloro-2-((1-methyl-1H-pyrazol-5-yl)amino)pyridin-4-yl)-2-(3-fluoro-2-(hydroxymethyl(yl)benzyl)-3-(methoxymethyl)-3,4-dihydropyrrolo[1,2-a]pyrazine-1(2H)-one;
99) (R)-7-(5-chloro-2-((1-methyl-1H-pyrazol-5-yl)amino)pyridin-4-yl)-2-(4-fluoro-2-(hydroxymethyl(yl)benzyl)-3-(methoxymethyl)-3,4-dihydropyrrolo[1,2-a]pyrazine-1(2H)-one;
100) (R)-2-(5-fluoro-2-(hydroxymethyl)benzyl)-3-(methoxymethyl)-7-(2-((1-methyl-1H-pyrazole-5-yl)

amino)-5-(trifluoromethyl)pyridin-4-yl)-3,4-dihydropyrrolo[1,2-a]pyrazine-1(2H)-one;

101) (R)-4-(2-(5-Fluoro-2-(hydroxymethyl)benzyl)-3-(methoxymethyl)-1-oxo-1,2,3,4-tetrahydro pyrrolo[1,2-a]pyrazin-7-yl)-6-((1-methyl-1H-pyrazol-5-yl)amino)nicotinonitrile;

102) (R)-2-(5-Fluoro-2-(hydroxymethyl)benzyl)-3-(methoxymethyl)-7-(5-methyl-2-((1-methyl-1H-pyrazol-5-yl)amino)pyridin-4-yl)-3,4-dihydropyrrolo[1,2-a]pyrazine-1(2H)-one;

103) (R)-7-(5-Chloro-2-((1-methyl-1H-pyrazol-5-yl)amino)pyridin-4-yl)-2-(2-(hydroxymethyl)-5-(trifluoromethyl)benzyl)-3-(methoxymethyl)-3,4-dihydropyrrolo[1,2-a]pyrazine-1(2H)-one;

104) (R)-7-(5-Chloro-2-((1-methyl-1H-pyrazol-5-yl)amino)pyridin-4-yl)-2-((3-(hydroxymethyl)-6-methylpyridin-2-yl)methyl)-3-(methoxymethyl)-3,4-dihydropyrrolo[1,2-a]pyrazine-1(2H)-one;

105) (R)-7-(5-chloro-2-((1-methyl-1H-pyrazol-5-yl)amino)pyridin-4-yl)-2-((4-(hydroxymethyl)-6-methylpyridin-3-yl)methyl)-3-(methoxymethyl)-3,4-dihydropyrrolo[1,2-a]pyrazine-1(2H)-one;

106) (R)-7-(5-chloro-2-((1-methyl-1H-pyrazol-5-yl)amino)pyridin-4-yl)-2-((2-(hydroxymethyl)-6-(trifluoromethyl)pyridin-3-yl)methyl)-3-(methoxymethyl)-3,4-dihydropyrrolo[1,2-a]pyrazine-1(2H)-ketone;

107) (R)-7-(5-chloro-2-((1-methyl-1H-pyrazol-5-yl)amino)pyridin-4-yl)-2-((3-(hydroxymethyl)pyridine-2-yl)methyl)-3-(methoxymethyl)-3,4-dihydropyrrolo[1,2-a]pyrazine-1(2H)-one;

108) (R)-7-(5-chloro-2-((1-methyl-1H-pyrazol-5-yl)amino)pyridin-4-yl)-2-((4-(hydroxymethyl)pyridine-3-yl)methyl)-3-(methoxymethyl)-3,4-dihydropyrrolo[1,2-a]pyrazine-1(2H)-one;

109) (R)-7-(5-chloro-3-fluoro-2-(isopropylamino)pyridin-4-yl)-2-(5-fluoro-2-(hydroxymethyl)benzyl)-3-(methoxymethyl)-3,4-dihydropyrrolo[1,2-a]pyrazine-1(2H)-one;

110) 7-(2-((1-Acetylpiperidin-4-yl)amino)-5-chloropyridin-4-yl)-2-(5-fluoro-2-(hydroxymethyl)benzyl)-3-(methoxymethyl)-3,4-dihydropyrrolo[1,2-a]pyrazine-1(2H)-one;

111) (R)-7-(5-chloro-2-((4-methoxycyclohexyl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

112) (R)-N-(5-chloro-4-(2-(5-fluoro-2-(hydroxymethyl)benzyl)-3-(methoxymethyl)-1-oxo-1,2,3,4-tetrahydropyrrolo[1,2-a]pyrazin-7-yl)pyridin-2-yl)acetamide;

113) (R)-7-(5-chloro-2-(((1-methyl-1H-pyrazol-5-yl)methyl)amino)pyridin-4-yl)-24(5-fluoro-2-(hydroxymethyl)benzyl)-3-(methoxymethyl)-3,4-dihydropyrrolo[1,2-a]pyrazine-1(2H)-one;

114) (R)-7-(5-chloro-2-((1-(2,2-difluoroethyl)-1H-pyrazol-3-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

115) (R)-7-(5-chloro-2-((1-(2,2-difluoroethyl)-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

116) (R)-7-(5-chloro-2-((oxazole-4-methylene)amino)pyridin-4-yl)-2-(5-fluoro-2-(hydroxymethyl)benzyl)-3-(methoxymethyl)-3,4-dihydropyrrole[1,2-a]pyrazine-1(2H)-one;

117) (R)-N-(5-chloro-4-(2-(5-fluoro-2-(hydroxymethyl)benzyl)-3-(methoxymethyl)-1-oxo-1,2,3,4-tetrahydropyrrolo[1,2-a]pyrazin-7-yl)pyridin-2-yl)-2-methylthiazole-4-carboxamide;

118) (R)-7-(5-chloro-2-((1-methyl-3-(trifluoromethyl)-1H-pyrazol-5-yl)amino)pyridin-4-yl)-2-(5-fluoro-2-(hydroxymethyl)benzyl)-3-(methoxymethyl)-3,4-dihydropyrrolo[1,2-a]pyrazine-1(2H)-one;

119) (R)-3-((7-(5-chloro-2-((1-methyl-1H-pyrazol-5-yl)amino)pyridin-4-yl)-3-(methoxymethyl)-1-oxo-3,4-dihydropyrrolo[1,2-a]pyrazine-2(1H)-yl)methyl)-4-(hydroxymethyl)benzonitrile;

120) (R)-7-(5-chloro-2-((1-methyl-1H-pyrazol-5-yl)amino)pyridin-4-yl)-2-((2-(hydroxymethyl)pyridine-3-yl)methyl)-3-(methoxymethyl)-3,4-dihydropyrrolo[1,2-a]pyrazine-1(2H)-one;

121) 2-(5-Fluoro-2-(hydroxymethyl)benzyl)-7-(2-((1-hydroxyprop-2-yl)amino)-5-methyl pyrimidin-4-yl)-3,4-dihydropyrrolo[1,2-a]pyrazine-1(2H)-one;

122) N-(5-Fluoro-2-(hydroxymethyl)benzyl)-4-(5-methyl-2-(oxetan-3-ylamino)pyrimidin-4-yl)-1H-pyrrole-2-carboxamide;

123) 2-(5-Fluoro-2-(hydroxymethyl)benzyl)-7-(2-(isopropylamino)-5-methylpyrimidin-4-yl)-3,4-dihydropyrrolo[1,2-a]pyrazine-1(2H)-one;

124) 7-(5-Chloro-2-((2,2,2-trifluoroethyl)amino)pyridin-4-yl)-2-(5-fluoro-2-(hydroxymethyl)benzyl)-3,4-dihydropyrrolo[1,2-a]pyrazine-1(2H)-one;

125) 7-(2-((2-Chloro-4-fluorophenyl)amino)-5-methylpyrimidin-4-yl)-2-(5-fluoro-2-(hydr oxymethyl)benzyl)-3,4-dihydropyrrolo[1,2-a]pyrazine-1(2H)-one;

126) 7-(5-Chloro-2-((tetrahydro-2H-pyran-4-yl)amino)pyridin-4-yl)-2-(5-fluoro-2-(hydroxymethyl)benzyl)-3,4-dihydropyrrolo[1,2-a]pyrazine-1(2H)-one;

127) (R)-2-(5-Fluoro-2-(hydroxymethyl)benzyl)-7-(2-(isopropylamino)pyrimidin-4-yl)-3-(methoxymethyl)-3,4-dihydropyrrolo[1,2-a]pyrazine-1(2H)-one;

128) 7-(5-Chloro-2-((3,3-difluorocyclobutyl)amino)pyridin-4-yl)-2-(5-fluoro-2-(hydroxymethyl)benzyl)-3,4-dihydropyrrolo[1,2-a]pyrazine-1(2H)-one;

129) 7-(5-Chloro-2-((2-chloro-4-fluorophenyl)amino)pyridin-4-yl)-2-(5-fluoro-2-(hydroxymethyl)benzyl)-3,4-dihydropyrrolo[1,2-a]pyrazine-1(2H)-one;

130) (R)-7-(5-chloro-2-((tetrahydro-2H-pyran-4-yl)amino)pyrimidin-4-yl)-2-(5-fluoro-2-(hydroxymethyl)benzyl)-3-(methoxymethyl)-3,4-dihydropyrrolo[1,2-a]pyrazine-1(2H)-one;

131) (R)-7-(5-chloro-2-(ethylamino)pyrimidin-4-yl)-2-(5-fluoro-2-(hydroxymethyl)benzyl)-3-(methoxymethylyl)-3,4-dihydropyrrolo[1,2-a]pyrazine-1(2H)-one;

132) 7-(2-((2-ethylphenyl)amino)-5-methylpyrimidin-4-yl)-2-(5-fluoro-2-(hydroxymethyl)benzyl)-3,4-dihydropyrrolo[1,2-a]pyrazine-1(2H)-one;

133) 7-(2-(Benzo[d][1,3]dioxol-4-ylamino)-5-methylpyrimidin-4-yl)-2-(5-fluoro-2-(hydroxyl(methyl)benzyl)-3,4-dihydropyrrolo[1,2-a]pyrazine-1(2H)-one;

134) 2-(5-Fluoro-2-(hydroxymethyl)benzyl)-7-(5-methyl-2-((1-methyl-1H-indazol-5-yl)amino)pyrimidin-4-yl)-3,4-dihydropyrrolo[1,2-a]pyrazine-(2H)-one;

135) 7-(2-((2,3-Dihydrobenzo[b][1,4]dioxen-5-yl)amino)-5-methylpyrimidin-4-yl)-2-(5-fluoro-2-(hydroxymethyl)benzyl)-3,4-dihydropyrrolo[1,2-a]pyrazine-1(2H)-one;

136) 7-(2-((2,3-Dimethylphenyl)amino)-5-methylpyrimidin-4-yl)-2-(5-fluoro-2-(hydroxymethyl)benzyl)-3,4-dihydropyrrolo[1,2-a]pyrazine-1(2H)-one;

137) 2-(5-Fluoro-2-(hydroxymethyl)benzyl)-7-(5-methyl-2-(phenylamino)pyrimidin-4-yl)-3,4-dihydropyrrolo[1,2-a]pyrazine-1(2H)-one;
138) 7-(2-((4-Chloro-2-methylphenyl)amino)-5-methylpyrimidin-4-yl)-2-(5-fluoro-2-(hydroxymethyl)benzyl)-3,4-dihydropyrrolo[1,2-a]pyrazine-1(2H)-one;
139) 4-(5-Chloro-2-((1-methyl-1H-pyrazol-5-yl)amino)pyridin-4-yl)-N-(4,5-difluoro-2-(hydroxymethyl)benzyl)-1H-pyrrole-2-carboxamide;
140) 2-(5-Fluoro-2-(hydroxymethyl)benzyl)-7-(5-methyl-2-((1-methyl-1H-indazol-7-yl)amino)pyrimidin-4-yl)-3,4-dihydropyrrolo[1,2-a]pyrazine-1(2H)-one;
141) 2-(5-Fluoro-2-(hydroxymethyl)benzyl)-7-(5-methyl-2-((1-methyl-1H-indazol-4-yl)amino)pyrimidin-4-yl)-3,4-dihydropyrrolo[1,2-a]pyrazine-1(2H)-one;
142) 7-(2-((2,2-Difluorobenzo[d][1,3]dioxol-4-yl)amino)-5-methylpyrimidin-4-yl)-2-(5-fluoro-2-(hydroxymethyl)benzyl)-3,4-dihydropyrrolo[1,2-a]pyrazine-1(2H)-one;
143) 7-(2-(Benzo[d]oxazol-4-ylamino)-5-methylpyrimidin-4-yl)-2-(5-fluoro-2-(hydroxymethyl)benzyl)-3,4-dihydropyrrolo[1,2-a]pyrazine-1(2H)-one;
144) 2-(5-Fluoro-2-(hydroxymethyl)benzyl)-7-(5-methyl-2-((1-methyl-1H-pyrazolo[3,4-b]pyridine-3-yl)amino)pyrimidinepiperidin-4-yl)-3,4-dihydropyrrolo[1,2-a]pyrazine-1(2H)-one;
145) 7-(2-((2,3-Dihydrobenzofuran-4-ylamino)-5-methylpyrimidin-4-yl)-2-(5-fluoro-2-(hydroxymethyl)benzyl)-3,4-dihydropyrrolo[1,2-a]pyrazine-1(2H)-one;
146) 7-(2-((2,3-Dihydrobenzofuran-7-yl)amino)-5-methylpyrimidin-4-yl)-2-(5-fluoro-2-(hydroxymethyl)benzyl)-3,4-dihydropyrrolo[1,2-a]pyrazine-1(2H)-one;
147) 7-(5-Chloro-2-((1-methyl-1H-pyrazol-5-yl)amino)pyridin-4-yl)-2-(4-chloro-5-fluoro-2-(hydroxymethyl)benzyl)-3,4-dihydropyrrolo[1,2-a]pyrazine-1(2H)-one;
148) 7-(5-Chloro-2-((1-methyl-1H-pyrazol-5-yl)amino)pyridin-4-yl)-2-(3,5-difluoro-2-(hydroxymethyl)benzyl)-3,4-dihydropyrrolo[1,2-a]pyrazine-1(2H)-one;
149) 7-(5-Chloro-2-((1-methyl-1H-pyrazol-5-yl)amino)pyridin-4-yl)-2-(4-fluoro-2-(hydroxymethyl)benzyl)-3,4-dihydropyrrolo[1,2-a]pyrazine-1(2H)-one;
150) 7-(5-Chloro-2-((1-methyl-1H-pyrazol-5-yl)amino)pyridin-4-yl)-2-(3-fluoro-2-(hydroxymethyl)benzyl)-3,4-dihydropyrrolo[1,2-a]pyrazine-1(2H)-one;
151) 4-(2-(5-Fluoro-2-(hydroxymethyl)benzyl)-1-oxo-1,2,3,4-tetrahydropyrrolo[1,2-a]pyrazine-7-yl)-6-((1-methyl-1H-pyrazol-5-yl)amino)nicotinonitrile;
152) 2-(5-fluoro-2-(hydroxymethyl)benzyl)-7-(5-methyl-2-((1-methyl-1H-pyrazol-5-yl)amino)pyridin-4-yl)-3,4-dihydropyrrolo[1,2-a]pyrazine-1(2H)-one;
153) 7-(5-Chloro-2-((1-methyl-1H-pyrazol-5-yl)amino)pyridin-4-yl)-2-(2-(hydroxymethyl)-5-(trifluoromethyl(yl)benzyl)-3,4-dihydropyrrolo[1,2-a]pyrazine-1(2H)-one;
154) 7-(5-Chloro-2-((1-methyl-1H-pyrazol-5-yl)amino)pyridin-4-yl)-2-((3-(hydroxymethyl)-6-methylpyridine-2-yl)methyl)-3,4-dihydropyrrolo[1,2-a]pyrazine-1(2H)-one;
155) 7-(5-Chloro-2-((1-methyl-1H-pyrazol-5-yl)amino)pyridin-4-yl)-2-((2-(hydroxymethyl)pyridin-3-yl)(methyl)-3,4-dihydropyrrolo[1,2-a]pyrazine-1 (2H)-one;
156) 7-(5-Chloro-2-((2-methoxyethyl)amino)pyridin-4-yl)-2-(5-fluoro-2-(hydroxymethyl)benzyl)-3,4-dihydropyrrolo[1,2-a]pyrazine-1(2H)-one;
157) (R)-2-(5-Fluoro-2-(hydroxymethyl)benzyl)-7-(2-((2-methoxyethyl)amino)pyrimidin-4-yl)-3-(methyl(oxymethyl)-3,4-dihydropyrrolo[1,2-a]pyrazine-1(2H)-one;
158) 7-(2-((2,3-Dimethoxyphenyl)amino)-5-methylpyrimidin-4-yl)-2-(5-fluoro-2-(hydroxylmethyl)benzyl)-3,4-dihydropyrrolo[1,2-a]pyrazine-1(2H)-one;
159) 2-(5-Fluoro-2-(hydroxymethyl)benzyl)-7-(2-((6-isopropoxypyridin-3-yl)amino)-5-methylpyrimidin-4-yl)-3,4-dihydropyrrolo[1,2-a]pyrazine-1(2H)-one;
160) 7-(5-Chloro-2-((1-methyl-1H-pyrazol-5-yl)amino)pyridin-4-yl)-2-(4,5-difluoro-2-(hydroxymethyl)benzyl)-3,4-dihydropyrrolo[1,2-a]pyrazine-1(2H)-one;
161) 2-(5-Fluoro-2-(hydroxymethyl)benzyl)-7-(2-((1-methyl-1H-pyrazol-5-yl)amino)-5-(trifluoromethyl)pyridine-4-yl)-3,4-dihydropyrrolo[1,2-a]pyrazine-1(2H)-one;
162) 2-(5-Fluoro-2-(hydroxymethyl)benzyl)-7-(2-(isopropylamino)-5-(trifluoromethyl)pyridin-4-yl)-3,4-dihydropyrrolo[1,2-a]pyrazine-1(2H)-one;
163) (R)-2-(5-Fluoro-2-(hydroxymethyl)benzyl)-3-(methoxymethyl)-7-(2-((1-methyl-1H-pyrazole-5-yl)amino)-5-(trifluoromethyl)pyrimidin-4-yl)-3,4-dihydropyrrolo[1,2-a]pyrazine-1(2H)-one;
164) 2-(5-Fluoro-2-(hydroxymethyl)benzyl)-7-(2-((1-methyl-1H-pyrazol-5-yl)amino)-5-(trifluoromethyl)pyrimidine-4-yl)-3,4-dihydropyrrolo[1,2-a]pyrazine-1(2H)-one;
165) 7-(5-Chloro-2-((1-methyl-1H-pyrazol-5-yl)amino)pyridin-4-yl)-2-((3-(hydroxymethyl)pyridin-2-yl)(methyl)-3,4-dihydropyrrolo[1,2-a]pyrazine-1(2H)-one;
166) 7-(5-Chloro-2-((1-methyl-1H-pyrazol-5-yl)amino)pyridin-4-yl)-2-((2-(hydroxymethyl)pyridin-3-yl)(methyl)-3,4-dihydropyrrolo[1,2-a]pyrazine-1(2H)-one;
and
168) (R)-7-(5-chloro-2-((1-methyl-1H-pyrazol-5-yl)amino)pyridin-4-yl)-3-(methoxymethyl)-2-(3,4,5-trifluoro-2-(hydroxymethyl)benzyl)-3,4-dihydropyrrolo[1,2-a]pyrazine-1(2H)-one.

23. A pharmaceutical composition comprising a therapeutically effective amount of at least one compound of the Formula (I) or a pharmaceutically-acceptable salt, solvate, or prodrug thereof as claimed in claim 1 and at least one pharmaceutically acceptable carrier.

24. The pharmaceutical composition as claimed in claim 23, wherein the weight ratio of the compound of the Formula (I) or a pharmaceutically-acceptable salt, solvate, or prodrug thereof to the pharmaceutically acceptable carrier is 0.0001:1-10.

25. A method for treating a disease mediated by ERK, comprising administering to a subject in need thereof a therapeutically effective amount of the compound of the Formula (I) or a pharmaceutically-acceptable salt, solvate, or prodrug thereof as claimed in claim 1, or a pharmaceutical composition—comprising a therapeutically effective amount of at least one compound of the Formula (I) or a pharmaceutically-acceptable salt, solvate, or prodrug thereof as claimed in claim 1 and at least one pharmaceutically acceptable carrier:
wherein the disease mediated by ERK is a cancer selected from the group consisting, of breast cancer, multiple myeloma, bladder cancer, endometrial cancer, gastric cancer, cervical cancer, rhabdomyosarcoma, non-small cell lung cancer, small cell lung cancer, pleomorphic lung cancer, ovarian cancer, esophageal cancer, melanoma, colorectal cancer, hepatocellular carcinoma, head and neck cancer, hepatobiliary cell carcinoma, myelodysplastic syndrome, malignant glioma, prostate cancer, thyroid cancer, schwann cell tumor, lung squamous cell carcinoma, lichenoid keratosis, synovial sarcoma, skin cancer, pancreatic cancer testicular cancer, and liposarcoma.

26. The method as claimed in claim 25, wherein the ERK includes ERK1 and/or ERK2.

27. The method as claimed in claim 25, wherein the subject in need thereof is a human.

* * * * *